(12) United States Patent
Krisky et al.

(10) Patent No.: US 12,275,949 B2
(45) Date of Patent: *Apr. 15, 2025

(54) HIGH-TRANSDUCING HSV VECTORS

(71) Applicant: PeriphaGen, Inc., Pittsburgh, PA (US)

(72) Inventors: David M. Krisky, Pittsburgh, PA (US); James B. Wechuck, Pittsburgh, PA (US); James R. Goss, Pittsburgh, PA (US)

(73) Assignee: PeriphaGen, Inc., Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/359,013

(22) Filed: Jul. 26, 2023

(65) Prior Publication Data

US 2024/0158809 A1 May 16, 2024

Related U.S. Application Data

(62) Division of application No. 16/088,393, filed as application No. PCT/US2017/024092 on Mar. 24, 2017, now Pat. No. 11,753,653.

(60) Provisional application No. 62/313,391, filed on Mar. 25, 2016.

(51) Int. Cl.
C12N 15/86 (2006.01)
A61K 48/00 (2006.01)
C12N 7/00 (2006.01)

(52) U.S. Cl.
CPC .......... C12N 15/86 (2013.01); A61K 48/0025 (2013.01); C12N 7/00 (2013.01); *C12N 2710/16621* (2013.01); *C12N 2710/16643* (2013.01); *C12N 2710/16662* (2013.01); *C12N 2830/008* (2013.01)

(58) Field of Classification Search
CPC ...... C12N 15/86; C12N 7/00; C12N 2710/16621; C12N 2710/16643; C12N 2710/16662; C12N 2830/008; C12N 2710/16641; C12N 2710/16652; C12N 2800/107; A61K 48/0025; A61K 31/713; A61K 38/27; A61K 48/0008; A61K 48/0058
See application file for complete search history.

(56) References Cited

U.S. PATENT DOCUMENTS

| | | | |
|---|---|---|---|
| 5,763,217 A | 6/1998 | Cynader et al. | |
| 5,849,571 A | 12/1998 | Glorioso et al. | |
| 5,879,934 A | 3/1999 | DeLuca | |
| 10,301,600 B2 | 5/2019 | Coffin | |
| 10,799,560 B2 | 10/2020 | Krisky et al. | |
| 11,753,653 B2* | 9/2023 | Krisky | C12N 7/00 435/320.1 |
| 2001/0026799 A1 | 10/2001 | DeLuca | |
| 2002/0098170 A1 | 7/2002 | Wechsler et al. | |
| 2005/0092374 A1 | 5/2005 | Kim et al. | |
| 2008/0289058 A1 | 11/2008 | Cascio et al. | |
| 2009/0156638 A1 | 6/2009 | Khanna | |
| 2014/0363469 A1 | 12/2014 | Meyers et al. | |
| 2017/0087185 A1 | 3/2017 | Crane et al. | |
| 2020/0199618 A1 | 6/2020 | Krisky et al. | |

FOREIGN PATENT DOCUMENTS

| | | |
|---|---|---|
| CN | 1705438 A | 12/2005 |
| CN | 103667175 A | 3/2014 |
| WO | WO-98/015637 A1 | 4/1998 |
| WO | WO-2003/105750 A2 | 12/2003 |
| WO | WO-2005/011722 A2 | 2/2005 |
| WO | WO-2005/092374 A2 | 12/2005 |
| WO | WO-2013/109604 A1 | 7/2013 |
| WO | WO-2017/165806 A1 | 9/2017 |
| WO | WO-2017/165813 A1 | 9/2017 |
| WO | WO-2023/205661 A2 | 10/2023 |
| WO | WO-2023/211425 A1 | 11/2023 |

OTHER PUBLICATIONS

Liu, M. et al., ICP0 Antagonizes ICP4-Dependent Silencing of the Herpes Simplex Virus ICP0 Gene PLoS One, 2010, vol. 5, No. 1, e8837; pp. 1-16; p. 8, col. 2, second paragraph.
'Transcriptional Regulator ICP4 [Human Alphaherpesvirus 1]; 13TCD6' Publication (online]. Sep. 5, 2012 [retrieved Jul. 10, 2017]. Retrieved from the Internet: <URL: https://www.ncbi.nlm.nih.gov/protein/38852 <http://www.ncbi.nlm.nih.gov/protein/388521993?report-genbank&log$=prottop&blast_rank=1&RID=PCWCCB3C014>; p. 1.
UniProtKB Accession No. 13TC55 "Immediate early protein ICP0" Sep. 5, 2012 [online]. [Retrieved on Aug. 29, 2022]. Retrieved from the internet: <URL: https://www.uniprot.org/uniprotkb/13TC55/entry><http://www.uniprot.org/uniprotkb/13TC55/entry> Entire document; full sequence.
Santiago-Ortiz et al., "Adena-Associated Virus (MV) Vectors in Cancer Gene Therapy" J Control Release. 28; 240:287-301 (2016).
Fink et al., Gene therapy for pain: results of a phase I clinical trial. Ann Neural. Aug. 2011; 70(2):207-12. doi: 10.1002/ana.22446. Epub Jul. 27, 2011. Author Manuscript, 12 pages.
Johnson et al., "Cytotoxicity of a replication-defective mutant of herpes simplex virus type 1." J Viral. May 1992;66(5):2952-65. doi: 10.1128/JVI.66.5.2952-2965.1992.
Kolb et al., "Sequence variation in the herpes simplex virus U(S) 1 ocular virulence determinant." Invest Ophthalmol Vis Sci. Jun. 28, 2011;52(7):4630-38. doi: 10.I 167/iovs.10-7032.
Krisky et al., "Deletion of multiple immediate-early genes from herpes simplex virus reduces cytotoxicity and permits long-term gene expression in neurons" Gene Ther. Dec. 1998;5(12):1593-603. doi: 10.1038/si.gt.3300766.
Lau et al., "Herpes simplex virus vector-mediated expression of interleukin-10 reduces below-level central neuropathic pain after spinal cord injury" Neurorehabil Neural Repair. Sep. 2012;26(7):889-97. doi: 10.1177/1545968312445637. Epub May 15, 2012.

(Continued)

Primary Examiner — Jeremy C Flinders
Assistant Examiner — Alexander W Nicol
(74) Attorney, Agent, or Firm — Goodwin Procter LLP

(57) ABSTRACT

Disclosed herein are high transducing replication defective herpes simplex virus (HSV) vectors of McKrae strain.

14 Claims, 110 Drawing Sheets

Specification includes a Sequence Listing.

(56) References Cited

OTHER PUBLICATIONS

Wu et al., "Prevention of diabetic neuropathy by regulatable expression of HSV-mediated ervthropoietin" Mol Ther. Feb. 2011; I9(2):310-7. doi: 10.1038/mt.2010.215. Epub Oct. 5, 2010.
International Preliminary Report on Patentability for Application No. PCT/US2017/024092, mailed Oct. 4, 2018.
International Preliminary Report on Patentability for Application No. PCT/US2017/024083, mailed Oct. 4, 2018.
Extended European Search Report mailed Aug. 16, 2019 for Application No. EP 17771265.0.
Extended European Search Report mailed Aug. 22, 2019 for Application No. EP 17771260.1.
Burton et al., "Multiple applications for replication-defective herpes simplex virus vectors" Stem Cells. Jan. 2001;I9(5):358-77.
Chattopadhyay et al., "Long-term neuroprotection achieved with latency-associated promoter-driven herpes simplex virus gene transfer to the peripheral nervous system" Mol Ther. Aug. 2005;I2(2):307-13.
Chattopadhyay et al., Protective effect of herpes simplex virus-mediated neurotrophin gene transfer in cisplatin neuropathy. Brain. Apr. 2004;I27(4):929-39.
DeLuca et al., "Isolation and characterization of deletion mutants of herpes simplex virus type 1 in the gene encoding immediate-early regulatory protein ICP4" J Virol. Nov. 1985;56(2):558-70.
Goss et al., "Herpes simplex-mediated gene transfer of nerve growth factor protects against peripheral neuropathy in streptozotocin-induced diabetes in the mouse" Diabetes. Jul. 2002;51(7):2227-32.
Goss et al., "PGN-503, a herpes simplex virus based vector expressing neurotrophin-3, prevents and reverses neuropathy in a mouse model of paclitaxel-induced peripheral neuropathy" Mol Ther. May 2016;24(Suppl. 1):S72.
Macdonald et al., "Genome sequence of herpes simplex virus 1 strain" McKrae. J Virol. Sep. 2012;86(17):7540-1.
Shepard et al., "Activities of heterodimers composed of DNA-binding- and transactivation-deficient subunits of the herpes simplex virus regulatory protein ICP4" J Virol. Jan. 1991;65(1):299-307.
Wang et al., "HSV-1 strain McKrae is more neuroinvasive than HSV-1 KOS after corneal or vaginal inoculation in mice" Virus Res. Jan. 20, 2013;173(2):436-40.
Watson et al., "Sequence and comparative analysis of the genome of HSV-1 strain" McKrae. Virology. Nov. 2012;433(2):528-37. Epub Sep. 25, 2012.
Accession No. 13TCD6, Transcriptional Regulator ICP4 [Human Alphaherpesvirus 1], 1 pages, Sep. 5, 2012 [Retrieved Jul. 10, 2017] URL: <https://www.ncbi.nlm.nih.gov/protein/388524993?report=genbank&log$=prottop&blast_rank=<http://www.ncbi.nlm.nih.gov/protein/388524993?report=genbank&log%24=prottop&blast_rank> 1 &RID=PCWCCB3C014>.
International Search Report for PCT/US2017/024083, 4 pages (Jul. 13, 2017).
International Search Report for PCT/US2017/024092, 4 pages (Aug. 1, 2017).
Liu, M. et al. ICP0 Antagonizes ICP4-Dependent Silencing of the Herpes Simplex Virus ICP0 Gene, PLoS One, 5(1): e8837 1-16 (2010).
Written Opinion for PCT/US2017/024083, 9 pages (Jul. 13, 2017).
Written Opinion for PCT/US2017/024092, 9 pages (Aug. 1, 2017).
U.S. Appl. No. 16/088,393, filed Mar. 24, 2017, High-Transducing HSC Vectors.
U.S. Appl. No. 16/088,408, filed Sep. 25, 2018, HSV vectors for delivery of NT3 and treatment of CIPN.

* cited by examiner

HSV McKrae strain nucleotide sequence (SEQ ID NO: 1)

Accession no. JQ730035.1

```
   1 gcagcccggg cccccgcgc gcgggcggc gcgcaaaaaa ggcggcggc ggtccggcg
  61 gcgtgcgcgc gcgcggcggg cgtggggc ggggccgcgg gagcggggga ggagcccac
 121 ccacagacgg ggaggagcgg gggaggagcg ggggaggagc ggggaggag ccccaccac
 181 agacggggag gagcggggga ggagcggcca gacccaaaa acgggcccc ccgaaacaca
 241 ccccccgggg gtcgcgcgcg gcccttaaa gcgcggcggc gggcagcccg gccccccgc
 301 ggccgagact agcgagttag acaggcaagc actactcgcc tctgcacgca catgcttgcc
 361 tgtcaaactc taccacccg gcacgctctc tgtctccatg gcccgccgcc gccgccatcg
 421 cggccccgc cgcccccggc cgcccgggcc cacgggcgcc gtcccaaccg cacagtccca
 481 ggtaacctcc acgcccaact cggaacccgc ggtcaggagc gcgcccgcgg ccgccccgcc
 541 gccgcccccc gcggtgggc cccgccttc ttgttcgctg ctgctgcgcc agtggctcca
 601 cgttcccgag tccgcgtccg acgacgacga tgacgacgac tggccggaca gccccccgcc
 661 cgagccggcg ccagaggccc ggcccaccgc cgccgccccc cggccccggt cccaccgcc
 721 cggcgtgggc ccgggggcg gggctgaccc ctcccacccc ccctcgcgcc ccttccgcct
 781 tccgccgcgc ctcgccctcc gcctgcgcgt caccgcggag cacctggcgc gcctgcgcct
 841 gcgacgcgcg gcggggagg gggcgccgga gccccccgcg accccgcga ccccgcgac
 901 ccccgcgacc cccgcgaccc ccgcgacccc cgcgaccccc gcgaccccg cgcgggtgcg
 961 cttctcgccc cacgtccggg tgcgccacct ggtggtctgg gcctcggccg cccgcctggc
1021 gcgccgcggc tcgtgggccc gcgagcgggc cgaccgggct cggttccggc gcgggtggc
1081 ggaggccgag gcggtcatcg ggccgtgcct ggggcccgag gcccgtgccc gggccctggc
1141 ccgcggagcc ggcccggcga actcggtcta acgttacacc cgaggcgcct gggtcttccg
1201 cggagctccc gggagctccg caccaagccg ctctccggag agacgatggc aggagccgcg
1261 catatatacg ctgggagccg gtccgccccc aaggcgggcc cgcctcgggg gcgggactgg
1321 ccaatcggcg gccgccagcg cggcggggcc cggccaacca gcgtccgcc agtcttcggg
1381 gcccggccca ttgggcggga gttaccgccc aatgggccgg gcgcccact tcccggtatg
1441 gtaattaaaa acttgcaaga ggccttgttc cgcttcccgg tatggtaatt agaaactcat
1501 taatgggcgg cccggccgc ccttccgct tccggcaatt ccgcgggcc ttaatgggca
```

FIGURE 9

```
1561 accccggtat tccccgcctc ccgcgccgcg cgtaaccact ccctgggt tccgggttat
1621 gctaattgct tttttggcgg aacacacggc ccctcgcgca ttggcccgcg ggtcgctcaa
1681 tgaacccgca ttggtcccct ggggttccgg gtatggtaat gagtttcttc gggaaggcgg
1741 gaagcccgg ggcaccgacg caggccaagc ccctgttgcg tcggcgggag gggcatgcta
1801 atggggttct ttgggggaca ccgggttggt cccccaaatc ggggccggg ccgtgcatgc
1861 taatgatatt ctttggggc gccgggttgg tccccgggga cggggccgcc ccgcggtggg
1921 cctgcctccc ctgggacgcg cggccattgg gggaatcgtc actgccgccc ctttggggag
1981 gggaaaggcg tggggtataa gttagccctg cccgacggt ctggtcgcat ttgcacctcg
2041 gcactcggag cgagacgcag cagccaggca gactcgggcc gccccctctc cgcatcacca
2101 cagaagcccc gcctacgttg cgaccccag ggaccctccg tccgcgaccc tccagccgca
2161 tacgaccccc atggagcccc gccccgagc gagtacccgc cggcctgagg gccgccccca
2221 gcgcgaggtg aggggccggg cgccatgtct ggggcgccat attgggggc gccatgttgg
2281 gggacccccg acccttaccc tggaaccggc cccatgttg ggggaccccc actcatacac
2341 gggagccggg cgccatgttg gggcgccatg ttaggggcg tggaacccg tgacactata
2401 tatacaggga ccgggggcgc catgttaggg ggcgcggaac ccctgaccc tatatataca
2461 gggaccgggg tcgccctgtt ggggtcgcc atgtgacccc ctgactttat atatacagac
2521 ccccaacaca tacacatggc ccctttgact cagacgcagg gcccggggtc gccgtgggac
2581 ccctgactc atacacagag acacgccccc acaacaaaca cacagggacc gggtcgccg
2641 tgttggggc gtggtcccca ctgactcata cgcaggcccc ccttactcac acgcatctag
2701 ggggtgggg aggagccgcc cgccatattt ggggacgcc gtgggacccc cgactccggt
2761 gcgtctggag ggcgggagaa gaggaagaa gagggtcgg gatccaaagg acggacccag
2821 accacctttg gttgcagacc cctttctccc cctcttccg aggccagcag ggggcagga
2881 ctttgtgagg cggggggga gaggggaac tcgtgggcgc tgattgacgc gggaaatccc
2941 cccccattct tacccgcccc cctttttcc ccttagcccg cccggatgt ctgggtgttt
3001 ccctgcgacc gagacctgcc ggacagcagc gactctgagg cggagaccga agtggggggg
3061 cgggggacg ccgaccacca tgacgacgac tccgcctccg aggcggacag cacggacacg
3121 gaactgttcg agacggggct gctgggccg cagggcgtgg atgggggggc ggtctcgggg
3181 gggagccccc ccgcgagga agacccggc agttgcgggg gcgcccccc tcgagaggac
```

```
3241 gggggggagcg acgagggcga cgtgtgcgcc gtgtgcacgg atgagatcgc gccccacctg
3301 cgctgcgaca ccttcccgtg catgcaccgc ttctgcatcc cgtgcatgaa aacctggatg
3361 caattgcgca acacctgccc gctgtgcaac gccaagctgg tgtacctgat agtgggcgtg
3421 acgccagcg ggtcgttcag caccatcctg atcgtgaacg acccccagac ccgcatggag
3481 gccgaggagg ccgtcagggc gggcacggcc gtggacttta tctggacggg caatcagcgg
3541 ttcgccccgc ggtacctgac cctggggggg cacacggtga gggccctgtc gcccacccac
3601 ccggagccca ccacggacga ggatgacgac gacctggacg acgtgaggc gggggggcggc
3661 aaggaccctg ggggaggagg aggagggagg aatgggcggg cgggcgagga agggcgggc
3721 cggggagggg gcgtaacctg atcgcgcccc ccgttgtctc ttgcagcaga ctacgtcccg
3781 cccgcccccc gccggacgcc ccgcgccccc ccacgcagag gcaccgccgc gcccccgtg
3841 acgggcgggg cgtctaacgc agccccccag ccggccgcgg ctggacagc gccccctcg
3901 gcgcccatcg ggccacacgg cagcagtaac accaacacca ccaccaacag cagcggcggc
3961 ggcggctccc gccagtcgcg agccgcggcg ccgcggggg cgtctggccc ctccggggg
4021 gttggggttg gggttggggt tgttgaagcg gaggcggggc ggccgagggg ccggacgggc
4081 cccttgtca acagacccgc ccccccttgca aacaacagag acccccatagt gatcagcgac
4141 tcccccccgg cctctcccca caggcccccc gggcgcccca tgccaggctc cgcccccgc
4201 cccgggcccc ccgcgtcctc ggccgcgtcg ggacccgcgc gccccgcgc ggccgtggcc
4261 ccgtgcgtgc gagcgccgcc tccggggccc ggccccgcg cccggccc cggggcggag
4321 ccggccgccc gccccgcgga cgcgcgccgt gtgcccagt cgcactcgtc cctggctcag
4381 gccgcgaacc aagaacagag tctgtgccgg gcgcgtgcga cggtggcgcg cggctcgggg
4441 gggccgggcg tggagggtgg gcacgggccc tcccgcggcc gcacccctc cggcgccgcc
4501 ccgctccct ccgccgtctc tgtcgagcag gaggcggcgg tgcgtccgag gaagaggcgc
4561 gggtcgggcc aggaaaaccc ctcccccag tccacgcgtc ccccctcgc gcggcaggg
4621 gccaagaggg cggcgacgca ccccccctcc gactcagggc cggggggcg cggccagggt
4681 gggcccggga cccccctgac gtcctcggcg gcctccgcct cttcctcctc tgcctcttcc
4741 tcctcggccc cgacccccgc ggggccgcc tcttccgccg ccgggccgc gtcctcctcc
4801 gcttccgcct cctcgggcgg ggccgtcggt gccctgggag ggagacaaga ggaaacctcc
4861 ctcggccccc gcgctgcttc tgggccgcgg gggccgagga agtgtgcccg gaagacgcgc
```

FIGURE 9 (Continued)

```
4921 cacgcggaga cttccggggc cgtccccgcg ggcggcctca cgcgctacct gcccatctcg 4981 gggtctcta gcgtggtcgc cctgtcgcct tacgtgaaca agactatcac ggggactgc 5041 ctgcccatcc tggacatgga gacggggaac atcggggcgt acgtggtcct ggtggaccag 5101 acgggaaaca tggtgaccgg gctgcggcc gcggtcccg gctggagccg ccgcaccctg 5161 ctccccgaga ccgcgggtaa ccacgtgatg cccccgagt acccgacggc ccccgcgtcg 5221 gagtggaaca gcctctggat gaccccgtg gggaacatgc tgttcgacca gggcaccta 5281 gtgggcgccc tggacttccg cagcctgcgg tctcggcacc cgtggtccgg ggagcagggg 5341 gcgtcgaccc gggacgaggg aaaacaataa gggacgcccc ccgtgtttgt ggggaggggg 5401 gtcgggtgct gggtggtctc tggccgcgcc cactacacca gccaatccgt gtcggggagg 5461 ggaaagtgaa agacacgggc accacacacc agcgggtctt tagtgttggc cctaataaaa 5521 aactcagggg attttgctg tctattggga ataaaggtt tacttttgta tcttttccct 5581 gtctgtgttg gatggatctt gggggtgcgt gggagtgggg gtgcgtggga gtggggtgc 5641 gtgggagtgg ggtgcgtgg gagtgggggt cgtgggagt ggggtgcgt gggagtgggg 5701 gtgcgtggga gtggggggtgc gtgggagtgg ggtgcgtgg gagtgggggt cgtgggagt 5761 ggggggtgcgt gggagtgggg gtgcgtggga gtggggggtgc gtgggagtgg ggtgccatg 5821 ttgggcaggc tctggtgtta accacagagc cgcggcccgg gctgcctgac caccgatccc 5881 cgaaagcatc ctgccactgg catggagcca gaaccacagt gggctgggtg tgggtgttaa 5941 gtttccgcga gcgcctgccc gcccggactg acctggcctc tggccgccac aaagggcggg 6001 ggggggtta actacactat agggcaacaa aggacgggag gggtggcggg acgggcgcc 6061 caaaggggg tcggccacac cacagacgtg ggtgttgggg gtgggggcgg agggtgggg 6121 gggagacaga aacaggaaca tagttagaaa acaagaatgc ggtgcagcca gagaatcaca 6181 ggagacgagg ggatgggcgt gttggttacc aacccacacc caggcatgct cggtggtatg 6241 aaggaggggg ggcggtgctt cttagagacc gccggggac gtggggttgg tgtgcaaagg 6301 cacgcgcacc cgcgtcggcc aggtgggccg gtaccccatc cccccctccc ccgaccttc 6361 cccccccgcg tgccagagat cacccccgtc ccccggcacc cgccactcct ccatatcctc 6421 gctttaggaa caactttggg gggggggtac acacgcgccg tgcatttcct tccacacccc 6481 ccctccccg catcccccc cccaggcagt aagacccaag catagagagc caggcacaaa 6541 aacacaggcg gggtgggaca catgccttct tggagtacgt gggtcattgg cgtgggggt
```

```
6601 tacagcgaca ccggccgacc ccctggcggt cttccagccg gcccttagat aagggggcag
6661 ttggtggtcg gacgggtaag taacagagtc tgactaaggg tgggagggggg ggaaaagaac
6721 gggctggtgt gctgtaacac gagcccaccc gcgagtggcg tggccgacct tagcctctgg
6781 ggcgccccct gtcgtttggg tccccccccc tctattgggg agaagcaggt gtctaaccta
6841 cctggaaacg cggcgtcttt gttgaacgac accggggcgc cctcgacgag tgggataacg
6901 gggaggaag ggagggagga gggtactggg ggtgaagaag gggggggggga agaagcgaga
6961 acaggaaagg cgacggagcc cggcagaaca ccgaggaaaa aaaaaacaca gcgcatgcgc
7021 cgggccgttg tgggccccg gccggggcc ccttgggtcc gccggggccc cggccgggc
7081 cgccacgggg gcggccgtt ggcggtaacc ccgattgttt atctcaggcc ccggccgggg
7141 aacccggaaa agcctccggg gggccttttt cgcgtcgcgt gccggcgagc gggcccggac
7201 ggggccggga ccgccgcggt cggggccccc tcgtcccggg ccgtacgcgg ccttcgcccc
7261 gtgaggggcc gaacgaacga aacatcccgg cgacggaacg aaaaacaccc cagacgggtt
7321 taaaaaacag aaaccgtaac ccccccacc cccgaaacgg ggaaaacaaa aaacagacca
7381 gcggccggcc ggcgcttagg gggaggatgt cgccgacgcc ccttggccgc cccggctgca
7441 ggggggcccg gagagccgcg gcacccggac gcgcccggaa agtctttcgc accacccgcg
7501 atcggcacgg ccgcgccccc gcttttataa aggctcagat gacgcagcaa aaacaggcca
7561 cagcaccacg tgggtaggtg atgtaattt tattttcctcg tctgcggcct aatggatttc
7621 cgggcgcggt gccctgtct gcagagcact taacggattg atatctcgcg ggcacgcgcg
7681 cccttaatgg accggcgcgg ggcgggggc cggatacccca cacggcgggg ggggtgtcgc
7741 gggccgtctg ctggcccgcg gccacataaa caatgactcg gggccttct gcctctgccg
7801 cttgtgtgtg cgcgcgccgg ctctgcggtg tcggcggcgg ctgcggcggc tgcggcggcc
7861 gccgtgttcg gtctcggtag ccggccggcg ggtggactcg cgggggccg gagggtggaa
7921 ggcagggggg tgtaggatgg gtatcaggac ttccacttcc cgtccttcca tcccccgttc
7981 ccctcggttg ttcctcgcct cccccaacac ccgccgctt tccgttgggg ttgttattgt
8041 tgtcgggatc gtgcgggccg ggggtcgccg gggcagggggc gggggcgggg gtgctcgtcg
8101 atcgaccggg ctcagtgggg gcgtgggggtg ggtgggaaaa ggcgaggaga ctggggtggg
8161 gggtgtcggg ggtggctgtt ttttgtggt tgttttttgt gtctgttccc gtccccgtc
8221 accccctcc ctccgtcccc ccgtcgcggg tgtttgtgtt tgtttattcc gacatcggtt
```

FIGURE 9 (Continued)

```
8281 tatttaaata aacacagccg ttctgcgtgt ctgttcttgc gtgtggctgg gggcttatat
8341 gtggggtccc gggggcggga tggggtttag cggcgggggg cggcgcgccg gacggggcgc
8401 tggagataac ggcccccggg aacgggggga ccggggctgg gtctcccgcg gtgggtgggt
8461 gggcggcggt ggcgggccg ggcgggccg ggtgggcggg gtttgaaaa acgaggagga
8521 ggagaaggag gaggaggggg ggggagacgg ggggaaagca aggacacggc cccgggggg
8581 gggagcgcg ggccgggccg cttggcaacc ccctgtttc ttccggaaac caggcttgtg
8641 gccccacccg acatcacaag ggacctcttg tcgggcctcc cgacgtacgc cgaggctatg
8701 tcggaccacc cccaaccta agaggggaga ggggagaggg gagagggag aggggagagg
8761 ggagagggga ggagaggggg tatataaacc aacgaaaagc gcgggaacgg ggatacgggg
8821 cttgtgtggc acgacgtcgt ggttgtgtta ctgggcaaac acttggggac tgtaggtttc
8881 tgtggtgccg accctaggcg ctatgggat tttgggttgg gttgggctta ttgccgttgg
8941 ggttttgtgt gtgcgggggg gcttgccttc aaccgaatat gttattcgga gtcgggtggc
9001 tcgagaggtg gggatatat taaaggtgcc ttgtgtgccg ctcccgtctg acgatcttga
9061 ttggcgctac gagacccct cggctataaa ctatgctttg atagacggta tattttgcg
9121 ttatcactgt cccggattgg acacggtctt gtgggatagg cacgccaga gggcgtattg
9181 ggttaacccc tttttgtttg gggcgggttt tttggaggac ttgagtcatc ccgcgtttcc
9241 tgccgacacc caggaaacag aaacgcgctt ggcccttat aaagagatac gccaggcgct
9301 ggacagtcgc aagcaggccg ccagccacac acctgtgaag gctgggtgtg tgaactttga
9361 ctattcgcgc accgccgct gtgtaggcg ccaggatttg ggacttacca acagaacgtc
9421 tggacggacc ccggttctgc cgtcggacga tgaagcgggc ctgcagccga agcccctcac
9481 cacgccgtcg cccatcatcg ccacgtcgga ccccaccccg cgacgggacg ccgccacaaa
9541 aagcagacgc cgacgacccc attcccggcg catctaatga tgcctcgacg gaaaaccgtc
9601 cgggtttggg gggcgaaccg gccgcctgtc gctcgtcagg gccggcgggc gctcctcgcc
9661 gccctagagg ctgtcccgct ggtgtgacgt tttcctcgtc cgcgccccc gacccctccca
9721 tggatttaac aaacgggggg gtgtcgcctg cggcgacctc ggccgctctg gactggacca
9781 cgtttcggcg tgtgtttctg atcgacgacg cgtggcggcc cctgttggag cctgagctgg
9841 cgaaccccctt aaccgcccac ctcctggccg aatataatcg tcggtgccag accgaagagg
9901 tgctgccgcc gcgggaggat gtgttttcgt ggactcgtta ttgcacccc gacgaggtgc
```

FIGURE 9 (Continued)

```
 9961 gcgtggttat catcggccag gacccatatc accaccccgg ccaggcgcac ggacttgcgt
10021 ttagcgtgcg cgcgaacgtg ccgcctcccc cgagtcttcg gaatgtcttg gcggccgtca
10081 agaactgtta tcccgaggca cggatgagcg ccacggttg cctggaaaag tgggcgcggg
10141 acggcgtcct gttactaaac acgacccgga ccgtcaagcg cggggcggcg gcgtcccact
10201 ctagaatcgg ttgggacgc ttcgtgggcg gagttatccg ccggttggct gcgcgccgcc
10261 ccggcctggt gtttatgctc tggggcgcac atgcccagaa tgccatcagg ccggaccctc
10321 gggtccattg cgtcctcaag ttttcgcacc cgtcgccct ctccaaggtt ccgttcggaa
10381 catgccagca tttcctcgtg gcgaatcgat atctcgagac ccggtcgatt tcacccatcg
10441 actggtcggt ttgaaaggca tcgacgtccg ggttttcgt ctgtggggc ttttgggtat
10501 ttccgatgaa taaagacggt taatggttaa acctctggtc tcatacgggt cggtgatgtc
10561 gggcgtcggg ggagagggag ttccctctgc gcttgcgatt ctagcctcgt ggggctggac
10621 gttcgacacg ccaaaccacg agtcagggat atcgccagat acgactcccg cagattccat
10681 tcgggggcc gctgtggcct cacctgacca acctttacac gggggccgg aacgggaggc
10741 cacagcgccg tctttctccc caacgcgcgc ggatgacggc ccgccctgta ccgacgggcc
10801 ctacgtgacg tttgataccc tgtttatggt gtcgtcgatc gacgaattag ggcgtcgcca
10861 gctcacggac accatccgca aggacctgcg gttgtcgctg ccaagtttta gcattgcgtg
10921 caccaagacc tcctcgtttt cggaaacgc cccgcgccac cacagacgcg gggcgttcca
10981 gcgcggcacg cgggcgccgc gcagcaacaa aagccttcag atgtttgtgt tgtgcaaacg
11041 cgcccacgcc gctcgagtgc gagagcagct tcgggtcgtt attcagtccc gcaagccgcg
11101 caagtattac acgcgatctt cggacgggcg gctctgcccc gcgtccccg tgttcgtcca
11161 cgagttcgtc tcgtccgagc caatgcgcct ccacgagat aacgtcatgc tggcctcggg
11221 ggccgagtaa ccgccccccc ccgcgccac cctcactgcc cgtcgcgcgt gtttgatgtt
11281 aataaataac acataaattt ggctggttgt tgttgtcttt taatggaccg ccgcagggg
11341 gggtggcatt tcagtgtcgg gtgacgagcg cgatccggcc gggatcctag gaccccaaaa
11401 gtttgtctgc gtattccagg gcggggctca gttgaatctc ccgcagcacc tctaccagca
11461 ggtccgcggt gggctggaga aactcggccg tcccggggca ggcggtcgtc gggagtggag
11521 gcgggcgcc caccccgtgt gccgcgcctg gcgtctcctc tggggcgac ccgtaaatgg
11581 ttgcagtgat gtaaatggtg tccgcggtcc agaccacggt caaaatgccg gccgtggtgc
```

FIGURE 9 (Continued)

```
11641 tccgggcgct ttcgccgcgc gaggagctga cccaggagtc gaacggatac gcgtacatat
11701 gggcgtccca cccgcgttcg agcttctggt cgctgtcccg gcctataaag cggtaggcac
11761 aaaattcggc gcgacagtcg ataatcacca acagcccaat ggggggtgtgc tggataacaa
11821 cgcctccgcg cggcaggcgg tcctggcgct ccggccccg taccataatc gcgcgggtgc
11881 cgtactcaaa aacatgcacc acctgcgcgg cgtcgggcag tgcgctggtc agcgaggccc
11941 tggcgtggca taggctatac gcgatggtcg tctgtggatt ggacatctcg cggtgggtag
12001 tgagtccccc gggccgggtt cggtagaact gtaaggggac ggcgggttaa tagacaatga
12061 ccacgttcgg atcgcgcaga gccgatagta tgtgctcact aatgacgtca tcgcgctcgt
12121 ggcgctcccg gagcggattt aagttcatgc gaaggaattc ggaggaggtg gtgcgggaca
12181 tggccacgta cgcgctgttg aggcgcaggt tgccgggcgt aaagcagatg gcgaccttgt
12241 ccaggctaag gccctgggag cgcgtgatgg tcatggcaag cttggagctg atgccgtagt
12301 cggcgtttat ggccatggcc agctccgtag agtcaatgga ctcgacaaac tcgctgatgt
12361 tggtgttgac gacggacatg aagccgtgtt ggtcccgcaa gaccacgtaa ggcaggggg
12421 cctcttccag taactcggcc acgttggccg tcgcgtgccg cctccgcagc tcgtccgcaa
12481 aggcaaacac ccgtgcgtac gtgtatccca tgagcgtata attgtccgtc tgcagggcga
12541 cggacatcag ccccccgcgc ggcgagccgg tcagcatctc gcagcccgg aagataacgt
12601 tgtccacgta cgtgctaaag gggcgccttt caaatgcctc cccgaagagc tcttggagga
12661 ttcggaatct cccgaggaag gcccgcttca gcagcgcaaa ctgggtgtga acggcggcgg
12721 tggtctccgg ttccccgggg gtgtagtggc agtaaaacac gtcgagctgt tgttcgtcca
12781 gccccgcgaa ataacgtcg aggtcgtcgt cggaaaaatc gtccgggccc ccgtcccgcg
12841 gccccagttg cttaaaatca aacgcacgct cgccggggc gcctgcgtcg gctattaccg
12901 acgcctgcgt cggcgccccc gaagatttgg ggcgcagaga cagaatctcc gccgttagtt
12961 ctcccatgcg ggcgtaggcg agggtcctct gggtcgcatc caggcccggg cgctgcagaa
13021 agttgtaaaa ggagataagc ccgctaaata tgagccgcga caggaacctg taggcaaact
13081 ccaccgaagt ctccccctga gtctttacaa agctgtcgtc acgcaacact gcctcgaagg
13141 cccggaacgt cccactaaac ccaaaaacca gttttcgcag gcgcgcggtc accgcgatct
13201 ggctgttgag gacgtaagtg acgtcgttgc gggccacgac cagctgctgt ttgctgtgca
13261 cctcgcagcg catgtgcccc gcgtcctggt cctggctctg cgagtagttg gtgatgcggc
```

FIGURE 9 (Continued)

```
13321 tggcgttggc cgtgagccac ttttcaatag tcaggccggg ctggtgtgtc agccgtcggt
13381 attcgtcaaa ctccttgacc gacacgaacg taagcacggg gagggtgaac acgacgaact
13441 ccccctcacg ggtcaccttc aggtaggcgt ggagcttggc catgtacgcg ctcacctctt
13501 tgtgggagga gaacagccgc gtccagcggg ggaggttggc ggggttggtg atgtagcttt
13561 ccgggacgac gaagcgatcc acgaactgca tgtgctcctc ggtgatgggc aggccgtact
13621 ccagcaccct catgaggtta ccgaactcgt gctcgacgca ccgtttgttg ttaataaaaa
13681 tggcccagct atacgagagg cgggcgtact cgcgcagcgt gcggttgcag atgaggtacg
13741 tgagcacgtt ctcgctctgg cggacggaac accgcagttt ctggtgctcg aaggtcgact
13801 ccagggacgc cgtctgcgtc ggcgagccca cacaccaa cacgggccgc aggcgggccg
13861 catactgggg ggtgtggtac agggcgttaa tcatccacca gcaatacacc acggccgtga
13921 ggaggtgacg cccaaggagc ccggcctcgt ctatgacgat cacgttgctg cgggtaaagg
13981 ccggcagcgc cccgtgggtg gccggggcca accgcgtcag ggcgccctcg gccaacccca
14041 gggtccgttc cagggcggcc agggcgcgaa actcgttccg cgactcctcg cccccggagg
14101 cggccagggc gcgcttcgtg aggtccaaaa tcacctccca gtagtacgtc agatctcgtc
14161 gctgcaggtc ctccagcgag gcggggttgc tggtcagggt gtacgggtac tgtcccagtt
14221 gggcctggac gtgattcccg cgaaacccaa attcatgaaa gatggtgttg atgggtcggc
14281 tgagaaaggc gcccgagagt ttggcgtaca tgttttgggc cgcaatgcgc gtggcgcccg
14341 tcaccacaca gtccaagacc tcgttgattg tctgcacgca cgtgctcttt ccggagccag
14401 cgttgccggt gataagatac accgcgaacg gaaactccct gagggcaggg cctgcggggg
14461 actctaaggc cgccacgtcc cggaaccact gcagacgggg cacttgcgct ccgtcgagct
14521 gttgttgcga gagctctcgg atgcgcttaa ggattggctg cacccgtgc atagacgtaa
14581 aatttaaaaa ggcctcggcc ctccctggaa cggctggtcg gtccccgggt tgctgaaggt
14641 gcggcgggcc gggtctctgt ccgtctagct ggcgctcccc gccggccgcc gccatgaccg
14701 caccacgctc gcgggccccc actacgcgtg gcgggggga cacggaagcg ctgtgctccc
14761 ccgaggacgg ctgggtaaag gttcaccca ccccggtac gatgctgttc cgtgagattc
14821 tccacgggca gctgggtat accgagggcc aggggtgta caacgtcgtc cggtccagcg
14881 aggcgaccac ccggcagctg caggcggcga tctttcacgc gctcctcaac gccaccactt
14941 accgggacct cgaggcggac tggctcggcc acgtggcggc ccgcggtctg cagccccaac
```

FIGURE 9 (Continued)

```
15001 ggctggttcg ccggtacagg aacgcccggg aggcggatat cgccggggtg gccgagcggg
15061 tgttcgacac gtggcggaac acgcttagga cgacgctgct ggactttgcc cacgggttgg
15121 tcgcctgctt tgcgccgggc ggcccgagcg gccgtcaag cttcccaaa tatatcgact
15181 ggctgacgtg cctggggctg gtcccatat tacgaagcg acaagaggg ggtgtgacgc
15241 agggtctgag ggcgtttctc aagcagcacc cgctgacccg ccagctggcc acgtcgcgg
15301 aggccgcgga gcgcgccggc cccgggtttt ttgagctggc gctggccttc gactccacgc
15361 gcgtggcgga ctacgaccgc gtgtatatct actacaacca ccgccgggc gactggctcg
15421 tgcgagaccc catcagcggg cagcgcggag aatgtctggt gctgtggcct cccttgtgga
15481 ccggggaccg tctggtcttc gattcgcccg tccagcggct gtttcccgag atcgtcgcgt
15541 gtcactccct ccgggaacac gcgcacgtct gccggctgcg caataccgcg tccgtcaagg
15601 tgctgctggg gcgcaagagc gacagcgagc gcggggtggc cggcgccgcg cgggtcgtta
15661 acaaggtgtt gggggaggac gacgagacca aggccgggtc ggccgcctca cgcctcgtgc
15721 ggcttatcat caacatgaag ggcatgcgcc acgtaggcga cattaacgac ccgtgcgtg
15781 cctacctcga cgaggccggg gggcacctga tagacgcccc ggccgtcgac ggtaccctcc
15841 ctggattcgg caagggcgga aacagccgcg ggtctgcggg ccaggaccag gggggcggg
15901 cgccgcagct tcgccaggcc ttccgcacgg ccgtggttaa caacatcaac ggcgtgttgg
15961 agggctatat aaataacctg tttggaacca tcgagcgcct gcgcgagacc aacgcgggcc
16021 tggcgaccca attgcaggag cgcgaccgcg agctccggcg cgcaacagcg ggggccctgg
16081 agcgccagca gcgcgcggcc gacctggcgg ccgagtccgt gaccggtgga tgcggcagcc
16141 gccctgcggg ggcggacctg ctccgggccg actatgacat tatcgacgtc agcaagtcca
16201 tggacgacga catgtacgtc gccaacagct ttcagcaccc gtacatccct tcgtacgccc
16261 aggacctgga gcgcctgtcg cgcctctggg agcacgagct ggtgcgctgt tttaaaattc
16321 tgtgtcaccg caacaaccag ggccaagaga cgtcgatctc gtactccagc ggggcgatcg
16381 ccgcattcgt cgccccctac tttgaggcag tgcttcgggc cccccgggta ggcgcgccca
16441 tcacgggctc cgatgtcatc ctggggagg aggagttatg ggatgcggtg tttaagaaaa
16501 cctgcctgca aacgtacctg acagacatcg cggccctgtt cgtcgcggac gtccagcacg
16561 cagcgctgcc ccgccccc tcccggtcg gcgccgattt ccggcccggc gcgtccccgc
16621 ggggccggtc cagatcgcgg tcgcccggaa gaactgcgcg aggcgcaccg gaccagggcg
```

FIGURE 9 (Continued)

```
16681 ggggcatcgg gcaccgggat ggccgccgcg acggccgacg atgaggggtc ggccgtcacc
16741 atcctcaagc aggccatcgc cggggaccgc agcctggtcg aggcggccga ggcgattagc
16801 cagcagacgc tgctccgcct ggcctgcgag gtgcgccagg tcggcgaccg ccagccgcgg
16861 tttacgcca ccagcatcgc gcgcgtcgac gtcgcgcctg ggtgccggtt gcggttcgtt
16921 ctggacggga gtcccgagga cgcctatgtg acgtcggagg attactttaa gcgctgctgc
16981 ggccagtcca gttatcgcgg cttcgcggtg gcggtcctga cggccaacga ggaccacgtg
17041 cacagcctgg ccgtgccccc cctcgttctg ctgcaccggt tctccctgtt caaccccagg
17101 gacctcctgg actttgagct tgcctgtctg ctgatgtacc tggagaactg ccccgaagc
17161 cacgccaccc cgtcgacctt tgccaaggtt ctggcgtggc tcggggtcgc gggtcgccgc
17221 acgtccccat tcgaacgcgt tcgctgcctt ttcatccgca gttgccactg ggtcctaaac
17281 acactcatgt tcatggtgca cgtaaaaccg ttcgacgacg agttcgtcct gccccactgg
17341 tacatggccc ggtacctgct ggccaacaac ccgccccccg ttctctcggc cctgttctgt
17401 gccaccccga cgagctcctc attccggctg ccggggccgc cccccgctc cgactgcgtg
17461 gcctataacc ccgccgggat catggggagc tgctgggcgt cggaggaggt gcgcgcgcct
17521 ctggtctatt ggtggctttc ggagacccca aaacgacaga cgtcgtcgct gttttatcag
17581 ttttgttgaa ttttagtaaa taaacccggt tttgtttcta tggcctcctg acggatgcgc
17641 gtgtccttac tccgttttgg tgggtgggtg gctgtgtatg gcgtccatc tgtgcgggga
17701 gggggcaagt cggcacgtat tcggacagac tcaagcacac acggggagc gctcttggct
17761 cagggcaatg ttttttattgg tcaaactcag gcaaacagaa acaacatctt gtcgtcaaag
17821 ggatacacaa acttcccccc ctcgcccat actcccgcca gcacccggt aaacaccaac
17881 tcaatctcgc gcaggatttc gcgcaggtga tgagcgcagt ccacgggggg gagcacaagg
17941 ggccgcgggt atagatcgac ggggacgccg accgactccc cgcctccggg acagacacgc
18001 acgacgcgcc gccagtagtg ctctgcgtcc aacaaggcgc gccgcggaa ggcagtgggg
18061 ggcaagggt cgctggcctc aaaggggac acccgaacgc tccagtactc cgcgtccaac
18121 cgtttattaa acgcgtccac gataaggcgg tgcaggcgt cctccataag gcccggcc
18181 gtgagcgcgt cctcctccgg cacgcctgcc gttgtcaggc ccaggacccg tcgcagcgtg
18241 tcgcgtacga ccccggccgc cgtggtgtac gcgggccgc ggagaggaaa tccccaaga
18301 tggtcagtgt tgtcgcggga gttccagaac cacactcccg cttggctcca ggcgacggcg
```

```
18361 tgggtgtaga cgccctcgag cgccaggcac agtgggtgcc gcagccggag gccgttggcc
18421 ataagcacgg ctcccacggc cgtctcgatg gccgccggg cgtcctcgat caccccggaa
18481 gccgcatccg cgtcttgggg gtccacgtta aagacacccc agaacgcacc cccatcgccc
18541 ccgcagaccg cgaacttaac cgagctggcc gtcctcaa tctgcaggca gacggcggcc
18601 atcaccccgc ccaggagctg ccgcagcgca gggcaggcgt cgcacgtgtc cgggaccagg
18661 cgctccaaga cggccccggc ccagggctct gagggagcgg ccaccaccag cgcgtccagt
18721 cttgctaggc ccgtccggcc gtggggttcc gccagcccgc tcccccgag gtcggccagg
18781 gccgccagga gctgggcgcg aagtccgggg aagcaaaacc gcgccgtcca gacgggcccg
18841 acggccgcgg gcgggtctaa cagttggatg atttagtgg cgggatgcca ccgcgccacc
18901 gcctcccgca ccgcgggcag gaggcatccg gctgccgccg aggccacgcc gggccaggct
18961 cgcgggggga ggacgaccct ggccccacc gcgggccagg ccccaggag cgcggcgtaa
19021 gcggccgcgg ccccgcgcac caggtcccgt gccgactcgg ccgtggccgg cacggtgaac
19081 gtgggccaac ccggaaaccc caggacggca aagtacggga cgggtccccc ccgggacctca
19141 aactcgggcc ccagaaaggc aaagacgggg gccagggccc cggggcggc gtggaccgtg
19201 gtatgccact gccggaaaag ggcgacgagc gccggcgcgg agaacttctc gccggcgctt
19261 acaaagtagt cgtaatcgcg gggcagcagc acccgtgccg tgactcgttg cgggtgcccg
19321 cgtggccgca ggcccacctc gcacacctcg accaggtccc cgaacgctcc ctccttcttg
19381 atcggcggaa acgcaagagt ctggtattcg cgcgcaaata gcgcggttcc ggtggtgatg
19441 ttaacggtca gcgaagcggc ggacgcgcac tgggggtgt cgcgaatggc cgccaggcgc
19501 gcccacgcca gccgcgcgtc gggatgctcg gcaacgcgcg ccgccagggc cataggtcg
19561 atgtcaatgt tggcctccgc gaccaggaga gcggcgcgag gggcggcggg cgggccccac
19621 gacgctctct caactttcac caccagtccc gtgcgtgggt ccgagccgat acgcagcggg
19681 gcgaacaggg ccaccggccc ggtctggcgc tccagggccg ccaggacgca cgcgtacagc
19741 gcccgccaca gagtcgggtt ctccagggc tccagcgggg aggcggccgg cgtcgtcgcg
19801 gcgcgggcgg ccgccacgac ggcctggacg gagacgtccg cggagccgta gaaatcccgc
19861 agctccgtcg cggtgacgga gacctccgca aagcgcgcgc gaccctcccc tgcggcgttg
19921 cgacatacaa aatacaccag ggcgtggaag tactcgcgag cgcgggggg cagccatacc
19981 gcgtaaaggg taatggcgct gacgctctcc tccacccaca cgatatctgc ggtgtccatc
```

FIGURE 9 (Continued)

```
20041 gcacggcccc taaggatcac gggcggtctg tgggtcccat gctgccgtgc ctggccgggc
20101 ccggtgggtc gcggaaaccg gtgacggggg ggggcggttt tgggggttgg ggtggggggtg
20161 ggaaacggcc cgggtccggg gccaacttg gccctcggt gcgttccgc aacagcgccg
20221 ccggtccgcg gacgaccacg taccgaacga gtgcggtccc gagacttata gggtgctaaa
20281 gttcaccgcc ccctgcatca tgggccaggc ctcggtgggg agctccgaca gcgccgcctc
20341 caggatgatg tcagcgttgg ggttggcgct ggatgagtgc gtgcgcaaac gcgccccca
20401 cgcgggcacg cgtagcttga agcgcgcgcc cgcaaactcc cgcttgtggg ccataagcag
20461 ggcgtacagc tgcctgtggg tccggcaggc gctgtggtcg atgtggtggg cgtccaacaa
20521 ccccacgatt gtctgtttgg tgaggttttt aacgcgcccc gccccgggaa acgtctgcgt
20581 gcttttggcc atctgcacgc caaacagttc gccccagatt atcttgaaca gcgccaccgc
20641 gtggtccgtc tgctaacgg accgcgcgg gggacagccg cttagggcgt cggcgacgcg
20701 cttgacggct tcctccgaga gcagaagtcc gtcggttacg ttacagtggc ccagttcgaa
20761 caccagctgc atgtagcggt cgtagtgggg ggtcagtagg tccagcacgt catcggggcc
20821 gaaggtcctc ccagatcccc cggccgccga gtcccaatgc aggcgcgcgg ccatggtgct
20881 gcacaggcac aacagctccc agacgggggt tacgttcagg gtggggggca gggccacgag
20941 ctccagctct ccggtgacgt tgatcgtggg gatgacgccc gtggcgtagt ggtcatagat
21001 ccgccgaaat atggcgctgc tgcgggtggc catgggaacg cggagacagg cctccagcaa
21061 cgccaggtaa ataaaccgcg tgcgtcccat caggctgttg aggttgcgca tgagcgcgac
21121 aatttccgcc ggcgcgacat cggaccggag gtattttcg acgaaagac ccacctcctc
21181 cgtctcggcg gcctgggccg gcagcgacgc ctcggatcc cggcaccgca gctcccgtag
21241 atcgcgctgg gccctgaggg cgtcgaaatg tacgcccgc aaaaacagac agaagtcctt
21301 tggggtcagg gtatcgtcgt gtccccagaa gcgcacgcgt atgcagttta gggtcagcag
21361 catgtgaagg atgttaaggc tgtccgagag cacgccagc gtgcatctct caaagtagtg
21421 tttgtaacgg aatttgttgt agatgcgcga ccccgcccc agcgacgtgt cgcatgccga
21481 cgcgtcacag cgcccttga accggcgaca cagcaggttt gtgacctggg agaactgcgc
21541 gggccactgg ccgcaggaac tgaccacgtg gttcaggagc atgggcgtaa agacgggctc
21601 cgagcgcgcc ccggagccgt ccatgtaaat cagtagctcc ccttgcgga gggtgcgcac
21661 ccgtcccagg gactggtaca cggacaccat gtccggtccg tagttcatgg gtttcacgta
```

FIGURE 9 (Continued)

```
21721 ggcgaacatg ccatcaaagt gcaggggatc gaagctgagg cccacggtta cgaccgtcgt
21781 gtatataacc acgcggtatt ggccccacgt ggtcacgtcc ccgagggggg tgagcgagtg
21841 aagcaacagc acgcggtccg taaactgacg gcagaaccgg gccacgatct ccgcgaagga
21901 gaccgtcgat gaaaaatgc agatgttatc gccccgcca aggcgcctt ccagtcccc
21961 aaagaacgtg gcccccggg cgtccggaga ggcgtccgga gacgggccgc ttggcggccc
22021 gggcgggcgc agggcagcct gcaggagctc ggtccccaga cgcgggagaa acaggcaccg
22081 gcgcgccgaa aacccgggca tggcgtactc gccgaccacc acatgcacgt ttttttcgcc
22141 ccggagaccg cacaggaagt ccaccaactg cgcgttggcg gttgcgtcca tggcgatgat
22201 ccgaggacag gtgcgcagca ggcgtagcat taacgcatcc acgcggccca gttgctgcat
22261 cgttggcgaa tagagctggc ccagcgtcga cataacctcg tccagaacga ggacgtcgta
22321 gttgttcaga aggttggggc ccacgcgatg aaggctttcc acctggacga taagtcggtg
22381 gaaggggcgg tcgttcataa tgtaattggt ggatgagaag taggtgacaa agtcgaccag
22441 gcctgactca gcgaaccgcg tcgccagggt ctgggtaaaa ctccgacgac aggagacgac
22501 gagcacactc gtgtccggag agtggatcgc ttcccgcagc cagcggatca gcgcggtagt
22561 ttttcccgac cccattggcg cgcggaccac agtcacgcac ctggccgtcg gggcgctcgc
22621 gttggggaag gtgacgggtc cgtgctgctg ccgctcgatc gttgttttcg ggtgaacccg
22681 gggcacccat tcggccaaat ccccccgta caacatccgc gctagcgata cgctcgacgt
22741 gtactgttcg cactcgtcgt ccccaatggg acgcccggcc ccagaggat ccccgactc
22801 cgcgccccc acgaaaggca tgaccggggc gcggacggcg tggtgggtct ggtgtgtgca
22861 ggtggcgacg tttgtggtct ctgcggtctg cgtcacgggg cttctcgtcc tggcctctgt
22921 gttccgggca cggtttccct gcttttatgc cacggcgagc tcttatgccg gggtgaactc
22981 cacggccgag gtgcgcgggg gtgtagccgt gccctcagg ttggacacgc agagccttgt
23041 gggcacttat gtaatcacgg ccgtgttgtt gttggccgcg gccgtgtatg ccgtggtcgg
23101 cgccgtgacc tcccgctacg accgcgccct ggacgcgggc cgccgtctgg ctgcggcccg
23161 catggccatg ccgcacgcca cgctgatcgc cggaaacgtc tgctcttggt tgctgcagat
23221 caccgtcctg ttgctggccc atcgcatcag ccagctggcc cacctggttt acgtcctgca
23281 ctttgcgtgt ctggtgtatt ttgcggccca tttttgcacc aggggggtcc tgagcgggac
23341 gtatctgcgt caggtgcacg gcctgatgga gccggccccg actcatcatc gcgtcgtcgg
```

```
23401 ccoggctcga gccgtgctga caaacgcctt gctgttgggc gtcttcctgt gcacggccga
23461 cgccgcggta tccctgaata ccatcgccgc gttcaacttt aattttttcgg ccccgggcat
23521 gctcatatgc ctgaccgtgc tgttcgccct tctcgtcgta tcgctgttgt tggtggtcga
23581 ggggggtgttg tgtcactacg tgcgcgtgtt ggtgggcccc cacctggggg ccgtggccgc
23641 cacggcatc gtcggctggc cctgcgagca ctattacacc aacggctact acgttgtgga
23701 gacgcagtgg ccgggggccc agacgggagt ccgcgtcgcc ctcgccctgg tcgccgcctt
23761 tgccctcggc atggccgtgc tccgctgcac ccgcgcctat ctgtatcaca ggcggcacca
23821 caccaaattt tttatgcgca tgcgcgacac gcgacaccgc gcacattccg ccctcaggcg
23881 cgtacgcagt tccatgcgcg gatcgcgaga cggccgccac aggcccgcac ccggcagccc
23941 gcccgggatt cccgaatatg cggaagaccc ctacgcgatc tcatacggcg ccagctcga
24001 ccggtacgga gattccgacg gggagccgat tacgacgag gtggctgacg accaaaccga
24061 cgtattgtac gccaagatac aacacccgcg gcacctgccc gacgacgagc ccatctatga
24121 caccgttggg gggtacgacc ccgagcccgc cgaggacccc gtgtacagca ccgtccgccg
24181 ttggtagctg tttggttccg ttttaataaa ccgtttgtgt ttaacccgac cgtggtgtat
24241 gtctggtgtg tggcgtccga tcccgttact atcaccgttt cccccccccc ccctcaacc
24301 ccggcgattg tgggttttt aaaaacgaca cgcgtgcgac cgtatacaga acattgtttt
24361 ggttttatt cgctatcgga catgggggt ggaaactggg tggcggggca ggcgcctccg
24421 ggggtccgcc ggtgagtgtg gcgcgagggg gggtccgacg aacgcaggcg ctgtctcccc
24481 ggggcccgcg taaccacgcg catatccggg ggcacgtaga aattaccttc ctcttcggac
24541 tcgatatcca cgacatcaaa gtcgtgggcg gtcagcgaga cgacctcccc gtcgtcggtg
24601 atgaggacgt tgtttcggca gcagcaggc cgggcccgg agaacgagag gcccatagct
24661 cggcgagcgt gtcgtcgaac gccaggcggc tgcttcgctg gatggcctta tagatctccg
24721 gatcgatgcg gacgggggta atgatcaggg cgatcggaac ggcctggttc gggagaatgg
24781 acgccttgct gggtcctgcg gccccgagag cccggcgcc gtcctccagg cggaacgtta
24841 cgccctcctc cgcgctggtg cggtgcctgc cgataaacgt caccagatgc gggtgggggg
24901 ggcagtcggg gaagtggctg tcgagcacgt agccctgcac caagatctgc ttaaagttcg
24961 ggtgacgggg gttcgcgaag acgggctcgc ggcggaccag atccccggag ctccaggaca
25021 cgggggagat ggtgtggcgt ccgaggtcgg gggcgccaaa cagaagcacc tccgagacaa
```

```
25081 cgccgctatt taactccacc aaggcccgat ccgcggcgga gcaccgcctt ttttcgcccg
25141 aggcgtgggc ctctgaccag gcctggtctt gcgtgacgag agcctcctcc gggccgggga
25201 cgcgcccggg cgcgaagtat cgcacgctgg gcttcgggat cgaccggata aatgcccgga
25261 acgcctccgg ggaccggtgt gtcatcaagt cctcgtaccgc ggaggccgtg gggtcgctgg
25321 ggtccatggg gtcgaaagcg tacttggccc ggcatttgac ctcgtaaaag gccaggggg
25381 tcttggggac tggggccagg tagccgtgaa tgtcccgagg acagacgaga atatccaggg
25441 acgccccgac catccccgtg tgaccgtcca tgaggacccc acacgtatgc acgttctctt
25501 cggtgaggtc gctgggttcg tggaagataa agcgccgcgt gtcggcgccg gcctcgccgc
25561 cgtcgtccgc gcggcccacg cagtagcgaa acagcaggct tcgggccgtc ggctcgttca
25621 cccgcccgaa catcaccgcc gaagactgta catccggccg caggctggcg ttgtgcttca
25681 gccactgggg cgagaaacac ggaccctggg ggccccagcg gagggtggat gcggtcgtga
25741 ggccccgccg gagcagggcc catagctggc agtcggcctg gttttgcgtg gccgcctcgt
25801 aaaacccat gagggccggg ggcgccacgg cgtccgcggc ggccgggggc ccgcggcgcg
25861 tcaggcgcca taggtgccgg ccgagtccgc ggtccaccat acccgcctcc tcgaggacca
25921 cggccaggga acacagataa tccaggcggg cccagagggg accgatggcc agagggcgc
25981 ggacgccgcg cagcaacccg cgcaggtggc gctcgaacgt ctcggctagt atatgggagg
26041 gcagcgcgtt gggatcacc gacgccgacc acatagagtc aaggtccggg gagtcgggat
26101 cggcgtccgg gtcgcgggcg tgggtgcccc caggagatag cggaatgtct ggggtcggag
26161 gccctgaggc gtcagaaagt gccggcgacg cggcccgggg cttttcgtct gcggtgtcgg
26221 tggcgtgctg atcacgtggg gggttaacgg gcgaatggga gctcgggtcc acagctgacg
26281 tcgtctgggg tgggggggc aggggacgga aggtggttgt cagcggaaga ctgttagggc
26341 gggggcgctt gggggggctg tcggggccac gagggtgtc ctcggccagg gccagggac
26401 gcttagtcac ggtgcgtccc ggcggacatg ctgggcctac cgtggactcc atttccgaga
26461 cgacgtgggg gagcggtggt tgagcgcgcc gccggtgaa cgctgattct cacgacagcg
26521 cgtgccgcgc gcacggggttg gtgtgacaca ggcgggacac cagcaccagg agaggcttaa
26581 gctcgggagg cagcgccacc gacgacagta tcgccttgtg tgtgtgctgg taatttatac
26641 accgatccgt aaacgcgcgc cgaatcttgg gattgcggag gtggcgccgg atgccctctg
26701 gtacgtcata cgccaggccg tgggtgttgg tctcggccga gttgacaaac agggctgggt
```

FIGURE 9 (Continued)

```
26761 gcagcacgca gcgataggcg agcagggcca gggcgaagtc cggcgacagc tggttgttga
26821 aatactggta accgggaaac cgggtcacgg gtacgcccag gctcggggcg acgtacacgc
26881 taaccaccaa ctccagcagc gtctggccaa gggcgtacag gtcaaccgct aacccgacgt
26941 cgtgcttcag gcggtggttg gtaaattcgg ccgttcgtt gttaaggtat ttcaccaaca
27001 gctccggggg ctggttatac ccgtgaccca ccagggtgtg aaagttggct gtggttaggg
27061 cggtgggcat gccaaacatc cgggggact tgaggtccgg ctcctggagg caaaactgcc
27121 cccggcgat cgtggagttg gagttgaggg tgacgaggct aaagtcggcg aggacggccc
27181 gccggagcga gacggcgtcc gacgcagca tgacgaggat gttggcgcac ttgatatcca
27241 ggtggctgat cccgcaggtg gtgtttaaaa acacaacggc gcgggccagc tccgtgaagc
27301 actggtggag ggccgtcgag accgaggggt ttgttgtgcg cagggacgcc agttggccga
27361 tatacttacc gaggtccatg tcgtacgcgg ggaacactat ctgtcgttgt tgcagcgaga
27421 acccgagggg cgcgatgaag ccgcggatgt tgtgggtgcg gccggcgcgt agagcgcact
27481 ccccgaccaa cagggtcgcg atgagctcaa cggcaaacca ctccttttcc tttatggtct
27541 taacggcaag cttatgttcg cgaatcagtt ggacgtcgcc gtatccccca gacccccga
27601 agcttcgggc cccggggatc tcgagggtcg tgtagtgtag ggcgggttg atggcgaaca
27661 cggggctgca tagcttgcgg atgcgcgtga gggtaaggat gtgcgagggg gacgagggg
27721 gtgcggttaa cgccgcctgg gatctgcgca gggcgggcg gttcagtttg gccgccgtac
27781 cgggcgtctc ggggacgcg cggcgatgag acgagcggct cattcgccat cgggatagtc
27841 ccgcgcaag ccgctcgcgg aggccggatc ggtggcggga cccgtgggag gagcgggagc
27901 cggcggcgtc ctggagagag gggccgctgg ggcgcccgga ggcccgtgt gggttggagt
27961 gtatgtagga tgcgagccaa tccttgaagg accgttggcg tgcaccttgg gggctgaggt
28021 tagctgccac atgaccagca ggtcgctgtc tgcgggactc atccatcctt cggccaggtc
28081 gccgtctccc cacagagaag cgttggtcgc tgcttcctcg agttgctcct cctggtccgc
28141 aagacgatcg tccacggcgt ccaggcgctc accaagcgcc ggatcgaggt acgtcggtg
28201 tgcggttaga aagtcacgac gcgccgcttg ctcctccacg cgaattttaa cacaggtcgc
28261 gcgctgtcgc atcatctcta agcgcgcgcg ggactttagc cgcgcctcca attccaagtg
28321 ggccgccttt gcagccataa aggcgccaac aaaccgagga tcttgggtgc tgacgccctc
28381 ccggtgcagc tgcagggtct ggtccttgta aatctcggct cggaggtgcg tctcggccag
```

FIGURE 9 (Continued)

```
28441 gcgtcggcgc agggccgcgt gggcggcatc tcggtccatt ccgccaccct gcggcgacc
28501 cgggggtgc tctgatagtc tcgcgtgccc aaggcccgtg atcggggtac ttcgccgcg
28561 cgacccgcca cccggtgtgc gcgatgtttg gtcagcagct ggcgtccgac gtccagcagt
28621 acctggagcg cctcgagaaa cagaggcaac ttaaggtggg cgcggacgag gcgtcggcgg
28681 gcctcacaat gggcggcgat gccctacgag tgccctttt agatttcgcg accgcgaccc
28741 ccaagcgcca ccagaccgtg gtccgggcg tcgggacgct ccacgactgc tgcgagcact
28801 cgccgctctt ctcggccgtg gcgcggcggc tgctgtttaa tagcctggtg ccggcgcaac
28861 taaaggggcg tgatttcggg ggcgaccaca cggccaagct ggaattcctg ccccccgagt
28921 tggtacgggc ggtggcgcga ctgcggttta aggagtgcgc gccggcggac gtggtgcctc
28981 agcgtaacgc ctactatagc gttctgaaca cgtttcaggc cctccaccgc tccgaagcct
29041 ttcgccagct ggtgcacttt gtgcgggact ttgcccagct gcttaaaacc tccttccggg
29101 cctccagcct cacggagacc acgggccccc ccaaaaaacg ggccaaggtg gacgtggcca
29161 cccacggccg gacgtacggc acgctggagc tgttccaaaa aatgatcctt atgcacgcca
29221 cctactttct ggccgccgtg ctcctcgggg accacgcgga gcaggtcaac acgttcctgc
29281 gtctcgtgtt tgagatcccc ctgtttagcg acgcggccgt gcgccacttc cgccagcgcg
29341 ccaccgtgtt tctcgtcccc cggcgccacg gcaagacctg gtttctagtg cccctcatcg
29401 cgctgtcact ggcctccttt cggggatca agatcggcta cacggcgcac atccgcaagg
29461 cgaccgagcc ggtgtttgag gagatcgacg cctgcctgcg gggctggttc ggttcggccc
29521 gagtggacca cgttaaaggg gaaaccatct ccttctcgtt tccggacggg tcgcgcagta
29581 ccatcgtgtt tgcctccagc cacaacacaa acgtaagtcc tctttctttt cgcatggctc
29641 tcccaagggg ccccgggtcg accgaccca caccaccca ccacccaca tacacacaca
29701 accagacgcg ggaggaaagt ctgccccgtg ggcactgatt tttattcggg atcgcttgag
29761 gaggcccggg caacggcccg ggcaacggtg gggcaactcg tagcaaatag gcgactgatg
29821 tacgaagaga agacacacag gcgccaccg gcgctggtcg ggggatgtt gtccgcgccg
29881 caccgtcccc cgacgacctc ttgcagacgg tccgtgatgc aaggacggcg ggggcctgc
29941 agcaggtga ccgtatccac gggatggcca aagagaagcg gacacaggct agcatccccc
30001 tggaccgcca gggtacactg ggccatcttg cccacagac acggggcgac gcagggacag
30061 gactccgtta cgacggagga gagccacagt gcgttggcgg aatcgatgtg gggcggcggg
```

```
30121 gcgcaggact cgcagccccc cgggtggttg gtgatcctgg ccaggagcca tcccagatgg
30181 cgggccctgc ttcccggtgg acagagcgac cccaggtcgc tgtccatggc ccagcagtag
30241 atctggccgc tggggaggtg ccaccaggcc cccgggccca aggcgcagca cgcgcccggc
30301 tccggggggg tcttcgcggg gaccagatac gcgccatcca gctcgccgac cactggctcc
30361 tccgcgagct gttcggtggt tgggtcgggg gtttcctccg gggggtggc cgcccgtatg
30421 cgggcgaacg tgagggtgca caggagcggg gtcaggggt gcgtcacgct ccggaggtgg
30481 acgatcgcgc agtagcggcg ctcgcggtta agaaaaaga gggcaaagaa ggtgttcggg
30541 ggcaaccgca gcgccttggg gcgcgtcaga tacagaaaaa tctcgcagaa gagggcgcgc
30601 ccggggtctg ggttaggaag ggccacctga cacagaggct cggtgaggac cgttagacac
30661 cgaaagatct tgagccgctc gtccgcccga acgacgcgcc acacaaagac ggagttgaca
30721 atgcgcgcga tagagtcgac gtccgtcccc aggtcgtcga ctctgtcgcg cgtgccgcga
30781 gctccggccc gggaatccgg ccggggcaag gtccccgggg gaccaggcgg cgccaggggc
30841 cgccggggtc ccagctgcgc catgccgggg gcgggggag ggcaaacccc agaggcgggg
30901 gccaacggcg cggggaggag tgggtgggcg aggtggccgg ggaaggcgc ccgctagcga
30961 gaacggccgt tcccggacga caccttgcga caaaacctaa ggacagcggc ccgcgcgacg
31021 gggtccgaga ggctaaggta ggccgcgatg ttaatggtga acgcaaagcc gccgggaaag
31081 acaactatgc cacagaggcg gcgattaaac cccaggcaga ggtaggcgta gctttccccg
31141 ggcaggtatt gctcgcagac cctgcgtggg gctgtggagg ggacggcctc catgaagcga
31201 catttactct gctcgcgttt actgacgtca ccatccatcg ccacggcgat tggacgattg
31261 ttaagccgca gcgtgtctcc gcttgtgctg tagtagtcaa aaacgtaatg gccgtcggag
31321 tcggcaaagc gggccgggag gtcgtcgccg agcgggacga cccgccgccc ccgaccgccc
31381 cgtccccca ggtgtgccag gacggccagg gcatacgcgg tgtgaaaaaa ggagtcgggg
31441 gcggtcccct cgacggcgca catcaggttc tcgaggagaa tggggaagcg cctggtcacc
31501 tccccaacc acgcgcgttg gtcggggcca aagtcatagc gcaggcgctg tgagattcgc
31561 gggccgccct gaagcgcggc ccggatggcc tggcccaggg cccggaggca cgccagatgt
31621 atgcgcgcgg taaaggcgac ctcggcggcg atgtcaaagg gcggcaggac ggggcgcggg
31681 tggcgcaggg gcacctcgag cgcgggaaag cgtagcagca gctccgcctg cccagcggga
31741 gacagctggt gggggcgcac gacgcgttct gcggcgcagg cctcggtcag ggccgtggcc
```

```
31801 agcgccgagg acagcagcgg agggcgggcg cgtcgcccgc ccacgccac ggagttctcg
31861 taggagacga cgacgaagcg ctgcttggtt ccgtagtggt ggcgcaggac cacggagata
31921 gaacgacggc tccacagcca gtccggccgg tcgccgccgg ccagggcttc ccatccgcga
31981 tccaatcact cgaccagcga ccgtggcttt gcggtaccag gggtcagggt tagaacgtcg
32041 ttcaggatgt cctcgccccc gggcccgtgg ggcacggggg ccacaaagcg ccccgcct
32101 gggggctcca gacccgccaa caccgcatct gcgtcagccg ccccatggc gccccgctg
32161 acggcctggt gaaccagggc gccctggcgg agccccgatg caacgccaca ggccgcacgc
32221 ccggtccgag cgcggaccgg gtggcggcgg gtgacgtcct gcactgcccg ctgaaccaac
32281 gcgaggatct cctcgttctc ctgcgcgatg acacgtcct gggccgcggt cgtgtcgccg
32341 ccggggccg tcagctgctc ctccggggag atggggggt cggacgcccc gacgatgggc
32401 gggtctgcgg gcgccccgc gtggggccgg gccaagggct gcggacgcgg ggacgcgctt
32461 tccccagac ccatggacag gtgggccgca gcctccttcg cggccggcgg ggcggcggcg
32521 ccaagcagag cgacgtagcg gcacaaatgc cgacagacgc gcatgatgcg cgtgctgtcg
32581 gccgcgtagc gcgtgttggg ggggacgagc tcgtcgtaac taaacagaat cacgcgggca
32641 cagctcgccc ccgagcccca cgcaaggcgc agcgccgcca cggcgtacgg gtcatagacg
32701 ccctgcgcgt tacacaccac gggcagggag acgaacaacc cccggcgct ggacgcacgc
32761 ggaaggaggc cagggtgtgc cggcacgacg ggggccagaa gctccccac cgcatccgcg
32821 ggcacgtagg cggcaaacgc cgtgcaccac ggggtacagt cgccggtggc atgagcccga
32881 gtctggatttt cgacctggaa gtttgcggcc gtcccgagtc cggggtggcc gcgcatcagg
32941 gcggccagag ggattcccgc ggccgccagg cactcgctgg atatgatgac gtgaaccaaa
33001 gacgagggcc gacccgggcc gtggccgaga tcgtactgga cctcgttggc caagtgcgcg
33061 ttcatggttc ggggtgggt gtgggtgtgt aggcgatgcg ggtccccga gtccgcggga
33121 agggcgtggg tttggcgcgc gtatgcgtat tcgccaacgg aggcgtgcgt gcttatgcgc
33181 ggcgcgtttc ttctgtctct agggaatccg aggccaggac tttaacctgc tctttgtcga
33241 cgaggccaac tttattcgcc cggatgcggt ccagacgatt atgggctttc tcaaccaggc
33301 caactgcaag attatcttcg tgtcgtccac caacaccggg aaggccagta cgagcttttt
33361 gtacaacctc cgcggggccg cagacgagct tctcaacgtg gtgacctata tatgcgatga
33421 tcacatgccg agggtggtga cgcacacaaa cgccacggcc tgttcttgtt atatcctcaa
```

```
33481 caagcccgtt ttcatcacga tggacggggc ggttcgccgg accgccgatt tgtttctggc
33541 cgattccttc atgcaggaga tcatcggggg ccaggccagg gagaccggcg acgaccggcc
33601 cgttctgacc aagtctgcgg gggagcggtt tctgttgtac cgccctcga ccaccaccaa
33661 cagcggctc atggcccg attgtacgt gtacgtggat ccgcgttca cggccaacac
33721 ccgagcctcc gggaccggcg tcgctgtcgt cgggcggtac cgcgacgatt atatcatctt
33781 cgccctggag cacttttttc tccgcgcgct cacgggctcg gccccgccg acatcgcccg
33841 ctgcgtcgtc cacagtctga cgcaggtcct ggccctgcat ccggggcgt ttcgcggcgt
33901 ccgggtggcg gtcgaggaa atagcagcca ggactcggcc gtcgccatcg ccacgcacgt
33961 gcacagag atgcaccgcc tactggcctc ggagggggcc gacgcgggct cgggcccga
34021 gcttctcttc taccactgcg agcctcccgg gagcgcggtg ctgtacccct ttttcctgct
34081 caacaaacag aagacgcccg cctttgaaca ctttattaaa aagtttaact ccggggcgt
34141 catggcctcc caggagatcg tttccgcgac ggtgcgcctg cagaccgacc cggtcgagta
34201 tctgctcgag cagctaaata acctcaccga aaccgtctcc cccaacactg acgtccgtac
34261 gtattccgga aaacggaacg gcgcctcgga tgaccttatg gtcgccgtca ttatggccat
34321 ctacctcgcg gcccaggccg gacctccgca cacattcgct cctatcacac gcgtcttgtg
34381 agcgcccaat aaacacaccc aggtatgcta cgcacgacca cggtgtcgtc tgttaagggg
34441 ggggggaagg gggtgttggc gggaagcgtg ggaacacggg ggattctctc acgaccggca
34501 ccagtaccac cccctgtga acacagaaac cccaacccaa atcccataaa catacgacac
34561 acaggcatat tttggaattt cttaggtttt tatttattta ggtatgctgg ggtttctccc
34621 tggatgccca ccccaccccc ccgtgggtc tagccgggcc ttagggatag cgtataacgg
34681 gggccatgtc tccggaccgc acaacggccg cgccgtcaaa ggtgcacacc cgaaccacgg
34741 gagccagggc caaggtgtct cctagttggc ccgcgtgggt cagccaggcg acgagcgcct
34801 cgtaaagcgg cagccttcgc tctccatcct gcatcagggc cggggcttcg gggtgaatga
34861 gctggcggc ctcccgcgtg acactctgca tctgcaggag agcgttcacg tacccgtcct
34921 gggcacttag cgcaaagagc cggggatta gcgtaaggat gatggtggtt ccctccgtga
34981 tcgagtaaac catgttaagg accagcgatc gcagctcggc gtttacggga ccgagttgtt
35041 ggacgtccgc cagcagcgag aggcgactcc cgttgtagta cagcacgttg aggtctggca
35101 gccctccggg gtttctgggg ctggggttca ggtcccggat gccctggcc acgagccgcg
```

FIGURE 9 (Continued)

```
35161 ccacgatttc gcgcgccagg ggcgatggaa gcggaacggg aaaccgcaac gtgaggtcca
35221 gcgaatccag gcgcacgtcc gtcgcttggc cctcgaacac gggcgggacg aggctgatgg
35281 ggtccccgtt acagagatct acggggaggg tgttgcgaag gttaacggtg ccggcgtggg
35341 tgaggccac gtccaggggg caggcgacga ttcgcgtgg aagcaccgg gtgatgacg
35401 cggggaagcg ccttcggtac gccagcaaca cccccaacgt gtcgggactg acgcctccgg
35461 agacgaagga ttcgtgcgcc acgtcggcca gcgtcagttg ccggcggatg gtcggcagga
35521 ataccaccog cccttgcag cgctgcagcg ccgccgcatc ggggcgcgag atgcccgagg
35581 gtatcgcgat gtcagtttca aagccgtccg ccagcatggc gccgatccac gcggcaggga
35641 gtgcagtggt gggtcgggtg gcgggaggag cgcggtgggg gtcagcggcg tagcagagac
35701 gggcgaccaa cctcgcatag gacgggggt gggtcttagg gggttgggag cgacaggga
35761 ccccagagca tgcgcgggga ggtctgtcgg gcccagacgc accgagagcg aatccgtccg
35821 cggagtcccg gcttgggttt tatggggccc ggccctcgga atcgcggctt gtcggcgggg
35881 acaaaggggg cggggctagg ggcttgcgga acagaagac gcgtgggata aagaatcgc
35941 actacccaa ggaagggcgg ggcggtttat tacagagcca gtcccttgag cggggatgcg
36001 tcatagacga gatactgcgc gaagtgggtc tcccgcgcgt gggcttcccc gttgcgggcg
36061 ctgcggagga gggcggggtc gctggcgcag gtgagcgggt aggcctcctg aaacaggcca
36121 cacgggtcct ccacgagttc gcggcacccc ggggggcgct taaactgtac gtcgctggcg
36181 gcggtggccg tggacaccgc cgaacccgtc tccacgatca ggcgctccag gcagcgatgt
36241 ttggcggcga tgtcggccga cgtaaagaac ttaaagcagg ggctgagcac cggcgaggcc
36301 ccgttgaggt ggtaggcccc gttatagagc aggtccccgt acgaaaatcg ctgcgacgcc
36361 cacgggttgg ccgtggccgc gaaggcccgg gacggtcgc tctggccgtg gtcgtacatg
36421 agggcggtga catccccctc cttgtccccc gcgtaaacgc cccggcggc gtgtccccgg
36481 gggttgcagg gccggcggaa gtagttgacg tcgtcgaca cggggtggc gataaactca
36541 cacacggcgt cctggccgtg gtccatccct gcgcgccgcg gcacctgggc gcacccgaac
36601 acggggacgg gctgggccgg cccaggcgg tttcccgcca cgaccgcgtt ccgcaggtac
36661 acggctgccg cgttgtccag gagaggggga gccccgcggc ccaggtaaaa gttttgggga
36721 aggttgccca tgtcggtgac ggggttgcgg acggttgccg tggccacgac ggcggtgtag
36781 cccacgccca ggtccacgtt cccgcgcggc tgggtgagcg tgaagtttac cccccgcca
```

FIGURE 9 (Continued)

```
36841 gtttcgtgcc gggccacctg gagctggccc aggaagtacg cctccgacgc gcgctccgag
36901 aacagcacgt tctcagtcac aaagcggtcc tgtcggacga cggtgaaccc aaacccggga
36961 tggaggcccg tcttgagctg atgatgcaag ccacgggac tgatcttgaa gtaccccgcc
37021 atgagtgcgt aggtcagcgc gttctcccg gccgcgtct cgcggacgtg ctgcacgacg
37081 ggctgtcgga tcgacgaaaa gtagttggcc cccagagccg gggggaccag ggggacctgc
37141 cgcgacaggt cgcgcagggc cgggggggaaa ttgggcgcgt cgccacgtg gtcggcccg
37201 gcgaacagcg cgtggacggg gaggggtaa aaatagtcgc cattttggat ggtatggtcc
37261 agatgctggg gggccatcag caggattccg gcgtgcaacg ccccgtcgaa tatgcgcatg
37321 ttggtggtgg acgcggtgtt ggcgcccgcg tcgggcgccg ccagcagag cagcgccgtt
37381 gtgcgttcgg ccatgttgtg ggccagcacc tgcagcgtga gcatggcggg cccgtccact
37441 accacgcgcc cgttgtgaaa catggcgttg accgtgttgg ccaccagatt ggccgggtgc
37501 aggggggtgcg cggggtccgt cacggggtcg ctggggcact cctcgccggg ggcgatctcc
37561 gggaccacca tgttctgcag ggtggcgtat acgcggtcga agcgaacccc cgcggtgcag
37621 cagcggcccc gcgagaaggc gggcaccatc acgtagtagt aaatcttgtg gtgcacggtc
37681 cagtccgccc ccggtgcgg ccgtcatcc gcggcgtccg cggctcgggc ctgggtgttg
37741 tgcagcagct ggccgtcgtt gcggttgaag tcgcggtcg ccacgttaca tgccgccgcg
37801 tacacggggt cgtggccccc cgcgctaacc cggcagtcgc gatggcggtc cagggccgcg
37861 cgccgcatca gggcgtcaca gtcccacacg agggtggca gcagcgccgg gtctcgcatt
37921 aggtgattca gctcggcttg cgcctgcccg ccagctccg ggccggtcag ggtaaagtca
37981 tcaaccagct gggccagggc ctcgacgtgc gccaccaggt cccggtacac ggccatgcac
38041 tcctcgggaa ggtctccccc gaggtaggtc acgacgtacg agaccagcga gtagtcgttc
38101 acgaacgccg cgcaccgcgt gttgttccag tagctggtga tgcactggac cacgagccgg
38161 gccagggcgc agaagacgtg ctcgctgccg tgtatggcgg cctgcagcag gtaaaacacc
38221 gccgggtagt tgcggtcgtc gaacgcccg cgaacggcgg cgatggtggc gggggccatg
38281 gcgtggcgtc ccaccccag ctccaggccc cggcgtccc ggaacgccgc cggacatagc
38341 gccaggggca agttgccgtt caccacgcgc caggtggcct ggatctcccc cgggccggcc
38401 ggggaacgt ccccccccgg cagctccacg tcggccaccc ccacaaagaa gtcgaacgcg
38461 gggtgcagct caagagccag gttggcgttg tcgggctgca taaactgctc cggggtcatc
```

FIGURE 9 (Continued)

```
38521 tggccttccg cgacccatcg gacccgcccg tgggccaggc gctgccccca ggcgttcaaa
38581 aacagctgct gcatgtctgc ggcggggccg gcggggccg ccacgtacgc cccgtacgga
38641 ttggcggctt cgacggggtc gcggttaagg ccccgaccg ccgcgtcaac gttcatcagc
38701 gaagggtggc acacggtccc gatgcgtgt tccagagaca ggcgcagcac ctggcggtcc
38761 ttccccaaa aaaacagctg gcggggcggg aaggcgcggg gatccgggtg gccgggggcg
38821 gggactaggt ccccggcgtg cgcggcaaac cgttccatga ccggattgaa caggcccagg
38881 ggcaggacga acgtcaggtc catggcgccc accaggggt agggaacgtt ggtggcggcg
38941 tagatgcgct tctccagggc ctccagaaag accagcttct cgccgatgga caccagatcc
39001 gcgcgcacgc gcgtcgtctg ggggcgctc tcgagctcgt ccagcgtctg ccggttcagg
39061 tcgagctgct cctcctgcat ctccagcagg tggcggccca cgtcgtccag acttcgcacg
39121 gccttgccca tcacgagcgc cgtgaccagg ttggccccgt tcaggaccat ctcgccgtac
39181 gtcaccggca cgtcggcttc ggtgtcctcc gctttcagga aggactgcag gaggcgctgt
39241 ttgatcgggg cggtggtgac gagcaccccg tcgaccggcc gcccgcgcgt gtcggcatgc
39301 gtcagacggg gcacggccac ggagggctgc gtggccgtgg tgaggtccac gagccaggcc
39361 tcgacggcct cccggcggtg gcccgccttg cccaggaaaa agctcgtctc gcagaagctt
39421 cgctttagct cggcgaccag ggtcgcccgg gccaccctgg tggccaggcg gccgttgtcc
39481 aggtatcgtt gcatcggcaa caacaaagcc aggggcggcg cctttccag cagcacgtgc
39541 agcatctggt cggccgtgcc gcgctcaaac gccccgagga cggcctggac gttgcgagcg
39601 agctgttgga tggcgcgcaa ctggcgatgc gcgccgatac ccgtcccgtc cagggcctcc
39661 cccgtgagca gggcgatggc ctcggtggcc aggctgaagg cggcgttcag ggcccggcgg
39721 tcgataatct tggtcatgta attgtgtgtg ggttgctcga tggggtgcgg gccgtcgcgg
39781 gcaatcagcg gctggtggac ctcgaactgt acgcgcccct cgttcatgta ggccagctcc
39841 ggaaacttgg tacacacgca cgccaccgac aacccgagct ccagaaagcg cacgagcgac
39901 agggtgttgc aatacgaccc cagcagggcg tcgaactcga cgtcgtacag gctgtttgca
39961 tcggagcgca cgcgggaaaa aaaatcgaac aggcgtcgat gcgacgccac ctcgatcgtg
40021 ctaaggaggg acccggtcgg caccatggcc gcggcatacc ggtatcccgg agggtcgcgg
40081 ttgggagctg ccatggggtc gcgtggagat cggctggatc tagcgatatt tgcccgggga
40141 ggctaagatc cacccaacg cccggccacc cgtgtacgtg cccgacggcc caaggtccac
```

FIGURE 9 (Continued)

```
40201 cgaaagacac gacgggcccg gacccaaaaa ggcgggggat gctgtgtgag gggccgggtg
40261 tcggtcgggg gggaaaggca ccggagaag gctgcggcct cgttccagga gaacccagtg
40321 tccccaacag acccggggac gtgggatccc aggccttata tacccccccc gccccacccc
40381 cgttagaacg cgacgggtgc attaagatg gccctggtcc aaaagcgtgc caggaagaaa
40441 ttggcagagg cggcaaagct gtccgccgcc gccacccaca tcgaggcccc ggccgcgcag
40501 gctatcccca gggccgtgt gcgcagggga tcggtgggcg gcagcatttg gttggtggcg
40561 ataaagtgga aaagcccgtc cggactgaag gtctcgtggg cggcggcgaa caaggcacac
40621 agggccgtgc ctcccaaaaa cacggacatc ccccaaaaca ctggcgccga caacggcaga
40681 cgatccctct tgatgttaac gtacaggagg agcgcccgca ccgcccacgt aacgtagtag
40741 ccgacgatgg cggccaggat acaggccggc gccaccaccc ttccggtcag cccgtaatac
40801 atgcccgctg ccaccatctc caacggcttc aggaccaaaa acgaccaaag gaacagaatc
40861 acgcgctttg aaaagaccgg ctgggtatgg ggcggaagac gcgagtatgc cgaactgaca
40921 aaaaaatcag aggtgccgta cgaggacaat gaaaactgtt cctccagcgg cagttctccc
40981 tcctccccc cgaaggcggc ctcgtcgacc agatctcgat ccaccagagg aagtcatcc
41041 cgcatggtca tggggtgtgc ggtggaggtg gggagaccga aaccgcaaag ggtcgcttac
41101 gtcagcagga tcccgagatc aaagacaccc gggttcttgc acaaacacca cccgggttgc
41161 atccgcggag gcgagtgttt tgataaggcc gttccgcgcc ttgatataac ctttgatgtt
41221 gaccacaaaa cccggaattt acgcctacgc cccaatgccc acgcaagatg aggtaggtaa
41281 cccccccgtg ggtgtgacgt tgcgtttagt tcattggagg ccaaggggaa aaatggggtg
41341 gggaggaaac ggaaaaccca gtaggccgtg tcgggaacac gccgggggtt gtcctcaaaa
41401 ggcagggtcc atactacgga agccgtcgtt gtattcgaga cctgcctgtg cgacgcacgt
41461 cggggttgcc tgtgtccggt tcggcccca ccgcgtgcgg cacgcacgag gacgagtccg
41521 cgtgctttat tggcgttcca agcgttgccc tccagtttct gttgtcggtg ttccccata
41581 cccacgccca catccaccgt aggggcctc tgggccgtgt tacgtcgccg cccgcgatgg
41641 agcttagcta cgccaccacc atgcactacc gggacgttgt gttttacgtc acaacggacc
41701 gaaaccgggc ctactttgtg tgcgggggt gtgtttattc cgtgggcgg ccgtgtgcct
41761 cgcagcccgg ggagattgcc aagtttggtc tggtcgttcg agggacaggc ccagacgacc
41821 gcgtggtcgc caactatgta cgaagcgagc tccgacaacg cggcctgcag gacgtgcgtc
```

FIGURE 9 (Continued)

```
41881 ccattgggga ggacgaggtg tttctggaca gcgtgtgtct tctaaacccg aacgtgagct
41941 ccgagctgga tgtgattaac acgaacgacg tggaagtgct ggacgaatgt ctggccgagt
42001 actgcacctc gctgcgaacc agcccgggtg tgctaatatc cgggctgcgc gtgcgggcgc
42061 aggacagaat catcgagttg tttgaacacc aacgatagt caacgtttcc tcgcactttg
42121 tgtataccoc gtcccatac gtgttcgccc tggcccaggc gcacctccc cggctcccga
42181 gctcgctgga ggccctggtg agcggcctgt ttgacggcat cccgcccca cgccagccac
42241 ttgacgccca aacccgcgc acggatgtgg ttatcacggg ccgccgcgcc ccacgaccca
42301 tcgccgggtc gggggcgggg tcgggggcg cgggcgccaa gcggccacc gtcagcgagt
42361 tcgtgcaagt caaacacatt gaccgcgtgg gccccgctgg cgtttcgccg gcgcctccgc
42421 caaacaacac cgactcgagt tccctggtgc ccggggccca ggattccgcc ccgccggcc
42481 ccacgctaag ggagctgtgg tgggtgtttt atgccgcaga ccgggcgctg gaggagcccc
42541 gcgccgactc tggcctcacc cgcgaggagg tacgtgccgt acgtgggttc cgggagcagg
42601 cgtggaaact gtttggctcc gcgggggccc cgcggcgtt tatcggggcc gcgttgggcc
42661 tgagccccct ccaaaagctg gccgtttact actatatcat ccaccgagag aggcgcctgt
42721 cccccttccc cgcgctagtc cggctcgtag gccggtacac acagcgccac ggcctgtacg
42781 tccctcggcc cgacgaccca gtcttggccg atgccatcaa cgggctggtt cgcgacgcgc
42841 tggcggccgg aaccacagcc gagcagctcc tcatgttcga ccttctcccc ccaaaggacg
42901 tgccggtggg aagcgacgtg caggccgaca gcaccgctct gctgcgcttt atagaatcgc
42961 aacgtctcgc cgtccccggg ggggtgatct ccccgagca cgtcgcgtac cttggtgcgt
43021 tcctgagcgt gctgtacgct ggccgcgggc gcatgtccgc agccacgcac accgcgcggc
43081 tgacagggt gacctccctg gtgctagcgg tgggtgacgt ggaccgtctt tccgcgtttg
43141 accgcggagc ggcgggcgcg ccagccgca gcgggccgc cgggtacctg gatgtgcttc
43201 ttaccgttcg tctcgctcgc tcccaacacg gacagtctgt gtaaaagacc ccaataaacg
43261 tatgtcgcta ctacaccctt gtgtgtcaat ggacgcctct ccgggggggg gaagggaaag
43321 caaagagggg ctggggagc ggcaccaccg gggcctgaac aaacaaacca cagacacggt
43381 tacagtttat tcggtcgggc ggagaaacgg ccgaagccac gcccacttta ttcgcgtctc
43441 caaaaaaacg ggacacttgt ccggagaacc tttaggatgc cagccagggc ggcggtaatc
43501 ataaccacgc ccagcgcaga ggcggccaga aacccgggcg caattgcggc cacgggctgc
```

FIGURE 9 (Continued)

```
43561 gtgtcaaagg ctagcaaatg aatgacggtt ccgtttggaa atagcaacaa ggccgtggac
43621 ggcacgtcgc tcgaaaacac gcttggggcg ccctccgtcg gccggcggc gatttgctgc
43681 tgtgtgttgt ccgtatccac cagcaacaca gacatgacct cccggccgg ggtgtagcgc
43741 atadatacgg cccdacgag cccaggtcg cgctggtttt gggtgcgcac cagccgcttg
43801 gactcgatat cccggtgga gccttcgcat gtcgcggtga ggtaggttag aacagtggg
43861 cgtcggacgt cgacgccggt gagcttgtag ccgatccccc ggggcagagg ggagtgggtg
43921 acgacgtagc tggcgctgtg ggtgatgggt accaggatcc gtggctcgac gttggcagac
43981 tgcccccgc accgatgtga ggcctcaggg acgaaggcgc ggatcagggc gttgtagtgt
44041 gcccaacgcg tcagggtcga ggcgaggccg tgggtctgct gggccaggac ttcgaccggg
44101 gtctcggatc gggtggcttg agccagcgcg tccaggataa acacgctctc gtctagatca
44161 aagcgcaggg aggccgcgca tggcgaaaag tggtccggaa gccaaaagag ggttttctgg
44221 tggtcggccc gggccagcgc ggtccggagg tcggcgttgg tcgctgcggc gacgtcggac
44281 gtacacaggg ccgaggctat cagaaggctc cggcgggcgc gttcccgctg caccgccgag
44341 gggacgccag ccaagaacgg ctgccggagg acagccgagg cgtaaaatag cgcccggtgg
44401 acgaccgggg tggtcagcac gcggcccct agaaactcgg catacagggc gtcgatgaga
44461 tgggctgcgc tgggcgccac tgcgtcgtac gccgaggggc tatccagcac gaaggccagc
44521 tgatagccca gcgcgtgtaa tgccaagctc tgttcgcgct ccagaatctc ggccaccagg
44581 tgctggagcc gagcctctag ctgcaggcgg gccgtgggat ccaagactga cacattaaaa
44641 aacacagaat ccgcggcaca gcccgcggcc ccgcgggcgg ccaacccggc aagcgcgcgc
44701 gagtgggcca aaaagcctag caggtcggag aggcagaccg cgccgtttgc gtgggcggcg
44761 ttcacgaaag caaaacccga cgtcgcgagc agcccgtta ggcgccagaa gagaggggg
44821 cgcgggccct gctcggcgcc cgcgtccccc gagaaaaact ccgcgtatgc ccgcgacagg
44881 aactgggcgt agttcgtgcc ctcctccggg tagccgccca cgcggcggag ggcgtccagc
44941 gcggagccgt tgtcggcccg cgtcagggac cctaggacaa agacccgata ccggggccg
45001 ccgggggcc cggaagagc ccgggggg ttttcgtccg cggggtcccc gacccgatct
45061 agcgtctggc ccgcggggac caccatcact tccaccggag ggctgtcgtg catggatatc
45121 acgagcccca tgaattcccg cccgtagcgc gcgcgcacca gcgcggcatc gcacccgagc
45181 accagctccc ccgtcgtcca gatgcccacg ggccacgtcg aggccgacgg ggagaaatac
```

```
45241 acgtacctac ctggggatct caacaggccc cggtggcca accaggtcgt ggacgcgttg 45301 tgcaggtgcg tgatgtccag ctccgtcgtc gggtgccgcc gggccccaac cggcggtcgg 45361 ggggcggtg tatcacgcgg cccgctcggg tggctcgccg tcgccacgtt gtctcccgc 45421 gggaacgtca gggcctcggg gtcaggacg gccgaaaacg ttaccaggc ccgggaacgc 45481 agcaacacgg aggcggctgg attgtgcaag agacccttaa ggggggcgac cgaggggga 45541 ggctgggcgg tcggctcgac cgtggtgggg gcgggcaggc tcgcgttcgg gggccggccg 45601 agcaggtagg tcttcgggat gtaaagcagc tggccggggt cccgcggaaa ctcggccgtg 45661 gtgaccaata caaaacaaaa gcgctcctcg taccagcgaa gaaggggcag agatgccgta 45721 gtcaggttta gttcgtccgg cggcgccaga atccgcgcg gtggttttg ggggtcgggg 45781 gtgtttggca gccacagacg cccggtgttc gtgtcgcgcc agtacatgcg gtccatgccc 45841 aggccatcca aaaaccatgg gtctgtctgc tcagtccagt cgtggacctg accccacgca 45901 acgcccaaaa taataacccc cacgaaccat aaaccattcc ccatggggga cccgtccct 45961 aacccacggg gcccgtggct atggcagggc ttgccgcccc gacgttggct gcgagccctg 46021 ggccttcacc cgaacttggg gggtggggtg gggaaaagga agaaacgcgg gcgtattggc 46081 cccaatgggg tctcggtggg gtatcgacag agtgccagcc ctggaccga ccccgcgtt 46141 tatgaacaaa cgacccaaca cccgtgcgtt ttattctgtc tttttattgc cgtcatagcg 46201 cgggttactt ccggtattgt ctccttccgt gtttcagtta gcctccccca tctcccggc 46261 aaacgtgcgc gccaggtcgc agatcgtcgg tatggagccg ggggtggtga cgtgggtctg 46321 gaccatcccg gaggtaagtt gcagcagggc gtcccggcag ccggcgggcg attggtcgta 46381 atccaggata aagacgtgca tgggacggag gcgtttggcc aagacgtcca aggcccaggc 46441 aaacacgtta tacaggtcgc cgttggggc cagcaactcg ggcgcccgaa acagggtaaa 46501 taacgtgtcc ccgatatggg gttgtgggcc cgcgttgctc tggggctcgg caccctgggg 46561 cggcacggcc gtccccgaaa gctgtcccca atcctcccgc cacgacccgc cgccctgcag 46621 ataccgcacc gtattggcaa gcagctcgta aacgcggcga atcgcggcca acatagccag 46681 gtcaagccgc tcgccgggc gctggcgttt ggccaggcgg tcgatgtgtc tgtcctccgg 46741 aaggccccc aacacgatgt ttgtgccggg caaggtcggc gggatgaggg ccacgaacgc 46801 cagcacggcc tgggggtca tgctgccat aaggtatcgc gcggccgggt aacacaggag 46861 ggcggcgatg ggatggcggt cgaagatgag ggtgagggcc ggggcgggg catgtgagct
```

FIGURE 9 (Continued)

```
46921 ccagcctcc ccccgatat gaggagccag aacggcgtcg gtcacggcat aaggcatgcc
46981 cattgttatc tgggcgcttg tcattaccac cgccgcgtcc ccggccgata tctcaccctg
47041 gtcgaggcgg tgttgtgtgg tgtagatgtt cgcgattgtc tcggaagccc ccaacacccg
47101 ccagtaagtc atcggctcgg gtacgtagac gatatcgtcg cgcgaaccca gggccaccag
47161 cagttgcgtg gtggtggttt tccccatccc gtggggaccg tctatataaa cccgcagtag
47221 cgtgggcatt ttctgctcca ggcggacttc cgtggctttt tgctgccggc gagggcgcaa
47281 cgccgtacgt cggttgttat ggccgcgaga acgcagcc tggtcgaacg cagacgcgtg
47341 ttgatggcag gggtacgaag ccatacgcgc ttctacaagg cgctggccga agaggtgcgg
47401 gagtttcacg ccaccaagat ctgcggcacg ctgttgacgc tgttaagcgg gtcgctgcag
47461 ggtcgctcgg tattcgaggc cacacgcgtc accttaatat gcgaagtgga cctgggaccg
47521 cgccgcccg actgcatctg cgtgttcgaa ttcgccaatg acaagacgct gggcggggtt
47581 tgtgtcatca tagaactaaa gacatgcaaa tatatttctt ccggggacac cgccagcaaa
47641 cgcgagcaac gggccacggg gatgaagcag ctgcgccact ccctgaagct cctgcagtcc
47701 ctcgcgcctc cgggtgacaa gatagtgtac ctgtgccccg tcctggtgtt tgtcgcccaa
47761 cggacgctcc gcgtcagccg cgtgacccgg ctcgtcccgc agaaggtctc cggtaatatc
47821 accgcagtcg tgcggatgct ccagagcctg tccacgtata cggtccccat tgagcctagg
47881 acccagcgag cccgtcgccg ccgcggcggc gccgcccggg ggtctgcgag cagaccgaaa
47941 aggtcacact ctggggcgcg cgacccgccc gagtcagcgg cccgccagtt accacccgcc
48001 gaccaaaccc ccgcctccac ggagggcggg ggggtgctta agaggatcgc ggcgctcttc
48061 tgcgtgcccg tggccaccaa gaccaaaccc cgagccgcct ccgaatgaga gtgtttcgtt
48121 ccttccccct ccccccgcgt cagacaaacc ctaaccaccg cttaagcggc cccgcgagg
48181 tccgaagact catttggatc cggcgggagc cacccgacaa cagcccccgg gttttcccac
48241 gccagacgcc ggtccgctgt gcatcgcgc ccctcatcc cacccccat cttgtcccca
48301 aataaaacaa ggtctggtag ttaggacaac gaccgcagtt ctgtgtgtt attttcgctc
48361 tccgcctctc gcagatggac ccgtactgcc catttgacgc tctggacgtc tgggaacaca
48421 ggcgcttcat agtcgccgat cccgaaact tcatcacccc cgagttcccc cgggactttt
48481 ggatgtcgcc cgtctttaac ctccccggg agacggcggc ggagcaggtg gtcgtcctac
48541 aggcccagcg cacagcggct gccgctgccc tggagaacgc cgccatgcag gcggccgagc
```

FIGURE 9 (Continued)

```
48601 tccccgtcga tatcgagcgc cggttacgcc cgatcgaacg gaacgtgcac gagatcgcag
48661 gcgccctgga ggcgctggag acggcggcgg ccgccgccga agaggcggat gccgcgcgcg
48721 gggatgagcc ggcgggtggg ggcgacgggg gggcgccccc gggtctggcc gtcgcggaga
48781 tggaggtcca gatcgtcgc aacgaccgc cgctacgata cgacccaac ctcccgtgg
48841 atctgctaca catggtgtac gcgggccgcg gggcgaccgg ctcgtcgggg gtggtgttcg
48901 ggacctggta ccgcactatc caggaccgca ccatcacgga ctttcccctg accacccgca
48961 gtgccgactt tcgggacggc cggatgtcca agaccttcat gacggcgctg gtcctgtccc
49021 tgcagtcgtg cggccggctg tatgtgggcc agcgccacta ttccgccttc gagtgcgccg
49081 tgttgtgtct ctacctgctg taccgaaaca cgcacggggc cgccgacgat agcgaccgcg
49141 ctccggtcac gttcggggat ctgctgggcc ggctgccccg ctacctggcg tgcctggccg
49201 cggtgatcgg gaccgagggc ggccggccac agtaccgcta ccgcgacgac aagctcccca
49261 agacgcagtt cgcggccggc gggggccgct acgaacacgg agcgctggcg tcgcacatcg
49321 tgatcgccac gctgatgcac cacggggtgc tcccggcggc cccggggac gtcccccggg
49381 acgcgagtac ccacgttaac cccgacggcg tggcgcacca cgacgacata aaccgcgccg
49441 ccgccgcgtt cctcagccgg ggccacaacc tattcctgtg ggaggaccag actctgctgc
49501 gggcaaccgc gaacaccata acggccctgg gcgttatcca gcggctcctc gcgaacggca
49561 acgtgtacgc ggaccgcctc aacaaccgcc tgcagctggg catgctgatc cccggagccg
49621 tcccttcgga ggccatcgcc cgtggggcct ccgggtccga ctcggggcc atcaagagcg
49681 gagacaacaa tctggaggcg ctatgtgcca attacgtgct tccgctgtac cgggccgacc
49741 cggcggtcga gctgacccag ctgtttcccg gcctggccgc cctgtgtctt gacgccagg
49801 cggggcggcc ggtcgggtcg acgcggcggg tggtggatat gtcatcgggg gcccgccagg
49861 cggcgctggt gcgcctcacc gccctggaac tcatcaaccg cacccgcaca aaccccaccc
49921 ccgtggggga ggttatccac gcccacgacg ccctggcgat ccaatacgaa cagggcttg
49981 gcctgctggc gcagcaggca cgcattggct tgggctccaa caccaagcgt ttctccgcgt
50041 tcaacgttag cagcgactac gacatgttgt actttttatg tctggggttc attccacagt
50101 acctgtcggc ggtttagtgg gtggtgggcg aggggggagg gggcattagg gagaaagaac
50161 aagagcctcc gttgggtttt ctttgtgcct gtactcaaaa ggtcataccc cgtaaacggc
50221 gggctccagt cccggcccgg tggttggcgt gaacgcaacg gcgggagctg ggttagcgtt
```

FIGURE 9 (Continued)

```
50281 tagtttagca ttcgctctcg cctttccgcc cgcccccga ccgttgcgcc ttttttttcg
50341 tccaccaaag tctctgtggg tgcgcgcatg gcagccgatg ccccgggaga ccggatggag
50401 gagcccctgc ccgacagggc cgtgcccatt tacgtggctg ggttttggc cctgtatgac
50461 agcggggact cgggcgagtt ggcattggat ccggatacgg tgcgggcggc cctgcctcg
50521 gataacccac tcccgattaa cgtggaccac cgcgctggct gcgaggtggg gcgggtgctg
50581 gccgtggtcg acgaccccg cgggccgttt tttgtgggc tgatcgcctg cgtgcagctg
50641 gagcgcgtcc tcgagacggc cgccagcgct gcgattttcg agcgccgcgg gccgccgctc
50701 tcccgggagg agcgcctgtt gtacctgatc accaactacc tgccctcggt ctccctggcc
50761 acaaaacgcc tgggggggcga ggcgcacccc gatcgcacgc tgttcgcgca cgtcgcgctg
50821 tgcgcgatcg ggcggcgcct cggcactatc gtcacctacg acaccggtct cgacgccgcc
50881 atcgcgccct ttcgccacct gtcgccggcg tctcgcgagg gggcgcggcg actggccgcc
50941 gaggccgaga tcgcgctgtc cgggcgcacc tgggcgcccg cgtggaggc gctgacccac
51001 acgctgcttt ccaccgccgt taacaacatg atgctgcggg accgctggag cctggtggcc
51061 gagcggcggc ggcaggccgg gatcgccgga cacacctacc tccaggcgag cgaaaaattc
51121 aaaatgtggg gggcggagcc tgtttccgcg ccgcgcgcg ggtataagaa cggggccccg
51181 gagtccacgg acataccgcc cggctcgatc gctgccgcgc cgcagggtga ccggtgccca
51241 atcgtccgtc agcgcggggt cgccttgtcc ccggtactgc cccccatgaa cccgttccg
51301 acatcgggca cccggcccc cgcgccgccc ggcgacggga gctacctgtg gatcccggcc
51361 tcccattaca accagctcgt cgccggccat gccgcgcccc aacccagcc gcattccgcg
51421 tttggttcc cggctgcggc ggggccgtg gcctatgggc ctcacggcgc gggtctttcc
51481 cagcattacc ctccccacgt cgcccatcag tatcccgggg tgctgttctc gggacccagc
51541 ccactcgagg cgcagatagc cgcgttggtg ggggccatag ccgcggaccg ccaggcgggc
51601 ggtcagccgg ccgcgggaga ccctggggtc cggggtcgg gaaagcgtcg ccggtacgag
51661 gcggggccgt cggagtccta ctgcgaccag gacgaaccgg acgcggacta cccgtactac
51721 cccggggagg ctcgaggcgg gccgcgcggg gtcgactctc ggcgcgcggc ccgccagtct
51781 cccgggacca acgagaccat cacggcgctg atggggcgg tgacgtcttt gcagcaggaa
51841 ctggcgcaca tgcgggctag gaccagcgcc cctatggga tgtacacgcc ggtggcgcac
51901 tatcgccctc aggtggggga gccggaacca acaacgaccc accggccct ttgtccccg
```

FIGURE 9 (Continued)

```
51961 gaggccgtgt atcgccgccc accacacagc gccgcctacg gtcctcccca gggtccggcg
52021 tcccatgccc ccactccccc gtatgcccca gctgcctgcc cgccaggccc gccaccgccc
52081 ccatgtcctt ccacccagac gcgcgccct ctaccgacgg agcccgcgtt cccgcccgcc
52141 gccatcggat cccaaccgga ggtatccaac gcggaggccg gggccttgt caacgccagc
52201 agcgcagcac acgtggacgt tgacacggcc cgcgccgccg atttgttcgt ctctcagatg
52261 atgggggccc gctgattcgc cccggtcttt ggtaccatgg gatgtcttac tgtatatctt
52321 tttaaataaa ccaggtaata ccaagaaga cccattggtg tatgttcttt ttttattggg
52381 aggcgcgggt aggcgggtag ctttacaatg caaaagcctt cgacgtggag gaaggcgtgg
52441 ggggaatcg gcactgacca aggggtccg ttttgtcacg ggaaaggaaa gaggaaacag
52501 gccgcggaca cccgggggag tttatgtgtt ccctttttctt tcttcccaca cacacaaaag
52561 gcgtaccaaa caaacaaacc aaagatgca catgcggttt aacacccgtg gtttttattt
52621 acaacaaacc cccgtcaca ggtcgtcctc gtcggcgtca ccgtctttgt tgggaacttg
52681 ggtgtagttg gtgttgcggc gcttgcgcat gaccatgtcg gtgaccttgg cgctgagcag
52741 cgcgctcgtg cccttcttct tggccttgtg ttccgtgcgc tccatggcag acaccagggc
52801 catgtaccgt atcatctccc gggcctcggc tagcttggcc tcgtcaaagt cgccgccctc
52861 ctcgccctcc ccggacgcgt ccgggttggt ggggttcttg agctccttgg tggttagcgg
52921 gtacagggcc ttcatggggt tgctctgcag ccgcatgacg tagcgaaagg cgaagaaggc
52981 cgccgccagg ccggccagga ccaacagacc cacggccagc gccccaaagg ggttggacat
53041 gaaggaggac acgcccgaca cggccgatac cacgccgccc acgatgccca tcaccacctt
53101 gccgaccgcg cgcccaggt cgcccatccc ctcgaagaac gcgccaggc ccgcaaacat
53161 ggcggcgttg gcgtcggcgt ggatgaccgt gtcgatgtcg gcgaagcgca ggtcgtgcag
53221 ctggttgcgg cgctggacct ccgtgtagtc cagcaggccg ctgtccttga tctcgtggcg
53281 ggtgtacacc tccaggggga caaactcgtg atcctccagc atggtgatgt tgaggtcgat
53341 gaaggtgctg acggtggtga tgtcggcgcg gctcagctgg tgggagtacg cgtactcctc
53401 gaagtacacg tagccccac cgaaggtgaa gtagcgccgg tgtcccacgg tacacggctc
53461 gatcgcatcg cgcgtcagcc gcagctcgtt gttctccccc agctgcccct cgaccaacgg
53521 gccctggtct tcgtaccgaa agctgaccag ggggcggctg tagcaggccc cgggccgcga
53581 gctgatgcgc atcgagtttt ggacgatcac gttgtccgcg gcgaccggca cgcacgtgga
```

FIGURE 9 (Continued)

```
53641 gacggccatc acgtcgccga gcatccgcgc gctcacccgc cggcccacgg tggccgaggc
53701 gatggcgttg gggttcagct tgcgggcctc gttccacagg gtcagctcgt gattctgcag
53761 ctcgcaccac gcgatggcaa cgcggcccaa catatcgttg acatggcgct gtatgtggtt
53821 gtacgaaac tgcagcctgg cgaactcgat ggaggagggtg gtcttgatgc gctccacgga
53881 cgcgttggcg ctggcccgg cggcggggg cgtggggttt ggggcttgc ggctctgctc
53941 tcggaggtgt tcccgcacgt acagctccgc gagcgtgttg ctgagaaggg gctggtacgc
54001 gatcagaaag cccccattgg ccaggtagta ctgcggctgg cccaccttga tgtgcgtcgc
54061 gttgtacctg cgggcgaaga tgcggtccat ggcgtcgcgg gcgtccttgc cgatgcagtc
54121 ccccaggtcc acgcgcgaga gcgggtactc ggtcaggttg gtggtgaagg tggtggatat
54181 ggcgtcggag gagaatcgga aggagccgcc gtactcggag cgcagcatct cgtccacctc
54241 ctgccacttg gtcatggtgc agaccgacgg gcgctttggc accagtccc aggccacggt
54301 gaacttgggg gtcgtgagca ggttccgggt ggtcggcgcc gtggcccggg ccttggtggt
54361 gaggtcgcgc gcgtagaagc cgtcgacctg cttgaagcgg tcgcggcgt agctggtgtg
54421 ttcggtgtgc gaccctccc ggtagccgta aaacggggac atgtacacaa agtcgccagt
54481 cgccagcaca aactcgtcgt acgggtacac cgagcgcgcg tccacctcct cgacgatgca
54541 gtttaccgtc gtcccgtacc ggtggaacgc ctccacccgc gagggttgt acttgaggtc
54601 ggtggtgtgc cagccccggc tcgtgcgggt cgcggcgttg gccggtttca gctccatgtc
54661 ggtctcgtgg tcgtcccggt gaaacgcggt ggtctccagg ttgttgcgca cgtacttggc
54721 cgtggaccga cagaccccct tggcgttgat cttgtcgatc acctcctcga aggggacggg
54781 ggcgcggtcc tcaaagatcc ccataaactg ggagtagcgg tggccgaacc acacctgcga
54841 aacggtgacg tctttgtagt acatggtggc cttgaacttg tacggggcga tgttctcctt
54901 gaagaccacc gcgatgccct ccgtgtagtt ctgaccctcg gccgggtcg ggcagcggcg
54961 cggctgctcg aactgcacca ccgtggcgcc cgtgggggt gggcacacgt aaaagtttgc
55021 atcggtgttc tccgccttga tgtcccgcag gtgctcgcgc agggtggcgt ggcccgcgc
55081 gacggtcgcg ttgtcgccgg cggggcgcgg cggctttggg ggtttcggtt ttttgttctt
55141 cttcggtttc gggtccccg ttgggggggc gccagggggcg ggcggcgccg gagtggcagg
55201 gccccgttc gccgctggg tcgcggccgc gacccaggc gtgccggggg aactcggagc
55261 cgccgacacc accaggaccc ccagcgtcaa cccccaagagc gcccatacga cgaaccaccg
```

FIGURE 9 (Continued)

```
55321 gcgccccgc gcggggcgc cctggcgcat ggcgggacta cggggccccg tcgtgcccc
55381 cgtcaggtag cctggggcg aggtgctgga ggaccgagta gaggatcgag aaaacgtctc
55441 ggtcgtagac cacgaccgac cggggccga tacagccgtc gggggcgctc tcgacgatgg
55501 ccaccagcgg acagtcggag tcgtacgtga gatatcgcc gggcgggtaa cggtaacgac
55561 cttcggaggt cgggcggctg cagtccgggc ggcgcaactc gagctccccg caccggtaga
55621 ccgaggcaaa gagtgtggtg gcgataatca gctcgcgaat atatcgccag gcggcgcgct
55681 gagtgggcgt tattccggaa atgccgtcaa acagtaaaa cctctgaaat tcgctgacgg
55741 cccaatcagc acccgagccc ccgccccca tgatgaaccg ggcgagctcc tccttcaggt
55801 gcggcaggag ccccacgttc tcgacgctgt aatacagcgc ggtgttgggg ggctgggcga
55861 agctgtgggt ggagtgatca agagggcc cgttgacgag ctcgaagaag cgatgggtga
55921 tgctggggag cagggccggg tccacctggt gtcgcaggag agacgctcgc atgaaccggt
55981 gcgcgtcgaa cacgcccggc gccgagcggt tgtcgatgac cgtgcccgcg ccgccgtca
56041 gggcgcagaa gcgcgcgcgc gccgcaaagc cgttggcgac cgcggcgaac gtcgcgggca
56101 gcacctcgcc gtggacgctg acccgcagca tcttctcgag ctccccgcgc tgctcgcgga
56161 cgcagcgccc caggctggcc aacgaccgct tcgtcaggcg gtccgcgtac agccgccgtc
56221 gctcccgcac gtccgcggcc gcttgcgtgg cgatgtcccc ccacgtctcg ggccctgcc
56281 ccccgggccc gcggcgacgg tcttcgtcct cgcccccgcc ccgggagct cccaaccccc
56341 gtgcccttc ctctacggcg acacggtccc cgtcgtcgtc ggggcccgcg ccgcccttgg
56401 gcgcgtccgc cgcgcccccc gccccatgc gcgccagcac gcgacgcagc gcctcctcgt
56461 cgcactgttc ggggctgacg aggcgccgca agagcggcgt cgtcaggtgg tggtcgtagc
56521 acgcgcggat gagcgcctcg atctgatcgt cgggtgacgt ggcctgaccg ccgattatta
56581 gggcgtccac catatccagc gccgccaggt ggctcccgaa cgcgcgatcg aaatgctccg
56641 cccgccgccc gaacagcgcc agttccacgg ccaccgcggc ggtctcctgc tgcaactcgc
56701 gccgcgccag cgcggtcagg ttgctggcaa acgcgtccat ggtggtctgg ccggcgcggt
56761 cgccggacgc gagccagaat cgcaattcgc tgatggcgta caggccgggc gtggtggcct
56821 gaaacacgtc gtgcgcctcc agcagggcgt cggcctcctt gcggaccgag tcattctcgg
56881 gcgacgggtg gggctgcccg tcgccccccg cggtccgggc cagcgcatgg tccaacacgg
56941 agagcgcccg cgcgcggtcg gcgtccgaca gcccggcggc gtggggcagg taccgccgca
```

FIGURE 9 (Continued)

```
57001 gctcgttggc gtccagccgc acctgcgcct gctgggtgac gtggttacag atacggtccg
57061 ccaggcggcg ggcgatcgtc gccccctggt tcgccgtcac acacagttcc tcgaaacaga
57121 ccgcgcaggg gtgggacggg tcgctaagct ccgggggggac gataaggccc gaccccaccg
57181 cccccaccat aaactcccga acgtgctcca gcgcggcggt ggcgccgcgc gagggggtga
57241 tgaggtggca gtagtttagc tgctttagaa agttctcgac gtcgtgcagg aaacacagct
57301 ccatatggac ggtcccgcca tacgtatcca gcctgacccg ttggtgatac ggacagggtc
57361 gggccaggcc catggtctcg gtgaaaaacg ccgcgacgtc tcccgcggtc gcgaacgtct
57421 ccaggctgcc caggagccgc tcgccctcgc gccacgcgta tctagcagc aactccaggg
57481 tgaccgacag cggggtgaga aaggcccgg cctgggcctc caggcccggc ctcagacgac
57541 gccgcagcgc ccgcacctga agcgcgttca gcttcagttg ggggagcttc ccccgtccga
57601 tgtgggggtc gcaccgccgg agcagctcta tctgaaacac ataggtctgc acctgcccga
57661 gcagggctaa caacttttga cgggccacgg tgggctcgga caccggggcg gccatctcgc
57721 ggcgccgatc tgtaccgcgg ccggagtatg cggtggaccg aggcggtccg tacgctaccc
57781 ggcgtctggc tgagccccgg ggtcccctc ttcggggcgg cctcccgcgg gcccgccgac
57841 cggcaagccg ggagtcggcg gcgcgtgcgt ttctgctcta ttcccagaca ccgcggagag
57901 gaatcacggc ccgcccagag atatagacac ggaacacaaa caagcacgga tgtcgtagca
57961 ataatttatt ttacacacat tcccgcccc gccctaggtt cccccacccc caaccctca
58021 cagcatatcc aacgtcaggt ctccttttt gtcggggggc ccctcccaa acgggtcatc
58081 cccgtggaac gcccgtttgc ggccggcaaa tgccggtccc gggccccg ggccgccgaa
58141 cggcgtcgcg ttgtcgtcct cgcagccaaa atccccaaag ttaaacacct cccccggcgtt
58201 gccgagttgg ctgactaggg cctcggcctc gtgcgccacc tccagggccg cgtccgtcga
58261 ccactcgccg ttgccgcgct ccagggcacg gcggtcagc tccatcatct cctcgcttag
58321 gtactcgtcc tccaggagcg ccagccagtc ctcgatctgc agctgctggg tgcggggccc
58381 caggcttttc acgtcacca cgaacacgct actggcgacg gcgccccgc cctcggagat
58441 aatgccccgg agctgctcgc acagcgagct ttcgtgcgct ccgccgccga ggctcgaggc
58501 cgcgcacaca aacccggccc ggggacaggc caggacgaac ttgcgggtgc ggtcaaaaat
58561 aaggagcggg cacgcgtttt tgccgcccat caggctggcc cagttcccgg cctgaaacac
58621 acggtcgttg ccggccatgc cgtagtactt gctgatgctc aaccccaaca cgaccatggg
```

FIGURE 9 (Continued)

```
58681 gcgcgccgcc atgacgggcc gcagcaggtt gcagctggcg aacatggacg tccacgcgcc
58741 cggatgcgcg tccacggcgt ccatcagcgc gcgggcccg gcctccaggc ccgcccgcc
58801 ctgcgcggac cacgcggccg cagcctgcac gctggggga cggcgggacc ccgcgatgat
58861 ggccgtaagg gtgttgatga agtacgtcga gtgatcgcag taccgcagaa tctggtttgc
58921 catgtagtac atcgccagct cgctcacgtt gttggggcc aggttaataa agtttatcgc
58981 gccgtagtcc agggaaaact ttttaatgaa cgcgatggtc tcgatgtcct cgcgcacag
59041 gagccgggcg ggaagctggt tgcgttggag ggccgtccag aaccactgcg ggttcgctg
59101 gttggacccc gggggcttgc cgttggggaa gatggccgcg tggaactgct tcagcagaaa
59161 gcccagcggt ccgaggagga tgtccacgcg cttgtcgggc ttctggtagg cgctctggag
59221 gctggcgacc cgcgccttgg cggcctcgga cgcgttggcg ctcgcgcccg cgaacaacac
59281 gcggctcttg acgcgcagct ccttgggaaa cccagggtc acgcgggcaa cgtcgccctc
59341 gaagctgctc tcggcggggg ccgtctggcc ggccgttagg ctggggcgc agatagccgc
59401 cccctccgag agcgcgaccg tcagcgtttt ggccgacaga acccgttgt taaacatgtc
59461 catcacgcgc cgccgcagca ccggttggaa ttgattgcga agttgcgcc cctcgaccga
59521 ctgcccggcg aacaccccgt ggcactggct cagggccagg tcctgataca cggcgaggtt
59581 ggatcgccgc ccgagaagct gaagcagggg gcatggcccg cacgcgtacg ggtccagcgt
59641 cagggacatg gcgtggttgg cctcgcccag accgtcgcga aacttgaagt tcctcccctc
59701 caccaggttg cgcatcagct gctccacctc gcggtccacg acctgcctga cgttgttcac
59761 caccgtatgc agggcctcgc ggttggtgat gatggtctcc agccgcccca tggccgtggg
59821 gaccgcctgg tccacgtact gcagggtctc gagttcggcc atgacgcgct cggtcgccgc
59881 gcggtacgtc tcctgcatga tggtccgggc ggtctcggat ccgtccgcgc gttcagggc
59941 cgagaaggcg gcgtagtttc ccagcacgtc gcagtcgctg tacatgctgt tcatggtccc
60001 gaagacgccg atggctccgc gggcggcgct ggcgaacttg ggatggcgcg ccggaggcg
60061 catgagcgtc gtgtgtacgc aggcgtggcg cgtgtcgaag gtgcacaggt tgcagggcac
60121 gtcggtctgg ttggagtccg cgacgtatcg aaacacgtcc atctcctggc gcccgacgat
60181 cacgccgccg tcgcagcgct ccaggtaaaa cagcatcttg ccagcagcg ccggggaaaa
60241 cccacacagc atggccaggt gctcgccggc aaattcctgg gttccgccga cgagggcgc
60301 ggtgggccga ccctcgaacc cgggcaccac gtgtccctcg cggtccacct gtgggttggc
```

FIGURE 9 (Continued)

```
60361 cgccacgtgg gtcccgggca cgaggaagaa gcggtaaaag gagggtttgc tgtggtcctt
60421 tgggtccgcc ggaccggcgt cgtccacctc ggtgagatgg agggccgagt tggtgctaaa
60481 taccatggcc cccacgagtc ccgcggcgcg cgccaggtac gccccgacgg cgttggcgcg
60541 ggccgtggcc gtgtcctggc cctgcacag cggccatgcg gagatgtcgg tgggcggctc
60601 gtcgaagacg gccatcgaca cgatagactc gagggccagg gcggcgtctc cggccatgac
60661 ggaggccagg cgctgttcga acccgccgc cgggcccttg ccgccgccgt cgcgcccacc
60721 ccgcggggtc ttaccctggc tggcttcgaa ggccgtgaac gtaatgtcgg cggggagggc
60781 ggcgccctcg tggttttcgt caaacgccag gtgggcggcc gcgcgggcca cggcgtccac
60841 gtttcggcat cgcagtgcca cggcggcggg tcccacgacc gcctcgaaca ggaggcggtt
60901 gaggggggcgg ttaaaaaacg gaagcgggta ggtaaaattc tccccgatcg atcggtggtt
60961 ggcgttgaac ggctcggcga tgacccggct aaaatccggc atgaacagct gcaacggata
61021 cacgggtatg cggtgcacct ccgcccgcc tatggttacc ttgtccgagc ctcccaggtg
61081 cagaaaggtg ttgttgatgc acacggcctc cttgaagccc tcggtaacga ccagatacag
61141 gagggcgcgg tccgggtcca ggccgaggcg ctcacacagc gcctccccg tcgtctcgtg
61201 tttgaggtcg ccgggccggg gggtgtagtc cgaaaagcca aaatggcggc gtgcccgctc
61261 gcagagtcgc gtcaggtttg gggcctggct gttggggtcc aggtgccggc cgccgtgaaa
61321 gacgtacacg gacgagctgt agtgcgatgg cgtcagtttc agggacaccg cggtacccc
61381 gagcccgtc gtgcgagaac ccacgaccac ggctacgttg cctcaaagc cgctctccac
61441 ggtcaggccc acgaccaggg gcgccacggc gacgtcggca tcgccgctgc gcgccgacag
61501 taacgccaga agctcgatgc cttcggatgg acacgcgcga gcgtacacgt atcccagggg
61561 cccggggggg accttgatgg tggttgccgt cttgggcttt gtctccatgt cctcctggca
61621 atcggtccgc aaacggaggt aatcccggca cgacgacgga cgcccgacga ggtatgtctc
61681 ccgagcgtca aaatccgggg ggggcggcga cggtcaaggg gagggtggga gaccggggtt
61741 ggggaatgaa tccctaccct tcaccgacaa ccccccggta ccacggggt gccgatgaac
61801 cccggcggct ggcaacgcgg ggtccctgcg agaggcacag atgcttacgg tcaggtgctc
61861 cgggccgggt gcgtctgata tgcggttggt atatgtacac tttacctggg ggcgtgccgg
61921 accgcaccag cccctcccac acccgcgcg tcatcagccg gtgggcgnnn nnnnnnnnn
61981 nnnnnnnnnn nnnnnnnnnn nnnnnnnnnn nnnnnnnnnn nnnnnnnnnn nnnnnnnnnn
```

```
62041 nnnnnnnnnn nnnnnnnnnn nnnnnnnnnt ttttataata gcggccacgc ccaccggcta
62101 cgtcacgctc ctgtcggccg ccggcggtcc ataagcccgg ccggccgggc cgacgcgaat
62161 aaaccgggcc gccggccggg gcgccgcgca gcagctcgcc gcccggatcc gccagacaaa
62221 caaggccttt gcacatgccg gccgggcga gcctggggggt ccggtaattt tgccatccca
62281 cccaagcggc ttttggggtt tttcctcttc ccccctcccc acctcccccc tctttagggg
62341 ttcggtgggg aacaaccgcg atgttttccg gtggcggcgg cccgctgtcc cccggaggaa
62401 agtcggcggc cagggcggcg tccgggtttt ttgcgcccgc cggccctcgc ggagccggcc
62461 ggggacccccc gccttgtttg aggcaaaact tttacaaccc ctacctcgcc ccagtcggga
62521 cgcaacagaa gccgaccggg ccaacccagc gccatacgta ctatagcgaa tgcgatgaat
62581 ttcgattcat cgccccgcgg gtgctggacg aggatgcccc cccggagaag cgcgccgggg
62641 tgcacgacgg tcacctcaag cgcgccccca aggtgtactg cggggggggac gagcgcgacg
62701 tcctccgcgt cgggtcgggc ggcttctggc cgcggcgctc gcgcctgtgg ggcggcgtgg
62761 accacgcccc ggcgggttc gaccccaccg tcaccgtctt tcacgtgtat gacatcctgg
62821 agaacgtgga gcacgcgtac ggcatgcgcg cggcccagtt ccacgcgcgg tttatggacg
62881 ccatcacacc gacggggacc gtcatcacgc tcctgggcct gactccggaa ggccaccggg
62941 tggccgttca cgtttacggc acgcggcagt acttttacat gaacaaggag gaggttgaca
63001 ggcacctaca atgccgcgcc ccacgagatc tctgcgagcg catggccgcg gccctgcgcg
63061 agtccccggg cgcgtcgttc cgcggcatct ccgcggacca cttcgaggcg gaggtggtgg
63121 agcgcaccga cgtgtactac tacgagacgc gccccgctct gttttaccgc gtctacgtcc
63181 gaagcgggcg cgtgctgtcg tacctgtgcg acaacttctg cccggccatc aagaagtacg
63241 agggtggggt cgacgccacc accccggttca tcctggacaa ccccgggttc gtcaccttcg
63301 gctggtaccg tctcaaaccg ggccggaaca acacgctagc ccagccgcgg gccccgatgg
63361 ccttcgggac atccagcgat gtcgagttta actgtacggc ggacaacctg gccatcgagg
63421 ggggcatgag cgacctaccg gcatacaagc tcatgtgctt cgatatcgaa tgcaaggcgg
63481 gggggggagga cgagctggcc tttccggtgg ccgggcaccc ggaggacctg gtcatccaga
63541 tatcctgtct gctctacgac ctgtccacca ccgccctgga gcacgtcctc ctgttttcgc
63601 tcggttcctg cgacctcccc gaatcccacc tgaacgagct ggcggccagg ggcctgccca
63661 cgcccgtggt tctggaattc gacagcgaat tcgagatgct gttggccttc atgacccttg
```

```
63721 tgaaacagta cggccccgag ttcgtgaccg ggtacaacat catcaacttc gactggccct
63781 tcttgctggc caagctgacg gacatttaca aggtccccct ggacgggtac ggccgcatga
63841 acggccgggg cgtgtttcgc gtgtgggaca taggccagag ccacttccag aagcgcagca
63901 agataaaggt gaacggcatg gtgaacatcg acatgtaggg gattataacc gacaagatca
63961 agctctcgag ctacaagctc aacgccgtgg ccgaagccgt cctgaaggac aagaagaagg
64021 acctgagcta tcgcgacatc cccgcctact acgccgccgg gcccgcgcaa cgcggggtga
64081 tcggcgagta ctgcatacag gattccctgc tggtgggcca gctgtttttt aagttttttgc
64141 cccatctgga gctctcggcc gtcgcgcgct ggcgggtat taacatcacc cgcaccatct
64201 acgacggcca gcagatccgc gtctttacgt gcctgctgcg cctggccgac cagaagggct
64261 ttattctgcc ggacacccag gggcgattta ggggcgccgg gggggaggcg cccaagcgtc
64321 cggccgcagc ccgggaggac gaggagcggc cagaggagga gggggaggac gagaacgaac
64381 gcgaggaggg cggggcgag cgggagccgg agggcgcgcg ggagaccgcc ggccggcacg
64441 tggggtacca ggggggccagg gtccttgacc ccacttccgg gtttcacgtg aacccgtgg
64501 tggtgttcga ctttgccagc ctgtacccca gcatcatcca ggcccacaac ctgtgcttca
64561 gcacgctctc cctgagggcc gacgcagtgg cgcacctgga ggcgggcaag gactacctgg
64621 agatcgagat ggggggggcga cggctgttct tcgtcaaggc tcacgtgcga gagagcctcc
64681 tcagcatcct cctgcgggac tggctcgcca tgcgaaagca gatccgctcg cggattcccc
64741 agagcagccc cgaggaggcc gtgctcctgg acaagcagca ggccgccatc aaggtcgtgt
64801 gtaactcggt gtacgggttc acgggagtgc agcacggact cctgccgtgc ctgcatgttg
64861 ccgcgacggt gacgaccatc ggccgcgaga tgctgctcgc gacccgcgag tacgtccacg
64921 cgcgctggc ggccttcgaa cagctcctgg ccgatttccc ggaggcggcc gacatgcgcg
64981 cccccgggcc ctattccatg cgcatcatct acggggacac ggactccata tttgtgctgt
65041 gccgcggcct cacggccgcc gggctgacgg ccatgggcga caagatggcg agccacatct
65101 cgcgcgcgct gtttctgccc cccatcaaac tcgagtgcga aaagacgttc accaagctgc
65161 tgctgatcgc caagaaaaag tacatcggcg tcatctacgg gggtaagatg ctcatcaagg
65221 gcgtggatct ggtgcgcaaa aacaactgcg cgtttatcaa ccgcacctcc agggccctgg
65281 tcgacctgct gttttacgac gataccgtat ccggagcggc cgccgcgtta gccgagcgcc
65341 ccgcagagga gtggctggcg cgacccctgc ccgagggact gcaggcgttc ggggccgtcc
```

```
65401 tcgtagacgc ccatcggcgc atcaccgacc cggagaggga catccaggac tttgtcctca
65461 ccgccgaact gagcagacac ccgcgcgcgt acaccaacaa gcgcctggcc cacctgacgg
65521 tgtattacaa gctcatggcc cgccgcgcgc aggtcccgtc catcaaggac cggatcccgt
65581 acgtgatcgt ggccagacc cgcgaggtag aggagacggt cgcgcggctg gccgcctcc
65641 gcgagctaga cgccgccgcc ccaggggacg agcccgcccc cccgcggcc ctgccctccc
65701 cggccaagcg ccccccggag acgccgtcgc atgccgaccc cccgggaggc gcgtccaagc
65761 ccgcaagct gctggtgtcc gagctggccg aggatcccgc atacgccatt gcccacggcg
65821 tcgccctgaa cacggactat tacttctccc acctgttggg ggcggcgtgc gtgacattca
65881 aggccctgtt tgggaataac gccaagatca ccgagagtct gttaaaaagg tttattcccg
65941 aagtgtggca ccccccggac gacgtggccg cgcggctccg ggccgcaggg ttcggggcgg
66001 tgggtgccgg cgctacggcg gaggaaactc gtcgaatgtt gcatagagcc tttgatactc
66061 tagcatgagc cccccgtcga agctgatgtc cctcatttta caataaatgt ctgcggccga
66121 cacggtcgga atctccgcgt ccgtgggttt ctctgcgttg cgccggacca cgagcacaaa
66181 cgtgctctgc cacacgtggg cgacgaacct gtaccccggg cacgcggtga gcatccggtc
66241 tatgagccgg tagtgcaggt gggcggacgt gccgggaaag atgacgtaca gcatgtggcc
66301 cccgtaagtg gggtccgggt aaaacaacag ccgcgggtcg cacgcccgc ctccgcgcag
66361 gatcgtgtgg acgaaaaaaa gctcgggttg gccaagaatc ccggccaaga ggtcctggag
66421 gggggcgttg tggcggtcgg ccaacacgac caaggaggcc aggaaggcgc gatgctcgaa
66481 tatcgtgttg atctgctgca cgaaggccag gattagggcc tcgcggctgg tgcggcgaa
66541 ccgcccgtct cccgcgttgc acgcgggaca gcaaccccg atgcctaggt agtagcccat
66601 cccggagagg gtcaggcagt tgtcggccac ggtctggtcc agacagaagg gcagcgacac
66661 gggagtggtc ttcaccaggg gcaccgagag cgagcgcacg atggcgatct cctcggaggg
66721 cgtctgggcg agggcggcga aaaggccccg atagcgctgg cgctcgtgta aacacagctc
66781 ctgtttgcgg gcgtgaggcg gcaggctctt ccggaggcc cgacgcacca cgcccagagt
66841 cccgccggcc gcagaggagc gcgaccgccg gcgctccttg ccgtgatagg gcccgggccg
66901 ggagccgcgg cgatgggggt cggtatcata cataggtaca cagggtgtgc tccaggaca
66961 ggagcgagat cgagtggcgt ctaagcagcg cgcccgcctc acggacaaat gtggcgagcg
67021 cggtgggctt tggtacaaat acctgatacg tcttgaaggt gtagatgagg gcacgcaacg
```

```
67081 ctatgcagac acgcccctcg aactcgttcc cgcaggccag cttggccttg tggagcagca
67141 gctcgtcggg atgggtggcg ggggatggc cgaacagaac ccaggggtca acctccatct
67201 ccgtgatggc gcacatgggg tcacagaaca tgtgcttaaa gatggcctcg ggccccgcgg
67261 cccgcagcag gctcacaaac cggcccccgt cccgggctg cgtctggggg tccgcctcga
67321 gctggtcgac gacgggtacg atacagtcga agaggctcgt gttgttttcc gagtagcgga
67381 ccacggaggc ccggagtctg cgcagggcca gccagtaagc ccgcaccagt aacaggttac
67441 acagcaggca ttctccgccg gtgcgcccgc gccccggcc gtgtttcagc acggtggcca
67501 tcagagggcc caggtcgagg tcgggctggg catcgggttc ggtaaactgc gcaaagcgcg
67561 gagccacgtc gcgcgtgcgt gccccgcgat gcgcttccca ggactggcgg accgtggcgc
67621 gacgggcctc cgcggcagcg cgcagctggg gccccgactc ccagacggcg ggggtgccgg
67681 cgaggagcag caggaccaga tccgcgtacg cccacgtatc cggcgactcc tccggctcgc
67741 ggtccccggc gaccgtctcg aattccccgt tgcgagcggc ggcgcgcgta cagcagctgt
67801 ccccgccccc gcgccgaccc tccgtgcagt ccaggagacg ggcgcaatcc ttccagttca
67861 tcagtgcggt ggtaagcgac ggctgcgtgc cggataccgc gccgaccccc gcccctcct
67921 cgccccgga ggccaaggtt ccgatgaggg cccgggtggc agactgcgcc aggaacgagt
67981 agttggagta ctgcaccttg gcggctcccg gggagggcga gggcttgggt tgcttctggg
68041 catgccgccc gggcacccg ccgtcggtac ggaagcagca gtggagaaaa aagtgccggt
68101 ggatgtcgtt tatggtgagg gcaaagcgtg cgaaggagcc gaccagggtc gccttcttgg
68161 tgcgcagaaa gtggcggtcc atgacgtaca caaactcgaa cgcggccacg aagatgctag
68221 cggcgcagtg gggcgccccc aggcatttgg cacagagaaa cgcgtaatcg gccacccact
68281 gaggcgagag gcggtaggtt tgcttgtaca gctcgatggt gcggcagacc agacagggcc
68341 ggtccagcgc gaaggtgtcg atggccgccg cggaaaaggg cccggtgtcc aaaagcccct
68401 cccacaggg atccggggc gggttgcggg gtcctccgcg cccgcccgaa cccctccgt
68461 cgcccgcccc cccgcgggcc cttgaggggg cggtgaccac gtcggcggcg acgtcctcgt
68521 cgagcgtacc gacgggcggc acacctatca cgtgactggc cgtcaggagc tcgcgcaga
68581 gagcctcgtt aagagccagg aggctgggat cgaaggccac atacgcgcgc tcgaacgccc
68641 ccgccttcca gctgctgccg gggactctt cgcacaccgc gacgctcgcc aggacccgg
68701 ggggcgaagt tgccatggct gggcgggagg ggcgcacgcg ccagcgaact ttacgggaca
```

```
68761 caatccccga ctgcgcgctg cggtcccaga ccctggagag tctagacgcg cgctacgtct
68821 cgcgagacgg cgcgcatgac gcggccgtct ggttcgagga tatgaccccc gccgagctgg
68881 aggttgtctt cccgactacg gacgccaagc taaactacct gtcgcggacg cagcggctgg
68941 cctccctcct gacgtacgcc gggcctataa aagcgccga cgacgccgcc gcccgcaga
69001 ccccggacac cgcgtgtgtg cacggcgagc tgctcgcccg caagcgggaa agattcgcgg
69061 cggtcattaa ccggttcctg gacctgcacc agattctgcg gggctgacgc gcgcgctgtt
69121 gggcgggacg gttcgcgaac cctttggtgg gttacgcgg gcacgcacgc tcccatcgcg
69181 ggcgccatgg cgggactggg caagccctac accggccacc caggtgacgc cttcgagggt
69241 ctcgttcagc gaattcggct tatcgtccca tctacgttgc ggggcgggga cggggaggcg
69301 ggccctact ctccctccag cctcccctcc aggtgcgcct ttcagtttca tggccatgac
69361 gggtccgacg agtcgtttcc catcgagtat gtactgcggc ttatgaacga ctgggccgag
69421 gtcccgtgca acccttacct gcgcatacag aacaccggcg tgtcggtgct gtttcagggg
69481 ttttttcatc gcccacacaa cgccccgggg ggcgcgatta cgccagagcg gaccaatgtg
69541 atcctggggt ccaccgagac gacggggttg tccctcggcg acctggacac catcaagggg
69601 cggctcggcc tggatgcccg gccgatgatg ccagcatgt ggatcagctg ctttgtgcgc
69661 atgccccgcg tgcagctcgc gtttcggttc atgggcccg aagatgccgg acggacgaga
69721 cggatcctgt gccgcgccgc cgagcaggct attacccgtc gccgccgaac ccggcggtcc
69781 cgggaggcgt acggggccga ggccgggctg ggggtggccg gaacgggttt ccgggccagg
69841 ggggacggtt ttggcccgct cccttgtta acccaagggc cctcccgccc gtggcaccag
69901 gccctgcggg gtcttaagca cctacggatt ggcccccccg cgctcgtttt ggcggcggga
69961 ctcgtcctgg gggccgctat ttggtgggtg gttggtgctg gcgcgcgcct ataaaaaagg
70021 acgcaccgcc gccctaatcg ccagtgcgtt ccggacgcct tcgccccaca cagccctccc
70081 gaccgacacc cccatatcgc tccccgacct ccgtcccga tggccgtccc gcaatttcac
70141 cgccccagca ccgttaccac cgatagcgtc cgggcgcttg catgcgcgg gctcgtcttg
70201 gccaccaata actctcagtt tatcatggat acaaccacc cacaccccca gggcacccaa
70261 ggggccgtgc gggagtttct ccgcggtcag gcggcggcac tgacggacct tggtctggcc
70321 cacgcaaaca acacgtttac ccccgcagcct atgttcgcgg gcgacgcacc ggccgcctgg
70381 ttgcggcccg cgtttggcct gcggcgcacc tattcaccct ttgtcgttcg agaaccttcg
```

FIGURE 9 (Continued)

```
70441 acgcccggga ccccgtgagg cccagggagt tccttctggg gtgttttaat caataaaaga
70501 ccacaccaac gcacgagcct tgcgtttaat gtcgtgttta ttcaagggag tgggataggg
70561 ttcgacggtt cgaaacttaa cacaccaaat aatcgagcgc gtctagccca gtaacatgcg
70621 cacgtgatgt aggctggtca gcacggcgtc gctgtgatga agcagcgccc ggcgggtccg
70681 ctgtaactgc tgttgtaggc ggtaacaggc gcggatcagc accgccaggg cgctacgacc
70741 ggtgcgttgc acgtagcgtc gcgacagaac tgcgtttgcc gatacgggcg ggggccgaa
70801 ttgtaagcgc gtcacctctt gggagtcatc ggcgtataac gcactgaatg gttcgttggt
70861 tatggggag tgtggttccc cagggagtgg gtcgagcgcc tcggcctcgg aatccgagag
70921 gaacaacgag gtggcgtcgg agtcttcgtc gtcagagaca tacagggtct gaagcagcga
70981 cacgggcgtg ggggtagcgt cgatgtgtag cgcgagggag gatgcccacg aagacacccc
71041 agacaaggag ctgcccgtgc gtggatttgt ggaagacgcg gaagccggga cggatgggcg
71101 gttttgcggt gcccggaacc gaaccgccgg atactccccg ggtgctacat gcccgttttg
71161 gggctgggt tggggctggg gcgcggacag gcggctgacg gtcaaatgcc cccggggcg
71221 cgcagatgtg gcgggcgtgg ccaccggctg ccgtgtagtg gggcggcggg aaaccgggcc
71281 tccgggcgta acaccgccct ccagcgtcaa gtatgtgggg ggcggcctg acgtcggggg
71341 cggggtgacg ggttggaccg cgggaggcgg gggagaggga cctgcgggag aggatgaggt
71401 cggctcggcc gggttgcggc ctaaacagg ggccgtgggg tcgcggggt cccagggtga
71461 agggagggat tcccgcgatt cggacagcga cgcgacagcg gggcgcgtaa ggcgccgctg
71521 cggcccgcct acgggaaccc tggggggggt tggcgcggga cccgaggtta gcggggggcg
71581 gcggttttcg ccccgggca aaaccgtgcc ggttgcgacc gggggcggaa cgggatcgat
71641 agggagagcg ggagaagcct ggccggcgga ctggggaccg agcgggaggg gcacaccaga
71701 caccaaagcg tggggcgctg gctctggggg tttgggaggg gccggggggc gcgcgaaatc
71761 ggtaaccggg gcgaccgtgt cggggagggc aggcggccgc caaccctggg tggtcgcgga
71821 agcctgggtg gcgcgcgcca gggagcgtgc ccggcggtgt cggcgcgcgc gcgacccgga
71881 cgaagaagcg gcagaagcgc gggaggaggc ggggggcgg ggggcggtgg catcggggg
71941 cgccggggaa ctttgggggg acggcaagcg ccggacgtcg tcgcggggc ccacgggcgc
72001 cggccgcgtg ctttcggccg ggacgcccgg tcgtgcttcg cgagccgtga ctgccggccc
72061 agggggccgc ggtgcacact gggatgtggg gacggactga tcggcggtgg gcgaaagggg
```

FIGURE 9 (Continued)

```
72121 gtccgggggca aggaggggcg cggggccgcc ggagtcgtca gacgcgagct cctccaggcc
72181 gtgaatccat gcccacatgc gagggggac gggctcgccg gggtggcgt cggtgaatag
72241 cgtggggggcc aggcttccgg gccccaacga gccctccgtc ccaacaaggt ccgccgggcc
72301 gggggtcggg ttcgggaccg aggggctctg gtcgtcgggg gcgcgctggt acaccggatg
72361 ccccgggaat agctccccg acaggaggga ggcgtcgaac ggccgcccga ggatagctcg
72421 tgcgaggaag gggtcctcgt cggtggcgct ggcggcgagg acgtcctcgc cgcccgccac
72481 aaacgggagc tcctcggtgg cctcgctgcc aacaaaccgc acgtcggggg ggccggggggg
72541 tccgggtttt cccacaacac cgcgaccggg gtcatggaga tgtccacgag caccagacac
72601 ggcgggcccc gggcgagggg ccgctcggcg atgagcgcgg acaggcgcgg gagctgtgcc
72661 gccagacacg cgttttcgat cgggttcagg tcggcgtgca ggaggcggac ggcccacgtc
72721 tcgatgtcgg acgacacggc atcgcgcaag gcggcgtccg gcccgcgagc gcgtgagtca
72781 aacagcgtga ggcacagctc cagctccgac tcgcgggaaa aggccgtggt gttgcggagc
72841 gccacgacga cgggcgcgcc caggagcact gccgccagca ccaggtccat ggccgtaacg
72901 cgcgccgcgg gggtgcggtg ggtggcggcg ccggcacgg cgacgtgctg gcccgtgggc
72961 cggtagaggg cgttgggggg agcgggggt gacgcctcgc gccccccga ggggctcagc
73021 gtctgcccag attccagacg cgcggtcaga agggcgtcga aactgtcata ctctgtgtag
73081 tcgtccggaa acatgcaggt ccaaagagcg gccagcgcgg tgcttgggag acacatgcgc
73141 ccgaggacgc tcaccgccgc cagcgcctgg gcgggactca gctttcccag cgcggcgccg
73201 cgctcggttc ccagctcggg gaccgagcgc cagggcgcca ggggtcggt ttcggacaac
73261 ttgccgcggc gccagtctgc cagccgcgtg ccgaacatga ggccccgggt cggagggcct
73321 ccggccgaaa acgctggcag cacgcggatg cgggcgtctg gatgcggggt caggcgctgc
73381 acgaatagca tggaatctgc tgcgttctga aacgcacggg ggagggtgag atgcatgtac
73441 tcgtgttggc ggaccagatc caggcgccaa aaggtgtaaa tgtgttccgg ggagctggcc
73501 accagcgcca ccagcacgtc gttctcgtta aaggaaacgc ggtgcctagt ggagctctgg
73561 ggtccgagcg gcggccccgg ggccgccgcg tcaccccccc attccagctg ggcccagcga
73621 cacccaaact cgcgcgtgag agtggtcgcg acgagggcga cgtagagctc ggccgccgca
73681 tccatcgagg ccccccatct cgcctggcgg tggcgcacaa agcgtccgaa gagctgaaag
73741 ttggcggcct gggcgtcgct gagggccagc tgaagccggt tgatgacggt gaggacgtac
```

FIGURE 9 (Continued)

```
73801 atggccgtga cggtcgaggc cgactccagg gtgtccgtcg gaagcggggg gcgaatgcat
73861 gccgcctcgg gacacatcag cagcgcgccg agcttgtcgg tcacggccgg gaagcagagc
73921 gcgtactgca gtggcgttcc atccgggacc aaaaagctgg gggcgaacgg ccgatccagc
73981 gtactggtgg cctcgcgcag caccagggc cccggcctc cgctcactcg caggtacgcc
74041 tcgccccggc ggcgcagcat ctgcgggtcg gcctcttggc cgggtggggc ggacgcccgg
74101 gcgcgggcgt ctagggcgcg aagatccacg agcaggggcg cgggcgcggc ggccgcgccc
74161 gcgcccgtct ggcctgtggc cttggcgtac gcgctatata agcccatgcg gcgttggatg
74221 agctcccgcg cgccccggaa ctcctccatc gcccatgggg ccaggtcccc ggccaccgcg
74281 tcgaattccg ccaacaggcc cccagggta tcaaagttca tctcccaggc caccttggc
74341 accacctcgt cccgcagccg ggcgctcagg tcggcgtgtt gggccacgcg cccccgagc
74401 tcctccacgg cccggccg ctcggcgctc ttggcgccca ggacgccctg gtacttggcg
74461 ggaaggcgct cgtagtcccg ctgggctcgc agccccgaca cagtgttggt ggtgtcctgc
74521 agggcgcgaa gctgctcgca tgccgcgcga atccctcgg gcgatttcca ggcccccccg
74581 cgaacgcggc cgaagcgacc ccatacctcg tcccactccg cctcggcctc ctcgagagac
74641 ctccgcaggg cctcgacgcg gcgacgggtg tcgaagagcg cctgcaggcg cgcgccctgt
74701 cgcgtcagga ggcccgggcc gtcgctgctg ccgcgctta gcgggtgcgt ctcaaaggta
74761 cgctgggcat gttccaacca ggcgaccgcc tgcacgtcga gctcgcgcgc cttctccgtc
74821 tggtccaaca gaatttcgac ctgatccgcg atctcctccg ccgagcgcgc ctggtccagc
74881 gtcttggcca cggtcgccgg gacggcgacc accttcagca gggtcttcag attggccaga
74941 ccctcggcct cgagctgggc ccggcgctcg cgcgcggcca gcacatcccg cagccccgcc
75001 gtgacccgct cggtggcttc ggcgcgctgc tgtttggcgc gcaccacggc gtccttggta
75061 tcggccaggt cctgtcgggt cacgaatgcg acgtagtcgg agtacgccgt gtccttcacg
75121 gggctctggt ccacgcgctc cagcgccgcc acgcacgcca ccagcgcgtc ctcgtcggg
75181 cagggcaggg tgacccctgc ccggacaagc tcggcggccg ccgccgggtc gttgcgcacc
75241 gcggatatct cctccgcggc ggcggccagg tccagcgcca cgcttccgat cgcgcgccgc
75301 gcgtcggccc ggagggcgtc caggcgatcg cggatatcca cgtactcggc gtagcccttt
75361 tgaaaaaacg gcacgtactg gcgcagggcc ggcacgcccc ccaagtcttc cgacaggtgt
75421 agtacggcct cgtggtagtc gataaacccg tcgttcgcct gggcccgctc cagcagcccc
```

FIGURE 9 (Continued)

```
75481 cccgcgagcc gcagaagccg cgccaggggc tcggtgtcca cccgaaacat gtcggcgtac
75541 gtgtcggccg cggccccaaa ggccgcgctc cagtcgatgc ggtgaatggc tgcgagcggg
75601 gggagcatgg ggtggcgctg gttctcgggg gtgtatgggt taaacgcaag ggccgtctcc
75661 agggcaaggg tcaccgcctt ggcgttggtt ccagcgcct gtcggccg ctttcggaag
75721 tcccgggggt tgtagccgtg cgtgcccgcc agcgcctgca ggcgacggag ctcgaccacg
75781 tcaaactcgg cactgctttc cacgcggtcc agcacggcct ccacgtcggc ggcccagcgc
75841 tcgtggctac tgcgggcgcg ctgggccgcc atcttctctc tgaggtcggc ggtggcggcc
75901 tcaagttcgt cggcgcggcg tcgcgtggcg ccgatgacct ttcccagctc ctgcagggcg
75961 cgcccgctgg gggagtggtc cccggccgtc ccttcggcgt gcaacaggcc cccgaacctg
76021 ccctcgtggc ccgcgaggct ttcccgcgcg ccggtggtcg cgcgcgtcgc ggcttggatc
76081 agggaggcat gctctccctt cggttggttg gcggcccggc gcacctggac gacaaggtcg
76141 gcggcagccg accctaaggt cgtgagctgg gcgatggccc ccgcgcgtc cagggccaac
76201 cgagtcgcct tgacgtatcc ccggcgctg tcggccatgg ccgctaggaa ggccaggggg
76261 gaggccgggt cgctggcggc cgcgcccagg gccgtcaccg cgtcgaccag gacgcggtgc
76321 gcccgcacgg ccgcatccac cgtcgacgcg gggtctgccg tcgcgacggc ggcgctgccg
76381 gcgttgatgg cgttcgagac ggcgtgggct atgatcgggg cgtgatcggc gaagaactgc
76441 aagagaaacg gagtctcggg ggcgtcggcg aacaggttct tcagcaccac cacgaagctg
76501 ggatgcaagc cggacagagc cgtcgccgtg tccggagtcg ggtgctccag ggcatctcgg
76561 tactgcccca gcagccccca catgtccgcc cgcagcgccg ccgtaacctc aggggcgcc
76621 ccccgaacgg cctcggggag gtccgaccag cccgccggca gggaggcccg cagggtcgcc
76681 aggacggccg gacaggcctt tagccccaca aagtcaggga ggggggcgcag gaccccctgg
76741 agtttgtgca agaacttctc ccgggcgtcg cggccacct tcgcccgctc ccgcgctccc
76801 tcgagcattg cctccaggga gcgcgcgcgc tcccgcaaac ggacacgcgc atcggggcg
76861 agctctgccg tcagcttggc ggcatccatg gcccgcgcct gccgcagcgc ttcctcggcc
76921 atgcgcgtgg cctctggcga cagcccgccg tcgtcggggt agggcgacgc gccgggcgca
76981 ggaacaaagg ccgcgtcgct gtccagctgc tgcccagggg ccgcatctag ggcgtcgaag
77041 cgccgcagct cggccagacc cgagctgcgg cgcgcctgct ggtcgttaat gtcgcggatg
77101 ctgcgcgcca gctcgtccag cggcttgcgt tctatcagcc cttggttggc ggcgtccgtc
```

FIGURE 9 (Continued)

```
77161 aggacggaga gccaggccgc caggtcctcg ggggcgtcca gcgtctggcc ccgctgtatc
77221 agatcccgca acaggatggc cgtggggctg gtcgcgatcg ggggcggggc gggaatggcg
77281 gcgcgctgcg cgatgtcccg cgtgtgctgg tcgaagacag gcagggactc gagcagctgg
77341 accacgggca cgacggcggc cgaagccacg tgaaacggc ggtcgttgtt gtcgctggcc
77401 tgtagagcct tggcgctgta tacggcccc cggtaaaagt actccttaac cgccccctcg
77461 atcgcccgac gggcctgggt ccgcacctcc tccagccgaa cctgaacggc ctcggggccc
77521 aggggggtg ggcgcggagc ccctgcggg gccgccccgg ccggggcggg cattacgccg
77581 aggggcccgg cgtgctgtga ccgcgtcg acccgcgag cgaggcgtc gaggcctcg
77641 cgcatctggc gatcctccgc ctccaccta atctcttcgc cacggcaaa tttggccaga
77701 gcctggactc tatacagaag cggttctggg tgcgtcgggg tggcggggc aaaaagggtg
77761 tccgggtggg cctgcgagcg ctccagaagc cactcgccga ggcgtgtata cagattggcc
77821 ggcggggccg cgcgaagctg cagctccagg tccgcgagtt cccccgtaaaa ggcgtccgtc
77881 tcccgaatga catccctagc cacaaggatc agcttcgcca gcgccaggcg accgatcaga
77941 gagtttcgt ccagcacgtg ctggacgagg ggcagatggg cggccacgtc ggccaggctc
78001 aggcgcgtgg aggccagaaa gtcccccacg gccgttttcc ggggcagcat gctcagggta
78061 aactccaaca gggcggcggc cgggccggcc accccggcct gggtgtgcgt ccgggccccg
78121 ttctcgatga gaaaggcgag gacgcgttca agaaaaaaa taacacagag ctccagcagc
78181 cccggagaag ccggatacgg cgaccgtaag gcgctgatgg tgagccgcga cacgcggcg
78241 acctcgcggg ccagggcggc ggagcacgcg gtgaacttaa ccgccgtggc ggccacgttt
78301 gggtgggcct cgaacagctg ggcaaggtct gcgcccgggg gctcgggtga gcggcgagtc
78361 ttcagcgcct cgagggcctg cgaggacgcc ggaacgtgg gcccgtcgtc ctcgcccgcc
78421 tcggcgaccg gcggcccggc cgggtcgggg ggtgccgagg cgaggacagg ctccggaacg
78481 gaggcgggga ccgcggcccc gacggggtt ttgcctttgg gggtggattt cttcttggtt
78541 ttggcagggg gggccgagcg tttcgtttc tccccgaag tcaggtcttc gacgctggaa
78601 ggcggagtcc aggtgggtcg gcggcgcttg ggatggccgg ccgagtagcg tgcccggtgc
78661 cgaccaaccg ggacgacgcc catctccagg acccgcatgt cgtcgtcatc ttcttcggcc
78721 gcctctgcgg cggggggctt ggggcggag ggaggcggtg gtgggatcgc ggagggtggg
78781 tcggcggagg ggggatccgt gggtggggta cccttcaggg ccaccgccca tacatcgtcg
```

```
78841 ggcgcccgat tcgggcgctt ggcctctggt tttgccgacg gaccggccgt cccccgggat
78901 gtctcggagg ccctgtcgtc gcgacgggcc cgggtcggtg gcggcgactg ggcggctgtg
78961 ggcgggtgtg gccccgtgcc ccctaccccc tcccggggc ccacgccgac gcaggctcc
79021 cccaggccg cgatctcgcc ccgcagggg tgcgtgatgg ccacgcgccg ttcgctgaac
79081 gcttcgtcct gcaggtaagt ctcgctggcc ccgtaaagat gcagagccgc ggccgtcaag
79141 tccgcaggag ccgcgggttc cgggcccgac ggcacgaaaa acaccatggc tcccgcccac
79201 cgtacgtccg ggcgatcgcg ggtgtaatac gtcaggtatg gatacatgtc ccccgcccgc
79261 actttggcga tgaacgcggg ggtgccctcc ggaaggccgt gcgggtcaaa aaggtatgcg
79321 gtgtcgccgt ccctgaacag cccatccct aggggccaa tggttaggag cgtgtacgac
79381 aggggcgca gggcccacgg gccggcgaag aacgtgtgtg cggggcattg tgtctccagc
79441 aggcccgccg cgggctcccc gaagaagccc acctcgccgt atacgcgcga aagacacag
79501 cgcagtccgc cgcgcgcccc tgggtactcg aggaagttgg ggagctcgac gatcgaacac
79561 atgcgcggcg gcccagggcc cgcggtcgcg cgcgtccact cgcccccctc gaccaaacaa
79621 ccctcgatgg cctccgcgga cagaacgtcg cgagggccca catcaaatat gaggctgaga
79681 aaggacagcg acgagcgcat gcacgatacc gaccccccg ctccaggtc gggcgcgaac
79741 tggttccgag caccggtgac cacgatgtcg cgatcccccc cgcgttccat cgtggagtgc
79801 ggtggggtgc ccgcgatcat atgtgcccta ctggccagag acccggcctg tttatggacc
79861 ggaccccgg ggttagtgtt gtttccgcca cccatgcccc cgtaccatgg ccccggttcc
79921 cctgattagg ctacgagtcg cggtgatcgc ttcccaaaaa ccgagctgcg tttgtctgtc
79981 ttgatcttcc ccccccccc cgcccgcccg cccgcccgcc cgcccgcaca ccataacacc
80041 gagaacaaca cacggggtg ggcgtaacat aataaagctt tattggtaac tagttaacgg
80101 caagtccgtg ggtggcgcga cggtgtcctc cgggctcatc tcgtcgtcct cgacgggggt
80161 gttggaatga ggcgcccct cgcggtccgc ctggcgtggg ccgtgcccat aggcctccgg
80221 cttctgtgcg tccatgggca taggcgcggg gagactgttt ccgcgtcgc ggacctccag
80281 gtccctggga gactccggtc cggctaacgg acgaaacgcg gaagcgcgaa acacgccgtc
80341 ggtgacccgc aggagctcgt tcatcagtaa ccaatccata ctcagcgtaa cggccagccc
80401 ctggcgagac agatccacgg agtccggaac cgcggtcgtc tggcccaggg ggccgaggct
80461 gtagtccccc caggcccta ggtcgcgacg gctcgtaagc acgacgcggt cggccgcggg
```

FIGURE 9 (Continued)

```
80521 gctttgcggg ggggcgtcct cgggcgcatg cgccattacc tctcggatgg ccgcggcgcg
80581 ctggtcggcc gagctgacca agggcgccac gaccacggcg cgctccgtct gcaggccctt
80641 ccacgtgtcg tggagttcct ggacaaactc ggccacgggc tcgggtcccg cggccgcgcg
80701 cgcggcttga tagcaggccg agagacgccg ccagcgcgct agaaactgac ccatgaagca
80761 aaacccgggg acctggtctc ccgacagcag cttcgacgcc cgggtgtgaa tgccggacac
80821 aacggacaga aacccgtgaa tttcgcgccg gaccacggcc agcacgttgt cctcgtgcga
80881 cacctgggcc gccagctcgt cgcacacctc caggtgcgcc gtggtttcgg tgatgacgga
80941 acgcaggctc gcgagggacg cgaccagcgc gcgcttggcg tcgtgataca tgctgcagta
81001 ctgactcacc gcgtccccca tggcctcggg gggccagggc cccaggcggt cgggagtgtc
81061 cccgaccacc gcatacaggc ggcgcccgtc gctctcgaac cgacactcga aaaggcgga
81121 gagcgtgcgc atgtgcagcc gcagcagcac gatggcgtcc tccagttggc gaatcagggg
81181 gtctgcgcgc tcggcgaggt cctgcagcac ccccggggcg ccagggcgt acatgctaat
81241 caacaggagg ctggtgccca cctcgggggg cgggggggc tgcagctgga ccaggggccg
81301 cagctgctcg acggcacccc tggagatcac gtacagctcc cggagcagct gctctatgtt
81361 gtcggccatc tgcatagtgg ggccgaggcc gccccgggcg ccggttcga ggagggtaat
81421 cagcgcgccc agtttggtgc gatggccctc gaccgtgggg agatagccca gcccaaagtc
81481 ccgggcccag gccaacacac gcagggcgaa ctcgaccggg cgtggaaggt aggccgcgct
81541 acacgtggcc cccaacgcgt ccccgaccac cagggccaga acgtagggga cgaagcccgg
81601 gtcggcgagg acgttggggt gaatgccctc gagggcgggg aagcggatct gggtcgccgc
81661 ggccaggtgg acagaggggg cgtggctggg ctgcccgacg gggagaagcg cggacagcgg
81721 cgtggccggg gtggtggggg tgatgtccca gtgggtctga ccatacacgt cgatccagat
81781 gagcgccgtc tcgcggagaa ggctgggttg accggaacta aagcggcgct cggccgtctc
81841 aaactccccc acgagcgccc gccgcaggct cgccagatgt ccgtcggca cggccggacc
81901 catgatacgc gccagtgtct ggctcagaac gcccccgac aggccgaccg cctcgcagag
81961 ccgcccgtgc gtgtgctcgc tggcgccctg gacccgcctg aaagttttta cgtagttggc
82021 atagtacccg tattccgcg ccagaccaaa cacgttcgac cccgcgaggg caatgcaccc
82081 aaagagctgc tggacttcgc cgagtccgtg gccggcgggc gtccgcgcgg ggacgcccgc
82141 cgccagaaac ccctccaggg ccgaaaggta gtgcgtgcag tgcgagggcg tgaacccagc
```

```
82201 gtcgatcagg gtgttgatca ccacggaggg cgaattggta ttctggatca acgtccacgt
82261 ctgctgcagc agagccagca gccgctgctg ggcgccggcg gagggctgct ccccgagctg
82321 cagcaggctg gagacggcag gctggaagac tgccagtgcc gacgaactca ggaacggcac
82381 gtcgggatca aacacgcca cgtccgtccg cacgcgcgcc attagcgtcc ccggggcgc
82441 acaggccgag cgcgggctga cgcggctgag ggccgtcgac acgcgcacct cctcgcggct
82501 gcgaaccatc ttgttggcct ccagtggcgg aatcattatg gccgggtcga tctcccgcac
82561 ggtgtgctga aactgcgcca acagggggcgg cgggaccaca gcccccgct cggggtcgt
82621 caggtactcg tccaccaggg ccaacgtaaa gagggcccgt gtgaggggag tgagggtcgc
82681 gtcgtctatg cgctggaggt gcgccgagaa cagcgtcacc cgattactca ccagggccaa
82741 gaaccggagg ccctcttgca cgaacggggc ggggaagagc aggctgtacg ccggggtggt
82801 aaggttcgcg ctgggctgcc ccaacgggac cggcgccatc ttgagtgacg tctccccaag
82861 ggcctcgatg gaggtccgcg ggctcatggc caagcagctc ttggtgacgg tttgccagcg
82921 gtctatccac tccacggcgc actggcggac gcggaccggc cccagggccg ccgcggtgcg
82981 caggccggcg gaatccagcg catgggacgt gtcggagccg gtgaccgcga ggatggtgtc
83041 cttgatgacc tccatctccc ggaaggcctg gtcgggggcc tcggggagag ccaccaccaa
83101 gcggtgtacg agcaacccgg ggaggttctc ggccaagagc gccgtctccg gaagcccgtg
83161 ggcccggtgg agcgcgcaca ggtgttccag cagcggccgc cagcatgccc gcgcgtctac
83221 cggggcaatg gccgttcccg acaacagaaa cgccgccatg gcggcgcgca gcttggccgt
83281 ggccagaaac gccgggtcgt ccgccccgtt tgccgtctcg gccgtggggg ttggcggttg
83341 gcgaaggccg gctaggctcg ccaataggcg ctgcataggt ccgtccgagg gcggaccggc
83401 gggtgaggtc gtgacgacgg gggcctcgga cgggagaccg cggtctgcca tgacgcccgg
83461 ctcgcgtggg tgggggacag cgtagaccaa cgacgagatc gggcgggaat gactgtcgtg
83521 cgctgtaggg agcggcgaat tatcgatccc ccgcggccct ccaggaaccc cgcaggcgtt
83581 gcgagtaccc ccgcgtcttcg cggggtgtta tacggccact taagtcccgg catcccgttc
83641 gcggacccag gcccggggga ttgtccggat gtgcgggcag cccggacggc gtgggttgcg
83701 gactttctgc ggggcggccc aaatggccct ttaaacgtgt gtatacggac gcgccgggcc
83761 agtcggccaa cacaacccac cggaggcggt agccgcgttt ggctgtgggg tgggtggttc
83821 cgccttgcgt gagtgtcctt tcgaccccc tccccgggt tttgttaggt cgcgatctgc
```

FIGURE 9 (Continued)

```
83881 agtcgcaatg aagaccaatc cgctacccgc aacccottcc gtgtggggcg ggagtaccgt
83941 ggaactcccc cccaccacac gcgataccgc gggacagggc ctgcttcggc gcgtcctgcg
84001 cccccgatc tctgccgcg acggcccagt gctcccagg gggtcgggac cccggagggc
84061 ggccagcacg ctgtggttgc ttggcctgga cggcacagac gcgcccctg gggcgctgac
84121 ccccaacgac gataccgaac aggccctgga caagatcctg cggggcacca tgcgcggggg
84181 ggcggccctg atctgctccc cgcgccatca tctaacccgc caagtgatcc tgacggatct
84241 gtgccaaccc aacgcggatc gtgccgggac gctgcttctg gcgctgcggc accccgccga
84301 cctgcctcac ctggcccacc agcgcgcccc gccaggccgg cagaccgagc ggctgggcga
84361 ggcctggggc cagctgatgg aggcgaccgc cctggggtcg gggcgagccg agagcgggtg
84421 cacgcgcgcg ggcctcgtgt cgtttaactt cctggtggcg gcgtgtgccg cctcgtacga
84481 cgcgcgcgac gccgccgatg cggtacgggc ccacgtcacg gccaactacc gcgggacgcg
84541 ggtgggggcg cgcctggatc gttttttccga gtgtctgcgc gccatggttc acacgcacgt
84601 cttcccccac gaggtcatgc ggttttcgg ggggctggtg tcgtgggtca cccaggacga
84661 gctagcgagc gtcaccgccg tgtgcgccgg ccacaggag gcggcgcaca ccggccaccc
84721 gggccggccc cgctcggccg tgatcctccc ggcgtgtgcg ttcgtggacc tggacgccga
84781 gctggggctg gggggccggg gtgcggcgtt tctgtacctg gtattcactt accgccagcg
84841 ccgggaccag gagctgtgtt gtgtgtacgt gatcaagagc cagctcccc cgcgcgggtt
84901 ggagccggcc ctggagcggc tgtttgggcg cctccggatc accaacacga ttcacggcac
84961 cgaggacatg acgcccccgg ccccaaaccg aaacccgac ttccccctcg cgggcctggc
85021 cgccaatccc caaacccgc gttgctcggc tggccaggtc acgaacccc agttcgccga
85081 caggctgtac cgctggcagc cggacctgcg ggggcgcccc accgcacgca cctgtacgta
85141 cgccgccttt gcagagctcg gcatgatgcc cgaggatagt cccgctgcc tgcaccgcac
85201 cgagcgcttt ggggcggtca gcgtccccgt tgtcatcctg gaaggcgtgg tgtggcgccc
85261 cggcgagtgg cgggcatgcg cgtgagcgta gcaaacgccc cgcccacaca cgctccgcc
85321 cccaacccct tccccgctgt cactcgtggt tcgttgaccc ggacgtccgc caaataaagc
85381 cactgaaacc cgaaacgcga gtgttgtaac gtcctttggg cgggaggaag ccacaaaatg
85441 caaatgggat acatggaagg aacacacccc cgtgactcag gacatcggcg tgtcctttg
85501 ggtttcactg aaactggccc gcgccccacc cctgcgcgat gtggataaaa agccagcgcg
```

FIGURE 9 (Continued)

```
85561 ggtggtttag ggtaccacag gtgggtgctt tggaaacttg tcggtcgccg tgctcctgtg
85621 agcttgcgtc cctccccggt ttcctttgcg ctcccgcctt ccggacctgc tcttgcctat
85681 cttctttggc tctcggtgcg attcgtcagg cagcggcctt gtcgaatctc gaccccacca
85741 ctcgccggac ccgccgacgt ccctctcga gccaccgaa accgccgcg tctgttgaaa
85801 tggccagccg cccagccgca tcctctcccg tcgaagcgcg ggccccggtt gggggacagg
85861 aggccggcgg cccagcgca gccacccagg gggaggccgc cggggcccct ctcgcccacg
85921 gccaccacgt gtactgccag cgagtcaatg gcgtgatggt gctttccgac aagacgcccg
85981 ggtccgcgtc ctaccgcatc agcgatagca actttgtcca atgtggttcc aactgcacca
86041 tgatcatcga cggagacgtg gtgcgcgggc gccccagga cccgggggcc gcggcatccc
86101 ccgctccctt cgttgcggtg acaaacatcg gagccggcag cgacggcggg accgccgtcg
86161 tggcattcgg gggaacccca cgtcgctcgg cggggacgtc taccggtacc cagacggccg
86221 acgtccccac cgaggccctt gggggccccc ctcctcctcc ccgcttcacc ctgggtggcg
86281 gctgttgttc ctgtcgcgac acacggcgcc gctctgcggt attcgggggg gaggggatc
86341 cagtcggccc cgcggagttc gtctcggacg accggtcgtc cgattccgac tcggatgact
86401 cggaggacac ggactcggag acgctgtcac acgcctcctc ggacgtgtcc ggcggggcca
86461 cgtacgacga cgcccttgac tccgattcgt catcggatga ctccctgcag atagatggcc
86521 ccgtgtgtcg cccgtggagc aatgacaccg cgccctgga tgtttgcccc gggaccccg
86581 gcccgggcgc cgacgccggt ggtccctcag cggtagaccc acgcgccg acgccagagg
86641 ccggcgctgg tcttgcggcc gatcccgccg tggcccggga cgacgcggag gggctttcgg
86701 accccggcc acgtctggga acggcacgg cctaccccgt ccccctggaa ctcacgcccg
86761 agaacgcgga ggccgtggcg cgctttctgg gagatgccgt gaaccgcgaa cccgcgctca
86821 tgctggagta cttttgccgg tgcgcccgcg aggaaaccaa gcgtgtcccc cccaggacat
86881 tcggcagccc ccctcgcctc acggaggacg actttgggct tctcaactac gcgctcgtgg
86941 agatgcagcg cctgtgtctg gacgttcctc cggtcccgcc gaacgcatac atgccctatt
87001 atctcaggga gtatgtgacg cggctggtca acgggttcaa gccgctggtg agccggtccg
87061 ctcgccttta ccgcatcctg ggggttctgg tgcacctgcg gatccggacc cgggaggcct
87121 cctttgagga gtggctgcga tccaaggaag tggccctgga ttttggcctg acggaaaggc
87181 ttcgcgagca cgaagcccag ctggtgatcc tggcccaggc tctggaccat tacgactgtc
```

FIGURE 9 (Continued)

```
87241 tgatccacag cacaccacac acgctggtcg agcgggggct gcaatcggcc ctgaagtatg
87301 aggagtttta cctaaagcgt tttggcgggc actacatgga gtccgtcttc cagatgtaca
87361 cccgcatcgc cggcttttttg gctgccggg ccacgcgcgg catgcgccac atcgccctgg
87421 ggcgagaggg gtcgtggtgg gaaatgttca agttcttttt ccaccgcctc tacgaccacc
87481 agatcgtacc gtcgaccccc gccatgctga acctggggac cgcaactac tacacctcca
87541 gctgctacct ggtaaacccc caggccacca caaacaaggc gaccctgcgg gccatcacca
87601 gcaacgtcag tgccatcctc gcccgcaacg ggggcatcgg gctatgcgtg caggcgtta
87661 acgactccgg ccccgggacc gccagcgtca tgcccgccct caaggtcctt gactcgctgg
87721 tggcggcgca acaaagag agcgcgcgtc cgaccggcgc gtgcgtgtac ctggagccgt
87781 ggcacaccga cgtgcgggcc gtgctccgga tgaagggggt cctcgccggc gaagaggccc
87841 agcgctgcga caatatcttc agcgccctct ggatgccaga cctgttttc aagcgcctga
87901 ttcgccacct ggacggcgag aagaacgtca catggaccct gttcgaccgg gacaccagca
87961 tgtcgctcgc cgactttcac ggggaggagt cgagaagct ctaccagcac ctcgaggtca
88021 tggggttcgg cgagcagata cccatccagg agctggccta tggcattgtg cgcagcgcgg
88081 ccacgaccgg gagccccttc gtcatgttca agacgcggt gaaccgccac tacatctacg
88141 acacccaggg ggcggccatc gccggctcca acctctgcac cgagatcgtc catccggcct
88201 ccaagcgatc cagtggggtc tgcaacctgg aagcgtgaa tctggcccga tgcgtctcca
88261 ggcagacgtt tgactttggg cggctccgcg acgccgtgca ggcgtgcgtg ctgatggtga
88321 acatcatgat cgacagcacg ctacaaccca cgccccagtg cacccgcggc aacgacaacc
88381 tgcggtccat gggaatcggc atgcagggcc tgcacacggc ctgcctgaag ctgggctgg
88441 atctggagtc tgccgaattt caggacctga acaaacacat cgccgaggtg atgctgctgt
88501 cggcgatgaa gaccagcaac gcgctgtgcg ttcgcggggc ccgtccttc aaccactta
88561 agcgcagcat gtatcgcgcc ggcgctttc actgggagcg cttccggac gcccggccgc
88621 ggtacgaggg cgagtgggag atgctacgcc agagcatgat gaaacacggc ctgcgcaaca
88681 gccagtttgt cgcgctgatg cccaccgccg cctcggcgca gatctcggac gtcagcgagg
88741 gcttttgcccc cctgttcacc aacctgttca gcaaggtgac ccgggacggc gagacgctgc
88801 gccccaacac gctcctgcta aaggaactgg aacgcacgtt tagcgggaag cgcctcctgg
88861 aggtgatgga cagtctcgac gccaagcagt ggtccgtggc gcaggcgctc ccgtgcctgg
```

FIGURE 9 (Continued)

```
88921 agcccaccca cccccteegg cgattcaaga ccgcgtttga ctacgaccag aagttgttga
88981 tcgacctgtg tgcggaccgc gcccectacg tcgaccatag ccaatccatg accctgtatg
89041 tcacggagaa ggcggacggg accctcccag cctccaccct ggtccgcctt ctggtccacg
89101 catataagcg cggactaaaa acagggatgt actactgcaa ggttcgcaag gcgaccaaca
89161 gcggggtctt tggcggcgac gacaacattg tctgcacgag ctgcgcgctg tgaccgacaa
89221 accccctccg cgccaggccc gccgccactg tcgtcgccgt cccacgctct ccctgctgc
89281 catggattcc gcggccccag ccctctcccc cgctctgacg gcccttacgg gccagagcgc
89341 gacggcggac ctggcgatcc agattccaaa gtgccccgac cccgagaggt acttctacac
89401 ctcccagtgt ccgacatta accacctgcg ctccctcagc atccttaacc gctggctgga
89461 aaccgagctt gttttcgtgg gggacgagga ggacgtctcc aagctttccg agggcgagct
89521 cagcttttac cgcttcctct tcgctttcct gtcggccgcc gacgacctgg ttacggaaaa
89581 cctgggcggc ctctccggcc tgtttgagca gaaggacatt ctccactact acgtggagca
89641 ggaatgcatc gaagtcgtac actcgcgcgt gtacaacatc atccagctgg tgcttttcca
89701 caacaacgac caggcgcgcc gcgagtacgt ggccggcacc atcaaccacc cggccatccg
89761 cgccaaggtg gactggttgg aagcgcgggt gcgggaatgc gcctccgttc cggaaaagtt
89821 cattctcatg atcctcatcg agggcatctt ttttgccgcc tcgtttgccg ccatcgccta
89881 ccttcgcacc aacaaccttc tgcgggtcac ctgccagtca acgacctca tcagccggga
89941 cgaggccgtg cacacgacgg cctcgtgtta catctacaac aactacctcg gcgggcacgc
90001 caagcccccg cccgaccgcg tgtacgggct gttccgccag gcggtcgaga tcgagatcgg
90061 atttatccga tcccaggcgc cgacggacag ccatatcctg agcccggcgg cgctggcggc
90121 catcgaaaac tacgtgcgat tcagcgcgga tcgctgttg ggccttatcc acatgaagcc
90181 actgttttcc gccccaccc ccgacgccag ctttccgctg agcctcatgt ccaccgacaa
90241 acacaccaat ttttcgagt gtcgcagcac ctcctacgcc ggggcggtcg tcaacgatct
90301 gtgagtgtcg cggcgcgctt ctaccgtgt ttgcccataa taaacctctg aaccaaactt
90361 tgggtctcat tgtgattctt gtcaggacg cggggtggg agaggataaa aggcggcgca
90421 aaaagcagta accaggtccg tccagattct gcggcatag aataccataa ttttattggt
90481 gggtcgtttg ttcggggaca agcgcgctcg tctgacgttt gggctactcg tcccagaatt
90541 tggccaggac gtccttgtag aacgcgggtg ggggggcctg ggtccgcaac tgctccagaa
```

```
90601 acctgtcggc gatatcaggg gccgtgatat gccgggtcac gatagatcgc gccaggtttt
90661 cgtcgcggat gtcctggtag ataggcaggc gtttcagaag agtccacggc ccccgctcct
90721 tggggccgat aagcgatatg acgtacttaa tgtagcggtg ttccaccagc tcggtgatgg
90781 tcatgggatc ggggagccag tccagggact ctggggcgtc gtggatgacg tggcgtcgcc
90841 ggttggccac ataactgcgg tgctcttcca gcagctgcgc gttcgggacc tggacgagct
90901 cgggcggggt gagtatctcc gaggaggacg acctggggcc ggggtggccc ccggtaacgt
90961 cccgggatc caggggagg tcctcgtcgt cttcgtatcc gccggcgatc tgttgggtta
91021 gaatttcggt ccacgagacg cgcgtctcgg tgccgccggc ggccggcggc agaggggccc
91081 tggtttccgt ggagcgcgag ctggtgtgtt cccggcggat ggcccgccgg gtctgagagc
91141 gactcggggg ggtccagtga cattcgcgca gcacatcctc cacggaggcg taggtgttat
91201 tgggatggag gtcggtgtgg cagcggacaa agagggccag gaactggggg tagctcatct
91261 taaagtactt cagtatatcg cgacagttga tcgtgggaat gtagcaggcg ctaatatcca
91321 acacaatatc acagcccatc aacaggaggt cagtgtccgt ggtgtacacg tacgcgaccg
91381 tgttggtgtg atagaggttg gcgcaggcat cgtccgcctc caactgaccc gagttaatgt
91441 aggcgtaccc cagggcccgg agaacgcgaa tacagaacag atgcgccaga cgcagggccg
91501 gcttcgaggg cgcggcggac ggcagcgcgg ctccggaccc ggccgtcccc cgggtccccg
91561 aggccagaga ggtgccgcgt cggcgcatgt tggaaaaggc agagctgggt ctggagtcgg
91621 tgatggggga aggcggtgga gaggcgtcca cgtcactggc ctcctcgtcc gtccggcact
91681 gggccgtcgt gcgggccagg atggccttgg ctccaaacac aaccggctcc atacaattga
91741 ccccgcgatc ggtaacgaag atggggaaaa gggacttttg ggtaaacacc tttaataagc
91801 gacagaggca gtgtagcgta atggcctcgc ggtcgtaact ggggtatcgg cgctgatatt
91861 tgaccaccaa cgtgtacatg acgttccaca ggtccacggc aatggggtg aagtacccgg
91921 ccggggcccc aaggccccgg cgcttgacca gatggtgtgt gtgggcaaac ttcatcatcc
91981 cgaacaaacc catgtcaggt cgattgtaac tgcggatcgg cctaactaag gcgtggttgg
92041 tgcgacggtc cgggacaccc gagcctgtct ctctgtgtat ggtgacccag acaacaacac
92101 cgacacaaga ggacaataat ccgttagggg acgctcttta taatttcgat ggcccaactc
92161 cacgcggatt ggtgcagcac cctgcatgcg ccgtgcggg ccaaccttcc ccccgctcat
92221 tgcctcttcc aaaagggtgt ggcctaacga gctggggcg tatttaatca ggctagcgcg
```

FIGURE 9 (Continued)

```
92281 gcgggcctgc cgtagttcct ggctcggtga gcgacggtcc ggttgcttgg gtccctggc
92341 tgccatcaaa accccaccct cgcagcggca tacgcccct ccgcgtcccg cacccgagac
92401 cccggcccgg ctgccctcac caccgaagcc cacctcgtca ctgtggggtg ttcccagccc
92461 gcgttgggat gacggattcc cctggcggtg tggcccccgc ctcccacgtg gaggacgcgt
92521 cggacgcgtc cctcgggcag ccggaggagg gggcgccctg ccaggtggtc ctgcagggcg
92581 ccgaacttaa tggaatccta caggcgtttg cccgctgcg cacgagcctt ctggactcgc
92641 ttctggttat gggcgaccgg ggcatcctta tccataacac gatctttggg gagcaggtgt
92701 tcctgccct ggaacactcg caattcagtc ggtatcgctg gcgcggaccc acggcggcgt
92761 tcctgtctct cgtggaccag aagcgctccc tcctgagcgt gtttcgcgcc aaccagtacc
92821 cggacctacg tcgggtggag ttggcgatca cgggccaggc ccgtttcgc acgctggttc
92881 agcgcatatg gacgacgacg tccgacggcg aggccgttga gctagccagc gagacgctga
92941 tgaagcgcga actgacgagc tttgtggtgc tggttcccca gggaaccccc gacgttcagt
93001 tgcgcctgac gaggccgcag ctcaccaagg tccttaacgc gaccggggcc gatagtgcca
93061 cgcccaccac gttcgagctc ggggttaacg gcaaaatttc cgtgttcacc acgagtacct
93121 gcgtcacatt tgctgcccgc gaggagggcg tgtcgtccag caccagcacc caggtccaga
93181 tcctgtccaa cgcgctcacc aaggcgggcc aggcggccgc caacgccaag acggtgtacg
93241 gggaaaatac ccatcgcacc ttctctgtgg tcgtcgacga ttgcagcatg cgggcggtgc
93301 tccggcgact gcaggtcggc gggggcaccc tcaagttctt cctcacgacc cccgtcccca
93361 gtctgtgcgt caccgccacc ggtcccaacg ctgtatcggc ggtatttctc ctgaaacccc
93421 agaagatttg cctggactgg ctgggtcata gccagggggtc tccttcagcc gggagctcgg
93481 cctcccgggc ctctgggagc gagccaacag acagcaagga ctccgcgtcg gacgcggtca
93541 gccacggcga tccggaagac ctcgatggcg ctgcccgggc gggagaggcg ggggcctcgc
93601 acgcctgtcc gatgccgtcg tcgaccacgc gggtcactcc cacgaccaag cggggcgct
93661 cgggggcga ggatgcgcgc gcggacacgg ccctaaagaa acctaagacg gggtcgccca
93721 ccgcacccc gcccgcagat ccagtcccc tggacacgga ggacgactcc gatgcggcgg
93781 acgggacggc ggcccgtccc gccgctccag acgcccggag cggaagccgt tacgcgtgtt
93841 actttcgcga cctcccgacc ggagaagcaa gccccggcgc cttctccgcc ttccggggg
93901 ggccccaaac cccgtatggt tttggattcc cctgacgggg cggggccttg gcggccgccc
```

FIGURE 9 (Continued)

```
93961 aactctcgca ccatcccggg ttaatgtaaa taaacttggt attgcccaac actctcccgc
94021 gtgtcgcgtg tggttcatgt gtgtgcctgg cgtccccac cctcgggttc gtgtatttcc
94081 tttccctgtc cttataaaag ccgtatgtgg ggcgctgacg gaaccacccc gcgtgccatc
94141 acggccaagg cgcgggatgc tccgcaacga cagccaccgg gcgcgtccc cggaggacgg
94201 ccagggacgg gtcgacgacg gacggccaca cctcgcgtgc gtggggccc tggcgcgggg
94261 gttcatgcat atctggcttc aggccgccac gctgggtttt gcgggatcgg tcgttatgtc
94321 gcgcgggccg tacgcgaatg ccgcgtctgg ggcgttcgcc gtcgggtgcg ccgtgctggg
94381 ctttatgcgc gcacccctc ccctcgcgcg gcccaccgcg cggatatacg cctggctcaa
94441 actggcggcc ggtggagcgg cccttgttct gtggagtctc gggagcccg gcacgcagcc
94501 ggggcccg gccccgggcc cggccaccca gtgcctggcg ctgggcgccg cctatgcggc
94561 gctcctggtg ctcgccgatg acgtctatcc gctctttctc ctcgcccgg ggccctgtt
94621 cgtcggcacc ctggggatgg tcgtcggcgg gctgacgatc ggaggcagcg cgcgctactg
94681 gtggatcggt gggcccgccg cggccgcctt ggccgcggcg gtgttggcgg gccgggggc
94741 gaccaccgcc agggactgct ctccagggc gtgccccgac caccgccgcg tctgcgtcat
94801 cgtcgcaggc gagtctgttt cccgccgccc ccggaggac ccagagcgac ccggggaccc
94861 cgggccaccg tccccccga caccccaacg atcccagggg ccgccggccg atgaggtcgc
94921 accggccggg gtagcgcggc ccgaaaacgt ctgggtgccc gtggtcacct ttctgggggc
94981 gggcgcgctc gccgtcaaga cggtgcgaga acatgcccgg ggaacgccgg gcccgggcct
95041 gccgctgtgg ccccaggtgt ttctcggagg ccatgtggcg gtggccctga cggagctgtg
95101 tcaggcgctt gcgccctggg accttacgga cccgctgctg tttgttcacg ccggactgca
95161 ggtcatcaac ctcgggttgg tgtttcggtt ttccgaggtt gtcgtgtatg cggcgctagg
95221 gggtgccgtg tggatttcgt tggcgcaggt gctggggctc cggcgtcgcc tgcgcaggaa
95281 ggacccgggg acggggccc ggttggcggc gacgcttcgg ggcctcttct tctccgtgta
95341 cgcgctgggg tttggggtgg gggcgctgct gtgccctccg ggtcaacgg cgggcggtc
95401 gggcgattga tatattttc aataaaaggc attagtcccg aagaccgccg gtgtgtgatg
95461 atttcgccat aacacccaaa ccccggatgg ggcccgggta taaattccgg aagggacac
95521 gggctaccct cactaccgag ggcgcttggt cgggaggccg catcgaacgc acacccccat
95581 ccggtggtcc gtgtggaggt cgttttcagt gcccggtctc gctttgccgg gaacgctagc
```

FIGURE 9 (Continued)

```
95641 cgatccctcg cgagggggag gcgtagggca tggccccggg gcgggtgggc cttgccgtgg
95701 tcctgtggag cctgttgtgg ctcggggcgg gggtgtccgg gggctcggaa actgcctcca
95761 ccggcccac gatcaccgcg ggagcggtga cgaacgcgag cgaggccccc acatcggggt
95821 cccccgggtc agccgccagc ccggaagtca ccccacatc gaccccaaac cccaacaatg
95881 tcacacaaaa caaaaccacc cccaccgagc cggccagccc ccaacaacc cccaagccca
95941 cctccacgcc caaaagcccc cccacgtcca cccccgaccc caaacccaag aacaacacca
96001 ccccgccaa gtcgggccgc cccactaaac ccccgggcc cgtgtggtgc gaccgccgcg
96061 accattggc ccggtacggc tcgcgggtgc agatccgatg ccggtttcgg aattccaccc
96121 gcatggagtt ccgcctccag atatggcgtt actccatggg tccgtccccc ccaatcgctc
96181 cggctcccga cctagaggag gtcctgacga acatcaccgc cccaccgggg ggactcctgg
96241 tgtacgacag cgcccccaac ctgacggacc cccacgtgct ctgggcggag ggggccggcc
96301 cgggtgccga ccctccgttg tattctgtca ccgggccgct gccgacccag cggctgatta
96361 tcggcgaggt gacgccgcg acccagggaa tgtattactt ggcctggggc cggatggaca
96421 gcccgcacga gtacgggacg tgggtgcgcg tccgcatgtt ccgccccccg tctctgaccc
96481 tccagcccca cgcggtgatg gagggtcagc cgttcaaggc gacgtgcacg gccgacgcct
96541 actaccgcg taacccgtg gagttggtct ggttcgagga cgaccgccag gtgtttaacc
96601 cgggccagat cgacacgcag acgcacgagc accccgacgg gttcaccacc gtctctaccg
96661 tgacctccga ggctgtcggc ggccaggtcc cccgcggac cttcacctgc cagatgacgt
96721 ggcaccgcga ctccgtgaca ttctcgcgac gcaatgccac cgggctggcc ctggtgctgc
96781 cgcggccaac catcaccatg gaatttgggg tccggcatgt ggtctgcacg gccggctgcg
96841 tccccgaggg cgtgacgttt gcctggttcc tggggacga cccctcaccg gcggctaagt
96901 cggccgttac ggcccaggag tcatgcgacc accccgggct ggctacggtc cggtccaccc
96961 tgcccatttc gtacgactac agcgagtaca tctgtcggtt gaccggatat ccggccggga
97021 ttcccgttct agaacaccac ggcagtcacc agcccccacc cagggacccc accgagcggc
97081 aggtgatcga ggcgatcgag tgggtgggga ttggaatcgg ggttctcgcg gcggggtcc
97141 tggtcgtaac ggcgatcgtg tacgtcgtcc gcacatcaca gtcgcggcag cgtcatcggc
97201 ggtaacgcga gaccccccg ttacctttt aatatctata tagtttggtc cccctctat
97261 cccgcccacc gctgggcgct ataaagccgc caccctctct tccctcaggt catccttggt
```

FIGURE 9 (Continued)

```
97321 cgatcccgaa cgacacacgg cgtggagcaa aacgcctccc cctgagccgc tttcctacca
97381 acacaccggc atgcctctgc gggcatcgga acacgcctac cggcccctgg gccccgggac
97441 accccccatg cgggctcggc tccccgccgc ggcctggqtt ggcgtcggga ccatcatcgg
97501 gggagttgtg atcattgccg cgttggtcct cgtgccctcg cgggcctcgt gggcactttc
97561 cccatgcgac agcggatggc acgagttcaa cctcgggtgc atatcctggg atccgacccc
97621 catggagcac gagcaggcgg tcggcggctg tagcgcccg gcgaccctga tccccgcgc
97681 ggctgccaaa cagctggccg ccgtcgcacg cgtccagtcg gcaagatcct cgggctactg
97741 gtgggtgagc ggagacggca ttcgggcctg cctgcggctc gtcgacggcg tcggcggtat
97801 tgaccagttt tgcgaggagc ccgcccttcg catatgctac tatccccgca gtcccggggg
97861 ctttgttcag tttgtaactt cgacccgcaa cgcgctgggg ctgccgtgag gcgcgtgtac
97921 tgcggtctgt ctcgtctcct cttctcccct tccctcccc tccgcatccc aggatcacac
97981 cggccaacga gggttggggg gtccggcacg gacccaaaat aataaacaca caatcacgtg
98041 cgataaaaag aacacgcggt cccctgtggt gttttggtt attttatta aatctcgtcg
98101 acaaacaggg ggaagggc gtggtctagc gacggcagca cgggcggagg cgttccacgg
98161 ctccggcgtc cttcgcgttt aagcttggtc aggagggcgc tcaggcggc gacgttggtc
98221 gggccgtcgt tggtcagggc gttggctcga tggcgggcga ggacgggcga ggggctcaac
98281 ggcggggggcg ggggcccggt gcggcccggg ggggaaaata gggcggatcc ccccagtcg
98341 tacagggat tttccgcctc aatgtacggg gaggccggcg ctgcattcgc cgtgttcacg
98401 cagacgtttt cgtagacccg catccatggt atttcctcgt agacacgccc ccgtcctcg
98461 cgcaccgtct cgtatattga ctcgtcgtcc tcgtaggggg cgtgccgttc gcgggccgag
98521 gcggcgtggg tggctttgcg gcgggcgtcg tcgtcgtcgt cgtcggccgt cagatacgtg
98581 gcttccatct ggtcgggttc tccctccggg gcgggtcccc acaccgtgg ccgatcgagg
98641 ctccccagag acgcgcgccg gacgaggagg gggcacgtcg ccgccggcgg tcgcctgtcg
98701 ggtcccgcga cgttacgggc cgggaggcgc ggggcacct cccccatgtg cgtgtaatac
98761 gtggccggct gtgcggccgc agcggggggc tcggcgaccg ggtcgttcgc atccggaagc
98821 gggggccccg cgccgtccgc gccggcgcctc cggaacctcc gggtggacgc gggggtcgag
98881 tgtaggcgag gtcgggggag gggcgggggc tcgttgtcgc gccgcgcccg ctgaatcttt
98941 tcccgacagg tcccacccccc cgcgcgatgc ccccccgggc cgctggccat gtcgtccggg
```

FIGURE 9 (Continued)

```
99001 ggaggccccg cggaccacgt cgtccggcga gacgccacga gccgcaggat ggactcgtag
99061 tggagcgacg gcgccccgct gcggagcaga tccgcggcca gggcggcccc gaaccaagcc
99121 ttgatgctca actccatccg ggcccagctg ggggcggtca tcgtggggaa caggggggcg
99181 gtggtccgac agaaacgctc ctggctgtcc accgcggccc gcagatactc gttgttcagg
99241 ctgtcggtgg cccagacgcc gtacccggtg agggtcgcgt tgatgatata ctgggcgtgg
99301 tgatggacga tcgacagaac ctccaccgtg gatacgacgg tatccacggt cccgtacgta
99361 ccgccgctcc gcttgccggt ctgccacagg ttggctaggc gcgtcaggtg gcccaggacg
99421 tcgctgaccg ccgcctgag cgccatgcac tgcatggagc cggttgtgcc gctgggaccc
99481 cggtccagat ggcgcgcgaa cgtttccgcg ggcgcctccg ggctgccgcc gagcgggagg
99541 aaccggcgat tggagggact cagccggtga catacgtgct tgtctgtcgt ccacagcatc
99601 caggacgccc accggtacag cacggagacg taggccagga gctcgttgag ccgcagtgcg
99661 gtgtcggtgc tggggcggct tgggtccgcc gggcgcataa agaacatgta ctgctgaatc
99721 cgatggaggg cgtcgcgcag gccggccacg gtggcggcgt acttggccgc cacggcccg
99781 ctcttgaacg gggtgcgcgc cagcagcttt ggcgccaggg tgggccgcag cagcacgtga
99841 aggctggggt cgcagtcgcc cacggggtcc tcggggacgt ccaggccgct gggcaccacc
99901 gtctgcaggt acttccagta ctgcgtgagg atggcgcggc tcaactggcc gccgggcagc
99961 tccacctcgc ccagcgcctg ggtggcggcc gaagcgtagt gccggatgta ctcgtagtgc
100021 gggtcgctgg cgagcccgtc cacgatcaaa ctctcgggaa ccgtgttgtg ttgccgcgcg
100081 gccaaccgga cgctgcgatc ggtgcaggtc agaaacgccg gctgcgcgtc gtcggagcgc
100141 tgccgcaagg cgcccacggc cgcgctaagg agcccctccg gggtggggag cagacacccg
100201 ccgaagatgc gccgctcggg aacgcccgcg ttgtcgccgc ggatcaggtt ggcaggcgtc
100261 aggcaccgcg ccagccgcag ggagctcgcg ccgcgcgtcc ggcgctgcat ggtgacgccc
100321 gttcggtcgg gacccgccgg tcggagttat gccgcgtcca gggccatcgg ggcgcttttt
100381 atcgggagga gcttatgggc gtggcgggcc tccagcccg gtcgcgcgcc tcccgacac
100441 gtgcgccgc agggcggcgg cccctcgtc tcccatcagc agtttcctaa actgggacat
100501 gatgtccacc acgcggaccc gcgggcccaa cacggacccg ccgcttacgg gggcgggggg
100561 gaagggctcc aggtccttga gaagaaaggc ggggtctgcc gtcccggaca cggggggccg
100621 gggcgctgag gaggcggggc gcagatccac gtgctccgcg gccgcgcgga cgtccgccca
```

```
100681 gaacttggcg ggggtggtgc gcgcgtacag gggctgggtc gctcggagga cgcacgcgta
100741 gcgcaggggg gtgtacgtgc ccacctcggg ggccgtgaat ccccgtcaa acgcggccag
100801 tgtcacgcac gccaccacgg tgtcggcaaa gccagcagc gctgcagga cgagcccggc
100861 ggccagaatg gcgcgcgtgg ccgccgcgtc gtccggcgc cggtgcgcgt cccgcacgc
100921 ccgggcgtac tttaaggtca cggtcgccag ggccgtgtgc agcgcgtaca ccgcagcgcc
100981 cagcacggcg ttgagcccgc tgttggcgag cagccggcgc gctgcggtgt cgcccagcgc
101041 ctcgtgctcg gccccacga ccgcgggct cccaggggc agggcgcgaa acagctcctc
101101 ccgcgccacg tccgcaaagg cggggtggtg cacgtgcggg tgcaggcgcg ccccacgac
101161 caccgagagc cactggaccg tctgctccgc catcaccgcc agcacatcca gcacgcgccc
101221 caggaaggcg gcctcccgcg tcaaaacgca ccggacggcg tcgggattga agcgggcgag
101281 cagggccccg gtggccaggt acgtcatgcg gccggcatag cgggcggcca cgcgacagtc
101341 gcggtccagc agcgcgcgca ccccgggcca gtacagcagg gaccccagcg agctgcggaa
101401 caccgcggcg tcggggccgg attggggga cactaaccc ccgcgctca gtaacggcac
101461 ggccgcggcc ccgacgggac gcaacgccgt gaggctcgcg aactgccgcc tcagctcggc
101521 cgccctgtcg tccaggtcag accgcgcgc ctccgcgtga aggcgcgtcc cgcacaccca
101581 cccgttgatg gccagccgca cgacggcatc cgccaaaaag ctcatcgcct gggcggggct
101641 ggtttttgtt cgacgatccg tcaggtcaag aatcccatcg cccgtgatat accaggccaa
101701 cgcctcgccc tgctgcaggg tttggcggaa aaacaccgcg gggttgtcgg gggaggcgaa
101761 gtgcatgacc cccacgcgcg ataacccgaa cgcgctatcc ggacacgggt aaaacccggc
101821 cggatgcccc agggctaggg cggagcgcac ggactcgtcc cacacggcaa cctgaggggc
101881 cagtcgatcc aacgggaatg ccgcccggag ctccgggccc ggcacgcgtc cctccagaac
101941 ctccaccttg gcggggaac gggccccgcc gccgtcctcc ggcccgacgg cttcgggta
102001 gtcgtcctcc tcgtactgca gctcctctag gaacagcggc gacggcgcca cccgcgaacc
102061 gccgacccgc cccaaaatag ccgcgcgtc gacgggaccc aggtatcccc cctgccgggc
102121 ctgcggagga ccgcggggaa cctcatcatc atcgtccagg cgaccgcgca ccgactggct
102181 acgggccgca tcgggcccgg ggcgctgccg ggacgctcgg cgatgggatg tgggcggggc
102241 ttccgacgcg cgccgtcgtc gggctcgcgg gccttcccgt cgacggcgca cgggcggctc
102301 gtcgcccgcc atctcctcca gagcctctag ctcgctgtcg tcatcccgc ggaacaccgc
```

```
102361 acgcaggtac cccatgaacc ccaccccatc gcccgctggc tcgtccgcca cgggcgaggc
102421 gcggggcgg tggatgcgc gcctcctgcg ccccgcgggt tcgcgagccg acatggtggc
102481 gatagacgcg ggttatcgga tgtccgctac cccccaaaaa agaaaaagac cccacagcgc
102541 ggatggaggc cggggtaggt gccgccggac ccctcgcga tgggaatgga cgggagcgac
102601 ggggccggcg caaaaaaacg cagtatctcc cgcgaaggct acccgccgcc ccagccccg
102661 gccaaatgcg gaaacggtcc cgcgctctcg cctttatacg cgggccgccc tgcgacacaa
102721 tcacccgtcc gtggtttcga atctacacga caggcccgca gacgcggcta acacacacgc
102781 cggcaaccca gaccccagtg ggttggttgc gcggtcccgt ctcctggcta gttctttccc
102841 ccaccaccaa ataatcagac gacaaccgca ggttttgtaa tgtatgtgct cgtgtttatt
102901 gtggatacga accggtgacg ggagggaaa acccagacgg gggatgcggg tccggtcgcg
102961 ccccctaccc accgtactcg tcaattccaa gggcatcggt aaacatctgc tcaaactcga
103021 agtcggccat atccagagcg ccgtagggg cggagtcgtg ggggtaaat cccggcccg
103081 gggaatcccc gtccccaac atgtccagat cgaaatcgtc tagcgcgtcg gcatgcgcca
103141 tcgccacgtc ctcgccgtct aagtggagct cgtcccccag gctgacatcg gtcggggggg
103201 ccgtcgacag tctgcgcgtg tgtcccgcgg ggagaaagga caggcgcgga gccgccagcc
103261 ccgcctcttc gggggcgtcg tcgtccggga gatcgagcag gccctcgatg gtagacccgt
103321 aattgttttt cgtacgcgcg cggctgtacg cgtgttcccg catgaccgcc tcggagggcg
103381 aggtcgtgaa gctggaatac gagtccaact tcgcccgaat caacaccata aagtacccag
103441 aggcgcgggc ctgggtgcca tgcagggtgg gagggggtcgt caacggcgcc cctggctcct
103501 ccgtagccgc gctgcgcacc agcgggaggt taaggtgctc gcgaatgtgg tttagctccc
103561 gcagccggcg ggcctcgatt ggcactcccc ggacggtgag cgctccgttg acgaacatga
103621 agggctggaa cagacccgcc aactgacgcc agctctccag gtcgcaacag aggcagtcaa
103681 acaggtcggg ccgcatcatc tgctcggcgt acgcggccca taggatctcg cgggtcaaaa
103741 atagatacaa atgcaaaaac agaacacgcg ccagacgagc ggtctctcgg tagtacctgt
103801 ccgcgatcgt ggcgcgcagc atttctccca ggtcgcgatc gcgtccgcgc atgtgcgcct
103861 ggcggtgcag ctgccggacg ctggcgcgca ggtaccggta cagggccgag cagaagttgg
103921 ccaacacggt tcgatagctc tcctcccgcg cccgtagctc ggcgtggaag aaacgagaga
103981 gcgcttcgta gtagagcccg aggccgtcgc gggtggccgg aagcgtcggg aaggccacgt
```

```
104041 cgccgtgggc gcgaatgtcg atttgggcgc gttcggggac gtacgcgtcc ccccattcca
104101 ccacatcgct gggcagcgtt gataggaatt tacactcccg gtacaggtcg gcgttggtcg
104161 gtagcgccga aaacagatcc tcgttccagg tatcgagcat ggtacatagc gcggggcccg
104221 cgctaaagcc caagtcgtcg aggagacggt taaagagggc ggcggggggg acgggcatgg
104281 gtggggaggg catgagctgg gcctggctca ggcgcccgt tgcgtacagc gggggggccg
104341 ccggggtgtt tttgggaccc ccggctgggc ggggggcgg tggcgaagcg ccgtccgcgt
104401 tcatgtcggc aaacagctcg tcgaccaaga ggtccattgg gtggggttga tacgggaaag
104461 acgatatcgg gcttttgatg cgatcgtccc cgcccgccca gagagtgtgg gacgcccgac
104521 ggcgcgggaa gagaaaaacc cccaaacgcg ttagaggacc ggacggacct tatgggggga
104581 agtgggcagc gggaaccccg tccgttcccg aggaatgaca gcccgtggtc gccaccacgc
104641 atttaagcaa cccgcacggg ccgcccgta cctcgtgact tcccccaca ttggctcctg
104701 tcacgtgaag gcgaaccgag ggcggctgtc caacccaccc ccgccaccc agtcccggtc
104761 cccgtcggat tgggaaacaa aggcacgcaa cgccaacacc gaatgaaccc ctgttggtgc
104821 tttattgtct gggtacggaa gttttcactc gacgggccgt ctggggcgag aagcggagcg
104881 ggctggggct cgaggtcgct cggtggggcg cgacgccgca gaacgccctc gagtcgccgt
104941 ggccgcgtcg acgtcctgca ccacgtctgg attcaccaac tcgttggcgc gctgaagcag
105001 gttttgccc tcgcagaccg tcacgcggat ggtggtgatg ccaaggagtt cgttgaggtc
105061 ttcgtctgtg cgcggacgcg acatgtccca gagctggacc gccgccatcc gggcatgcat
105121 ggccgccagg cgcccgaccg cggcgcagaa gacgcgcttg ttaaagccgg ccacccgggg
105181 ggtccatggc gcgtcggggt ttgggggggc ggtgctaaag tgcagctttc tggccagccc
105241 ctgcgcgggt gtcttggatc gggttggcgc cgtcgacgcg ggggcgtctg ggagtgcggc
105301 ggattctggc tgggccgatt tcctgccgcg ggtggtctcc gccgccgggg ccgcggggc
105361 cttagtcgcc acccgctggg ttcggggggc ccggggggcg gtggtgggtg tgcgtccggc
105421 ccctccggac ccagcgggtg gcggaggtgc ccgcgcaggc cccgggccgg acaaaaccgc
105481 cccggaaacg ggacgccgcg tccggggac ctccgggtgt tcgtcgtctt cggatgacga
105541 gccccgtag agggcataat ccgactcgtc gtactggacg aaacggacct cgcccctctg
105601 gcgcgagcgt gtctgtaggg cgccacggcg ggaggtgtca ggcggactat cgggactcgc
105661 catacctgaa gacggggtgt agtacagatc ctcgtactca tcgcgcggaa cctcccgcgg
```

```
105721 acccgacttc acggagcggc gagaggtcat ggttccacga acacgctagg gtcggatgcg
105781 cggacaatta ggcctgggtt cggacggcgg gggtggtgca ggtgtggaga ggtcgagcga
105841 tagggcggc ccgggagaga agagagggtc cgcaaaaccc actggggatg cgtgagtggc
105901 cctctgtggg cggtggggga gagtcttata ggaagtgcat ataaccacaa cccatgggtc
105961 taaccaatcc ccaggggcca agaaacagac acgcccaaa cggtctcggt ttccgcgagg
106021 aagggaagt cctgggacac cctccacccc caccctcac cccacacagg gcgggttcag
106081 gcgtgcccgg cagccagtag cctctggcag atctgacaga cgtgtgcgat aatacacacg
106141 cccatcgagg ccatgcctac ataaagggc accagggccc ccggggcaga catttggcca
106201 gtgttttggg tctcgcaccg cgcgccccg atcccatcgc gcccgccctc ctcgccgggc
106261 ggctccccgt gcgggcccgc gtctcccgcc gctaaggcga cgagcaagac aaacaacagg
106321 cccgcccgac agacccttct ggggggcccc atcgtcccta acaggaagat gagtcagtgg
106381 ggatccgggg cgatccttgt ccagccggac agcttgggtc gggggtacga tggcgactgg
106441 cacacggccg tcgctactcg cggggggcgga gtcgtgcaac tgaacctggt caacaggcgc
106501 gcggtggctt ttatgccgaa ggttagcggg gactccggat gggccgtcgg gcgcgtctct
106561 ctggacctgc gaatggctat gccggctgac ttttgcgcga ttattcacgc cccgcgcta
106621 gccagccccg ggcaccacgt aatactgggt cttatcgact cggggtaccg cggaaccgtt
106681 atggccgtgg tcgtagcgcc taaaaggacg cgggaatttg ccccgggac cctgtgggtc
106741 gacgtgacgt tcctggacat cctggcgacc cccccggccc tcaccgagcc gatttccctg
106801 cggcagttcc cgcaactggc gccccccct ccaaccgggg ccgggatacg cgaagatcct
106861 tggttggagg gggcgctcgg ggccccaagc gtgactacgg ccctaccggc gcgacgccga
106921 gggcggtccc tcgtctatgc cggcgagctg acgccggttc agacggaaca cggggacggc
106981 gtacgagaag ccatcgcctt ccttccaaaa cgcgaggagg atgccggttt cgacattgtc
107041 gtccgtcgcc cggtcaccgt cccggcaaac ggcaccacgg tcgtgcagcc atccctccgc
107101 atgctccacg cggacgccgg gcccgcggcc tgctatgtgt tgggcggtc gtcgctcaac
107161 gcccgcggcc tcctggtcgt cctacgcgc tggctccccg gcacgtatg tgcgtttgtt
107221 gtttacaacc ttacgggggt tcctgtgacc ctcgaggccg gcgccaaggt cgcccagctc
107281 ctggttgcgg gggcggacgc tcttccttgg atccccccgg acaactttca cggggaccaaa
107341 gcgcttcgaa actaccccag gggtgttccg gactcaaccg ccgaacccag gaacccgccg
```

```
107401 ctcctggtgt ttacgaacga gtttgacgcg gaggccccc cgagcgagcg cgggaccggg
107461 ggttttggct ctaccggtat ttagcccaca gctttgggtt cgttccgggc aataaaaaac
107521 gtttgtatcg catctttcct gtgtgtagtt gtttatgttg gatgcctgtg ggtctatcac
107581 acccgcccct ccatcccaca aacacaaaac acacggrttg gatgaaaaca cgcatttatt
107641 gacccaaaac acacggagct gctcgagatg ggccagggcg aggtgcggtt ggggaggctg
107701 taggtctggg aacggacacg cggggacacg attccggttt ggggtccggg agggcgtcgc
107761 cgtttcgggc ggcaggcgcc agcgtaacct ccggggggcgg cgtgtggggg tgccccaagg
107821 agggcgcctc ggtcaccca atcccccccg accgggttcc cccggcaacc ccgaaggcgg
107881 agaggccaag ggcccgttcg gcgatggcca catcctccat gaccacgtca ctctcggcca
107941 tgctccgaat agcctgggag acgagcacat ccgcggactt gtcagccgcc cccacggaca
108001 tgtacatctg caggatggtg gccatacacg tgtccgccag gcgccgcatc ttgtcctgat
108061 gggccgccac ggccccgtcg atcgtggggg cctcgagccc ggggtggtgg cgcgccagtc
108121 gttctaggtt caccatgcag gcgtggtacg tgcgggccaa ggcgcgggcc ttcacgaggc
108181 gtcgggtgtc gtccagggac cccagggcgt catcgagcgt gatggggcg ggaagtagcg
108241 cgttaacgac cgccagggcc tcctgcagcc gcggctccgc ctccgagggc ggaacggccg
108301 cgcggatcat ctcatattgt tcctcgggc gcgctcccca gccacatata gccccgagaa
108361 gagaagccat cgcgggcggg tactggccct tgggcgcgcg gacgcaatgg ggcaggaaga
108421 cgggaaccgc ggggagaggc gggcggccgg gactcccgtg gaggtgaccg cgctttatgc
108481 gaccgacggg tgcgttatta cctcttcgat cgccctcctc acaaactctc tactggggc
108541 cgagccggtt tatatattca gctacgacgc atacacgcac gatggccgtg ctgacgggcc
108601 cacggagcaa gacaggttcg aagagagtcg ggcgctctac caagcgtcgg gcgggctaaa
108661 tggcgactcc ttccgagtaa ccttttgttt attggggacg gaagtgggtg ggacccacca
108721 ggcccgcggg cgaacccgac ccatgttcgt ctgtcgcttc gagcgagcgg acgacgtcgc
108781 cgcgctacag gacgccctgg cgcacggac cccgctacaa ccggaccaca tcgccgccac
108841 cctggacgcg gaggccacgt tcgcgctgca tgcgaacatg atcctggctc tcaccgtggc
108901 catcaacaac gccagcccc gcacggacg cgacgccgcc gcggcgcagt atgatcaggg
108961 cgcgtcccta cgctcgctcg tggggcgcac gtccctggga caacgcggcc ttaccacgct
109021 atacgtccac cacgaggcgc gcgtgcttgc cgcgtaccgc agggcgtatt atggaagcgc
```

```
109081 gcagagtccc ttctggtttc ttagcaaatt cgggccggac gaaaaaagcc tggtgctcac
109141 cactcggtac tacctgcttc aggcccagcg tctgggggc gcggggcca cgtacgacct
109201 gcaggccatc aaggacatct gcgccaccta cgcgattccc cacgccccc gccccgacac
109261 cgtcagcgct gcgtccctga cctcgtttgc cgccatcacg cggttctgtt gcacgagcca
109321 gtacgcccgc ggggccgcgg cggccgggtt ccgctttac gtggagcgcc gtattgcggc
109381 cgacgtccgc gagaccagtg cgctggagaa gttcataacc cacgatcgca gttgcctgcg
109441 cgtgtccgac cgtgaattca ttacgtacat ctacctggcc cattttgagt gtttcagccc
109501 cccgcgccta gccacgcatc ttcgggccgt gacgacccac gaccccaacc ccgcggccag
109561 cacggagcag ccctcgcccc tgggcaggga ggccgtggaa caatttttt gtcacgtgcg
109621 cgcccaactg aatatcgggg agtacgtcaa acacaacgtg accccgggg agaccgtcct
109681 ggatggcgat acggccaagg cctacctgcg cgctcgcacg tacgcgcccg ggccctgac
109741 gcccgccccc gcgtattgcg gggccgtgga ctccgccacc aaaatgatgg ggcgtttggc
109801 ggacgccgaa aagctcctgg tcccccgcgg gtggcccgcg tttgcgcccg ccagtcccgg
109861 ggaggacacg gcgggcggca cgccgccccc acagacctgc ggaattgtca gcgcctcct
109921 gagactggcc gccacggaac agcagggcac cacaccccg gcgatcgcgg cgcttatccg
109981 taatgcggcg gtgcagactc ccctgcccgt ctaccggata tccatggtcc ccacgggaca
110041 ggcatttgcc gcgctggcct gggacgactg ggcccgcata acgcgggacg ctcgcctggc
110101 cgaagcggtc gtgtccgccg aagcggcggc gcaccccgac cacggcgcgc tgggcaggcg
110161 gctcacggat cgcatccgcg cccagggccc cgtgatgccc cctggcggcc tggatgccgg
110221 ggggcagatg tacgtgaatc gcaacgagat attcaacggc gcgctggcaa tcacaaacat
110281 catcctggat ctcgacatcg ccctgaagga gcccgtcccc tttcgccggc tccacgaggc
110341 cctgggccac tttaggcgcg gggctctggc tgcggttcag ctcctgtttc ccgcggcccg
110401 cgtggacccc gacgcatatc cctgttattt tttcaaaagc gcatgtcggc ccggccggc
110461 gtccgtgggt tccggcagcg gactcggcaa cgacgacgac ggggactggt ttccctgcta
110521 cgacgacgcc ggtgatgagg agtgggcgga ggacccgggc gccatggaca catcccacga
110581 tccccggac gacgaggttg cctactttga cctgtgccac gaagtcggcc cacggcgga
110641 acctcgcgaa acggattcgc ccgtgtgttc ctgcaccgac aagatcggac tgcgggtgtg
110701 catgcccgtc cccgccccgt acgtcgtcca cggttctcta acgatgcggg gggtggcacg
```

```
110761 ggtcatccag caggcggtgc tgttggaccg agattttgtg gaggccatcg ggagctacgt
110821 aaaaaacttc ctgttgatcg atacgggagt gtacgcccac ggccacagcc tgcgcttgcc
110881 gtattttgcc aaaatcgccc ccgacgggcc tgcgtgcgga aggctgctgc cagtgtttgt
110941 gatccccccc gcctgcaaag acgttccggc gtttgtcgcc gcgcacgccg accgcggcg
111001 cttccatttt cacgccccgc ccacctatct cgcttccccc cgggagatcc gtgtcctgca
111061 cagcctgggt ggggactatg tgagcttctt tgaaaggaag gcgtcccgca acgcgctgga
111121 acactttggg cgacgcgaga ccctgacgga ggtcctgggt cggtacaacg tacagccgga
111181 tgcgggaggg accgtcgagg ggttcgcatc ggaactgctg gggcggatag tcgcgtgcat
111241 cgaaacccac tttcccgaac acgccggcga atatcaggcc gtatccgtcc ggcgggccgt
111301 cagtaaggac gactgggtcc tcctacagct agtccccgtt cgcggtaccc tgcagcaaag
111361 cctgtcgtgt ctgcgcttta agcacggccg ggcgagtcgc gccacggcgc ggacattcgt
111421 cgcgctgagc gtcggggcca acaaccgcct gtgcgtgtcc ttgtgtcagc agtgctttgc
111481 cgccaaatgc gacagcaacc gcctgcacac gctgtttacc attgacgccg gtacgccatg
111541 ctcgccgtcc gttccctgca gcacctctca accgtcgtct tgataacggc gtacggcctc
111601 gtgctcgtgt ggtacaccgt cttcggtgcc agtccgctgc accgatgtat ttacgcggta
111661 cgccccaccg gcaccaacaa cgacaccgcc ctcgtgtgga tgaaaatgaa ccagacccta
111721 ttgtttctgg ggccccgac gcacccccc aacgggggct ggcgcaacca cgcccatatc
111781 tgctacgcca atcttatcgc gggtagggtc gtgcccttcc aggtcccacc cgacgccatg
111841 aatcgtcgga tcatgaacgt ccacgaggca gttaactgtc tggagaccct atggtacaca
111901 cgggtgcgtc tggtggtcgt agggtggttc ctgtatctgg cgttcgtcgc cctccaccaa
111961 cgccgatgta tgtttggtgt cgtgagtccc gcccacaaga tggtggcccc ggccacctac
112021 ctcttgaact acgcaggccg catcgtatcg agcgtgttcc tgcagtaccc ctacacgaaa
112081 attacccgcc tgctctgcga gctgtcggtc cagcggcaaa acctggttca gttgtttgag
112141 acggacccgg tcaccttctt gtaccaccgc ccgccatcg gggtcatcgt aggctgcgag
112201 ttgatgctac gctttgtggc cgtgggtctc atcgtcggca ccgctttcat atcccggggg
112261 gcatgtgcga tcacatacc cctgtttctg accatcacca cctggtgttt tgtctccacc
112321 atcggcctga cagagctgta ttgtattctg cggcggggcc cggcccccaa gaacgcagac
112381 aaggccgccg ccccggggcg atccaagggg ctgtctggcg tctgcgggcg ctgttgttcc
```

FIGURE 9 (Continued)

```
112441 atcatcctct cgggcatcgc agtgcgattg tgttatatcg ccgtggtggc cggggtggtg
112501 ctcgtggcgc ttcactacga gcaggagatc cagaggcgcc tgtttgatgt atgacgtcac
112561 atccaggccg gcggaaaccg gaacggcata tgcaaattgg aaactgtcct gtcttgggc
112621 ccacccaccc gacgcgtcat atgcaaatga aaatcggtcc cccgaggcca cgtgtagcct
112681 ggatcccaac gacccccgccc atgggtccca attggccgtc ccgttaccaa gaccaaccca
112741 gccagcgtat ccaccccgc ccgggtcccc gcggaagcgg aacggtgtat gtgatatgct
112801 aattaaatac atgccacgta cttatggtgt ctgattggtc cttgtctgtg ccggaggtgg
112861 ggcggggccc ccgcccgggg ggcggaacga ggagggttt gggagagccg gccccggcac
112921 cacgggtata aggacatcca ccacccggcc ggtggtggtg tgcagccgtg ttccaaccac
112981 ggtcacgctt ctgtgcctct cccgattcg ggcccggtcg ctcgctaccg gtgcaccacc
113041 accagaggcc atatccgaca ccccagcccc gacggcagcc gacagcccgg tcatggcgac
113101 tgacattgat atgctaattg acctcggcct ggacctctcc gacagcgatc tggacgagga
113161 cccccccgag ccggcggaga gccgccgcga cgacctggca tcggacagca gcggggagtg
113221 ttcctcgtcg gacgaggaca tggaagaccc ccacggagag gacggaccgg agccgatact
113281 cgacgccgct cgcccggcgg tccgcccgtc tcgtccagaa gaccccggcg tacccagcac
113341 ccagacgcct cgtccgacgg agcggcaggg ccccaacgat cctcaaccag cgccccacag
113401 tgtgtggtcg cgcctcgggg cccggcgacc gtcttgctcc ccgagcagc acggggcaa
113461 ggtggcccgc ctccaacccc caccgaccaa agcccagcct gcccgcggcg gacgccgtgg
113521 gcgtcgcagg ggtcggggtc gcggtggtcc cggggccgcc gatggtttgt cggaccccg
113581 ccggcgtgcc cccagaacca atcgcaaccc ggggggaccc cgccccgggg cggggtggac
113641 ggacggcccc ggcgcccccc atggcgaggc gtggcgcgga agtgagcagc ccgacccacc
113701 cggaggcccg cggacacggg gcgtgcgcca agcacccccc ccgctaatga cgctggcgat
113761 tgcccccccg cccgcggacc ccgcgcccc ggccccggag cgaaaggcgc ccgccgccga
113821 caccatcgac gccaccacgc ggttggtcct gcgctccatc tccgagcgcg gcgcggtcga
113881 ccgcatcagc gagagctttg gccgcagcgc acaggtcatg cacgacccct ttggggggca
113941 gccgtttccc gccgcgaata gcccctgggc cccggtgttg gcgggccaag gagggcccct
114001 tgacgccgag accagacggg tctcctggga aaccttggtc gcccacggcc cgagcctcta
114061 tcgcactttt gccggcaatc ctcgggccgc atcgaccgcc aaggccatgc gcgactgcgt
```

```
114121 gctgcgccaa gaaaatttca tcgaggcgct ggcctccgcc gacgagacgc tggcgtggtg
114181 caagatgtgc atccaccaca acctgccgct gcgccccag gaccccatta tcgggacggc
114241 cgcggctgtg ctggataacc tcgccacgcg cctgcggccc tttctccagt gctacctgaa
114301 ggcgcgaggc ctgtgcggcc tggacgaact gtgttcgcgg cggcgtctgg cggacattaa
114361 ggacattgca tccttcgtgt ttgtcattct ggccaggctc gccaaccgcg tcgagcgtgg
114421 cgtcgcggag atcgactacg cgaccttgg tgtcggggtc ggagagaaga tgcatttcta
114481 cctccccggg gcctgcatgg cgggcctgat cgaaatccta gacacgcacc gccaggagtg
114541 ttcgagtcgt gtctgcgagt tgacggccag tcacatcgtc gccccccgt acgtgcacgg
114601 caaatatttt tattgcaact ccctgtttta ggtacaataa aaacaaaaca tttcaaacaa
114661 atcgccccac gtgttgtcct tctttgctca tggccggcgg ggcgtgggtc acggcagatg
114721 gcggggtgg gcccggcgta cggcctgggt gggcggaggg aactaaccca acgtataaat
114781 ccgtccccgc tccaaggccg gtgtcatagt gcccttagga gcttccgcc cgggcgcatc
114841 cccctttttg cactatgaca gcgaccccc tcaccaacct gttcttacgg gccccggaca
114901 taaccacgt tgcccccct tactgcctca cgccacctg gcaggccgaa acggccatgc
114961 acaccagcaa aactgactcc gcttgcgtgg ccgtgtggag ttacctggtc gcgcctcct
115021 gtgagaccag cggcacaatc cactgctttt tctttgtggt atacaaggac acccaccata
115081 cccctccgct gattaccgag ctccgcaact ttgcggacct ggttaaccac cgccggtcc
115141 tacgcgaact ggaggataag cgcggggtgc ggctgcggtg tgcgcggccg tttagcgtcg
115201 ggacgattaa ggacgtctct gggtccggcg cgtcctcggc gggagagtac acgataaacg
115261 ggatcgtgta ccactgccac tgtcggtatc cgttctcaaa acatgctgg atggggcct
115321 ccgcggccct acagcacctg cgctccatca gctccagcgg catggccgcc cgcgcggcag
115381 agcatcgacg cgtcaagatt aaaattaagg cgtgatttcc aaccccccat gaatgtgtgt
115441 aacccccccc aaaaaaataa agagccgtaa cccaaccaaa ccaggcgtgg tgtgagtttg
115501 tggacccaaa gccctcagag acaacgcgac aggccagtat ggaccgtgag acttttattt
115561 attaactcac agggcgctt accgccacag gaataccaga ataatgacca ccacaatcgc
115621 gaccacccca aatacagcat ggcgccccac cacgccacaa cagccctgtc gccggtatgg
115681 ggcatgatca gacgagccgc gagccgcgcg ttgggccctg tacagctcgc gcgaattgac
115741 cctaggaggc cgccacgcgc ccgagttttg cgttcgtcgc tggtcgtcgg gcaccaaagc
```

```
115801 ccggacggc tgttcggtcg aacgaacggc cacgacagtg gcataggttg ggggtggtc
115861 cgacatagcc tcggcgtacg tcgggaggcc cgacaagagg tcccttgtga tgtcgggtgg
115921 ggccacaagc ctggtttccg gaagaaacag gggggttgcc aataacccgc cagggccaaa
115981 actccggccc tggcgcacgt cgttcggcgc ggcgccgggc gcgccgagcg gctcgctggg
116041 cggcttggcg tgagcggccc cgctccgacg cctcgccctc tccggaggag gttggtggaa
116101 ttggcacgga cgacagggc ccagcagagt acggtggagg tgggtccgtg ggggtgtcca
116161 gatcaataac gacaaacggc ccctcgttcc taccagacaa gctatcgtag ggggcgggg
116221 gatcaacaaa cgcgttcccc gcgctccata gacccgcgtc gggttgcgcc gcctccgaag
116281 ccatggatgc gccccaaagc cacgactccc gcgcgctagg tccttggggt aagggaaaag
116341 gccctactcc ccatccaagc cagccaagtt aacgggctac gccttcgggg atgggactgg
116401 cacccggcg gattttgttg ggctggcatg cgtcgcccaa ccgagggccg cgtccacggg
116461 acgcgccttt tataaccccg ggggtcattc ccaacgatca catgcaatct aactggctcc
116521 cctctcctcc cctctcccct ctccctctc ccctctccc tctccctct ccctcttag
116581 gttgggggt ggtccgacat agcctcggcg tacgtcggga ggcccgacaa gaggtccctt
116641 gtgatgtcgg gtggggccac aagcctggtt tccggaagaa acagggggt tgccaagcgg
116701 cccggccgc gctcccccc ccccggggcc gtgtccttgc tttcccccg tctccccccc
116761 cctcctcctc cttctcctcc tcctcgtttt tccaaaccccc gccacccgg ccggcccgg
116821 cccggccacc gccgcccacc cacccaccgc gggagaccca gccccggtcc cccgttcccc
116881 ggggccgtt atctccagcg ccccgtccgg cgcgccgccc ccgccgcta aacccatcc
116941 cgccccggg accccacata taagccccca gccacacgca agaacagaca cgcagaacgg
117001 ctgtgtttat ttaaataaac cgatgtcgga ataaacaaac acaaacaccc gcgacggggg
117061 gacggaggga gggggtgac ggggacggg aacagacaca aaaacaacc acaaaaaaac
117121 agccacccc gacaccccc accccagtct cctcgccttt tcccacccac cccacgcccc
117181 cactgagccc ggtcgatcga cgagcacccc cgccccgcc cctgccccgg cgaccccgg
117241 cccgcacgat cccgacaaca ataacaaccc caacggaaag cggcggggtg ttgggggagg
117301 cgaggaacaa ccgaggggaa cggggatgg aaggacggga agtggaagtc ctgatacccca
117361 tcctacaccc ccctgccttc caccctccgg cccccgcga gtccacccgc cggccggcta
117421 ccgagaccga acacggcggc cgccgcagcc gccgcagccg ccgccgacac cgcagagccg
```

```
117481 gcgcgcgcac acacaagcgg cagaggcaga aaggccccga gtcattgttt atgtggccgc
117541 gggccagcag acggcccgcg cacccccccc gcccgtgtgg gtatccggcc ccccgcccg
117601 cgccggtcca ttaagggcgc gcgtgcccgc gagatatcaa tccgttaagt gctctgcaga
117661 cagggcacc gcgcccggaa atccattagg ccgcagacga ggaaaataaa attacatcac
117721 ctacccacgt ggtgctgtgg cctgttttg ctgcgtcatc tgagccttta taaaagcggg
117781 ggcgcggccg tgccgatcgc gggtggtgcg aaagactttc cgggcgcgtc cgggtgccgc
117841 ggctctccgg gcccccctgc agccggggcg gccaaggggc gtcggcgaca tcctcccct
117901 aagcgccggc cggccgctgg tctgttttt gttttccccg tttcggggggt gggggggggtt
117961 acggtttctg ttttttaaac ccgtctgggg tgttttcgt tccgtcgccg ggatgtttcg
118021 ttcgttcggc ccctcacggg gcgaaggccg cgtacggccc gggacgaggg gccccgacc
118081 gcggcggtcc gggcccccgtc cgggcccgct cgccggcacg cgacgcgaaa aaggccccc
118141 ggaggctttt ccgggttccc ggcccggggc ctgagataaa caatcggggt taccgccaac
118201 ggccggcccc cgtggcggcc cggcccgggg ccccggcgga ccaaggggc cccggcccgg
118261 ggccccacaa cggcccggcg catgcgctgt gttttttttt tcctcggtgt tctgccgggc
118321 tccgtcgcct ttcctgttct cgcttcttcc ccccccctt cttcacccc agtaccctcc
118381 tccctccctt cctccccgt tatcccactc gtcgagggcg ccccggtgtc gttcaacaaa
118441 gacgccgcgt ttccaggtag gttagacacc tgcttctccc caatagaggg ggggggaccc
118501 aaacgacagg gggcgcccca gaggctaagg tcggccacgc cactcgcggg tgggctcgtg
118561 ttacagcaca ccagcccgtt cttttccccc cctcccaccc ttagtcagac tctgttactt
118621 acccgtccga ccaccaactg cccccttatc taagggccgg ctggaagacc gccaggggggt
118681 cggccggtgt cgctgtaacc ccccacgcca atgacccacg tactccaaga aggcatgtgt
118741 cccacccgc ctgtgttttt gtgcctggct ctctatgctt gggtcttact gcctgggggg
118801 ggggatgcgg gggagggggg gtgtggaagg aaatgcacgg cgcgtgtgta cccccccccc
118861 aaagttgttc ctaaagcgag gatatggagg agtggcgggt gccgggggac gggggtgatc
118921 tctggcacgc ggggggggaa gggtcggggg aggggggat ggggtaccgg cccacctggc
118981 cgacgcgggt gcgcgtgcct ttgcacacca accccacgtc ccccggcggt tctaagaag
119041 caccgccccc cctccttcat accaccgagc atgcctgggt gtgggttggt aaccaacacg
119101 cccatcccct cgtctcctgt gattctctgg ctgcaccgca ttcttgtttt ctaactatgt
```

```
119161 tcctgtttct gtctccccc cacccctccg ccccacccc caacacccac gtctgtggtg
119221 tggccgaccc cctttgggc gcccgtccc gccacccctc ccgtcctttg ttgccctata
119281 gtgtagttaa ccccccccc gcccctttgtg cggccagag gccaggtcag tccgggcggg
119341 caggcgctcg cggaaactta acacccacac ccagcccact gtggttctgg ctccatgcca
119401 gtggcaggat gctttcgggg atcggtggtc aggcagcccg ggccgcggct ctgtggttaa
119461 caccagagcc tgcccaacat ggcaccccca ctcccacgca ccccactcc cacgcacccc
119521 cactcccacg caccccact cccacgcacc cccactccca cgcaccccca ctcccacgca
119581 ccccactcc cacgcacccc cactcccacg caccccact cccacgcacc cccactccca
119641 cgcaccccca ctcccacgca ccccactcc cacgcacccc cactcccacg caccccaag
119701 atccatccaa cacagacagg gaaaagatac aaaagtaaac ctttatttcc caatagacag
119761 caaaaatccc ctgagttttt tattagggcc aacactaaag accgctggt gtgtggtgcc
119821 cgtgtctttc actttcccct ccccgacacg gattggctgg tgtagtgggc gcggccagag
119881 accacccagc acccgacccc cctccccaca aacacggggg gcgtcccta ttgttttccc
119941 tcgtcccggg tcgacgcccc ctgctcccg gaccacgggt gccgagaccg caggctgcgg
120001 aagtccaggg cgcccactag ggtgccctgg tcgaacagca tgttccccac gggggtcatc
120061 cagaggctgt tccactccga cgcgggggcc gtcgggtact cggggggcat cacgtggtta
120121 cccgcggtct cggggagcag ggtgcggcgg ctccagccgg ggaccgcggc ccgcagccgg
120181 gtcgccatgt ttcccgtctg gtccaccagg accacgtacg ccccgatgtt cccgtctcc
120241 atgtccagga tgggcaggca gtccccgtg atagtcttgt tcacgtaagg cgacagggcg
120301 accacgctag agaccccga gatgggcagg tagcgcgtga ggccgcccgc ggggacggcc
120361 ccggaagtct ccgcgtggcg cgtcttccgg gcacacttcc tcggcccccg cggcccagaa
120421 gcagcgcggg ggccgaggga ggtttcctct tgtctccctc ccagggcacc gacgccccg
120481 cccgaggagg cggaagcgga ggaggacgcg gccccggcgg cggaagaggc ggccccgcg
120541 ggggtcgggg ccgaggagga agaggcagag gaggaagagg cggaggccgc cgaggacgtc
120601 agggggtcc ccggcccacc ctggccgcgc cccccggcc ctgagtcgga gggggggtgc
120661 gtcgccgccc tcttggcccc tgccggcgcg agggggggac gcgtggactg gggggagggg
120721 ttttcctggc ccgacccgcg cctcttcctc ggacgcaccg ccgcctcctg ctcgacagag
120781 acggcggagg ggagcggggc ggcgccggag ggggtgcggc cgcgggaggg cccgtgccca
```

```
120841  cctccacgc  cggccccc   cgagccgcgc  gccacgtcg   cacgcccg   gcacagactc
120901  tgttcttggt  tcgcggcctg  agccagggac  gagtgcgact  ggggcacacg  gcgcgcgtcc
120961  gcggggcggg  cggccggctc  cgccccgggg  gccggggcgc  ggggccggg   cccggaggc
121021  ggcgctcgca  cgcacgggc   cacggccgcg  cggggcgcg   cgggtcccga  cgcggccgag
121081  gacgcggggg  gccgggggcg  ggggcggag   cctggcatgg  gcgccgcggg  gggcctgtgg
121141  ggagaggccg  gggggagtc   gctgatcact  atggggtctc  tgttgtttgc  aaggggggcg
121201  ggtctgttga  caaggggcc   cgtccggccc  ctcggccgcc  ccgcctccgc  ttcaacaacc
121261  ccaaccccaa  ccccaacccc  cccggagggg  ccagacgccc  ccgcggcgc   gcggctcgc
121321  gactggcggg  agccgccgcc  gccgctgctg  ttggtggtgg  tgttggtgtt  actgctgccg
121381  tgtggcccga  tgggcgccga  gggggcgct   gtccgagccg  cggccggctg  ggggctgcg
121441  ttagacgccc  cgcccgtcac  gggggcgcg   gcggtgcctc  tgcgtggggg  ggcgcgggc
121501  gtccggcggg  gggcgggcgg  gacgtagtct  gctgcaagag  acaacggggg  gcgcgatcag
121561  gttacgcccc  ctccccggcc  cgcccttcc   tcgcccgcc   gcccattcct  ccctcctcct
121621  cctcccccag  ggtccttgcc  gcccccgcc   tcaccgtcgt  ccaggtcgtc  gtcatcctcg
121681  tccgtggtgg  gctccgggtg  ggtgggcgac  agggccctca  ccgtgtgccc  cccagggtc
121741  aggtaccgcg  gggcgaaccg  ctgattgccc  gtccagataa  agtccacggc  cgtgcccgcc
121801  ctgacggcct  cctcggcctc  catgcgggtc  tgggggtcgt  tcacgatcgg  gatggtgctg
121861  aacgaccgc   tgggcgtcac  gcccactatc  aggtacacca  gcttggcgtt  gcacagcggg
121921  caggtgttgc  gcaattgcat  ccaggttttc  atgcacggga  tgcagaagcg  gtgcatgcac
121981  gggaaggtgt  cgcagcgcag  gtggggcgcg  atctcatccg  tgcacacggc  gcacacgtcg
122041  ccctcgtcgc  tccccccgtc  ctctcgaggg  gggcgcccc   cgcaactgcc  gggtcttcc
122101  tcgcggggg   ggctccccc   cgagaccgcc  ccccatcca   cgccctgcgg  cccagcagc
122161  ccgtctcga   acagttccgt  gtccgtgctg  tccgcctcgg  aggcggagtc  gtcgtcatgg
122221  tggtcggcgt  ccccccgcc   ccccacttcg  gtctccgcct  cagagtcgct  gctgtccggc
122281  aggtctcggt  cgcagggaaa  cacccagaca  tccggggcgg  gctaagggga  aaaaggggg
122341  gcgggtaaga  atgggggggg  atttcccgcg  tcaatcagcg  cccacgagtt  ccccctctcc
122401  cccccgcct   cacaaagtcc  tgccccctg   ctggcctcgg  aagagggggg  agaaagggt
122461  ctgcaaccaa  aggtggtctg  ggtccgtcct  ttggatcccg  accctctttc  ttccctcttc
```

FIGURE 9 (Continued)

```
122521 tcccgccctc cagacgcacc ggagtcgggg gtcccacggc gtcccccaaa tatggcgggc
122581 ggctcctccc caccccccta gatgcgtgtg agtaaggggg gcctgcgtat gagtcagtgg
122641 ggaccacgcc cccaacacgg cgaccccggt ccctgtgtgt ttgttgtggg ggcgtgtctc
122701 tgtgtatgag tcagggggtc ccacggcgac cccggccct gcgtctgagt caaaggggcc
122761 atgtgtatgt gttgggggtc tgtatatata aagtcagggg gtcacatggc gaccccccaac
122821 agggcgaccc cggtccctgt atatataggg tcaggggtt ccgcgccccc taacatggcg
122881 ccccccggtcc ctgtatatat agtgtcacgg ggttccacgc ccctaacat ggcgccccaa
122941 catggcgccc ggctcccgtg tatgagtggg ggtcccccaa catggggcc ggttccaggg
123001 taagggtcgg gggtccccca acatggcgcc cccaatatg gcgcccaga catggcgccc
123061 ggccctcac ctcgcgctgg gggcggccct caggccggcg ggtactcgct ccggggcggg
123121 gctccatggg ggtcgtatgc ggctggaggg tcgcggacgg agggtccctg ggggtcgcaa
123181 cgtaggcggg gcttctgtgg tgatgcggag aggggcggc ccgagtctgc ctggctgctg
123241 cgtctcgctc cgagtgccga ggtgcaaatg cgaccagacc gtcgggccag gctaactta
123301 tacccacgc ctttccctc cccaaggggg cggcagtgac gattcccca atggccgcgc
123361 gtcccagggg aggcaggccc accgcggggc ggccccgtcc ccggggacca acccggcgcc
123421 cccaaagaat atcattagca tgcacggccc ggccccgat ttgggggacc aacccggtgt
123481 ccccccaaaga accccattag catgcccctc ccgccgacgc aacagggggct tggcctgcgt
123541 cggtgccccg gggcttcccg ccttcccgaa gaaactcatt accatacccg gaacccccagg
123601 ggaccaatgc gggttcattg agcgacccgc gggccaatgc gcgaggggcc gtgtgttccg
123661 ccaaaaaagc aattagcata acccggaacc ccaggggagt ggttacgcgc ggcgcgggag
123721 gcggggaata ccggggttgc ccattaaggg ccgcgggaat tgccggaagc gggaagggcg
123781 gccggggccg cccattaatg agtttctaat taccataccg ggaagcggaa caaggcctct
123841 tgcaagtttt taattaccat accgggaagt gggcggcccg gcccattggg cggtaactcc
123901 cgcccaatgg gcgggcccc gaagactcgg cggacgctgg ttggccgggc ccgccgcgc
123961 tggcggccgc cgattggcca gtcccgcccc cgaggcgggc ccgccttggg ggcggaccgg
124021 ctcccagcgt atatatgcgc ggctcctgcc atcgtctctc cggagagcgg cttggtgcgg
124081 agctcccggg agctccgcgg aagacccagg cgcctcgggt gtaacgttag accgagttcg
124141 ccgggccggc tccgcgggcc agggcccggg cacgggcctc gggcccagg cacggcccga
```

FIGURE 9 (Continued)

```
124201 tgaccgcctc ggcctccgcc acccggcgcc ggaaccgagc ccggtcggcc cgctcgcggg
124261 cccacgagcc gcggcgcgcc aggcgggcgg ccgaggccca gaccaccagg tggcgcaccc
124321 ggacgtgggg cgagaagcgc acccgcgcgg gggtcgcggg ggtcgcgggg gtcgcggggg
124381 tcgcgggggt cgcggggggtc gcggggtcg cggggtcgc gggggctcc ggcgcccct
124441 ccccgcccgc gcgtcgcagg cgcaggcgcg ccaggtgctc cgcggtgacg cgcaggcgga
124501 gggcgaggcg cggcggaagg cggaaggggc gcgaggggggg gtgggagggg tcagccccgc
124561 ccccgggcc cacgccgggc ggtggggacc ggggccgggg ggcggcggcg gtgggccggg
124621 cctctggcgc cggctcgggc gggggctgt ccggccagtc gtcgtcatcg tcgtcgtcgg
124681 acgcggactc gggaacgtgg agccactggc gcagcagcag cgaacaagaa ggcgggggcc
124741 caccggcggg gggcggcggc ggggcggccg cgggcgcgct cctgaccgcg ggttccgagt
124801 tgggcgtgga ggttacctgg gactgtgcgg ttgggacggc gcccgtgggc ccgggcggcc
124861 ggggcggcg ggggccgcga tggcggcggc ggcgggccat ggagacagag agcgtgccgg
124921 ggtggtagag tttgacaggc aagcatgtgc gtgcagaggc gagtagtgct tgcctgtcta
124981 actcgctagt ctcggccgcg gggggcccgg gctgccgcc ccgcgcttt aaagggccgc
125041 gcgcgacccc cgggggggtgt gtttcggggg ggccgttttt tggggtctgg ccgctcctcc
125101 cccgctcctc cccgtctgtg ggtggggctc ctccccgct cctccccgc tcctccccg
125161 ctcctccccg tctgtgggtg gggctcctcc cccgctcccg cggcccgcc ccacgccc
125221 gccgcgcgcg cgcacgccgc ccggaccgcc gcccgccttt tttgcgcgcc gccccgcgcg
125281 cggggggccc gggctgccac aggtgtaaca acaccaacag aacaccaaca gcacggcgca
125341 ccggcgactc cggttcctca tccacacgtc acgtcatcca acacacctgc caacaacac
125401 aactcacagc gacaactcac cgcgcaacaa ctcctgttcc tcatccacac gtcaccgcgc
125461 acccccgct cctccagacg tccccagcg caacacgccg ctcctgtcac acaccacagc
125521 cccagccctc ccagccccca gccctcccca gcccagccc tcccagccc cagccctccc
125581 cagccccagc cctccccagc ccagccctc ccagcccca gccctcccca gcccagccc
125641 tccccagccc cagccctccc cagccccagc cctccccagc ccagccctc ccagccccca
125701 gccctcccca gccgcgtccc gcgctccctc gggggggttc gggcatctct acctcagtgc
125761 cgccaatctc aggtcagaga tccaaacct ccgggggcgc ccgcgcacca ccaccgcccc
125821 tcgcccctc ccgcccctcg cccctcccg ccctcgccc cctcccgccc ctcgccccct
```

FIGURE 9 (Continued)

```
125881  ccgcccctc  gcccctccc  gccctcgcc  cctcccgcc  cctcgccccc  tcccgccct
125941  cgcccctcc  cgccctcga  ataaacaacg  ctactgcaaa  acttaatcag  gtcgttgccg
126001  tttattgcgt  cttcgggttt  cacaagcgcc  ccgcccgtc  ccggccgtt  acagcaccc
126061  gtcccctcg  aacgcgccg  cgtcgtcttc  gtcccaggcg  ccttcccagt  ccacaacgtc
126121  ccgtcgcggg  ggcgtggcca  agcccgcctc  cgccccagc  acctccacgg  ccccgccgc
126181  cgccagcacg  gtgccgctgc  ggcccgtggc  cgaggccag  cgaatcccgg  gcggcgccgg
126241  cggcagggcc  cccgggccgt  cgtcgtcgcc  gcgcagcacc  agcgggggg  cgtcgtcgtc
126301  gggctccagc  agggcgcggg  cgcaaaagtc  cctccgcggc  ccgcgccacc  gggccgggcc
126361  ggcgcgcacc  gcctcgcgcc  ccagcgccac  gtacacgggc  cgcagcggcg  cgcccaggcc
126421  ccagcgcgcg  caggcgcggt  gcgagtgggc  ctcctcctcg  cagaagtccg  gcgcgccggg
126481  cgccatggcg  tcggtggtcc  ccgaggccgc  cgcccggccg  tccagcgccg  gcagcacggc
126541  ccggcggtac  tcgcgcgggg  acatgggcac  cggcgtgtcc  gggccgaagc  gcgtgcgcac
126601  gcggtagcgc  acgttgccgc  cgcggcacag  gcgcagcggc  ggcgcgtcgg  ggtacaggcg
126661  cgcgtgcgcg  gcctccacgc  gcgcaagac  ccccgggccg  aacacgcggc  ccgaggccag
126721  caccgtgcgg  cgcaggtcgc  gcgccgccgg  ccagcgcacg  gcgcactgca  cggcggcag
126781  caggtcgcac  gccaggtagg  cgtgctgccg  cgacaccgcg  ggcccgtcgg  cgggccagtc
126841  gcaggcgcgc  acggtgttga  ccacgatgag  ccgccggtcg  ccggcgctgg  cgagcagccc
126901  cagaaactcc  acggccccgg  cgaaggccag  gtcccgcgtg  acagcagca  gcacgccctg
126961  cgcgcccagc  gccgacacgt  cggggcgcc  ggtccagttg  cccgccagg  cggccgtgtc
127021  cggcccgcac  agccggttgg  ccagggccgc  cagcaggcag  gacagcccgc  cgcgctcggc
127081  ggaccactcc  ggcggccccc  ccgaggcccc  gccgccggcc  aggtcctcgc  ccggcagcgg
127141  cgagtacagc  accaccacgc  gcacgtcctc  ggggtcgggg  atctggcgca  tccaggccgc
127201  catgcggcgc  agcgggcccg  aggcgcgcag  ggggccaaag  aggcggcccc  cggcggcccc
127261  gtgggggtgg  gggttctcgt  cgtcgtcgcc  gccgccgcac  gcggcctggg  cggcggggc
127321  gggcccggcg  caccgcgcg  cgatcgaggc  cagggccgc  gggtcaaaca  tgagggccgg
127381  tcgccagggg  acggggaaca  gcgggtggtc  cgtgagctcg  gccacggcgc  gcggggagca
127441  gtaggcctcc  agggcggcgg  ccgcgggcg  cgccgtgtgg  ctgggcccg  ggggctgccg
127501  ccgccagccg  cccaggggt  cggggccctc  ggcgggccgg  cgcgacagcg  ccacggggcg
```

```
127561 cgggcgggcc tgcgccgcgg cggcccgggg cgccgcgggc tgggcggggg cgggctcggg
127621 ccccggggc gtggagggg gcgcgggcgc ggggagggg gcgcggcgt ccgagccggg
127681 ggcgtccgcg ccgctcttct tcgtcttcgg gggtcgcggg ccgccgcctc cgggcggccg
127741 ggccgggccg ggactcttgc gcttgcgccc ctcccgcggc gcggcggagg cggcggccgc
127801 gaccccgaa gacgaagaag agcggcgcgg acccgccgcc agcaggggc gcaggctctg
127861 gttctcaaac agcaggtccg cggcggcggc ggccgcggag ctcggcaggc gcgggtcccg
127921 cggcagcgcg ggacccaggg ccccggcgac caggctcacg gcgcgcacgg cggccacggc
127981 ggcctcgctg ccgccggcca cgcgcaggtc cccgcgcagg cgcatgagca ccagcgcgtc
128041 gcgcacgaac cgcagctcgc gcagccacgc gcgcaggcgg ggcgcgtcgg cgtgcggcgg
128101 cggcggggaa gcggggcccg cgggtccctc cggccgcggg gggctggcgg gccgggcccc
128161 ggccagcccc gggacggccg ccaggtcgcc gtcgaagccc tcggccagcg cctccaggat
128221 cccgcggcag gcggccaggc actccacggc cacgcggccg gcctgggcgc ggcgccggc
128281 gtcgtcgtcg gcgtcggcgt ggcgggcggc gtcggggtcg tcgcccccg cggggaggc
128341 gggcgcggcg gacagccgcc ccagggcggc gaggatcccc gcggcgccgt acccggcggg
128401 caccgcgcgc tcgcccggtg cggcggcggc ggcgacgacg gcggcggcga ccccctcgtc
128461 atctgcgccg gcgccggggc tccccgcggc ccccgtcagc gccgcgttct cgcgcgccaa
128521 caggggcgcg taggcgcggc gcaggctggt cagcaggaag cccttctgcg cgcggtcgta
128581 tcggcggctc atggccacgg cggccgccgc gtgcgccagg cccagccga agcggccggc
128641 cgccatggcg tagcccaggt ggggcacggc ccgcgccacg ctgccggtga tgaaggagct
128701 gctgttgcgc gcggcgcccg agatccggaa gcaggcctgg tccagcgcca cgtcccggg
128761 gaccacgcgc gggttctgga gccaccccat ggcctccgcg tccggggtgt acagcagccg
128821 cgtgatcagg gcgtactgct gcgcggcgtc gcccagctcg ggcgcccaca cggccgccgg
128881 ggcgcccgag gcctcgaacc ggcgtcgcgc ctcctccgcc tcgggcgccc ccagaggcc
128941 cgggcggctg tcgcccaggc cgccgtacag caccgcccc ggggcgggg gccgggcgcc
129001 gggccacggc tccccgctga cgtacccgtc gcgatagcgc gcgtagaagg cgccggaggc
129061 cgcgtcggcg tccagctcga cccgccggg ctgcccggcc gtgaagcggc ccgtggcgtc
129121 gcggccggcc accgccgcgc gggcccggcg gcgctcgatg cggcccgcgg aggccgcggg
129181 ggtcctcgcc gccgcccggg gcttgggcgc ggcctcggag agggggggtg gcccgggcgg
```

FIGURE 9 (Continued)

```
129241 gggcggcgtc cgcccggggg cttccggcgc cgcgctcgac ggaccccgcc cgacggcccg
129301 cgcctcgcgt gcgtggtcgg ccgcgtcgtt gccgtcgtcg tcctcgtcct cgtcggacga
129361 cgaggacgaa gaggatgcgg acgacgagga cgaggacccg gagtccgacg aggtcgatga
129421 cgccgatggc cgccgccggc cgtgacgacg tctctgcggc ggctgggcgg gcgggcgcgg
129481 cgacaggcgg tccgtggggt ccggatacgc gccgcgtagc ggggcctccc gtgcgcggcc
129541 ccggccgggg gcccggtcgc cggcggcgtc ggctgcgtcg tcgtactcgt cccgtcatc
129601 gtcgtcggct cgaaaggcgg gggtccgggg cggcgaggcc gcggggtcgg gcgtcgggat
129661 cgtccggacg gcctcctcta ccatggaggc cagcagggcc agctgtcgcg gcgagacggc
129721 gtccccggcg tcctcgccgg cgtcggtgcc cgccgcgggg gccctcccgt ccgccgggc
129781 gtcgtcgagg tcgtgggggt ggtcggggtc gtggtcgggg tcgtcccgc cctcctccgt
129841 ctccgcgccc caccgaggg ccccccgctc gtcgcggtct gggctcgggg tgggcggcgg
129901 cccgtcggtg gggcccgggg agccggggcg ctgcttgttc tccgacgcca tcgccgatgc
129961 ggggcgatcc tccggggata cgactgcgac ggcggacgta gcacggtagg tcacctacgg
130021 actctcgatg gggagggggc gagacccacg gaccccgacg accccgccg tcgacgcgga
130081 actagcgcgg accggtcgat gcttgggtgg gaaaaaggac agggacggcc gatcccctc
130141 ccgcgcttcg tccgcgtatc ggcgtcccgg cgcggcgagc gtctgacggt ctgtctctgg
130201 cggtcccgcg tcgggtcgtg gatccgtgtc ggcagccgcg ctccgtgtgg acgatcgggg
130261 cgtcctcggg ctcatatagt cccagggggcc ggcgggaagg aggagcagcg gaggccgccg
130321 gccccccgcc cccacggcgg gcccgcccg aacggaattc cattatgcac gaccccgccc
130381 cgacgccggc acgccggggg cccgtggccg cggcccgttg gtcgaacccc cggccccgcc
130441 catccgcgcc atctgccatg ggcggggcgc tagggcgggt gggcccgcgc cccgcccgc
130501 atggcatctc attaccgccc gatccggcgg tttccgcttc cgttccgcat gctaacgagg
130561 aacgggcagg gggcggggcc cgggccccga cttcccggtt cggcggtaat gagatacgag
130621 cccgcgcgc ccgttggccg tccccgggcc cccggtcccg ccgccggac gccgggacca
130681 acgggacggc gggcggccca agggccgccc gccttgccgc ccccccattg gccggcgggc
130741 gggaccgccc caagggggcg gggccgccgg gtaaaagaag tgagaacgcg aagcgttcgc
130801 acttcgtccc aatatatata tattattagg gcgaagtgcg agcactggcg ccgtgcccga
130861 ctccgcgccg gcccccgggg cgggcccggg cggcgggggg cgggtctctc cggcgcacat
```

```
130921 aaaggcccgg cgcgaccgac gcccgcagac ggcgccggcc acgaacgacg ggagctgctg
130981 cggagcacgc ggaccgggag cgggactcgc agagggccgt cggagcggac ggcgtcggca
131041 tcgcgacgcc ccggctcggg atcgggatcg catcggaaag ggacacgcgg aaagacccac
131101 ccacccace cacgaaacac agggacgca ccccggggc ctccgacgac agaaacccac
131161 cggtccgcct ttttgcacgg gtaagcacct tgggtgggcg gaggagggcg gaggaggggg
131221 gacgcggggg cggaggaggg gggacgcggg ggcggaggag gggggacgcg ggggcggagg
131281 aggggggacg cggggggcgga ggaggggggct cacccgcgtt cgtgccttcc cgcaggagga
131341 acgtcctcgt cgaggcgacc ggcggcgacc gttgcgtgga ccgcttcctg ctcgtcgggg
131401 cgaccggcgg cgaccgttgc gtggaccgct cctgctcgt cggggcgacc ggcggcgacc
131461 gttgcgtgga ccgcttcctg ctcgtcgggg ggggggggg gaagccactg tggtcctccg
131521 ggacgttttc tggatggccg acatttcccc aggcgctttt gcgccttgtg taaaagcgcg
131581 gcgtcccgct ctccgatccc cgcccctggg cacgcgcaag cgcaagcgcc ctgcccgccc
131641 cctctcatcg gagtctgagg tcgaaaccga tacagccttg gagtctgagg tcgaatccga
131701 gacagcatcg gattcgaccg agtctgggga ccaggaggaa gccccccgca tcggtggccg
131761 tagggccccc cggaggcttg ggggcggtt ttttctggac atgtcggcgg aatccaccac
131821 ggggacggaa acggatacgg cgtgtcgga cgaccccgac gacacgtccg actggtctta
131881 tgacgacatt ccccacgac ccaagcgggc ccgggtaaac ctgcggctca cgagctctcc
131941 cgatcggcgg gatggggtta ttttcctaa gatggggcgg gtccggtcta cccgggaaac
132001 gcagccccgg gccccaaccc cgtcggcccc aagcccaaat gcaatgctac ggcgctcggt
132061 gcgccaggcc cagaggcgga gcagcgcacg atggaccccc gacctgggct acatgcgcca
132121 gtgtatcaat cagctgtttc gggtcctgcg ggtcgcccgg gaccccacg gcagtgccaa
132181 ccgcctgcgc cacctgatac gcgactgtta cctgatggga tactgccgag ccgtctggc
132241 cccgcgcacg tggtgccgct tgctgcaggt gtccggcgga acctggggca tgcacctgcg
132301 caacaccata cgggaggtgg aggctcgatt cgacgccacc gcggaacccg tgtgcaaact
132361 tccttgtttg gaggccagac ggtacggccc ggagtgtgat cttagtaatc tcgagattca
132421 tctcagcgcg acaagcgatg atgaaatctc cgatgccacc gatctggagg ccgccggttc
132481 ggaccacacg ctcgcgtccc agtccgacac ggaggatgcc cctcccccg ttacgctgga
132541 aaccccagaa ccccgcgggt ccctcgctgt gcgtctggag gatgagtttg gggagtttga
```

FIGURE 9 (Continued)

```
132601 ctggaccccc caggagggct cccagccctg gctgtctgcg gtcgtggccg ataccagctc
132661 cgtggaacgc ccgggcccat ccgattctgg ggcgggtcgc gccgcagaag accgcaagtg
132721 tctggacggc tgccggaaaa tgcgcttctc caccgcctgc cctatccgt gtagcgacac
132781 gtttctccgg ccgtgagtcc ggtcgcccg acccctttgt atgtcaccaa aataaaagac
132841 caaaatcaaa gcgtttgtcc cagcgtctta atggcgggaa gggcggagag aaacagacca
132901 cgcggacatg gggggtgttt gggggtttat tggcaccggg gctaagggg tggtaaccgg
132961 atagcagatg tgaggaagtc ggggccgttc gccgcgaacg gcgatcagag ggtcagtttc
133021 ttgcggacca cggcccggcg atgtggttg ctcgtctggg acctcgggca tgcccataca
133081 cgcacaacac ggacgccgca ccggatggga cgtcgtaagg gggcctgggg tagctgggtg
133141 gggtttgtgc agagcaatca gggaccgcag ccagcgcata caatcgcgct cccgtccgtt
133201 tgtcccgggc agtaccacgc cgtactggta ttcgtaccgg ctgagcaggg tctccagggg
133261 gtggttgggg gccgcgggga acggggtcca cgccacggtc cactcgggca aaaaccgagt
133321 cggcacggcc cacggttctc ccacccacgc gtctggggtc ttgatggcga taaatcttac
133381 cccgagccgg attttttggg cgtattcgag aaacggcaca cacagatccg ccgcgcctac
133441 cacccacaag tggtagatgc gagggggct gggttggtct cggtgcagca gtcggaagca
133501 cgccacggcg tccacgacct cggtgctctc caagggctg tcctccgcaa acaggcccgt
133561 ggtggtgttt ggggggcagc gacaggacct agtgcgcacg atcgggcggg tgggtttggg
133621 taagtccatc agcggctcgg ccaaccgtcg aaggttggcc ggacgaacga cgaccggggt
133681 acccaggggt tctgatgcca aaatgcggca ctgcctaagc aggaagctcc acagggccgg
133741 gcttgcgtcg acggaagtcc ggggcagggc gttgttctgg tcaaggaggg tcattacgtt
133801 gacgacaaca acgcccatgt tggtatatta caggcccgtg tccgatttgg ggcacttgca
133861 gatttgtaag gccacgcacg gcggggagac aggccgacgc ggggctgct ctaaaaattt
133921 aagggcccta cggtccacag acccgcctc ccgggggggg ggccttgga gcgaccggca
133981 gcgtaggcgt ccggggggagg ggagggtgat ttacggggggg gtaggtcagg gggtgggtcg
134041 tcaaactgcc gctccttaaa acccggggc ccgtcgttcg gggtgctcgt tggttggcac
134101 tcacggtgcg gcgaatggcc tgtcgtaagt tttgtcgcgt ttacggggga cagggcagga
134161 ggaaggagga ggccgtcccg ccggagacaa agccgtcccg ggtgtttcct catggcccct
134221 tttataccc agccgaggac gcgtgcctgg actccccgcc cccggagacc cccaaaacctt
```

```
134281 cccacaccac accacccagc gaggccgagc gcctgtttca tctgcaggag atccttgccc
134341 agatgtacgg aaaccaggac tacccatag aggacgaccc cagcgcggat gccgcggacg
134401 atgtcgacga ggacgccccg gacgacgtgg cctatccgga ggaatacgca gaggagcttt
134461 ttctgcccgg ggacgcgacc ggtcccctta tcggggccaa cgaccacatc cctccccgt
134521 gtggcgcatc tccccccggt atacgacgac gcagccggga tgagattggg gccacgggat
134581 ttaccgcgga agagctggac gccatggaca gggaggcggc tcgagccatc agccgcggcg
134641 gcaagccccc ctcgaccatg gccaagctgg tgactggcat gggctttacg atccacggag
134701 cgctcacccc aggatcggag gggtgtgtct ttgatagcag ccacccagat taccccaac
134761 gggtaatcgt gaaggcgggg tggtacacga gcacgagcca cgaggcgcga ctgctgaggc
134821 gactggacca ccccgcgatc ctgcccctcc tggacctgca tgtcgtctcc ggggtcacgt
134881 gtctggtcct ccccaagtac caggccgacc tgtatacctc tctgagtagg cgcctgaacc
134941 cgctgggacg cccgcagatc gcagcggtct cccggcagct cctaagcgcc gttgactaca
135001 ttcaccgcca gggcattatc caccgcgaca ttaagaccga aaatatttt attaacaccc
135061 ccgaggacat ttgcctgggg gactttggtg ccgcgtgctt cgtgcagggt tcccgatcaa
135121 gcccttccc ctacggaatc gccggaacca tcgacaccaa cgccccgag gtcctggccg
135181 gggatccgta taccacgacc gtcgacattt ggagcgccgg tctggtgatc ttcgagactg
135241 ccgtccacaa cgcgtccttg ttctcggccc ccgcggccc caaaagggc ccgtgtgaca
135301 gtcagatcac ccgcatcatc cgacaggccc aggtccacgt tgacgagttt ccccgcatc
135361 cagaatcgcg cctcacctcg cgctaccgct cccgcgcggc cgggaacaat cgcccgcctt
135421 acacccgacc ggcctggacc cgctactaca agatggacat agacgtcgaa tatctggttt
135481 gcaaagccct caccttcgac ggcgcgcttc gccccagcgc cgcagagctg ctttgtttgc
135541 cgctgtttca acagaaatga ccgcccccgg ggggcggtgc tgtttgcggg ttggcacaaa
135601 aagaccccga cccgcgtctg tggtgttttt ggcatcatgt cgccgggcgc catgcgtgcc
135661 gttgttccca ttatcccatt ccttttggtt cttgtcggtg tatcggggt tcccaccaac
135721 gtctcctcca ccacccaacc ccaactccag accaccggtc gtccctcgca tgaagccccc
135781 aacatgaccc agaccggcac caccgactct cccaccgcca tcagccttac cacgcccgac
135841 cacacacccc ccatgccaag tatcggactg gaggaggagg aggaagagga ggagggggcc
135901 ggggatggcg aacatcttaa gggggagat gggacccgtg cacccctacc ccagtccccg
```

```
135961 ggtccagccg tcccgttggc cggggatgac gagaaggaca acccaaccg tcccgtagtc
136021 ccaccccccg gtcccaacaa ctccccgcg cgccccgaga ccagtcgacc gaagacaccc
136081 cccaccagta tcgggccgct ggcaactcga cccacgaccc aactcccctc aaagggcga
136141 ccctggttc cgacgcctca acatacccg ctgttctcgt tcctcactgc ctcccccgcc
136201 ctggacaccc tcttcgtcgt cagcaccgtc atccacacct tatcgttttt gtgtattggt
136261 gcgatggcga cacacctgtg tggcggttgg tccagacgcg ggcgacgcac acccctagc
136321 gtgcgttacg tgtgcctgcc gtccgaacgc gggtagggta tggggcgggg gatggggaga
136381 gcccacatgc ggaaagcaag aacaataaag gcggtggtat ctagttgata tgcatctctg
136441 ggtgtttttg gggtgtggcg gacgcgggc ggtcattgga cggggtgcag ttaaatacat
136501 gcccgggacc catgaagcat gcgcgacttc cgggcctcgg aacccacccg aaacggccaa
136561 cggacgtctg agccaggcct ggctatccgg agaaacagca cacgacttgg cgttctgtgt
136621 gtcgcgatgt ctctgcgcgc agtctggcat ctggggcttt tgggaagcct cgtgggggct
136681 gttcttgccg ccacccatcg gggacctgcg gccaacacaa cggacccctt aacgcacgcc
136741 ccagtgtccc ctcacccag cccctgggg ggctttgccg tcccctcgt agtcggtggg
136801 ctgtgcgccg tagtcctggg ggcggcgtgt ctgcttgagc tcctgcgtcg tacgtgccgc
136861 gggtgggggc gttaccatcc ctacatggac ccagttgtcg tataattccc cccccccctt
136921 ctccgcatgg gtgatgtcgg gtccaaactc ccgacaccac cagctggcat ggtataaatc
136981 accggtgcgc cccccaaacc atgtccggca gggggatggg ggggcgaatg cggagggcac
137041 ccaacaacac cgggctaacc aggaaatccg tggccccggc cccaataaa gatcgcggta
137101 gccggccgt gtgacactat cgtccatacc gaccacaccg acgaatcccc taaggggag
137161 ggccattttt acgaggagga ggggtataac aaagtctgtc tttaaaaagc aggggttagg
137221 gagttgttcg gtcataagct tcagcgcgaa cgaccaacta ccccgatcat cagttatcct
137281 taaggtctct tttgtgtggt gcgttccggt atggggggg ctgccgccag gttgggggcc
137341 gtgattttgt ttgtcgtcat agtgggcctc catgggtcc gcggcaaata tgccttggcg
137401 gatgcctctc tcaagatggc cgaccccaat cgctttcgcg gcaaagacct tccggtcctg
137461 gaccagctga ccgaccctcc ggggtccgg cgcgtgtacc acatccaggc gggcctaccg
137521 gacccgttcc agccccccag cctcccgatc acggtttact acgccgtgtt ggagcgcgcc
137581 tgccgcagcg tgctcctaaa cgcaccgtcg gaggccccc agattgtccg cggggcctcc
```

```
137641 gaagacgtcc ggaaacaacc ctacaacctg accatcgctt ggtttcggat gggaggcaac
137701 tgtgctatcc ccatcacggt catggagtac accgaatgct cctacaacaa gtctctgggg
137761 gcctgtccca tccgaacgca gccccgctgg aactactatg acagcttcag cgccgtcagc
137821 gaggataacc tggggttcct gatgcacgcc ccgcgtttg agaccgccgg cacgtacctg
137881 cggctcgtga agataaacga ctggacggag attacacagt ttatcctgga gcaccgagcc
137941 aagggctcct gtaagtacgc cctcccgctg cgcatccccc gtcagcctg cctgtccccc
138001 caggcctacc agcaggggt gacggtggac agcatcggga tgctgccccg cttcatcccc
138061 gagaaccagc gcaccgtcgc cgtatacagc ttgaagatcg ccgggtggca cgggcccaag
138121 gccccataca cgagcaccct gctgccccg gagctgtccg agacccccaa cgccacgcag
138181 ccagaactcg ccccggaaga ccccgaggat tcggccctct tggaggaccc cgtggggacg
138241 gtggcgccgc aaatcccacc aaactggcac ataccgtcga tccaggacgc cgcgacgcct
138301 taccatcccc cggccacccc gaacaacatg ggcctgatcg ccggcgcggt gggcggcagt
138361 ctcctggcag ccctggtcat ttgcggaatt gtgtactgga tgcgccgccg cactcaaaaa
138421 gccccaaagc gcatacgcct ccccacatc cgggaagacg accagccgtc ctcgcaccag
138481 cccttgtttt actagatacc ccccttaat gggtgcgggg gggtcaggtc tgcggggttg
138541 ggatgggacc ttaactccat ataaagcgag tctggaaggg gggaaaggcg acagtcgat
138601 aagtcggtag cggggacgc gcacctgttc cgcctgtcgc acccacagct ttttttgcga
138661 accgtccgt tccgggatgc cgtgccgccc gttgcaggc ctggtgctcg tgggcctctg
138721 ggtctgtgcc accagcctgg ttgtccgtgg ccccacggtc agtctggtat caaactcatt
138781 tgtggacgcc ggggccttgg ggcccgacgg cgtagtggag gaagacctgc ttattctcgg
138841 ggagcttcgc tttgtggggg accaggtccc ccacaccacc tactacgatg gggtcgtaga
138901 gctgtggcac tacccccatgg gacacaaatg cccacgggtc gtgcatgtcg tcacggtgac
138961 cgcgtgccca cgtcgccccg ccgtggcttt cgccctgtgt cgcgcgaccg acaacactca
139021 cagccccgca tatcccaccc tggagctgaa tctggcccaa cagccgcttt tgcgggtccg
139081 gagggcgacg cgtgactatg ccggggtgta cgtgttacgc gtatgggtcg tggacgcacc
139141 aaacgccagc ctgtttgtcc tggggatggc catagccgcc gaagggactc tggcgtacaa
139201 cggctcggcc catggctcct gcgacccgaa actgcttccg tattcggccc cgcgtctggc
139261 cccggcgagc gtataccaac ccgcccctaa cccggcctcc accccctcga ccaccacctc
```

```
139321 cacccccteg accaccacct ccaccccctc gaccaccacc tccaccccct cgaccaccac
139381 ctccaccccc tcgaccacca cctccacccc ctcgaccacc acctccaccc cctcgaccac
139441 catcccgct ccccaagcat cgaccacacc cttcccacg ggagacccaa aaccccaacc
139501 tcacgggtc aaccacgaac cccatcgaa tgccacgcga gcgaccgcg actcgcgata
139561 cgcgctaacg gtgacccaga taatccagat agccatcccc gcgtccatta tagccctggt
139621 gtttctgggg agctgtattt gctttataca cagatgtcaa cgccgctacc gacgctcccg
139681 ccgcccgatt tacaaccccc agatacccac gggcatctca tgcgcggtga acgaagcggc
139741 catggcccgc ctcggagccg agctcaaatc gcatccgagc acccccccca aatcccggcg
139801 ccggtcgtca cgcacgccaa tgccctccct gacggccatc gccgaagagt cggagcccgc
139861 ggggcggct gggcttccga cgcccccgt ggaccccacg acatccaccc caacgcctcc
139921 cctgttggta taggtccacg gccactggcc ggggcacca cataaccgac cgcagtcact
139981 gagttgggaa taaaccggta ttatttacct atatccgtgt atgtccattt ctttcccccc
140041 ccccccccc cggaaaccca aagaaggaag caaagaatgg atgggaggag ttcaggaagc
140101 cggggagagg gcccgcggcg catttaaggc gttgttgtgt tgactttggc tcttctggcg
140161 ggttggtgcg gtgctgtttg ttgggctccc attttacccg aagatcggct gctatccccg
140221 ggacatggat cgcggggcgg tggtggggtt tcttctcggt gtttgtgttg tatcgtgctt
140281 ggcgggaatg cccaaaacgt cctggagacg ggtgagtgtc ggcgaggacg tttcgttgct
140341 tccagctccg gggcctacgg ggcgcggccc gacccagaaa ctactatggg ccgtggaacc
140401 cctggatggg tgcggcccct tacacccgtc gtgggtctcg ctgatgcccc ccaagcaggt
140461 gcccgagacg gtcgtggatg cggcgtgcat gcgcgctccg gtcccgctgg cgatggcgta
140521 cgccccccg gccccatctg cgaccggggg tctacgaacg gacttcgtgt ggcaggagcg
140581 cgcggccgtg gttaaccgga gtctggttat tcacggggtc cgagagacgg acagcggcct
140641 gtataccctg tccgtgggcg acataaagga cccggctcgc caagtggcct cggtggtcct
140701 ggtggtgcaa ccggcccag ttccgacccc accccgacc ccagccgatt acgacgagga
140761 tgacaatgac gagggcgagg gcgaggacga aagtctagcc ggcactcccg ccagcgggac
140821 cccccggctc ccgcctcccc ccgccccccc gaggtcttgg cccagcgccc ccgaagtctc
140881 acacgtgcgt ggggtgaccg tgcgtatgga gactccggaa gctatcctgt tttcccccgg
140941 ggaggcgttt agcacgaacg tctccatcca tgccatcgcc cacgacgacc agacctacac
```

```
141001 catggacgtc gtctggttga ggttcgacgt gccgacctcg tgtgccgaga tgcgaatata
141061 cgaatcgtgt ctgtatcacc cgcagctccc agagtgtctg tccccggccg acgctccgtg
141121 cgccgcgagt acgtggacgt ctcgcctggc cgtccgcagc tacgcggggt gttccagaac
141181 aaaccccccg ccgcgctgtt cggccgaggc tcacatggag ccttccggg ggctggcgtg
141241 gcaggcggcc tccgtcaatc tggagttccg ggacgcgtcc ccacaacact ccggcctgta
141301 tctgtgcgtg gtgtacgtca acgaccatat tcacgcatgg ggccacatta ccatcagcac
141361 cgcggcgcag taccggaacg cggtggtgga acagcccctc ccacagcgcg gcgcggattt
141421 ggccgagccc acccacccgc acgtcggggc ccctccccac gcgccccaa ccacggcgc
141481 cctgcggtta ggggcggtga tggggccgc cctgctgctg tctgcgctgg ggttgtcggt
141541 gtgggcgtgt atgacctgtt ggcgcaggcg tgcctggcgg gcggttaaaa gcagggcctc
141601 gggtaagggg cccacgtaca ttcgcgtggc cgacagcgag ctgtacgcgg actggagctc
141661 ggacagcgag ggagaacgcg accaggtccc gtggctggcc cccccggaga gacccgactc
141721 tccctccacc aatggatccg gctttgagat cttatcacca acggctccgt ctgtataccc
141781 ccgtagcgat gggcatcaat ctcgccgcca gctcacaacc tttggatccg gaaggcccga
141841 tcgccgttac tcccaggcct ccgattcgtc cgtcttctgg taaggcgcc catcccgagg
141901 ccccacgtcg gtcgccgaac tgggcgaccg ccggcgaggt ggacgtcgga gacgagctaa
141961 tcgcgatttc cgacgaacgc ggacccccc gacatgaccg cccgcccctc gccacgtcga
142021 ccgcgccctc gccacacccg cgaccccgg gctacacggc cgttgtctcc ccgatggccc
142081 tccaggctgt cgacgccccc tccctgtttg tcgcctggct ggccgctcgg tggctccggg
142141 gggcttccgg cctgggggcc gtcttgtgtg ggattgcgtg gtatgtgacg tcaattgccc
142201 gaggcgcata aagggccggt ggtccgccta gccgcagcaa attaaaaatc gtgagtcact
142261 gcgaccgcaa cttcccaccc ggagctttct tccggcctcg atgacgtccc ggctctccga
142321 tcccaactcc tcagcgcgat ccgacatgtc cgtgccgctt tatcccacgg cctcgccagt
142381 ttcggtcgaa gcctactact cggaaagcga agacgaggcg ccaacgact tcctcgtacg
142441 catgggccgc caacagtcgg tattaaggcg tcgacgcaga cgcaccgct gcgtcggcat
142501 ggtgatcgcc tgtctcctcg tggccgttct gtcgggcgga tttggggcgc tcctgatgtg
142561 gctgctccgc taaaagaccg catcgacacg cgcgtccttc ttgtcgtctc tcttccccc
142621 atcaccccgc aatttgcacc cagcctttaa ctacattaaa ttgggttcga ttggcaatgt
```

```
142681 tgtctcccgg ttgatttttg ggtgggtggg gagtgggtgg gtgggagtg ggtgggtggg
142741 gagtgggtgg gtgggagtg ggtgggtggg gagtgggtgg gtgggagtg ggtgggtggg
142801 gagtgggtgg gtgggagtg ggtgggtggg gagtgggtgg gtgggagtg ggtgggtggg
142861 gagtgggtgg gtgggagtg ggtgggtggg gagtgggtgg gtgggagtg ggtgggtggg
142921 gagtgggtgg gtgggagtg gcaaggaaga aacaagcccg accaccagac agaaaatgta
142981 accataccca aaccgactct gggggctgtt tgtgggtcg gaaccatagg atgaacaaac
143041 caccccgtac ctcccgcacc cttgggtgcg ggtggctcat cggcatctgt ccggtatggg
143101 ttgttcccca cccactcgcg ttcggacgtc ttagaatcat ggcggtttct atgccgacat
143161 cggtttctcc cccgcaataa gacacgatgc gataaaatct gtttgtgaaa tttattaagg
143221 gtacaaattg ccctagcaca ggggtggggt tagggccggg tccccacacc caaacgcacc
143281 aaacagatgc aggcagtggg tcgagtacag ccccgcgtac gaacacgtcg atgcgtgtgt
143341 cagacagcac cagaaagcac aggccatcaa caggtcgtgc atgtgtcggt gggtttggac
143401 gcgggggggcc atggtgggtg ataaagttaa tggccgccgt ccgccagggc cacaggggcg
143461 acgtctcttg gttggcccgg agccactggg tgtggaccag ccgcgcgtgg cggcccaaca
143521 tggcccctgt agccgggggc gggggatcgc gcacgtttgc agcgcacatg cgagacacct
143581 cgaccacggt tcggaagaag gcccggtggt ccgcgggcaa catcaccagg tgcgcaagcg
143641 cccgggcgtc cagagggtag agccctgagt catccgaggt tggctcatcg cccgggtcat
143701 gccgcaagtg cgtgtgggtt gggcttccgg tgggcgggac gcgaaccgcg gtgtggagcc
143761 cgacgcgggc ccgagcgtac gctccatctt gtggggagaa ggggtctggg ctcgccaggg
143821 gggcatactt gcccgggcta tacagacccg cgagccgtac gtggttcgcg gggggtgcgt
143881 ggggtccggg gctcccgggg aggccggggc tcccggggtt gtcgtggatc cctggggtca
143941 cgcggtaccc tggggtctct gggagctcgc ggtactctgg gttccctagg ttctcgggt
144001 ggtcgcggaa cccggggctc ccggggaaca cgcggtgtcc tggggattgt tggcggtcgg
144061 acggcttcag atggcttcga gatcgtagtg tccgcaccga ctcgtagtag acccgaatct
144121 ccacattgcc ctgccgcttg atcattatca ccccgttgcg ggggtccgga gatcatgcgc
144181 gggtgtcctc gaggtgcgtg aacacctctg ggtgcatgc cggcggacgg cacgcctttt
144241 aagtaaacat ctgggtcgcc cggcccaact ggggccgggg gttgggtctg gctcatctcg
144301 agagccacgg ggggaaccac cctccgccca gaaacttggg cgatggtcgt acccgggact
```

```
144361 caacgggtta ccggattacg gggactgtcg gtcacggtcc cgccggttct tcgatgtgcc
144421 acacccaagg atgcgttggg ggcgattttg ggcagcagcc cgggagagcg cagcagagga
144481 cgctccgggt cgtgcacggc ggttctggcc gcctcccgt cctcacgccc ccttttattg
144541 atctcatcgc gtacgtcggc gtacgtcctg ggcccaaccc gcatgttgtc caggaaggtg
144601 tccgccattt ccagggccca cgacatgctc ccccccccc ccccgacgag caggaagcgg
144661 tccacgcaac ggtcgccgcc ggtcgccccg acgagcagga agcggtccac gcaacggtcg
144721 ccgccggtcg ccccgacgag caggaagcgg tccacgcaac ggtcgccgcc ggtcgcctcg
144781 acgaggacgt tcctcctgcg ggaaggcacg aacgcgggtg agccccctcc tccgccccg
144841 cgtccccct cctccgcccc cgcgtccccc ctcctccgcc cccgcgtccc cctcctccg
144901 ccccgcgtc cccctcctc cgccctcctc cgcccaccca agtgcttac ccgtgcaaaa
144961 aggcggaccg gtgggtttct gtcgtcggag gccccgggg tgcgtcccct gtgtttcgtg
145021 ggtggggtgg gtgggtcttt ccgcgtgtcc ctttccgatg cgatcccgat ccgagccgg
145081 ggcgtcgcga tgccgacgcc gtccgctccg acggcctct gcgagtcccg ctcccggtcc
145141 gcgtgctccg cagcagctcc cgtcgttcgt ggccggcgcc gtctgcgggc gtcggtcgcg
145201 ccgggccttt atgtgcgccg gagagacccg ccccccgccg ccgggcccg ccccgggc
145261 cggcgcggag tcgggcacgg cgccagtgct cgcacttcgc cctaataata tatatatatt
145321 gggacgaagt gcgaacgctt cgcgttctca cttctttttac ccggcggccc cgccccttg
145381 gggcggtccc gcccgccggc caatgggggg gcggcaaggc gggcggccct tgggccgccc
145441 gccgtcccgt tggtcccggc gtccggcggg cgggaccggg ggcccgggga cggccaacgg
145501 gcgcgcgggg ctcgtatctc attaccgccg aacgggaag tcgggcccg ggcccgccc
145561 cctgcccgtt cctcgttagc atgcggaacg gaagcggaaa ccgccggatc gggcggtaat
145621 gagatgccat gcggggcggg gcgcgggccc accgcccta gcgccccgcc catggcagat
145681 ggcgcggatg ggcggggccg ggggttcgac caacgggccg cggccacggg ccccggcgt
145741 gccggcgtcg ggcggggtc gtgcataatg gaattccgtt cggggcgggc cgccgtggg
145801 ggcgggggc cggcggcctc cgctgctcct ccttcccgcc ggccctggg actatatgag
145861 cccgaggacg ccccgatcgt ccacacggag cgcggctgcc gacacggatc cacgacccga
145921 cgcgggaccg ccagagacag accgtcagac gctcgccgcg ccgggacgcc gatacgcgga
145981 cgaagcgcgg gaggggatc ggccgtccct gtccttttc ccacccaagc atcgaccggt
```

```
146041 ccgcgctagt tccgcgtcga cggcgggggt cgtcggggtc cgtgggtctc gcccctccc
146101 catcgagagt ccgtaggtga cctaccgtgc tacgtccgcc gtcgcagtcg tatccccgga
146161 ggatcgcccc gcatcggcga tggcgtcgga gaacaagcag cgccccggct ccccgggccc
146221 caccgacggg ccgccgccca ccccgagccc agaccgcgac gagcgggggg ccctcgggtg
146281 gggcgcggag acggaggagg gcggggacga ccccgaccac gaccccgacc accccacga
146341 cctcgacgac gcccggcggg acgggagggc cccgcggcg gcaccgacg ccggcgagga
146401 cgccggggac gccgtctcgc cgcgacagct ggccctgctg gcctccatgg tagaggaggc
146461 cgtccggacg atcccgacgc ccgacccgc ggcctcgccg cccggaccc ccgcctttcg
146521 agccgacgac gatgacgggg acgagtacga cgacgcagcc gacgccgccg gcgaccgggc
146581 cccggcccgg ggccgcgcac gggaggcccc gctacgcggc gcgtatccgg accccacgga
146641 ccgcctgtcg ccgcgcccgc cggcccagcc ccgcagaga cgtcgtcacg gccggcggcg
146701 gccatcggcg tcatcgacct cgtcggactc cgggtcctcg tcctcgtcgt ccgcatcctc
146761 ttcgtcctcg tcgtccgacg aggacgagga cgacgacggc aacgacgcgg ccgaccacgc
146821 acgcgaggcg cgggccgtcg ggcggggtcc gtcgagcgcg cgccggaag ccccgggcg
146881 gacgccgccc ccgccgggc cacccccct ctccgaggcc gcgcccaagc cccgggcggc
146941 ggcgaggacc cccgcggcct ccgcgggccg catcgagcgc cgccgggccc gcgcggcggt
147001 ggccggccgc gacgccacgg gccgcttcac ggccgggcag cccggcgggg tcgagctgga
147061 cgccgacgcg gcctccggcg ccttctacgc gcgctatcgc gacgggtacg tcagcgggga
147121 gccgtggccc ggcgccgggc cccgccccc ggggcgggtg ctgtacggcg gcctgggcga
147181 cagccgcccg ggcctctggg gggcgccga ggcggaggag gcgcgacgcc ggttcgaggc
147241 ctcgggcgcc ccggcggccg tgtgggcgcc cgagctgggc gacgccgcgc agcagtacgc
147301 cctgatcacg cggctgctgt acaccccgga cgcggaggcc atggggtggc tccagaaccc
147361 gcgcgtggtc cccggggacg tggcgctgga ccaggcctgc ttccggatct cgggcgccgc
147421 gcgcaacagc agctccttca tcaccggcag cgtggcgcgg ccgtgcccc acctgggcta
147481 cgccatggcg gccggccgct tcggctgggg cctggcgcac gcggcggccg ccgtggccat
147541 gagccgccga tacgaccgcg cgcagaaggg cttcctgctg accagcctgc gccgcgccta
147601 cgcgcccctg ttggcgcgcg agaacgcggc gctgacgggg gccgcgggga gccccggcgc
147661 cggcgcagat gacgaggggg tcgccgccgc cgtcgtcgcc gccgccgccg caccgggcga
```

```
147721 gcgcgcggtg cccgccgggt acggcgccgc ggggatcctc gccgccctgg ggcggctgtc
147781 cgccgcgccc ggctccccg cgggggggcga cgaccccgac gccgccgcc acgccgacgc
147841 cgacgacgac gccgggcgcc gcgcccaggc cggccgcgtg gccgtggagt gcctggccgc
147901 ctgccgcggg atcctggagg cgctggccga gggcttcgac ggcgacctgg cggccgtccc
147961 ggggctggcc ggggcccggc ccgccagccc cccgcggccg gagggacccg cgggcccgc
148021 ttccccgccg ccgccgcacg ccgacgcgcc ccgcctgcgc gcgtggctgc gcgagctgcg
148081 gttcgtgcgc gacgcgctgg tgctcatgcg cctgcgcggg gacctgcgcg tggccggcgg
148141 cagcgaggcc gccgtggccg ccgtgcgcgc cgtgagcctg gtcgccgggg ccctgggtcc
148201 cgcgctgccg cgggacccgc gcctgccgag ctccgcggcc gccgccgccg cggacctgct
148261 gtttgagaac cagagcctgc gcccctgct ggcggcgggt ccgcgccgct cttcttcgtc
148321 ttcggggggtc gcggccgccg cctccgccgc gccgcgggag gggcgcaagc gcaagagtcc
148381 cggcccggcc cggccgcccg gaggcggcgg cccgcgaccc ccgaagacga agaagagcgg
148441 cgcggacgcc cccggctcgg acgcccgcgc cccctcccc gcgcccgcgc ccctccac
148501 gccccgggg cccgagcccg ccccgccca gcccgcggcg cccgggccg ccgcggcgca
148561 ggcccgcccg cgcccgtgg cgctgtcgcg ccggcccgcc gagggcccg accccctggg
148621 cggctggcgg cggcagcccc cggggcccag ccacacggcg gcgcccgcgg ccgccgccct
148681 ggaggcctac tgctccccgc gcgccgtggc cgagctcacg gaccaccgc tgttccccgt
148741 ccctggcga ccggccctca tgtttgaccc gcgggccctg gcctcgatcg ccgcgcggtg
148801 cgccgggccc gccccgccg cccaggccgc gtgcggcggc ggcgacgacg acgagaaccc
148861 ccaccccac ggggccgccg ggggccgcct ctttggcccc ctgcgcgcct cgggcccgct
148921 gcgccgcatg gcggcctgga tgcgccagat ccccgacccc gaggacgtgc gcgtggtggt
148981 gctgtactcg ccgctgccgg gcgaggacct ggccggcggc ggggcctcgg ggggccgcc
149041 ggagtggtcc gccgagcgcg gcggctgtc ctgcctgctg gcggccctgg ccaaccggct
149101 gtgcgggccg gacacggccg cctgggcggg caactggacc ggcgccccg acgtgtcggc
149161 gctgggcgcg cagggcgtgc tgctgctgtc cacgcgggac ctggccttcg ccggggccgt
149221 ggagtttctg gggctgctcg ccagcgccgg cgaccggcgg ctcatcgtgg tcaacaccgt
149281 gcgcgcctgc gactggcccg ccgacgggcc cgcggtgtcg cggcagcacg cctacctggc
149341 gtgcgacctg ctgcccgccg tgcagtgcgc cgtgcgctgg ccggcggcgc gcgacctgcg
```

```
149401 ccgcacggtg ctggcctcgg gccgcgtgtt cggcccgggg gtcttcgcgc gcgtggaggc
149461 cgcgcacgcg cgcctgtacc ccgacgcgcc gccgctgcgc ctgtgccgcg gcggcaacgt
149521 gcgctaccgc gtgcgcacgc gcttcggccc ggacacgccg gtgcccatgt cccgcgcga
149581 gtaccgcgg gccgtgctgc cggcgctgga cggccggcg gcggcctcgg ggaccaccga
149641 cgccatggcg cccggcgcgc cggacttctg cgaggaggag gcccactcgc accgcgcctg
149701 cgcgcgctgg ggcctgggcg cgccgctgcg gcccgtgtac gtggcgctgg ggcgcgaggc
149761 ggtgcgcgcc ggcccggccc ggtggcgcgg gccgcggagg gacttttgcg cccgcgccct
149821 gctggagccc gacgacgacg ccccccgct ggtgctgcgc ggcgacgacg acggcccggg
149881 ggccctgccg ccggcgccgc ccgggattcg ctgggcctcg ccacgggcc gcagcggcac
149941 cgtgctggcg gcggcggggg ccgtggaggt gctgggggcg gaggcgggct tggccacgcc
150001 cccgcgacgg gacgttgtgg actgggaagg cgcctgggac gaagacgacg gcggcgcgtt
150061 cgagggggac ggggtgctgt aacgggccgg gacggggcgg ggcgcttgtg aaacccgaag
150121 acgcaataaa cggcaacgac ctgattaagt tttgcagtag cgttgtttat tcgaggggcg
150181 ggaggggcg aggggcggga ggggcgagg ggcgggaggg ggcgagggc gggaggggc
150241 gagggcggg aggggcgag gggcgggagg gggcgagggg cgggaggggg cgaggggcgg
150301 gaggggcga gggcggtgg tggtgcgcgg gcgccccgg agggtttgga tctctgacct
150361 gagattggcg gcactgaggt agagatgccc gaacccccc gagggagcgc gggacgcggc
150421 tggggagggc tgggctggg gagggctggg gctggggagg gctggggctg ggagggctg
150481 ggctgggga gggctggggc tgggagggc tgggctggg gagggctggg gctggggagg
150541 gctggggctg gggagggctg gggctgggga gggctggggc tgggagggc tgggctggg
150601 gagggctggg gctgtggtgt gtgacaggag cggcgtgttg cgctggggga cgtctggagg
150661 agcgggggt gcgcggtgac gtgtggatga ggaacaggag ttgttgcgcg gtgagttgtc
150721 gctgtgagtt gtgttgttgg gcaggtgtgt tggatgacgt gacgtgtgga tgaggaaccg
150781 gagtcgccgg tgcgccgtgc tgttggtgtt ctgttggtgt tgttacacct gtggcagccc
150841 gggcccccg cgcgcgggc ggcgcgcaaa aaaggcgggc ggcggtccgg gcggcgtgcg
150901 cgcgcgcggc gggcgtgggg ggcggggccg cgggagcggg ggaggagccc cacccacaga
150961 cggggaggag cggggagga gcggggagg agcgggggag gagccccacc cacagacggg
151021 gaggagcggg ggaggagcgg ccagaccca aaaacgggcc ccccgaaac acaccccccg
```

FIGURE 9 (Continued)

```
151081 ggggtcgcgc gcggcccttt aaagcgcggc ggcgggcagc ccgggccccc cgcgg
```

FIGURE 9 (Continued)

McKrae ICP4 amino acid sequence (SEQ ID NO: 2)

```
   1 masenkqrpg spgptdgppp tpspdrderg algwgaetee ggddpdhdpd hphdlddarr
  61 dgrapaagtd agedagdavs prqlallasm veeavrtipt pdpaaspprt pafraddddg
 121 deyddaadaa gdrapargra reaplrgayp dptdrlsprp paqppqrrrh grrrpsasst
 181 ssdsgsssss sasssssssd ededdgnda adharearav grgpssaape apgrtppppg
 241 ppplseaapk praaartpaa sagrierrra raavagrdat grftagqprr veldadaasg
 301 afyaryrdgy vsgepwpgag ppppgrvlyg glgdsrpglw gapeaeearr rfeasgapaa
 361 vwapelgdaa qqyalitrll ytpdaeamgw lqnprvvpgd valdqacfri sgaarnsssf
 421 itgsvaravp hlgyamaagr fgwglahaaa avamsrrydr aqkgflltsl rrayapllar
 481 enaaltgaag spgagaddeg vaaavvaaaa apgeravpag ygaagilaal grlsaapasp
 541 aggddpdaar hadadddagr raqagrvave claacrgile alaegfdgdl aavpglagar
 601 paspprpegp agpasppph adaprlrawl relrfvrdal vlmrlrgdlr vaggseaava
 661 avravslvag algpalprdp rlpssaaaaa adllfenqsl rpllaagprr ssssgvaaa
 721 asaapregrk rkspgparpp ggggprppkt kksgadapgs daraplpapa ppstppgpep
 781 apaqpaapra aaaqarprpv alsrrpaegp dplggwrrqp pgpshtaapa aaaleaycsp
 841 ravaeltdhp lfpvpwrpal mfdpralasi aarcagpapa aqaacggggdd denphphgaa
 901 ggrlfgplra sgplrrmaaw mrqipdpedv rvvvlysplp gedlagggas ggppewsaer
 961 gglsclllaal anrlcgpdta awagnwtgap dvsalgaqgv lllstrdlaf agaveflgll
1021 asagdrrliv vntvracdwp adgpavsrqh aylacdllpa vqcavrwpaa rdlrrtvlas
1081 grvfgpgvfa rveaaharly pdapplrlcr ggnvryrvrt rfgpdtpvpm spreyrravl
1141 paldgraaas gttdamapga pdfceeeahs hracarwglg aplrpvyval greavragpa
1201 rwrgprrdfc arallepddd applvlrgdd dgpgalppap pgirwasatg rsgtvlaaag
1261 avevlgaeag latpprrdvv dwegawdedd ggafegdgvl
```

FIGURE 10

HSV McKrae strain amino acid sequence of ICP22 (SEQ ID NO: 3)

```
  1 madispgafa pcvkarrpal rspplgtrkr krparplsse sevetdtale sevesetasd
 61 stesgdqeea priggrrapr rlggrffldm saesttgtet dtavsddpdd tsdwsyddip
121 prpkrarvnl rltsspdrrd gvifpkmgrv rstretqpra ptpsapspna mlrrsvrqaq
181 rrssarwtpd lgymrqcinq lfrvlrvard phgsanrlrh lirdcylmgy crarlaprtw
241 crllqvsggt wgmhlrntir evearfdata epvcklpcle arrygpecdl snleihlsat
301 sddeisdatd leaagsdhtl asqsdtedap spvtletpep rgslavrled efgefdwtpq
361 egsqpwlsav vadtssverp gpsdsgagra aedrkcldgc rkmrfstacp ypcsdtflrp
```

FIGURE 11

HSV McKrae strain amino acid sequence of ICP47 (SEQ ID NO: 4)

```
 1 mswalemadt fldnmrvgpr tyadvrdein krgredreaa rtavhdperp llrspgllpk
61 iapnaslqva hrrtggtvtd sprnpvtr
```

FIGURE 12

HSV McKrae strain nucleotide sequence of ICP4 (SEQ ID NO: 5)

```
126001 tttattgcgt cttcgggttt cacaagcgcc ccgcccgtc ccggcccgtt acagcacccc
126061 gtcccctcg aacgcgccgc cgtcgtcttc gtcccaggcg ccttcccagt ccacaacgtc
126121 ccgtcgcggg ggcgtggcca agcccgcctc cgccccagc acctcacgg ccccgccgc
126181 cgccagcacg gtgccgctgc ggcccgtggc cgaggccag cgaatcccgg gcggcgccgg
126241 cggcagggcc ccgggccgt cgtcgtcgcc gcgcagcacc agcgggggg cgtcgtcgtc
126301 gggctccagc agggcgcggg cgcaaaagtc cctccgcggc ccgcgccacc gggccgggcc
126361 ggcgcgcacc gcctcgcgcc ccagcgccac gtacacgggc cgcagcggcg cgcccaggcc
126421 ccagcgcgcg caggcgcggt gcgagtgggc ctcctcctcg cagaagtccg gcgcgccggg
126481 cgccatggcg tcggtggtcc ccgaggccgc cgcccggccg tccagcgccg gcagcacggc
126541 ccggcggtac tcgcgcgggg acatgggcac cggcgtgtcc gggccgaagc gcgtgcgcac
126601 gcggtagcgc acgttgccgc cgcggcacag gcgcagcggc ggcgcgtcgg ggtacaggcg
126661 cgcgtgcgcg gcctccacgc gcgcgaagac ccccgggccg aacacgcggc ccgaggccag
126721 caccgtgcgg cgcaggtcgc gcgccgccgg ccagcgcacg cgcactgca cggcgggcag
126781 caggtcgcac gccaggtagg cgtgctgccg cgacaccgcg ggcccgtcgg cgggccagtc
126841 gcaggcgcgc acggtgttga ccacgatgag ccgccggtcg ccggcgctgg cgagcagccc
126901 cagaaactcc acggccccgg cgaaggccag gtcccgcgtg acagcagca gcacgccctg
126961 cgcgcccagc gccgacacgt cggggcgcc ggtccagttg cccgcccagg cggccgtgtc
127021 cggcccgcac agccggttgg ccagggccgc cagcaggcag gacagcccgc cgcgctcggc
127081 ggaccactcc ggcggccccc ccgaggcccc gccgccggcc aggtcctcgc ccggcagcgg
127141 cgagtacagc accaccacgc gcacgtcctc ggggtcgggg atctggcgca tccaggccgc
127201 catgcggcgc agcgggcccg aggcgcgcag ggggccaaag aggcggcccc cggcggcccc
127261 gtggggtgg gggttctcgt cgtcgtcgcc gccgccgcac gcggcctggg cggcggggc
127321 gggcccggcg caccgcgcgg cgatcgaggc cagggcccgc gggtcaaaca tgagggccgg
127381 tcgccagggg acggggaaca gcgggtggtc cgtgagctcg gccacggcgc gcggggagca
127441 gtaggcctcc agggcggcgg ccgcgggcgc cgccgtgtgg ctggcccccg ggggctgccg
127501 ccgccagccg cccaggggt cggggccctc ggcgggccgg cgcgacagcg ccacggggcg
127561 cgggcgggcc tgcgccgcgg cggcccgggg cgccgcgggc tgggcggggg cgggctcggg
```

FIGURE 13

```
127621 ccccgggggc gtggagggg gcgcggcgc ggggagggg gcgcgggcgt ccgagccggg
127681 ggcgtccgcg ccgctcttct tcgtcttcgg gggtcgcggg ccgccgcctc cgggcggccg
127741 ggccgggccg ggactcttgc gcttgcgccc ctcccgcggc gcggcggagg ccggcggccgc
127801 gaccccgaa gacgaagaag agcggcgcgg acccgccgcc agcaggggc gcaggctctg
127861 gttctcaaac agcaggtccg cggcggcgg ggccgcggag ctcggcaggc gcgggtcccg
127921 cggcagcgcg ggacccaggg ccccggcgac caggctcacg gcgcacgg cggccacggc
127981 ggcctcgctg ccgccggcca cgcgcaggtc cccgcgcagg cgcatgagca ccagcgcgtc
128041 gcgcacgaac cgcagctcgc gcagccacgc gcgcaggcgg ggcgcgtcgg cgtgcggcgg
128101 cggcggggaa gcggggcccg cgggtccctc cggccgcggg gggctggcgg gccgggcccc
128161 ggccagcccc gggacggccg ccaggtcgcc gtcgaagccc tcggccagcg cctccaggat
128221 cccgcggcag gcggccaggc actccacggc cacgcggccg gcctgggcgc ggcgcccggc
128281 gtcgtcgtcg gcgtcggcgt ggcgggcggc gtcggggtcg tcgccccccg cggggaggc
128341 gggcgcggcg gacagccgcc ccagggcggc gaggatcccc gcggcgccgt acccggcggg
128401 caccgcgcgc tcgcccggtg cggcggcggc ggcgacgacg gcggcggcga ccccctcgtc
128461 atctgcgccg gcgccggggc tccccgcggc ccccgtcagc ccgcgttct cgcgcgccaa
128521 cagggcgcg taggcgcggc gcaggctggt cagcaggaag cccttctgcg cgcggtcgta
128581 tcggcggctc atggccacgg cggccgccgc gtgcgccagg cccagccga agcggccggc
128641 cgccatggcg tagcccaggt ggggcacggc ccgcgccacg ctgccggtga tgaaggagct
128701 gctgttgcgc gcggcgcccg agatccggaa gcaggcctgg tccagcgcca cgtccccggg
128761 gaccacgcgc gggttctgga gccaccccat ggcctccgcg tccggggtgt acagcagccg
128821 cgtgatcagg gcgtactgct gcgcggcgtc gcccagctcg ggcgcccaca cggccgccgg
128881 ggcgcccgag gcctcgaacc ggcgtcgcgc ctcctccgcc tcgggcgccc ccagaggcc
128941 cgggcggctg tcgcccaggc cgccgtacag caccccgcccc ggggcggg gccggcgcc
129001 ggccacggc tcccgctga cgtacccgtc gcgatagcgc gcgtagaagg cgccggaggc
129061 cgcgtcggcg tccagctcga cccgccgggg ctgcccggcc gtgaagcggc ccgtggcgtc
129121 gcggccggcc accgccgcgc gggcccggcg gcgctcgatg cggcccgcgg aggccgcggg
129181 ggtcctcgcc gcgcccgggg gcttgggcgc ggcctcggag aggggggtg gcccgggcgg
129241 gggcggcgtc cgcccggggg cttccggcgc cgcgctcgac ggacccccgcc cgacggcccg
```

FIGURE 13 (Continued)

```
129301 cgcctcgcgt gcgtggtcgg ccgcgtcgtt gccgtcgtcg tcctcgtcct cgtcggacga
129361 cgaggacgaa gaggatgcgg acgacgagga cgaggacccg gagtccgacg aggtcgatga
129421 cgccgatggc cgccgccggc cgtgacgacg tctctgcggc ggctgggccg gcgggcgcgg
129481 cgacaggcgg tccgtggggt ccggatacgc gccgcgtagc ggggcctccc gtgcgcggcc
129541 ccgggccggg gcccggtcgc cggcggcgtc ggctgcgtcg tcgtactcgt cccgtcatc
129601 gtcgtcggct cgaaaggcgg gggtccgggg cggcgaggcc gcggggtcgg gcgtcgggat
129661 cgtccggacg gcctcctcta ccatggaggc cagcagggcc agctgtcgcg gcgagacggc
129721 gtccccggcg tcctcgccgg cgtcggtgcc cgccgcgggg gccctcccgt ccgccgggc
129781 gtcgtcgagg tcgtgggggt ggtcggggtc gtggtcgggg tcgtcccgc cctcctccgt
129841 ctccgcgccc cacccgaggg ccccccgctc gtcgcggtct gggctcgggg tgggcggcgg
129901 cccgtcggtg gggcccgggg agccggggcg ctgcttgttc tccgacgcca tgccgatgc
129961 ggggcgatcc tccggggata cgactgcgac ggcggacgta gcacggtagg tcacctacgg
```

FIGURE 13 (Continued)

HSV McKrae strain nucleotide sequence of ICP22 (SEQ ID NO: 6)

```
132481  ggtcctccgg gacgttttct gg<u>a</u>tggccga catttcccca ggcgcttttg tgccttgtgt
132541  aaaagcgcgg cgtcccgctc tccgatcccc gccctgggc acgcgaagc gcaagcgccc
132601  tgcccgcccc ctctcatcgg agtctgaggt cgaatccgag acagccttgg agtctgaggt
132661  cgaatccgag acagcatcgg attcgaccga gtctggggac caggaggaag cccccgcat
132721  cggtggccgt agggcccccc ggaggcttgg ggggcggttt tttctggaca tgtcggcgga
132781  atccaccacg gggacggaaa cggatgcgtc ggtgtcggac gaccccgacg acacgtccga
132841  ctggtcttgt gacgacattc ccccacgacc caagcgggcc cgggtaaacc tgcggctcac
132901  tagctctccc gatcggcggg atggggttat ttttcctaag atggggcggg tccggtctac
132961  ccgggaaacg cagccccggg cccccacccc gtcgcccca gcccaaatg caatgctccg
133021  gcgctcggtg cgccaggccc agaggcggag cagcgcacga tggaccccg acctgggcta
133081  catgcgccag tgtatcaatc agctgtttcg ggtcctgcgg gtcgcccggg accccacgg
133141  cagtgccaac cgcctgcgcc acctgatacg cgactgttac ctgatgggat actgccgagc
133201  ccgtctggcc ccgcgcacgt ggtgccgctt gctgcaggtg tccggcggaa cctggggcat
133261  gcacctgcgc aacaccatac gggaggtgga ggctcgattc gacgccaccg cagaacccgt
133321  gtgcaagctt ccttgtttgg aggccagacg gtacggcccg gagtgtgatc ttagtaatct
133381  cgagattcat ctcagcgcga caagcgatga tgaaatctcc gatgccaccg atctggaggc
133441  cgccggttcg gaccacacgc tgcgtccca gtccgacacg gaggatgccc cctcccccgt
133501  tacgctggaa ccccagaac cccgcgggtc cctcgctgtg cgtctggagg atgagtttgg
133561  ggagtttgac tggaccccc aggagggctc ccagccctgg ctgtctgcgg tcgtggccga
133621  taccagctcc gtggaacgcc cgggcccatc cgattctggg gcgggtcgcg cagcagaaga
133681  ccgcaagtgt ctggacggct gccggaaaat gcgcttctcc accgcctgcc cctatccgtg
133741  cagcgacacg tttctccggc cgtg<u>a</u>gtccg gtcgcccga ccccttgta tgtccccaaa
```

FIGURE 14

HSV McKrae strain nucleotide sequence of ICP47 (SEQ ID NO: 7)

```
145081 tccgcccaga gactcgggtg atggtcgtac ccgggactca acgggttacc ggattacggg 145141 gactgtcggt cacggtcccg ccggttcttc gatgtgccac acccaaggat gcgttggggg 145201 cgatttcggg cagcagcccg ggagagcgca gcagggacg ctccgggtcg tgcacggcgg 145261 ttctggccgc ctcccggtcc tcacgcccc ttttattgat ctcatcgcgt acgtcggcgt 145321 acgtcctggg cccaacccgc atgttgtcca ggaaggtgtc cgccatttcc agggcccacg 145381 acatgctttt cccccgacg agcaggaagc ggtccacgca acggtcgccg ccggtcgcct
```

FIGURE 15

Human cytomegalovirus enhancer nucleotide sequence (SEQ ID NO: 8)

```
gaagatctttggttatatagcataaatcaatattggctattggccattgcatacgttgtatccatatcataatatgt
acatttatattggctcatgtccaacattaccgccatgttgacattgattattgactagttattaatagtaatcaatt
acggggtcattagttcatagcccatatatggagttccgcgttacataacttacggtaaatggcccgcctggctgacc
gcccaacgaccccgcccattgacgtcaataatgacgtatgttcccatagtaacgccaataggggactttccattgac
gtcaatgggtggagtatttacggtaaactgcccacttggcagtacatcaagtgtatcatatgccaagtacgccccct
attgacgtcaatgacggtaaatggcccgcctggcattatgcccagtacatgaccttatgggactttcctacttggca
gtacatctacgtattagtcatcgctattaccatggtgatgcggttttggcagtacatcaat
```

FIGURE 16

Calcitonin gene-related peptide promoter (SEQ ID NO: 9)

```
aatgggtttg ggtgtgtgta aatgagtgtg
accggaagcg agtgtgagct tgatctaggc agggaccaca cagcactgtc acacctgcct
gctctttagt agaggactga agtgcggggg tgggggtacg gggccggaat agaatgtctc
tggacatct  tggcaaacag cagccggaag caaagggca  gctgtgcaaa cggctcaggc
aggtgatgga tggcagggta ggaaggggga ggtccagagg tctggatgga ggcttccgca
tctgtacctt gcaactcacc cctcaggccc agcaggtcat cggcccctc  ctcacacatg
taatgacgta gaagagtacc ccgggacagt ccggggagat ggagattcgg aaagtatcca
tggagctctt acagaatccc ctgtgcggac caggaaactc ttgtagatcc ctgcctatct
gaggcccagg cgctgggctg tttctcacaa tattccttca agatgagatt gtggtcccca
tttcaaagat gagtacactg agcctctgtg aagttacttg cccatgatca cacaaccagg
aattgggcca actgtaattg aactcctgtc taacaaagtt cttgctccca gctccgtctc
ttgtttccca cgagccctgg ccctctgtgg gtaataccag ctactggagt cagatttctt
gggcccagaa cccacccta  ggggcattaa cctttaaaat ctcacttggg caggggtctg
ggatcagagt tggaagagtc cctacaatcc tggacccttt ccgccaaatc gtgaaaccag
gggtggagtg gggcgagggt tcaaaaccag gccggactga gaggtgaaat tcaccatgac
gtcaaactgc cctcaaattc ccgctcactt taagggcgtt acttgttggt gcccccacca
tcccccacca tttccatcaa tgacctcaat gcaaatacaa gtgggacggt cctgctgacg
cctccaggtt ctggaagcat gaggg ccagg  gcaaaggacc cctccgccca
ttggttgctg tgcactggcg gaactttccc gacccacagc ggcggaata agagcagtcg
ctggcgctgg gaggcatcag agacactgcc cagcccaagt gtcgccgccg cttccacagg
gctctggctg gacgccgccg ccgccgctgc
```

FIGURE 17

Bovine growth hormone polyadenylation signal nucleotide sequence (SEQ ID NO: 10)

ggatcccgactgtgccttctagttgccagccatctgttgtttgcccctcccccgtgccttccttgaccctggaaggt
gccactcccactgtcctttcctaataaaatgaggaaattgcatcgcattgtctgagtaggtgtcattctattctggg
gggtggggtggggcaggacagcaaggggaggattgggaagacaatagcaggcatgctggggaagatcttc

FIGURE 18

HIGH-TRANSDUCING HSV VECTORS

CROSS REFERENCE TO RELATED APPLICATIONS

The present application is a Division of U.S. application Ser. No. 16/088,393, filed Sep. 25, 2018, which is the National Stage of International Application No. PCT/US17/24092, filed Mar. 24, 2017, which claims priority to U.S. Provisional Application No. 62/313,391, filed Mar. 25, 2016, the entire contents of which are herein incorporated by reference.

SEQUENCE LISTING

The contents of the electronic sequence listing (P113870000US02-SEQ-EMB.xml; Size: 180,145 bytes; and Date of Creation: Jul. 21, 2023) is herein incorporated by reference in its entirety.

BACKGROUND

Systemic delivery of certain therapeutic agents can be problematic for agents with poor pharmacokinetics and/or a risk of off target adverse effects. Local injection at particular target sites may require highly invasive techniques or be infeasible. Delivery of agents by viral vectors allows the ability to specifically target cell populations to provide local production and/or delivery of agents.

SUMMARY OF THE INVENTION

The present disclosure provides compositions and methods for viral vector delivery of agents to target cells.

In some embodiments, the disclosure provides variants of herpes simplex virus (HSV) McKrae strain whose genome contains an alteration such that the variant fails to express a functional protein characterized by an amino acid sequence of SEQ ID NO: 16.

In some embodiments, the disclosure provides variants of herpes simplex virus McKrae strain having a truncated genome of total size less than about 150,000 base pairs and including a deletion of one or more residues within an element corresponding to residues 126049 to 130014 of SEQ ID NO: 1.

In some embodiments, the disclosure provides vectors comprising a variant herpes simplex virus (HSV) McKrae strain genome which genome contains an alteration such that the variant fails to express a functional protein characterized by an amino acid sequence of SEQ ID NO: 2. In some embodiments, the vector comprises a neuron specific promoter. In some embodiments, the promoter is a calcitonin gene-related peptide (CGRP) promoter.

In some embodiments, the vector comprises a human cytomegalovirus (HCMV) enhancer. In some embodiments, the vector comprises a bovine growth hormone (BGH) polyadenylation signal. In some embodiments, the vectors comprise a nucleic acid that encodes a therapeutic polypeptide.

In some embodiments, the disclosure provides cells transduced with a HSV McKrae strain viral vector as described herein.

In some embodiments, the disclosure provides pharmaceutical compositions comprising an HSV McKrae strain viral vector as described herein and a pharmaceutically acceptable carrier.

In some embodiments, the disclosure provides methods of propagating a vector comprising a variant herpes simplex virus (HSV) McKrae strain genome which genome contains an alteration such that the variant fails to express a functional protein characterized by an amino acid sequence of SEQ ID NO: 16, the method comprising steps of: (i) infecting cultured ICP4 complementing cells containing DNA encoding HSV protein ICP4 with the vector, and (ii) isolating supernatant from the culture of step (i).

In some embodiments, the method comprises a step of purifying vector in the supernatant by chromatography. In some embodiments, the method comprises a step of concentrating the purified vector. In some embodiments, purified vector is concentrated by tangential flow filtration.

In some embodiments, the disclosure provides methods of preparing a vector comprising a variant herpes simplex virus (HSV) McKrae strain genome which genome contains an alteration such that the variant fails to express a functional protein characterized by an amino acid sequence of SEQ ID NO: 16, and wherein the vector expresses a marker element, the method comprising incubating cells transfected with:
 (a) a first nucleic acid molecule:
  (i) comprising a portion of HSV McKrae strain genome but does not encode a functional protein characterized by an amino acid sequence of SEQ ID NO: 16; and
  (ii) comprising a first homology region (HR1) and a second homology region (HR2), and
 (b) a second nucleic acid molecule comprising a sequence that encodes a marker element, wherein the sequence is flanked by a first homology region (HR1') and a second homology region (HR2'), wherein HR1 is homologous to HR1' and HR2 is homologous to HR2' such that the sequence that encodes the marker element in the second nucleic acid molecule integrates into the first nucleic acid molecule via homologous recombination.

In some embodiments, the cells are ICP4 complementing cells. In some embodiments, the cells complement ICP4 and at least one other viral gene. In some embodiments, the cells complement ICP4 and at least one immediate early gene. In some embodiments, the cells are ICP4, ICP27, and UL55 complementing cells. In some embodiments, the cells are ICP4, ICP22, and ICP47 complementing cells.

In some embodiments, the marker element is a polypeptide. In some embodiments, the polypeptide is detectable by fluorescence. In some embodiments, the marker element is a green fluorescent peptide. In some embodiments, the method comprises a step of purifying viral plaques that express the marker element.

In some embodiments, the disclosure provides methods of preparing a vector comprising a variant herpes simplex virus (HSV) McKrae strain genome which genome contains an alteration such that the variant fails to express a functional protein characterized by an amino acid sequence of SEQ ID NO. 16, and wherein the vector expresses an agent of interest, the method comprising incubating cells transfected with:
 a) a first nucleic acid molecule:
  (i) comprising a portion of HSV McKrae strain genome but does not encode a functional protein characterized by an amino acid sequence of SEQ ID NO: 16; and
  (ii) comprising a sequence that encodes a marker element, wherein the sequence that encodes the marker element is flanked by a first homology region (HR1) and a second homology region (HR2); and (b) a second nucleic acid molecule comprising a sequence that encodes an agent of interest, wherein the sequence encoding the agent of interest is flanked by a first homology region (HR1') and a second homology region (HR2'), wherein HR1 is homologous to HR1' and HR2 is homologous to HR2' such the sequence encoding the agent of interest is integrated into the first nucleic acid molecule via homologous recombination.

In some embodiments, the cells are ICP4 complementing cells. In some embodiments, the cells complement ICP4 and at least one other viral gene. In some embodiments, the cells complement ICP4 and at least one immediate early gene. In some embodiments, the cells are ICP4, ICP27, and UL55 complementing cells. In some embodiments, the cells are ICP4, ICP22, and ICP47 complementing cells.

In some embodiments the method comprises a step of purifying viral plaques that do not express the marker element.

In some embodiments, the disclosure provides methods of expressing a polypeptide in dorsal root ganglion (DRG) of a subject comprising administering to the subject an HSV McKrae strain vector as described herein. In some embodiments, the vector is administered in vivo. In some embodiments, the vector is administered by contact with skin. In some embodiments, the vector is administered by intradermal injection.

In some embodiments, the disclosure provides methods of measuring transduction efficiency in dorsal root ganglion (DRG) of an HSV McKrae strain viral vector comprising (a) contacting the skin of an animal with an HSV McKrae strain viral vector (b) removing DRG tissue from the animal, and (c) assaying the number of HSV genomes transduced in the DRG. In some embodiments, the number of genomes is measured by an amplification technique. In some embodiments, the number of genomes is measured by quantitative polymerase chain reaction (PCR).

In some embodiments, the disclosure provides methods of measuring transduction efficiency in dorsal root ganglion (DRG) of an HSV McKrae strain viral vector that contains an expression cassette comprising a polypeptide payload, the method comprising steps of: (a) contacting the skin of an animal with an HSV McKrae strain viral vector, (b) removing DRG tissue from the animal, and (c) assaying the amount of a polypeptide encoded by a nucleic acid of the expression cassette. In some embodiments, the amount of polypeptide is measured by an immunoassay. In some embodiments, the amount of polypeptide is measured by an enzyme linked immunosorbent assay (ELISA).

BRIEF DESCRIPTION OF THE DRAWINGS

The drawings are for illustration purposes only, not for limitation.

FIG. 9 depicts an exemplary HSV McKrae strain nucleotide sequence (SEQ ID NO: 1) which is identified as accession number JQ730035.1

FIG. 10 depicts an exemplary HSV McKrae strain ICP4 amino acid sequence (SEQ ID NO: 2).

FIG. 11 depicts an exemplary HSV McKrae strain ICP22 amino acid sequence (SEQ ID NO: 3).

FIG. 12 depicts an exemplary HSV McKrae strain ICP47 amino acid sequence (SEQ ID NO: 4).

FIG. 13 depicts an exemplary HSV McKrae strain nucleotide sequence of ICP4 (SEQ ID NO: 5).

FIG. 14 depicts an exemplary HSV McKrae strain nucleotide sequence of ICP22 (SEQ ID NO: 6).

FIG. 15 depicts an exemplary HSV McKrae strain nucleotide sequence ICP47 (SEQ ID NO: 7).

FIG. 16 depicts an exemplary human cytomegalovirus enhancer nucleotide sequence (SEQ ID NO: 8).

FIG. 17 depicts an exemplary calcitonin gene-related peptide nucleotide sequence (SEQ ID NO: 9).

FIG. 18 depicts an exemplary bovine growth hormone polyadenylation signal (SEQ ID NO: 10).

DEFINITIONS

Figure 1:
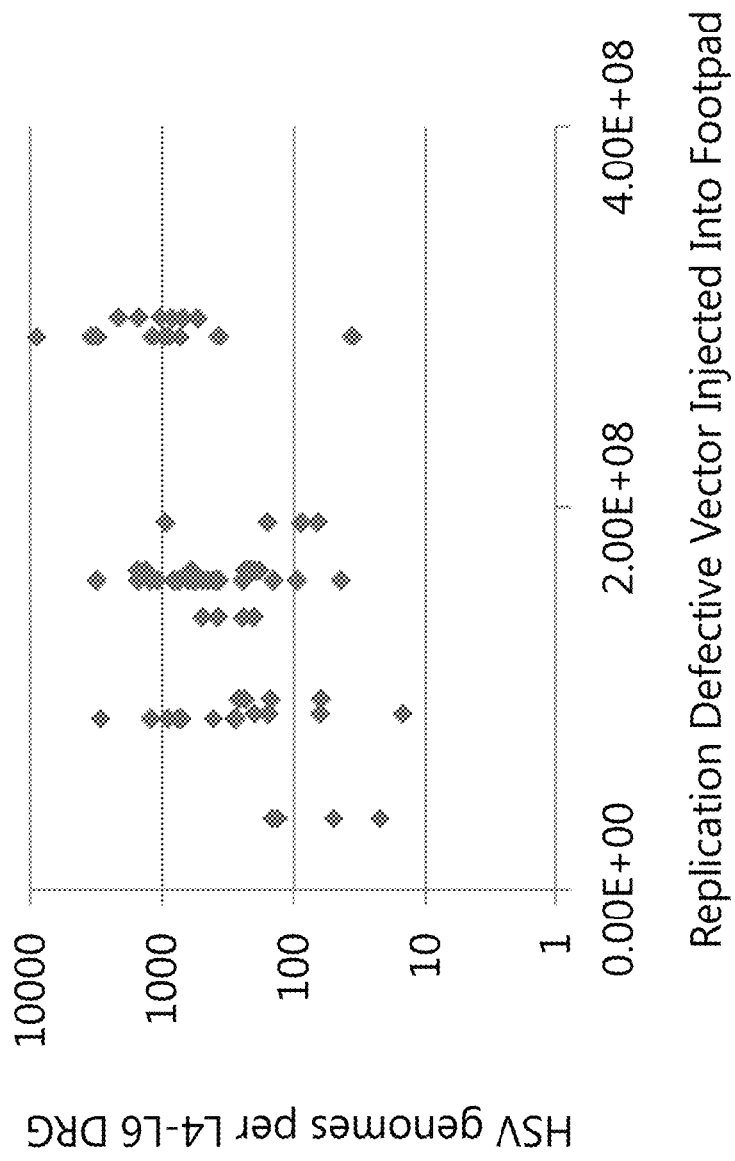
FIG. 1 depicts an exemplary graph that shows the number of HSV genomes per L4-L6 dorsal root ganglia (DRG) detected in a qPCR assay as a result of different doses of replication-defective viral vector injected into the footpad.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time.

Agent: As used herein, the term "agent" refers to a compound or entity of any chemical class including, for example, polypeptides, nucleic acids, saccharides, lipids, small molecules, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc.

Amelioration: As used herein, the term "amelioration" refers to the prevention, reduction or palliation of a state, or improvement of the state of a subject. Amelioration includes, but does not require complete recovery or complete prevention of a disease, disorder or condition.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%6, or less in either direction (greater than or less than) of the stated reference value unless otherwise stated or otherwise evident from the context (except where such number would exceed 100% f a possible value).

Characteristic sequence: As used herein, the term "characteristic sequence" refers to a sequence that is found in all members of a family of polypeptides or nucleic acids, and therefore can be used by those of ordinary skill in the art to define members of the family.

Combination therapy: As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens.

Composition: As used herein, the term "composition" or a "pharmaceutical composition" refers to the combination of two or more agents as described herein for co-administration or administration as part of the same regimen. It is not required in all embodiments that the combination of agents result in physical admixture, that is, administration as separate co-agents each of the components of the composition is possible; however many patients or practitioners in the field may find it advantageous to prepare a composition that is an admixture of two or more of the ingredients in a pharmaceutically acceptable carrier, diluent, or excipient, making it possible to administer the component ingredients of the combination at the same time.

Engineered: As used herein, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present disclosure, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% f the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Marker element: As used herein, the term "marker element" refers to a detectable or selectable agent. In some embodiments, a "marker element" is a detectable or selectable nucleic acid sequence. In some embodiments a "marker element" is an expression product (e.g., RNA or protein) whose presence or absence is detectable and/or selectable in cells. In some embodiments, an expression product is or comprises an enzyme. In some embodiments, an expression product is a fluorophore.

Nucleic acid: As used herein, the term "nucleic acid" refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present disclosure. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, CS-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof) In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation, topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include—sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevent or prevention: As used herein, the terms "prevent" or "prevention", when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Subject: As used herein, the term "subject" refers to a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Treatment: As used herein, the term "treatment" (also "treat" or "treating") refers to any administration of a substance that partially or completely alleviates, ameliorates, relieves, inhibits, delays onset of, reduces severity of, and/or reduces incidence of one or more symptoms, features, and/or causes of a particular disease, disorder, and/or condition (e.g., neuropathy). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated to a viral genome or portion thereof. Certain vectors are capable of autonomous replication in a host cell into which they are introduced (e.g., bacterial vectors having a bacterial origin of replication, episomal mammalian vectors, herpes simplex virus (HSV) vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION

Various aspects of the invention are described in detail in the following sections. The use of sections is not meant to limit the invention. Each section can apply to any aspect of the invention. In this application, the use of "or" means "and/or" unless stated otherwise or clear from context to be disjunctive.

The present disclosure provides, among other things, compositions comprising HSV vectors and methods for use and production of same. In particular, the present disclosure relates to McKrae strain vectors for the delivery of payloads to neuronal cells.

Viral Vectors and HSV

Viral vectors can be used to facilitate the transfer of nucleic acids into cells. Known viral vectors include those derived from retroviruses, adenoviruses, adeno-associated virus (AAV), vaccinia virus, and baculovirus. Vectors derived from herpes simplex viruses (HSV), such as herpes simplex virus 1 (HSV-1) and herpes simplex virus-2 (HSV-2) are particularly useful for delivery of agents to specifically targeted tissues. Considerations for choosing a particular vector and delivery system include, for example, characteristics of target cells, desired longevity of expression, virulence and invasiveness of the vector; and, size of the genetic material to be transferred.

HSV-1 vectors can typically accommodate up to 25 kb of foreign DNA sequences. HSV-1 has an approximate 152-kb double-stranded linear DNA genome that can be maintained episomally in the nucleus of cells. The HSV-1 virion is enveloped and approximately 110 nm in diameter. Viral infection is initiated in epithelial cells of the skin or mucosal membranes by binding of the viral envelope glycoproteins to heparin sulfate moieties on the plasma membrane. HSV is particularly well suited for the delivery of genes to the nervous system and possesses a natural tropism for sensory neurons. The virus can establish a latent state in which viral genomes persist for the life of the host as an intranuclear episomal element. The life-long persistence of latent genomes in human trigeminal ganglia without the development of sensory loss or histologic damage to the ganglia exemplifies the effectiveness of the latency mechanisms. Wild-type HSV virus may be reactivated from latency under the influence of a variety of stresses. However, recombinant viral vectors that are rendered replication defective retain the ability to establish a persistent quiescent state in neurons yet are unable to replicate (or reactivate) in the nervous system.

Vectors based upon HSV-1 may have one or more HSV genes necessary for replication rendered nonfunctional (e.g., by deletion or disruption). HSV genes necessary for replication include, for example, immediate early genes such as ICP4 and ICP 27. In some embodiments, the disclosure provides replication defective HSV vectors with one or more of ICP9, ICP4, ICP22, ICP27, and ICP47 deleted or disrupted. In some embodiments, the disclosure provides HSV vectors with a nonfunctional ICP4 gene. In some embodiments, the disclosure provides HSV vectors with nonfunctional ICP4, ICP22, and ICP47 genes. In some embodiments, the disclosure provides an HSV vector with ICP4 deleted and ICP22 and ICP47 disrupted. In some embodiments, the disclosure provides an HSV vector with ICP4 deleted and expression of ICP22 and ICP47 disrupted or delayed. In some embodiments, the disclosure provides an HSV vector with ICP4 deleted ICP0, ICP22, ICP27, and/or ICP47 not expressed as immediate early genes.

HSV-1 vectors that have deleted HSV genes can be produced in cell lines that express the deficient protein in trans. In some embodiments, HSV-1 vectors are produced in a mammalian cell line. In some embodiments, HSV-1 vectors are produced in a mammalian cell line of Vero lineage. In some embodiments, the cell line expresses ICP4. In some embodiments, the cell line expresses one or more of ICP0, ICP4, ICP22, ICP27, and ICP47. In some embodiments, the cell line expresses ICP4 and at least one additional immediate early gene. In some embodiments, the cell line expresses ICP4, ICP22, and ICP 47. In some embodiments, the cell line expresses ICP4, ICP22, and UL55. In some embodiments, the cell line expresses ICP4, ICP27 and UL55. In some embodiments, the cell line comprises a nucleic acid molecule having a simian virus 40 polyadenylation signal (SV40 pA) In some embodiments, viral vectors are produced in Vero 6-5C cells. In some embodiments, viral vectors are produced in Vero D cells.

McKrae Strain

At least 17 strains of HSV-1 have been isolated, including but not limited to, McKrae, strain 17, strain F, H129, HF10, MacIntyre, Strain HF, ATCC 2011 and KOS (for review, see Watson et al, *Virology* (2012)). A McKrae strain was isolated from a patient with herpes simplex keratitis and subsequently passaged in tissue culture. A partial genome sequence of McKrae is shown in FIG. 9 (SEQ ID NO: 1) (accession number JQ730035).

Inter-strain differences in HSV-1 peripheral replication and virulence are observed after injection into animals. McKrae undergoes spontaneous or induced reactivation at a higher frequency than other known strains and is among the most virulent HSV-1 strains. McKrae is also more neuroinvasive than other known strains, such as strain 17, KOS, F, and H129. In one study, KOS or McKrae was injected into the cornea and genital tract of mice to compare pathogenesis (Wang et al. (2013) Virus Res. 173(2):436-440. Each was found to replicate to a similar extent in the corneal epithelium and trigeminal ganglia; however, McKrae titers were over 100 fold higher in brainstem. Upon intravaginal injection, McKrae and KOS replicated to a similar extent except for a transient spike in McKrae titer at four days. McKrae, but not KOS, elicited significant inflammation of external genitalia along with weight loss in the animals. KOS was not detected in neural tissue and McKrae was rarely detected.

In some embodiments, the disclosure provides HSV viral vectors with deletion of genes that render HSV replication defective, but do not reduce HSV neuroinvasiveness. Thus, the HSV vectors are able to traverse the peripheral nervous system to reach neurons in the dorsal root ganglion upon administration to the skin.

HSV genes influence viral characteristics and phenotype. There are at least 9 genes and several non-coding sequences unique to McKrae strain. In addition to those associated with pathogenesis and latency reactivations, such as RL1, RS1, and RL2, three UL genes (UL36, UL49A, UL56) and three US genes (US7, US10, and US11) are unique for McKrae strain. In addition to gene variations, non-coding sequences such as LAT, 'a' sequence, and miRNAs contain variations unique to McKrae.

One or more of following gene and non-coding sequences can be considered characteristic of McKrae strain. In McKrae, RL1 (ICP34.5) has an extended P-A-T repeat between residues 159 and 160 that results in 8 iterations, while other strains contain only 3-5 iterations. The P-A-T repeat is thought to influence cellular localization of the ICP34.5 protein. (Mao & Rosenthal, J. Biol. Chem. 277(13):11423-31 (2012). ICP34.5 is thought to be a neurovirulence factor involved in viral replication and anti-host response.

McKrae strain also contains an extended repeat element of six iterations of the internal tandem repeat STPSTTT (SEQ ID NO: 11) located within the coding sequence of US07 (gI). Additionally in McKrae, UL 36 contains a premature stop codon introduced due to a G nucleotide deletion in a mononucleotide string encoding amino acid residue 2453 (nt 72,535) and UL 56 (180 aa) contains a single base pair insertion at nucleotide 115,992 (amino acid 97). McKrae strain also contains an extended ORF in US10 resulting from a single bp insertion at nucleotide 143,416 and the frameshift causes a stop codon loss in McKrae and a unique C-terminal protein sequence. McKrae has amino acid differences at UL49A at residues 28 and 51 compared to other strains. McKrae has histidine and threonine at residues 28 and 51, respectively, whereas strain 17 has arginine and threonine and other strains (e.g., KOS) have histidine and alanine. Also, McKrae strain contains reduced tandem repeats found at the UL-RL junction (49 bp in McKrae as opposed to 181 bp in strain 17 and KOS) and approximately 330 nucleotides missing immediately following the UL-RL junction repeat. McKrae also contains unique variation within the 'a' sequence direct repeat 2 (DR2) array. Instead of a series of unbroken tandem repeats, the McKrae DR2 repeats are interrupted twice by identical guanine-rich sequences.

Major variation within the LAT intron between strains is due to differences in a repeat element (GCACCCC-CACTCCCAC) (SEQ ID NO: 12) that varies in iteration number beginning at nucleotide 119,482 in McKrae strain, with McKrae containing 13 repeats while strains F, H129 and 17 contain 9 repeats and KOS contains 15 repeats. Also, tandem repeat variation between strains is found beginning in McKrae at base 125,520. McKrae repeat elements include twelve iterations of CCCCAGCCCTCCCCAG (SEQ ID NO: 13) and eight iterations of CCCCTCGCCCCCTCCCG (SEQ ID NO: 14). The first repeat unit is unique from other strains in that it contains a G-A transition, and strain McKrae contains three iterations more than any other strain. The McKrae strain second repeat element is collapsed, missing 188 nucleotides relative to all other strains, and separated from the upstream repeat by a 100% conserved sequence of 105 bp containing miR-H5.

McKrae further contains a unique coding sequence for ICP4 that is not found in other known strains. (Watson et al., Virology (2012)). ICP4 is an immediate early transcriptional regulator and has been implicated in reactivation. Whereas other strains contain an alanine rich region (AASAP-DAADALAAA) (SEQ ID NO: 15) between residues 707 and 720, in McKrae the alanine rich region is replaced by a serine rich sequence (GPRRSSSSSGVAA) (SEQ ID NO: 16). The serine rich block of substitutions present in McKrae is adjacent to the nuclear localization signal (NLS) (amino acid 728-734). A change in conformation of this region may alter the NLS and in turn affect localization of not only ICP4, but also other viral proteins (e.g. ICP0, ICP8) that are affected by ICP4 localization (Knipe and Smith, 1986). Thus, this region may influence viral phenotype in part by altering the localization of proteins to the nucleus.

Replication Defective McKrae Vector
McKrae Backbone

Viral genes are expressed in a tightly regulated, ordered cascade, which begins with the production of the immediate-early (IE) genes. The resulting IE proteins, which include infected cell proteins ICP0, ICP4, ICP22, ICP27, and ICP47, are responsible for regulating viral gene expression during subsequent phases of the replication cycle. Replication-defective variant viruses are defective for one or more functions that are essential for viral genome replication or synthesis and assembly of viral particles. Such viruses can be propagated in complementing cell lines expressing the missing gene product(s); however, in normal (i.e., non-complementing) cells, the viruses express viral gene products but do not replicate to form progeny virions.

Replication-defective viruses can be created through various methods known in the art for modifying genes. In some embodiments, one or more nucleotides are rendered different relative to the wild-type sequence. In some embodiments, one or more nucleotides are deleted. In some embodiments, the deletion of one or more nucleotides creates a premature stop codon. In some embodiments, the deletion of one or more nucleotides creates a gene encoding a truncated polypeptide. In some embodiments, the deletion of one or more nucleotides creates a gene encoding a nonfunctional polypeptide. In some embodiments, the deletion of one or more nucleotides renders a gene nonfunctional by disruption. In some embodiments, a gene is disrupted by deletion of its promoter.

In some embodiments, one or more genes are deleted to render a virus replication defective. In some embodiments, the gene encoding ICP0 is fully or partially deleted. In some embodiments, the gene encoding ICP4 is fully or partially deleted. In some embodiments, the gene encoding IC22 is fully or partially deleted. In some embodiments, the gene encoding ICP27 is fully or partially deleted. In some embodiments, the gene encoding ICP47 is fully or partially deleted. In some embodiments, the gene encoding ICP 4 is fully or partially deleted, without disrupting expression of any additional immediate early genes. In some embodiments, the gene encoding ICP4 is fully or partially deleted, and one or more other immediate early (IE) genes are disrupted. In some embodiments, the gene encoding ICP4 is deleted and ICP22 and ICP47 are disrupted.

HSV-1 IE promoters contain one or more copies of an IE-specific regulatory sequence of consensus TAATGARAT (SEQ ID NO: 19) (where R is a purine). These motifs are normally located within a few hundred base pairs of the proximal IE promoter sequences, but in conjunction with their flanking sequences they are discrete functional entities which can confer IE-specific regulation to other proximal promoter elements of different temporal class. In some embodiments, replication-defective viruses are created by deleting nucleotides in an IE-specific regulatory sequence. In some embodiments, an IE-specific regulatory sequence contains an internal deletion. In some embodiments, an IE-specific regulatory sequence contains a terminal deletion. In some embodiments, an IE-specific regulatory sequence is completely deleted.

A schematic of an exemplary replication defective McKrae strain viral vector is depicted below. The schematic shows complete deletions of both copies of the viral ICP4 gene, and a human cytomegalovirus (HCMV) immediate early promoter driven expression cassette inserted within both copies of the deleted ICP4 loci. The expression cassette contains a payload of interest for expression in target cells.

Figure 19:
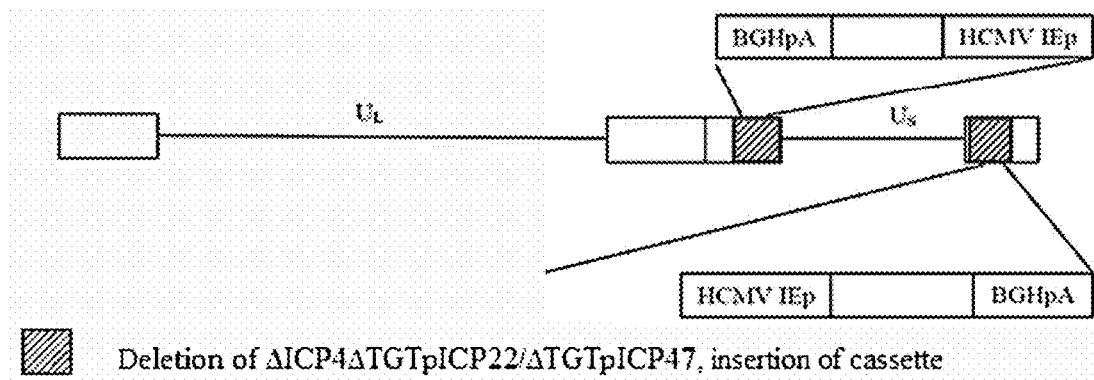
FIG. 19 depicts the extent of the ICP4 deletion resulting in the removal of the upstream promoter sequences of two additional immediate early viral genes: ICP22 and ICP47.

The extent of the ICP4 deletion results in the removal of the upstream promoter sequences of two additional immediate early viral genes: ICP22 and ICP47 (FIG. 19).

Payload

Viral vectors in accordance with the present disclosure contain a nucleic acid molecule comprising the payload of the vector. In some embodiments, a payload comprises a nucleic acid molecule that encodes a protein. In some embodiments, a payload comprises a nucleic acid molecule that comprises a sequence complementary to a nucleic acid sequence that encodes a protein. In some embodiments, a payload encodes a nucleic acid molecule that is regulatory. In some embodiments, a payload encodes a small interfering RNA (siRNA) polynucleotide. In some embodiments, a payload encodes a micro RNA (miRNA) polynucleotide.

In some embodiments, the payload is a nucleic acid molecule that encodes a protein that is exogenous to the target tissue or subject to which the vector is administered. In some embodiments, the payload is a nucleic acid molecule that encodes a protein that is endogenous to the target tissue or subject to which the vector is administered. In some embodiments, a nucleic acid molecule is codon optimized.

Regulatory Elements

The inclusion of non-native regulatory sequences, gene control sequences, promoters, non-coding sequences, introns, or coding sequences in a nucleic acid of the present disclosure is contemplated herein. The inclusion of nucleic acid tags or signaling sequences, or nucleic acids encoding protein tags or protein signaling sequences, is further contemplated herein. Typically, the coding region is operably linked with one or more regulatory nucleic acid components.

A promoter included in a nucleic acid of the present disclosure can be a tissue- or cell type-specific promoter, a promoter specific to multiple tissues or cell types, an organ-specific promoter, a promoter specific to multiple organs, a systemic or ubiquitous promoter, or a nearly systemic or ubiquitous promoter. Promoters having stochastic expression, inducible expression, conditional expression, or otherwise discontinuous, inconstant, or unpredictable expression are also included within the scope of the present disclosure. A promoter of the present disclosure may include any of the above characteristics or other promoter characteristics known in the art.

Examples of known promoters include, but are not limited to, the cytomegalovirus (CMV) promoter CMV/human beta 3 globin promoter GFAP promoter, chicken beta actin (CBA) promoter the β-glucuronidase (GUSB) promoter and ubiquitin promoters such as those isolated from human ubiquitin A, human ubiquitin B, and human ubiquitin C.

In some embodiments, a promoter is a neuron specific promoter in that it is a promoter having specific expression in neurons, preferential expression in neurons, or that typically drives expression of an associated coding sequence in neurons or a subset of neurons but not in one or more other tissues or cell types. Examples of such promoters include calcitonin gene-related peptide (CGRP), synapsin I (SYN), calcium/calmodulin-dependent protein kinase II, tubulin alpha I, neuron-specific enolase, microtubule-associated protein IB (MAPI B), and platelet-derived growth factor beta chain promoters, as well as derivatives thereof. In some embodiments, the promoter is a calcitonin gene-related peptide (CGRP) promoter or derivative thereof.

Other regulatory elements may additionally be operatively linked to the payload, such as an enhancer and a polyadenylation site. In some embodiments, an enhancer comprises a human cytomegalovirus (HCMV) sequence. In some embodiments, a polyadenylation site comprises a bovine growth hormone (BGH) polyadenylation signal.

In some embodiments, a promoter is a chimeric of one or more promoters or regulatory elements found in nature. In some embodiments, the viral vectors comprise a payload whose expression is driven by a CGRP promoter with an HCMV enhancer sequence.

Preparation of Vectors

The present disclosure relates particularly to McKrae strain viral vectors that are replication defective. In some embodiments, viral vectors are generated by deletion or disruption of one or more immediate early genes. Viral genes may be deleted or disrupted using methods of recombinant technology known in the art. In some embodiments a viral vector of the present disclosure may be rendered replication defective as a result of a homologous recombination event. In some embodiments, replication defective viral vectors are generated by deletion of an ICP4 gene. In some embodiments, replication defective viral vectors are generated by deletion of an ICP4 gene and deletion of a promoter for one or more other immediate early genes (e.g., ICP22 and/or ICP47).

In some embodiments, viral vectors of the present disclosure are generated by deletion of loci encoding one or more ICPs (e.g., ICP4) through homologous recombination. In some embodiments, generation of a viral vector of the present disclosure includes a step of homologous recombination of a first plasmid with a second plasmid. In some embodiments, the first plasmid contains nucleic acid sequences homologous to regions of an HSV genome that are adjacent to a nucleic acid region of an HSV genome that is intended to be replaced. In some embodiments, the second plasmid contains an HSV genome, or fragment thereof. In some embodiments, the first plasmid contains nucleic acid sequence encoding a gene of interest between the homologous nucleic acid sequences. In some embodiments, the gene of interest may be or include a marker protein that is detectable by fluorescence, chemiluminescense, or other property, which can be used to select for vectors resulting from successful homologous recombination.

In some embodiments, a viral vector of the present disclosure is generated by homologous recombination of a first plasmid containing a nucleic acid sequence homologous to regions upstream of the ICP4 promoter including the viral origin contained within the short inverted repeat regions of HSV, with a second plasmid containing an HSV McKrae strain genome.

In some embodiments, a vector is made by first replacing both copies of the ICP4 loci by homologous recombination using plasmid SASB3 and screening for green fluorescent protein (GFP)-expressing plaques. In some embodiments, a plasmid is constructed by cloning the Sph I to Afl III (Sal I linkered) fragment (1928 bp) of the HSV-1 KOS strain genome (nucleotides 124485-126413) into Sph I/Sal I digested pSP72 followed by insertion of the 695 bp Bgl II to BamH I fragment (nucleotides 131931 to 132626) containing regions upstream of the ICP4 promoter including the viral origin contained within the short inverted repeat regions into the Bgl 11 to BamH I sites of the vector plasmid. In some embodiments, a plasmid is constructed by cloning a HCMV-eGFP fragment in the BamHI site of a plasmid as described above. In some embodiments, a plasmid as described above is then recombined into a specific locus of a wild-type McKrae virus. In some embodiments, the resulting vector is isolated using a stable cell line that expresses one or more genes deleted or disrupted in the HSV genome that are required for replication.

In some embodiments, a vector is made by first replacing both copies of the ICP4 loci by homologous recombination using plasmid SDAXB and screening for green fluorescent protein (GFP)-expressing plaques. In some embodiments, a plasmid is constructed by cloning the Sph I to Afl III fragment (1928 bp) of the HSV-1 KOS strain genome (nucleotides 124346 to 126273 of accession KT899744) into Sph I/Afl III digested pSP72 to make SDA followed by changing the Afl III site to a BamHI site (SDAB). A BamHI to Bgl II DNA PCR fragment containing regions upstream of the ICP4 promoter including the viral origin (nucleotides 144933 to 145534 of accession JQ730035) contained within the short inverted repeat regions was cloned into the BamHI site of SDAB to make SDAXB. In some embodiments, a plasmid is constructed by cloning a HCMV-eGFP fragment in the BamHI site of a plasmid as described above. In some embodiments, a plasmid as described above is then recombined into a specific locus of a wild-type McKrae virus. In some embodiments, the resulting vector is isolated using a stable cell line that expresses one or more genes deleted or disrupted in the HSV genome that are required for replication.

Characterization of Vectors

Viral vectors in accordance with the present disclosure can be characterized by genomic sequencing in order to determine if the expected vector was successfully created. Any method of sequencing known in the art is acceptable for this purpose. Methods of sequencing include, for example, nanopore sequencing, single molecule real time sequencing (SMRT), DNA nanoball (DNB) sequencing, pyrosequencing and using DNA arrays.

The expression of a payload from a viral vector can be detected by any method known in the art for detecting proteins or nucleic acids. Methods of detecting protein expression include immunohistochemistry, flow cytometry, Western blotting, enzyme-linked immunosorbent assay (ELISA), immune-electron microscopy, individual protein immunoprecipitation (IP), protein complex immunoprecipitation (Co—IP), chromatin immunoprecipitation (ChIP), RNA immunoprecipitation (RIP), immunoelectrophoresis, spectrophotometry, and bicinchoninic acid assay (BCA). Methods of detecting nucleic acid expression include Southern blotting, Northern blotting, polymerase chain reaction (PCR), quantitative PCR, and RT-PCR.

In some embodiments, the present disclosure provides methods for testing the ability of viral vectors to transduce neurons. In some embodiments, the neurons are peripheral neurons. In some embodiments, the neurons are sensory neurons. In some embodiments, the neurons comprise dorsal root ganglia (DRG).

In some embodiments, a viral vector preparation may be injected into the one or more dermatomes corresponding to a section of DRG for example, the left and right L4, L5, and L6 DRG. DRG are removed are removed and DNA is isolated from the DRG and analyzed for vector genome copies using a qPCR assay that targets a sequence within HSV-1. In some embodiments, a qPCR assay targets a sequence within the HSV-1 glycoprotein ($U_L$-22) gene Applications/Uses Viral vectors in accordance with the present disclosure are useful for a wide variety of therapeutic applications. In some embodiments, vectors as described herein are useful to deliver one or more payloads to one or more target cells. In some embodiments, target cells reside in tissues that are poorly vascularized and difficult to reach by systemic circulation. In some embodiments, target cells are cells susceptible to infection by HSV. In some embodiments, target cells are particularly susceptible to infection by a McKrae strain of HSV. In some embodiments, target cells are or include one or more of neuronal cells. In some embodiments, target cells are dorsal root ganglion (DRG) cells.

Gene Therapy

Viral vectors in accordance with the present disclosure are useful in any context in which gene therapy is contemplated. For example, viral vectors comprising a heterologous nucleic acid segment operably linked to a promoter are useful for any disease or clinical condition associated with reduction or absence of the protein encoded by the heterologous nucleic acid segment, or any disease or clinical condition that can be effectively treated by expression of the encoded protein within the subject. Viral vectors that contain an expression cassette for synthesis of an RNAi agent (e.g., one or more siRNAs or shRNAs) are useful in treating any disease or clinical condition associated with overexpression of a transcript or its encoded protein in a subject, or any disease or clinical condition that may be treated by causing reduction of a transcript or its encoded protein in a subject. Viral vectors that comprise an expression cassette for synthesis of one or more RNAs that self-hybridize or hybridize with each other to form an RNAi agent targeted to a transcript encoding a cytokine may be used to regulate immune system responses (e.g., responses responsible for organ transplant rejection, allergy, autoimmune diseases, inflammation, etc.). Viral vectors that provide a template for synthesis of one or more RNAs that self-hybridize or hybridize with each other to form an RNAi agent targeted to a transcript of an infectious agent or targeted to a cellular transcript whose encoded product is necessary for or contributes to any aspect of the infectious process may be used in the treatment of infectious diseases.

Administration

Compositions comprising viral vectors as described herein may be formulated for delivery by any available route including, but not limited to parenteral (e.g., intravenous), intradermal, subcutaneous, oral (e.g., inhalation), transdermal (topical), transmucosal, rectal, and vaginal. Preferred routes of delivery include intradermal. In some embodiments, pharmaceutical compositions include a viral vector in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. In some embodiments, viral vectors are formulated in glycerol. In some embodiments, viral vectors are formulated in approximately 10% glycerol in phosphate buffered saline.

It is advantageous to formulate compositions in dosage unit form for ease of administration and uniformity of dosage. Dosage unit form as used herein refers to physically discrete units suited as unitary dosages for the subject to be treated; each unit containing a predetermined quantity of a viral vector calculated to produce the desired therapeutic effect in association with a pharmaceutical carrier.

The pharmaceutical composition can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a viral vector can include a single treatment or, in many cases, can include a series of treatments.

Compositions

In some embodiments, the active agents, i.e., a viral vector of the disclosure and/or other agents to be administered together with a viral vector of the disclosure, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. In some embodiments the composition is targeted to particular cell types or to cells that are infected by a virus.

Combination Therapy

According to the present disclosure, provided compositions may be administered in combination with one or more other active agents and/or therapeutic modalities, such as known therapeutic agents and/or independently active biologically active agents. In some embodiments, provided compositions include one or more such other active agents; in some embodiments, such other active agents are provided as part of distinct compositions. In some embodiments, combination therapy involves simultaneous administration of one or more doses or units of two or more different active agents and/or therapeutic modalities; in some embodiments, combination therapy involves simultaneous exposure to two or more different active agents and/or therapeutic modalities, for example through overlapping dosing regimens.

In some embodiments, provided compositions include or are administered in combination with one or more other active agents useful for the treatment of the relevant disease, disorder and/or condition.

EXAMPLES

Example 1: Assay for Assessment of Transduction of DRG

This Example shows an exemplary method for assaying transduction of viral vectors in dorsal root ganglion (DRG) tissue.

Subsequent to intradermal administration of a viral vector, L4, L5, and L6 DRG are removed and vortexed, with inversion, for 40 seconds in a pre-chilled Lysing Matrix A tube (MP Biomedicals) with 350 µL of a 0.5% Reagent DX (Qiagen) in Buffer RLT Plus/DTT solution.

DNA and RNA are isolated from the sample homogenate using the AllPrep DNA/RNA Mini Kit (Qiagen). The RNA isolation portion includes an on-column DNase treatment step. The DNA is eluted in 2×190 µL of UltraPure Distilled Water (Invitrogen) after a 10-15 minute room temperature incubation per elution. The RNA is eluted in 2×30 µL of RNase-free water* after a 3 minute room temperature incubation per elution. The DNA is concentrated by open incubation at 37° C. overnight.

Ten (10) µL of concentrated DNA is analyzed in a 50-µL reaction for HSV vector genomes by a qPCR assay that targets a region in the $U_L22$ (glycoprotein H) gene.

For mRNA expression analyses, 8 µL of RNA first undergoes reverse transcription using the SuperScript™ III First-Strand Synthesis SuperMix for qRT-PCR (Invitrogen) followed by RNase treatment. The RNase-treated cDNA can then be analyzed by any of a number of qPCR assays that target either a particular transgene (e.g., payload transcript), the stable 2 kb LAT intron, or the 5' LAT exon.

Example 2: Comparison of Nerve Transduction Capabilities of Different HSV Strains This example demonstrates that a McKrae strain vector transduces neurons more effectively than a KOS strain vector.

Two different wild-type strains of HSV-1 (McKrae and KOS) were prepared and injected into the dorsum and plantar surface of the right and left hind feet of three Sprague-Dawley (SD) rats each, at 100 µL per injection. All animals were euthanized five days after vector injection. During the terminal procedures, the left and right L4, L5, and L6 dorsal root ganglia (DRG) were removed, frozen at −70° C., and shipped on dry ice.

DNA was isolated from the left L4-L6 DRG of all animals in the study using a QIAamp DNA Mini Kit (Qiagen). The sample DNA was analyzed for vector genome copies using a qPCR assay that targets a sequence within the HSV-1 glycoprotein H (UL-22) gene on a Rotor-Gene Q Real-Time PCR Cycler (Qiagen). As shown in Table 1, McKrae strain appears to transduce the neurons significantly better than the KOS strain. The mean genome copy number detected in the DRG of the KOS group was 73, while that of the McKrae group was 21,347.

TABLE 1

| Strain | Name | Ct | Calc Conc (Copies) | Mean Ct | Mean Ct SD | Mean Calc Conc | Total DF | Total Sample Genomes |
|---|---|---|---|---|---|---|---|---|
| KOS | 5a1R A1G1 L-DRG | 35.27 | 7.00E±00 | 35.31 | 0.06 | 7.00E±00 | 20 | 1.40E±02 |
|  | 5a1R A1G1 L DRG | 35.36 | 6.00E±00 |  |  |  |  |  |
| KOS | 5a1R A2G1 L-DRG | 36.10 | 4.00E±00 | 36.05 | 0.07 | 4.00E±00 | 20 | 8.00E±01 |
|  | 5a1R A2G1 L DRG | 36.01 | 4.00E±00 |  |  |  |  |  |
| KOS | 5a1R A3G1 L-DRG | 37.15 | 2.00E±00 | 37.15 |  | 2.00E±00 | 34.97 | <LOQ |
|  | 5a1R A3G1 L-DRG |  |  |  |  |  |  |  |
| Mck | 5a1R A4G2 L-DRG | 37.31 | 2.00E±00 | 36.43 | 1.25 | 3.00E±00 | 40.65 | <LOQ |
|  | 5a1R A4G2 L ORG | 35.54 | 6.00E±00 |  |  |  |  |  |
| Mck | 5a1R A5G2 L-DRG | 26.73 | 1.95E±03 | 26.74 | 0.01 | 1.94E±03 | 32.89 | 6.38E±04 |
|  | 5a1R A5G2 L DRG | 26.74 | 1.93E±03 |  |  |  |  |  |
| Mck | 5a1R A6G2 L-DRG | 35.23 | 7.00E±00 | 34.79 | 0.61 | 9.00E±00 | 28.57 | 2.57E±02 |
|  | 5a1R A6G2 L-DRG | 34.36 | 1.20E±01 |  |  |  |  |  |

| Name | Ct | Calc Conc (Copies) | Mean Ct | Mean Ct SD | Mean Calc Conc | Spk (Cop) | % Recovery |
|---|---|---|---|---|---|---|---|
| 5aS2 A2G1 L-DRG | 36.93 | 2 | 37.22 | 0.42 | 2 | <LOQ |  |
| 5aS2 A2G1 L-DRG | 37.52 | 2 |  |  |  |  |  |
| 5aS2 A2G1 L-DRG spk-25 | 32.67 | 38 | 32.79 | 0.18 | 35 | 25 | 140% |
| 5aS2 A2G1 L-DRG spk-25 | 32.92 | 32 |  |  |  |  |  |

LOQ: Ct = 36.34

Example 3: Preparation of Vectors

This example describes methods of preparing and formulating exemplary vectors for gene therapy.

Genetic Structure of Vector

A vector is made by first replacing both copies of the ICP4 loci by homologous recombination using a plasmid and screening for marker element expressing plaques. A plasmid is constructed by cloning a fragment of a HSV-1 genome comprising regions upstream of the ICP4 promoter including the viral origin contained within the short inverted repeat regions. The plasmid is further modified by cloning a marker element, for example HCMV-eGFP, fragment into the plasmid. This plasmid is then recombined into the ICP4 locus of a wild-type HSV virus. The resulting vector is isolated using a stable ICP4 expressing Vero cell line, such as '6-5C'. Vero 6-5C cells are complementing cells that express ICP4.

In order to replace the marker element (e.g., GFP) with a gene of interest (GOI) in the vector described above, a plasmid is constructed by cloning HCMV-GOI-pA into the plasmid. Plaques which do not express the marker element are isolated and tested by ELISA for GOI expression Production of Crude Vector ICP4 complementing Vero cells are cultured in tissue culture flasks using complete media (DMEM supplemented with FBS, HEPES, and Pen Strep) and expanded into 6-12×T175 flasks at a seeding density of $3-4\times10^4$ cells/cm$^2$. The culture flasks are incubated at 37° C./7.5% $CO_2$ for 3-4 days.

When cells are 1-2 days over confluent, they are infected at a multiplicity of infection (MOI) of ~0.1 with a virus stock of known concentration. The infection is initiated by removing the culture supernatant from each flask and infecting with a total of 2.5 mL of complete media containing the appropriate amount of a virus stock. The virus is adsorbed on the cell monolayers by incubating the cultures for 1.5-2 hours, shaking and rotating the flasks every 15-20 minutes. After the adsorption step, an additional 10 mL of complete medium is added to each flask and the cultures are incubated again at 37° C./7.5% $CO_2$.

Approximately 48 hours after initiating the infection, the flasks are viewed by microscope to confirm cells show signs of cytopathogenic effect and detachment from the flask surface. At that point the cells and supernatant are harvested, pooled together, and centrifuged at ~1500×g for ~10 min. The supernatant is removed from the cell pellet and held separately for later processing.

The cell pellet is resuspended in 4-5 mL of complete media, homogenized, and then frozen at –80° C. After the cell suspension has been frozen for >20 minutes, it is thawed and centrifuged at ~1500×g for ~10 min. This second cell pellet supernatant is removed and combined with the first collected supernatant.

The pooled supernatant is aliquoted into centrifuge tubes. The virus is then centrifuged at ~40,000×g for ~30 minutes at 2-8° C. in order to pellet the virus. After the centrifugation step is completed, the supernatant from the tubes is removed and discarded. The following day the virus pellets are homogenized by pipetting and pooled together. The resuspended virus stock is then aliquoted into cryovials typically at volumes of ~120 µL per vial. Complete medium (200-300 µL) is added to the virus pellets in order to cover them with liquid and are stored at 2-8° C. overnight to loosen the virus particles. The vials are labeled and frozen at –80° C. Later, a frozen vial is thawed in order to perform a virus plaque titration assay to determine the concentration of the prepared virus stock prior to using in any in vivo or in vitro studies.

Manufacture of Clarified Vector

Cell Thaw and Expansion

Vero cells (e.g., Vero 6-5, VeroD cells) from a working cell bank are thawed at 37° C. and transferred to a conical tube and pooled. VeroD cells are complementing cells that express or ICP4, ICP27, and UL55. The cells are vialed at approximately $1.0\times10^7$ viable cells/mL/tube. The cells are gradually diluted with complete medium and a sample is removed to obtain viable cell counts. The cells are plated in tissue culture flasks at a density of $3.0-5.0\times10^4$ cells/cm$^2$.

The cells are incubated at 37° C., 7.5%; $CO_2$ and examined periodically by phase microscopy. The cells are passaged while subconfluent. The complete medium is removed, rinsed with PBS, and the cells are dissociated. The flasks are incubated until the cells detach, then they are re-suspended in complete medium, pooled, counted and seeded into new flasks at a density between $1.0-4.0\times10^4$ cells/cm$^2$. The cells are expanded and allowed to extend to 1-2 days post-confluence prior to infection.

Infection with Vector

When the cells reach the desired confluence, a model flask is subcultured and the cells are counted to estimate the number of cells per cell factory A master virus bank vector inoculum is prepared by thawing the appropriate volume required to obtain a multiplicity of infection (MOI) of 0.1 and diluting the stock with complete medium up to the target volume desired for the infection. The cell factories are infected by an initial adsorption period followed by incubation for the first day of infection in complete medium. After approximately 24 hours, the culture medium is removed and replaced with an equal volume of serum-free medium. The cell factories are placed in the incubator and the temperature is reduced to 33° C./with 7.5% $CO_2$. The cultures are monitored daily and the percent cytopathic effect estimated by visual inspection.

Crude Viral Harvest and Clarification

The infection is stopped by placing the cell factories in a biosafety cabinet and pooling the supernatant and cell debris into a sterile bag. This bulk unclarified harvest is sampled for adventitious agents. After sampling, the sodium chloride level of the harvest is increased and then it is mixed. The harvest is then aliquoted into centrifuge tubes and the cell debris removed by centrifugation. The supernatant is pooled into a sterile bag. After pre-treatment of a clarification filter capsule with sterile water, the virus-containing supernatant is then pumped through the filter capsule into another sterile bag, followed by sterile water to recover remaining virus in the capsule. The bag is mixed and the filtrate was stored overnight at 4° C.

Afterwards, the filtrate is warmed and adjusted to ~2 mM $MgCl_2$ by addition of 2 volumes of 3 mM $MgCl_2$ in sterile water. The diluted filtrate is mixed and treated with an endonuclease.

Cation Exchange Column Chromatography

A BPG 400 column is packed with SP high performance resin, sanitized with 0.5N NaOH and equilibrated with wash buffer (PBS pH 7.0) and strip buffer (1M NaCl—PBS pH 7.0) before loading endonuclease treated virus.

The process bag containing the endonuclease-treated filtrate is connected to the inlet using a tubing welder and the virus is loaded onto the column. The flow through is collected in a sterile bag. The virus capture step is followed by washing with PBS until the UV absorbance returns to baseline. The pump is stopped and a process bag containing 0.45 M NaCl—PBS (pH 7.0) is connected to the inlet. The outlet tubing is transferred to a sterile container in a biosafety cabinet. The buffer is pumped into the column and when the UV absorbance begins to increase sharply, the column outlet is transferred to a new sterile container to collect the eluted virus. The collection is stopped after the UV absorbance returns to near baseline. This is the purified viral elute fraction. A process bag containing strip buffer is connected to the inlet and the end of the outlet tubing is transferred into a sterile bottle to collect the strip fraction. The buffer is pumped through the column until UV absorbance reaches a peak and returns to near baseline. The collected elute is stored at 4° C. overnight.

Tangential Flow Filtration

The tangential-flow filtration system, using a 0.1 micrometer pore size hollow fiber filter cartridge is prepared by assembling the tubing and cartridge and sterilizing the system by autoclaving. The system is flushed with sterile PBS (pH 7.0) and the virus eluate fraction is added to the system reservoir and equilibrated by recirculation. After equilibration, the permeate collection pump is turned on and filtrate is collected. The system is run until the loaded volume is reduced to approximately 500 ml. The retentate in the reservoir is diluted with DPBS (pH 7.0) with continuous constant volume diafiltration, and the product in the retentate is recovered when the permeate conductivity is within 10% f the diafiltering buffer (DPBS pH 7.0).

Formulation, Final Filtration and Packaging

The recovered retentate is adjusted to 10% final volume with sterile glycerol and mixed well prior to filtering through a 0.45 μm disc filter unit. The product is dispensed into labeled cryovials for storage at ≤−65° C.

Example 4: Analysis of Transduction of McKrae Strain in DRG after Paw Injection This example demonstrates that administration of a McKrae strain-based vector results in transduction of dorsal root ganglia (DRG) in vivo.

A replication-defective HSV-1 vector as described above was injected into the footpad of rats. As shown in FIG. 1, a replication-defective HSV-1 vector can transduce the DRG neurons in a dose-dependent manner (five days after injection). The ordinate shows a portion of the total number of genomes detectable under assay conditions and indicates that the number of genomes increases relative to dose of vector injected.

Figure 2:
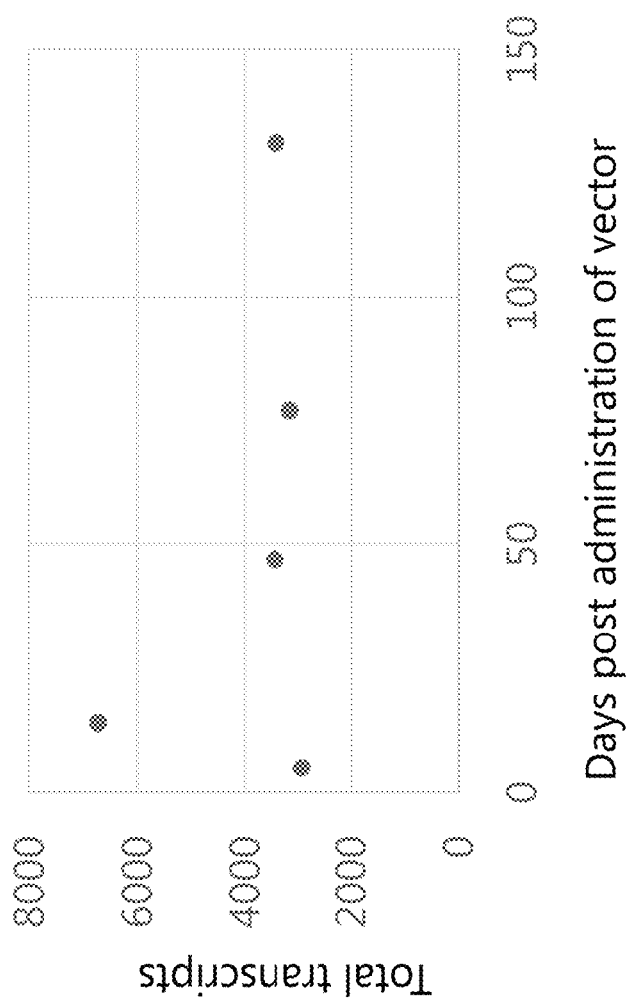
FIG. 2 depicts an exemplary graph that shows the total number of transcripts of payload in L4-L6 DRG at 5, 14, 47, 77, and 131 days post administration with HSV viral vectors having a HCMV promoter.
Figure 3:
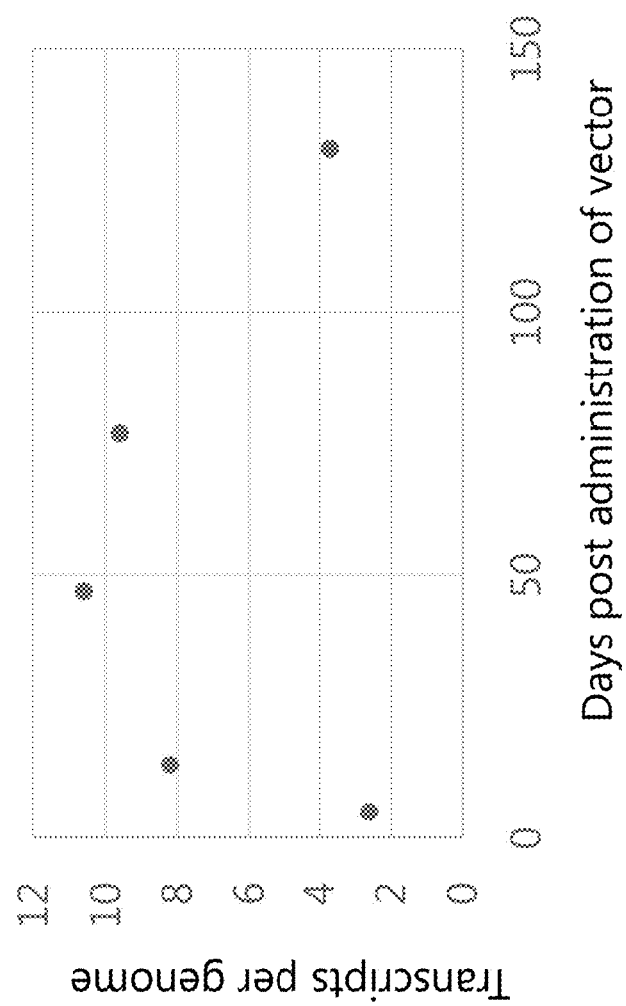
FIG. 3 depicts an exemplary graph that shows the number of transcripts of payload per genome in L4-L6 DRG at 5, 14, 47, 77, and 131 days post administration with HSV viral vectors having a HCMV promoter.

FIG. 2 shows the total number of transcripts of a payload in DRG at 5, 14, 47, 77, and 131 days after injection into the footpad of a rodent. FIG. 3 shows the data from the same experiment as number of transcripts of payload per genome. Expression of the payload was driven by the HCMV promoter.

Example 5: Analysis of Transduction and Expression of Payload with Different Promoters This example demonstrates increased gene expression can be obtained in DRG using a neuron specific promoter.

Figure 4:
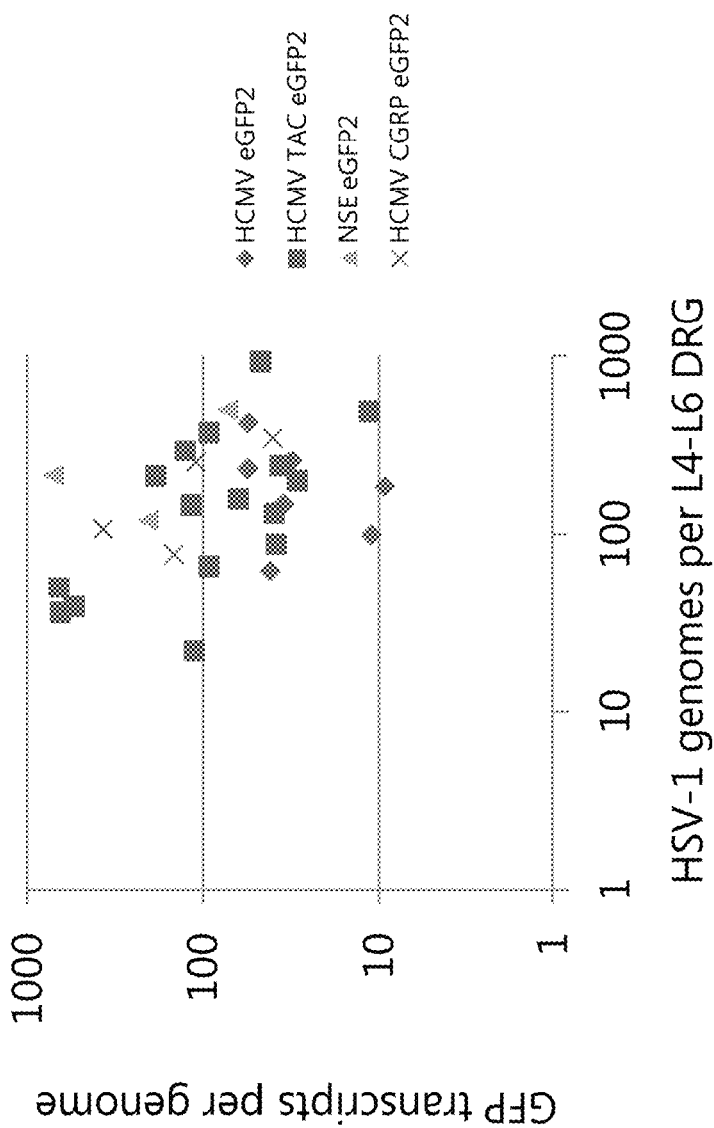
FIG. 4 depicts an exemplary graph that shows the number of GFP transcripts per genome and the number of HSV-1 genomes per L4-L6 DRG as a result of administering viral vectors with different promoters.

Four different promoters (HCMV, HCMV TAC, NSE and HCMV CGRP) were tested for efficacy in delivering HSV-1 vectors to DRG. The vector comprising a NSE promoter did not have a CMV enhancer, just a neuron-specific promoter. As shown in FIG. 4, a vector with an HCMV promoter averaged 29 transcripts per genome in DRG, while HCMV TAC, NSE and HCMV CGRP promoters averaged 176, 327 and 166 transcripts per genome, respectively.

Figure 5:
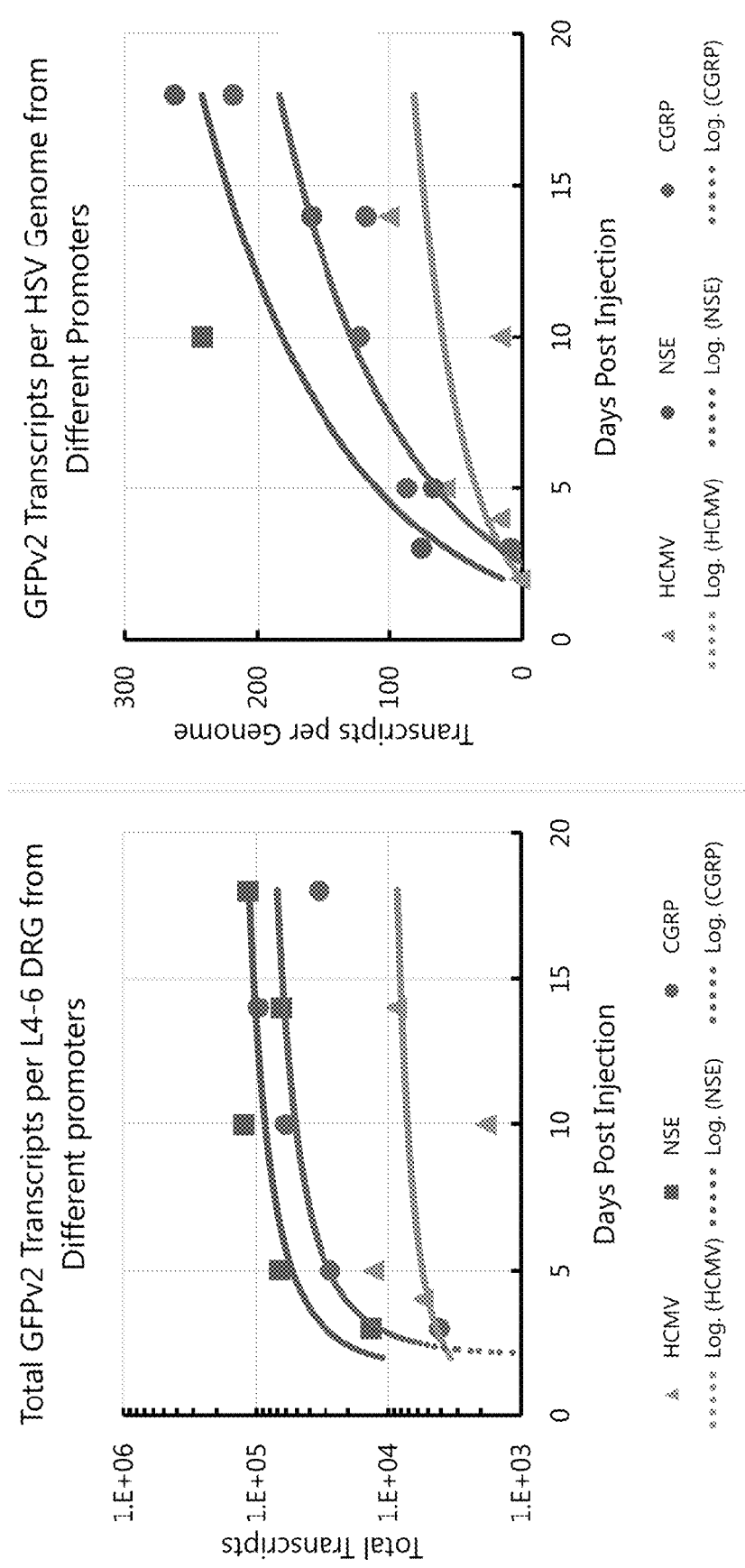
FIG. 5 depicts an exemplary graph that shows the total number of GFP transcripts and total transcripts per genome in L4-L6 DRG over 18 days after administration of HSV viral vectors with tissue specific promoters.

McKrae viral vectors comprising Green Fluorescent Protein (GFP) operatively linked to HCMV, NSE, or CGRP promoters were injected into the footpad of rats and GFP transcripts were measured in L4-L6 DRG over time. As shown in FIG. 5, tissue specific promoters improved transcription in DRG neurons between 5 and 18 days after footpad inoculation.

Figure 6:
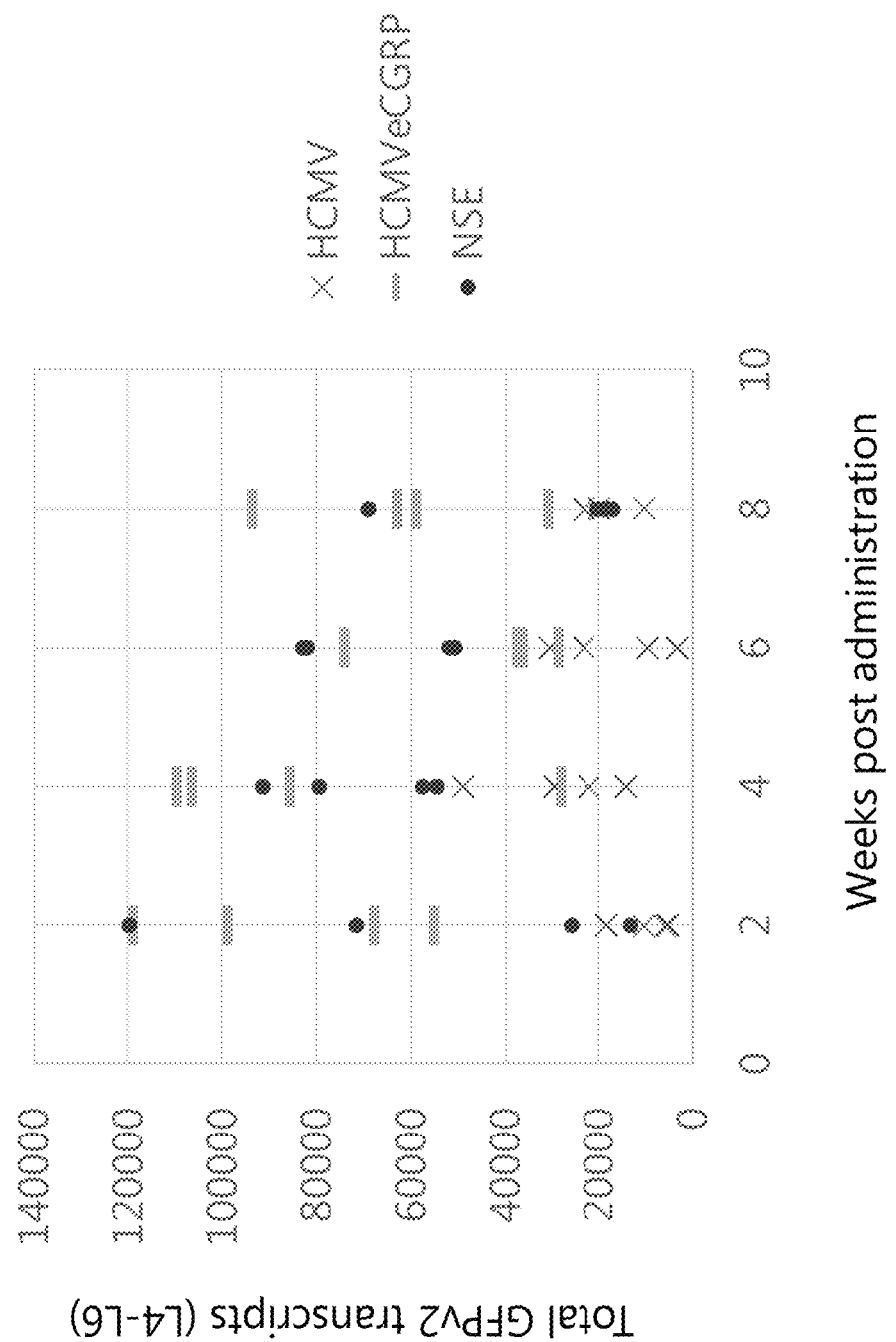
FIG. 6 depicts an exemplary graph that shows the number of total GFP transcripts in L4-L6 DRG over 8 weeks after administration of HSV viral vectors with tissue specific promoters.
Figure 7:
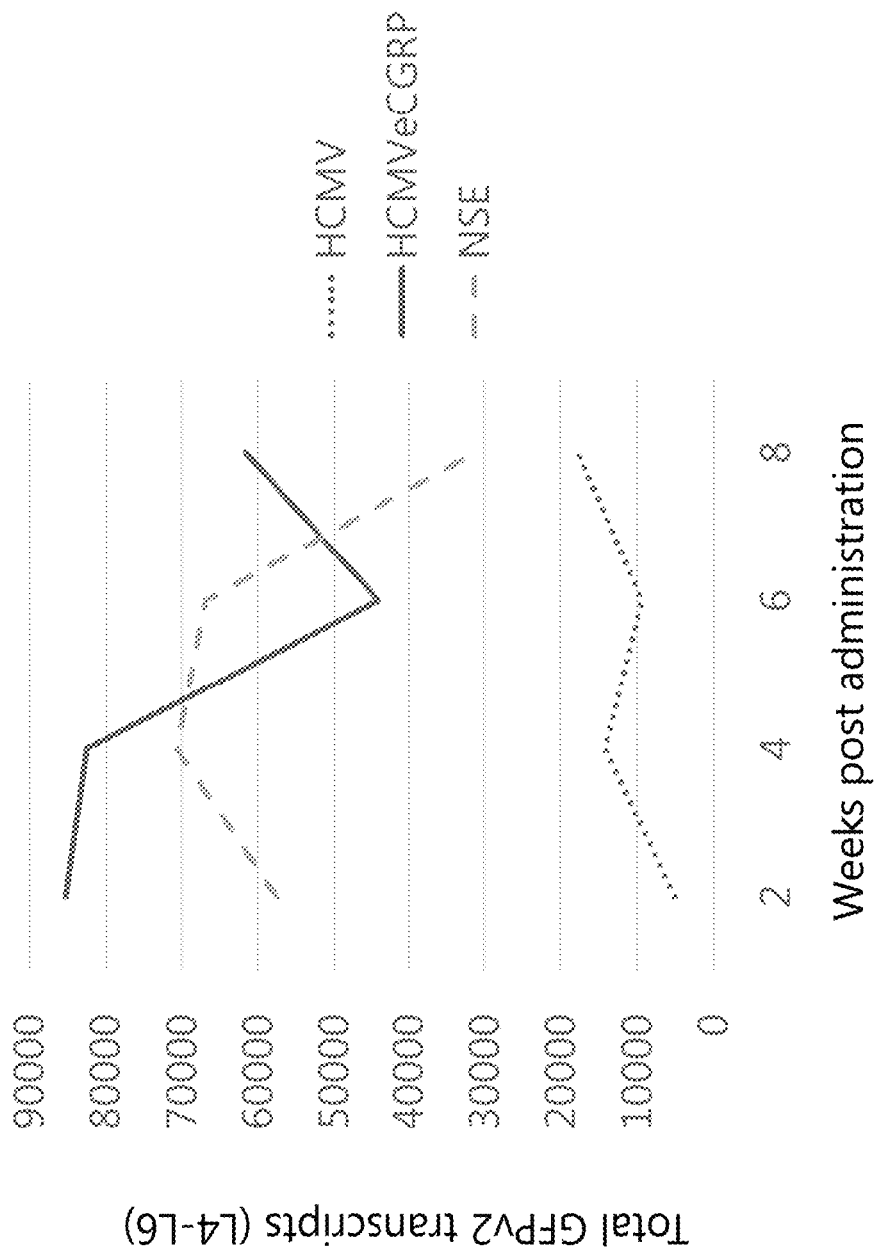
FIG. 7 depicts an exemplary graph that shows the total number of GFP transcripts in L4-L6 DRG over 8 weeks after administration of HSV viral vectors with tissue specific promoters.

Additionally, when three different promoters (HCMV, HCMVeCGRP and NSE) were compared over time (2-8 weeks), vectors containing either a NSE or HCMVeCGRP promoter resulted in more total transcripts in DRG than a vector containing a HCMV promoter (see FIGS. 6 and 7).

Figure 8:
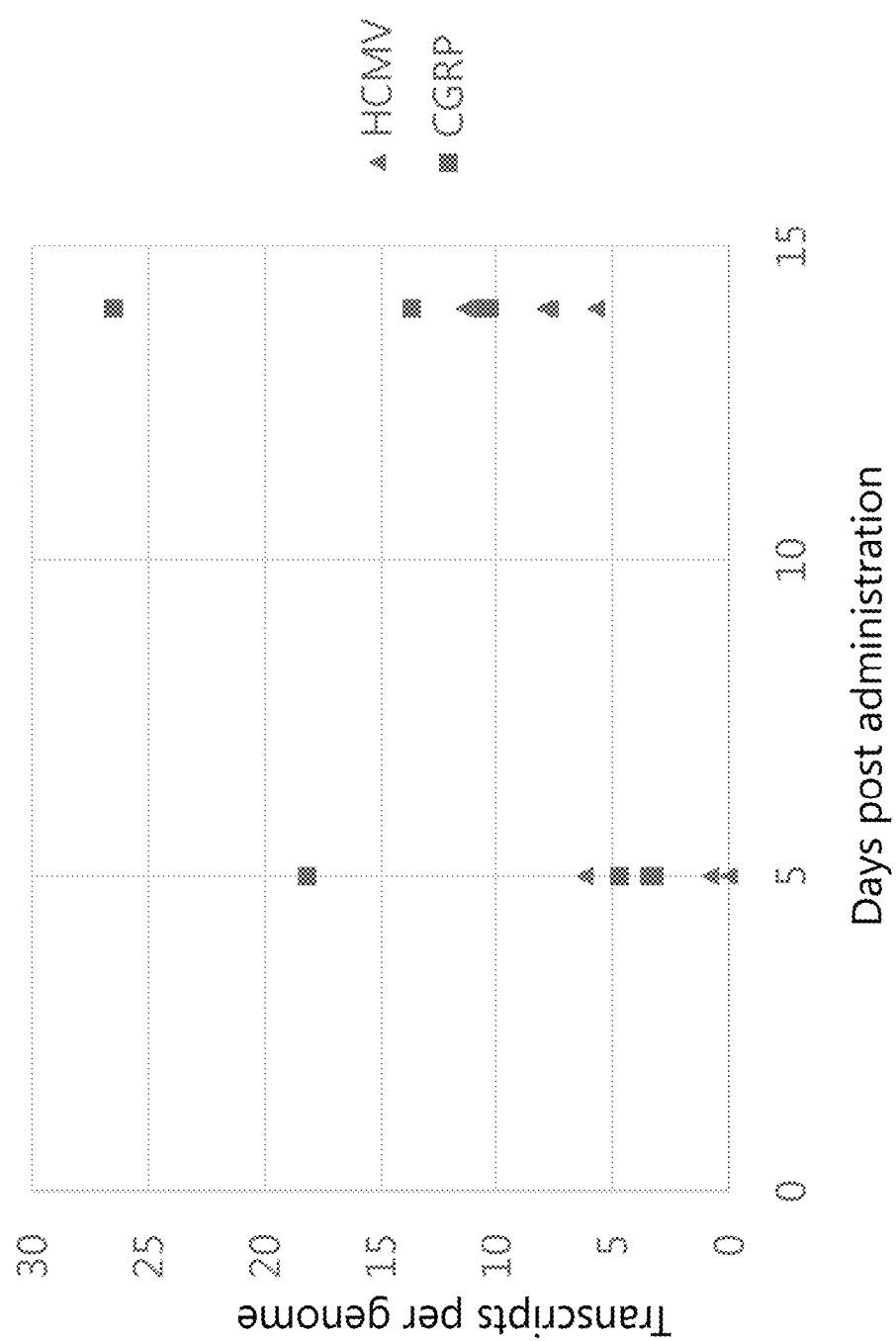
FIG. 8 depicts an exemplary graph that shows the total number of transcripts of payload per genome in L4-L6 DRG after administration with HSV viral vectors having a human cytomegalovirus (HCMV) promoter compared to HSV viral vectors having a chimeric calcitonin gene-related peptide (CGRP) promoter with an HCMV enhancer.

Transcripts of payload were measured in DRG of rats receiving an injection of a McKrae viral vector comprising a polypeptide payload operatively coupled to a CGRP chimeric promoter or an HCMV promoter. As measured at 5 and 14 days post-injection, the CGRP promoter, comprising an HCMV enhancer upstream of the promoter, showed higher transcript numbers of the polypeptide payload per genome than the HCMV promoter (FIG. 8).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

SEQUENCE LISTING

```
Sequence total quantity: 19
SEQ ID NO: 1            moltype = DNA  length = 151135
FEATURE                 Location/Qualifiers
misc_difference         61968..62069
                        note = n is a, c, g, or t
source                  1..151135
                        mol_type = genomic DNA
                        note = human herpesvirus 1 strain McKrae
                        organism = unidentified
SEQUENCE: 1
gcagcccggg ccccccgcgc gcggggcggc gcgcaaaaaa ggcgggcggc ggtccgggcg   60
gcgtgcgcgc gcgcggcggg cgtgggggc ggggccgcgg gagcggggga ggagcccac   120
ccacagacgg ggaggagcgg gggaggagcg ggggaggagc ggggggaggag ccccacccac  180
agacggggag gagcggggga ggagcggcca gaccccaaaa acgggccccc ccgaaacaca  240
cccccgggg gtcgcgcgcg gccctttaaa gcgcggcggc gggcagcccg ggccccccgc   300
ggccgagact agcgagttag acaggcaagc actactcgcc tctgcacgca catgcttgcc  360
tgtcaaactc taccacccg gcacgctctc tgtctccatg gcccgccgcc gccgccatcg   420
cggccccgc cgcccccggc cgcccgggcc cgccgcgcc gtcccaaccg cacagtccca   480
ggtaacctcc acgcccaact cggaaccccgc ggtcaggagc gcgcccgcgg ccgcccgcc  540
gccgcccccc gccggtgggc ccccgccttc ttgttcgctg ctgctgcgcc agtgctcca   600
cgttcccgag tccgcgtccg acgacgacga tgacgacgac tggccggaca gcccccgcc   660
cgagccggcg ccagaggccc ggcccaccgc cgccgccccc cggcccggt ccccaccgcc    720
cggcgtgggc ccggggggcg gggctgaccc ctcccacccc ccctcgccgc ccttccgcct   780
tccgccgcgc ctcgccctcc gcctgcgcgt caccgcggag cacctggcgc gcctgcgcct  840
gcgacgcgcg ggcggggagg gggcgccgga gcccccgcg accccccgcga ccccgcgac   900
ccccgcgacc cccgcgaccc ccgcgacccc cgcgaccccc gcgaccccg cgcgggtgcg   960
cttctcgccc cacgtccggg tgcgccacct ggtggtctgg gcctcggccg cccgcctggc  1020
gcgccgcggc tcgtgggccc gcgagcgggc cgaccgggct cggttccggc gccgggtggc  1080
```

```
ggaggccgag gcggtcatcg ggccgtgcct ggggcccgag gcccgtgccc gggccctggc    1140
ccgcggagcc ggcccggcga actcggtcta acgttacacc cgaggcgcct gggtcttccg    1200
cggagctccc gggagctccg caccaagccg ctctccggag agacgatggc aggagccgcg    1260
catatatacg ctgggagccg gtccgccccc aaggcgggcc cgcctcgggg gcgggactgg    1320
ccaatcggcg gccgccagcg cggcgggggcc cggccaacca gcgtccgccg agtcttcggg    1380
gcccggccca ttgggcggga gttaccgccc aatgggccgg gccgcccact tcccggtatg    1440
gtaattaaaa acttgcaaga ggccttgttc cgcttcccgg tatggtaatt agaaactcat    1500
taatgggcgg ccccggccgc ccttcccgct tccggcaatt cccgcggccc ttaatgggca    1560
accccggtat tccccgcctc ccgcgccgcg cgtaaccact ccctcggggt tccgggttat    1620
gctaattgct tttttggcgg aacacacggc ccctcgcgca ttggcccgcg ggtcgctcaa    1680
tgaacccgca ttggtcccct ggggttccgg gtatggtaat gagtttcttc ggggaaggcgg    1740
gaagccccgg ggcaccgacg caggccaagc ccctgttgcg tcgcgggag gggcatgcta    1800
atggggttct ttggggggaca ccgggttggt cccccaaatc ggggccggg ccgtgcatgc    1860
taatgatatt cttttggggc gccgggttgg tccccgggga ccccgcggtggg             1920
cctgcctccc ctgggacgcg cggccattgg gggaatcgtc actgccgccc ctttggggag    1980
gggaaaggcg tgggggtataa gttagccctg gcccgacggt ctggtcgcat ttgcacctcg    2040
gcactcggag cgagacgcag cagccaggca gactcgggcc gcccccctctc cgcatcacca    2100
cagaagcccc gcctacgttg cgaccccccag ggaccctccg tccgcgaccc tccagccgca    2160
tacgaccccc atggagcccc gcccggagc gagtacccgc cggcctgagg gccgccccca    2220
gcgcgagtg aggggccggg cgccatgtct gggcgccat attgggggc gccatgttgg    2280
gggacccccg acccttaccc tggaaccggc ccccatgttg ggggaccccc actcatacac    2340
gggagccggg cgccatgttg gggcgccatg ttaggggggg tggaaccccg tgacactata    2400
tatacaggga ccgggggcgc catgttaggg ggcgcgaac ccctgaccc tatatataca    2460
gggaccgggg tcgccctgtt gggggtcgcc atgtgacccc ctgactttat atatacagac    2520
ccccaacaca tacacatggc ccctttgact cagacgcagg gcccggggtc gccgtgggac    2580
ccctgactc atacacagag acacgccccc acaacaaaca cagggacc gggtcgccg    2640
tgttgggggc gtggtcccca ctgactcata cgcaggcccc ccttactcac acgcatctag    2700
gggggtgggg aggagccgcc cgccatattt ggggacgcc gtgggacccc cgactccggt    2760
gcgtctggag ggcgggagaa gagggaagaa gaggggtcgg gatccaaagg acggacccag    2820
accaccttg gttgcagacc cctttctccc ccctcttccg aggccagcag ggggggcagga    2880
ctttgtgagg cgggggggga gagggggaac tcgtggcgc tgattgacgc gggaaatccc    2940
ccccccattct tacccgcccc ccttttttcc ccttagcccg ccccgatgt ctgggtgttt    3000
ccctgcgacc gagacctgcc ggacagcagc gactctgagg cggagaccga agtggggggg    3060
cgggggggacg ccgaccacca tgacgacgac tccgcctccg aggcggagac cacggacacg    3120
gaactgttcg agacggggct gctggggccg cagggcgtgg atggggggc ggtctcgggg    3180
gggagccccc ccgcgagga agaccccggc agttgcgggg gcgcccccc tcgagggac    3240
gggggagcg acgagggcga cgtgtgcgcc gtgtgcacgg atgagatcgc gccccacctg    3300
cgctgcgaca ccttccccgtg catgcaccgc ttctgcatcc cgtgcatgaa aacctggatg    3360
caattgcgca acaacctgcc cgctgtgcaac gccaagctgc tgtacctgat agtgggcgtg    3420
acgcccagcg ggtcgttcag caccatcccg atcgtgaacg acccccagac ccgcatggag    3480
gccgaggagg ccgtcagggc gggcacggcc gtggactttta tctggacggg caatcagcgg    3540
ttcgccccgc ggtacctgac cctggggggg cacacggtga gggcccctgtc gcccaccac    3600
ccggagccca ccacggacga ggatgacgac gacctggacg acggtgaggc gggggggccg    3660
aaggaccctg ggggaggagg aggaggggag aatgggcggg cggcgagga aagggcgggc    3720
cggggagggg gcgtaacctg atcgcgcccc ccgttgtctc ttgcagcaga ctacgtcccg    3780
cccgccccc gccggacgcc ccgcgccccc ccacgcagag gcaccgccgc gccccccgtg    3840
acgggcgggg cgtctaacgc agccccccag ccggccgggg ctcggacgga gcccccctcg    3900
gcgcccatcg ggccacacgg cagcagtaac accaacacca ccaccaacag cagccggcgg    3960
ggcggctccc gccagtcgcg agccgcgcg ccgggggggg cgtctggccc ctccgggggg    4020
gttgggggttg gggttgggt tgttgaagcg gaggcgggggc ggccgagggg ccggacgggc    4080
ccccttgtca acagacccgc ccccccttgca aacaacagga accccatagt gatcagcgac    4140
tccccccgg cctctcccca caggcccccc gcggcgccca tgccaggctc cgccccccgc    4200
cccgggcccc ccgcgtcctc ggccgcgtcg ggacccgcgc gccccccgcg ggccgtggcc    4260
ccgtgcgtgc gagcgccgcc tccggggccc gggccccgcg ccccgccccc cggggcggag    4320
ccggccgccc gcccgcggga cgccggccgt gtgccccagt cgcactcgtc cctggctcag    4380
gccgcgaacc aagaacagag tctgtgccgg gcgcgtgcga cggtggcgcg cggctcgggg    4440
gggccggggc tggaggtggg gcacgggccc tcccgcggcc gcacccctc cggcgccgcc    4500
ccgctcccct ccgccgtctc tgtcgagcag gaggcggcgg tgcgtccgag gaagaggcgc    4560
gggtcgggcc aggaaaaccc ctccccccag tccacgcgtc ccccctcgc gccggcagga    4620
gccaagaggg cggcgacgca cccccccctcc gactcaggc cgggggggcg cggccagggt    4680
gggcccggga ccccctgac gtcctcggcg gcctccgcct cttcctcctc tgcctcttcc    4740
tcctcggccc cgaccccgc gggggccgcc tcttccgccg ccgggggccgc gtcctcctcc    4800
gcttccgcct cctcggcgg ggccgtcggt gccctggag ggagacaaga ggaaacctcc    4860
ctcggcccccc gcgctgcttc tgggcgcgg gggccgagga agtgtgccgg gaagacgcgc    4920
cacgcggaga cttccggggc cgtccccgcg ggcggcctca cgcgctacct gcccatctcg    4980
ggggtctcta gcgtggtcgc cctgtcgcct tacgtgaaca agactatcac ggggggactgc    5040
ctgcccatcc tggacatgga gacggggaac atcggggcgt acgtggtcct ggtggaccag    5100
acgggaaaca tggcgacccg gctgcgggcc gcggtccccg gctggagccg ccgcaccctg    5160
ctccccgaga ccgcgggtaa ccacgtgatg ccccccgagt accgacgcc ccccgtcg    5220
gagtggaaca gcctctggat gaccccccgtg gggaacatgc tgttcgacca gggcacccta    5280
gtgggcgccc tggacttccg cagcctgcgg tctcggcacc cgtggtccgg ggagcagggg    5340
gcgtcgaccc gggacgaggg aaaacaataa gggacgcccc ccgtgtttgt ggggaggggg    5400
gtcgggtgct gggtggtctc tggccgcgcc cactacacca gccaatccgt gtcggggagg    5460
ggaaagtgaa agacacgggc accacacacc agcgggtctt tagtgttggc cctaataaaa    5520
aactcagggg attttttgctg tctattggga aataaaggtt tacttttgta tcttttccct    5580
gtctgtgttg gatggatctt gggggtcgct gggagtgggg gtgcgtggga gtggggtgc    5640
gtgggagtgg gggtgcgtgg gagtggggg cgtgggagt ggggtgcgt gggagtgggg    5700
gtgcgtggga gtggggtgc gtgggagtgg ggtgcgtggg gagtggggt gcgtgggagt    5760
gggggtgcgt gggagtgggg gtgcgtggga gtggggtgc gtgggagtgg gggtgccatg    5820
```

```
ttgggcaggc tctggtgtta accacagagc cgcggcccgg gctgcctgac caccgatccc   5880
cgaaagcatc ctgccactgg catgagccaa gaaccacagt gggctgggtg tgggtgttaa   5940
gtttccgcga gcgcctgccc gcccggactg acctggcctc tggccgccac aaagggcggg   6000
ggggggggtta actacactat agggcaacaa aggacgggag gggtggcggg acggggcgcc   6060
caaaagggggg tcggccacac cacagacgtg ggtgttgggg ggtggggcag aggggtgggg   6120
gggagacaga aacaggaaca tagttagaaa acaagaatgc ggtgcagcca gagaatcaca   6180
ggagacgagg ggatgggcgt gttggttacc aacccacacc caggcatgct cggtggtatg   6240
aaggaggggg ggcggtgctt cttagagacc gccggggac gtggggttgg tgtgcaaagg   6300
cacgcgcacc cgcgtcggcc aggtgggccg gtaccccatc cccccctccc ccgacccttc   6360
ccccccgcg tgccagagat cacccccgtc ccccggcacc cgccactcct ccatatcctc   6420
gctttaggaa caactttggg gggggggtac acacgcgccg tgcatttcct tccacccccc   6480
ccctcccccg catcccccc cccaggcagt aagacccaag catagagagc caggcacaaa   6540
aacacaggcg gggtgggaca catgccttct tggagtacgt gggtcattgg cgtgggggt   6600
tacagcgaca ccggccgacc ccctggcggt cttccagccg gcccttagat aaggggggcag   6660
ttggtggtcg gacgggtaag taacagagtc tgactaaggg tgggagggg ggaaaagaac   6720
gggctggtgt gctgtaacac gagcccaccc gcgagtggcg tggccgacct tagcctctgg   6780
ggcgccccct gtcgtttggg tccccccccc tctattgggg agaagcaggt gtctaaccta   6840
cctggaaacg cggcgtcttt gttgaacgac accggggcgc cctcgacgag tggataacg   6900
gggggaggaag ggagggagga gggtactggg ggtgaagaag gggggggga agaagcgaga   6960
acaggaaagg cgacggagcc cggcagaaca ccgaggaaaa aaaaaacaca gcgcatgcgc   7020
cgggccgttg tgggccccg ggccggggcc ccttgggtcc gccggggccc cgggccgggc   7080
cgccacgggg gccggccgtt ggcggtaacc ccgattgttt atctcaggcc ccggggccggg   7140
aacccggaaa agcctccggg gggcctttt cgcgtcgcgt gccggcgagc gggcccggac   7200
ggggcccgga ccgccgcggt cggggccccc tcgtcccggg ccgtacgcgg ccttcgcccc   7260
gtgagggggcc gaacgaacga aacatcccgg cgacggaacg aaaaacaccc cagacggggtt   7320
taaaaaacag aaaccgtaac ccccccccacc cccgaaacgg ggaaaacaaa aaacagacca   7380
gcggccggcc ggcgcttagg gggaggatgt gccgacgcc ccttggccgc cccggctgca   7440
ggggggcccg gagagccgcg gcacccggac gcgcccggaa agtctttcgc caccccgcg    7500
atcggcacgg ccgcgccccc gcttttataa aggctcagat gacgcagcaa aaacaggcca   7560
cagcaccacg tgggtaggtg atgtaatttt attttcctcg tctgcggcct aatggatttc   7620
cgggcgcggt gccctgtct gcagagcact taacggattg atatctcgcg ggcacgcgcg   7680
cccttaatgg accggcgcgg ggcgggggc cggatccca cacgggcggg ggggtgtcgc   7740
gggccgtctg ctgcccgcg gccacataaa caatgactcg gggcctttct gcctctgccg   7800
cttgtgtgtg cgcggccgg ctctgcggtg tcggcgcgg ctgcggcggc tgcggcggcc   7860
gccgtgttcg gtctcggtag ccggccggcg ggtggactcg gagggtgggaa   7920
ggcagggggg tgtaggatgg gtatcaggac ttccacttcc cgtccttcca tccccgttc   7980
ccctcggttg ttcctcgcct cccccaacac cccgccgctt tccgttgggg ttgttattgt   8040
tgtcgggatc gtgcgggccg ggggtcgccg gggcagggc ggggggcggg gtgctcgtcg   8100
atcgaccggg ctcagtgggg gcgtgggggtg ggtgggaaaa gcgaggaga ctggggtggg   8160
gggtgtcggg ggtggctgtt ttttttgtggt tgttttttgt gtctgttccc gtcccccgtc   8220
accccccctcc ctccgtcccc ccgtcgcggg tgtttgtgtt tgtttattcc gacatcggtt   8280
tattttaaata aacacagccg ttctgcgtgt ctgttcttgc gtgtggctgg gggcttatat   8340
gtggggtccc gggggcgggga tgggggtttag cggcggggggg cggcgcgcg gacggggcgc   8400
tggagataac ggcccccggg gaacggggga ccggggctgg gtctcccgcg gtgggtgggt   8460
gggcggcggt ggccgggccg ggccgggccg ggtgggcggg gtttgaaaaa acgaggagga   8520
ggagaaggag gaggagggg ggggagacgg ggggaaagca aggacacggc cccgggggg    8580
gggggacgcg ggccggggccg cttggcaacc ccctgttttc ttccggaaac caggcttggg   8640
gccccacccg acatcacaag ggacctcttg tcgggcctcc cgacgtacgc cgaggctatg   8700
tcggaccacc ccccaaccta agaggggaga ggggagaggg gagaggggag aggggagagg   8760
ggagagggga ggagagggg tatataaacc aacgaaaagc gcgggaacgg ggatacgggg   8820
cttgtgtggc acgacgtcgt ggttgtgtta ctgggcaaac acttgggggac tgtaggtttc   8880
tgtggtgccg accctaggcg ctatgggggat tttgggttgg gttgggctta ttgccgttgg   8940
ggttttgtgt gtgcggggg gcttgccttc aaccgaatat gttattcgga gtcgggtggc   9000
tcgagaggtg ggggatatat taaaggtgcc ttgtgtgccg ctcccgtctg acgatcttga   9060
ttggcgctac gagaccccct cggctataaa ctatgctttg atagacggta tattttcg    9120
ttatcactgt cccggattgg acacggtctt gtgggatagg cacgcccaga gggcgtattg   9180
ggttaacccc tttttgtttg gggcgggttt tttgaggac ttgagtcatc ccgcgttcc    9240
tgccgacacc caggaaacag aaacgcgctt ggccccttat aaagagatac gccaggcgct   9300
ggacagtcgc aagcaggccg ccagccacac acctgtgaag gggcggtgtg tgaactttga   9360
ctattcgcgc acccgcgct gtgtagggcg ccaggatttg ggacttacca acagaacgtc   9420
tggacgacc ccggttctgc cgtcggacga tgaagcgggc ctgcagccga agcccctcac   9480
cacgccgtcg cccatcatcg ccacgtcgga cccacccccg cgacgggacg ccgccacaaa   9540
aagcagacgc cgacgacccc attcccgcgc catctaatga tgcctcgacg gaaaaccgtc   9600
cgggtttggg gggcgaaccg gccgcctgtc gctcgtcagg ccgggcggc gctcctcgcc    9660
gccctagagg ctgtcccgct ggtgtgacgt tttcctcgtc cgcgccccc gaccctccca   9720
tggatttaac aaacgggggg gtgtcgcctg cggcgacctc ggcgcctctg gactggacca   9780
cgtttcggcg tgtgtttctg atcgacgacg cgtggcggcc cctgttggag cctgagctgg   9840
cgaaccccctt aaccgcccac ctcctggccg aatataatcg tcggtgccag accgaagagg   9900
tgctgcccgc gcggaggat gtgttttcgt ggactcgtta ttgcaccccc gacgaggtgc   9960
gcgtggttat catcggccag gacccatatc accaccccgg ccaggcgcac ggacttgcgt  10020
ttagcgtgcg cgcgaacgtg ccgcctcccc cgagtcttcg gaatgtcttg gcggccgtca  10080
agaactgtta tcccgaggca cggatgagcg gccacggttg cctggaaaag tgggcgcggg  10140
acggcgtcct gttactaaac acgaccctga ccgtcaagcg cggggcggcg cgtcccact   10200
ctagaatcgg ttgggaccgc ttcgtgggcg gagttatccg ccggttcgct gcgcgccgcc  10260
ccggcctggt gtttatgctc tggggcgcac atgcccagaa tgccatcagg ccggaccctc  10320
gggtccattg cgtcctcaag ttttcgcacc cgtcgcccct ctcaaggtt ccgttcggaa   10380
catgccagca tttcctcgtg gcgaatcgat atctcgagac ccggtcgatt tcacccatcg  10440
actggtcggt ttgaaaggca tcgacgtccg gggttttcgt ctgtggggc ttttgggtat    10500
ttccgatgaa taaagacggt taatggttaa acctctggtc tcatacgggt cggtgatgtc  10560
```

```
gggcgtcggg ggagagggag ttccctctgc gcttgcgatt ctagcctcgt ggggctggac   10620
gttcgacacg ccaaaccacg agtcagggat atcgccagat acgactcccg cagattccat   10680
tcgggggggcc gctgtggcct cacctgacca acctttacac gggggccegg aacgggaggc   10740
cacagcgccg tctttctccc caacgcgcgc ggatgacggc ccgccctgta ccgacgggcc   10800
ctacgtgacg tttgataccc tgtttatggt gtcgtcgatc gacgaattag ggcgtcgcca   10860
gctcacggac accatccgca aggacctgcg gttgtcgctg gccaagttta gcattgcgtg   10920
caccaagacc tcctcgtttt cgggaaacgc cccgcgccac cacagacgcg gggcgttcca   10980
gcgcggcacg cgggcgccgc gcagcaacaa aagccttcag atgtttgtgt tgtgcaaacg   11040
cgcccacgcc gctcgagtgc gagagcagct tcgggtcgtt attcagtccc gcaagccgcg   11100
caagtattac acgcgatctt cggacggggcg gctctgcccc gccgtccccg tgttcgtcca   11160
cgagttcgtc tcgtccgagc caatgcgcct ccaccgagat aacgtcatgc tggcctcggg   11220
ggccgagtaa ccgcccccc cccgcgccac cctcactgcc cgtcgcgcgt gtttgatgtt   11280
aataaataac acataaattt ggctggttgt ttgttgtctt taatgaccg cccgcagggg   11340
gggtggcatt tcagtgtcgg gtgacgagcg cgatccggcc gggatcctag gaccccaaaa   11400
gtttgtctgc gtattccagg gcggggctca gttgaatctc ccgcagcacc tctaccagca   11460
ggtccgcggt gggctggaga aactcggccg tcccggggca ggcggtcgtc gggagtggag   11520
gcgcggcgcc caccccgtgt gccgcgcctg gcgtctcctc tgggggcgac ccgtaaatgg   11580
ttgcagtgat gtaaatggtg tccgcagtcc agaccacggt caaaatgccg gccgtggtgc   11640
tccgggcgct ttcgccgcgc gaggagctga cccaggagtc gaacggatac gcgtacatat   11700
gggcgtccca cccgcgttcg agcttctggt cgctgtcccg gcctataaag cggtaggcac   11760
aaaattcggc gcgacagtcg ataatcacca acagcccaat gggggtgtgc tggataacaa   11820
cgcctccgcg cggcaggcgg tcctggcgct cccggcctcg taccataatc gcgcgggtgc   11880
cgtactcaaa aacatgcacc acctgcgcgg cgtcgggcag tgcgctggtc agcgaggccc   11940
tggcgtggca taggctatac gcgatggtcg tctgtggatt ggacatctcg cggtgggtag   12000
tgagtccccc gggccgggtt cggtagaact gtaagggaga ggcgggttaa tagacaatga   12060
ccacgttcgg atcgcgcaga gccgatagta tgtgctcact aatgacgtca tcgcgctcgt   12120
ggcgctcccg gagcggattt aagttcatgc gaaggaattc ggaggaggtg gtgcgggaca   12180
tggccacgta cgcgctgttg aggcgcaggt tgccgggcgt aaagcagatg gcgaccttgt   12240
ccaggctaag gccctgggag cgcgtgatgg tcatggcaag cttggagctg atgccgtagt   12300
cggcgtttat ggccatggcc agctccgtag agtcaatgga ctcgacaaac tcgctgatgt   12360
tggtgttgac gacggacatg aagccgtgtt ggtcccgcaa gaccacgtaa ggcaggggg   12420
cctcttccag taactcggcc acgttggccg tcgcgtgccg cctccgcagc tcgtccgcaa   12480
aggcaaacac ccgtgcgtac gtgtatccca tgagcgtata attgtccgtc tgcagggcga   12540
cggacatcag cccccccgcg ggcgagccgg tcagcatctc gcagccccgg aagataacgt   12600
tgtccacgta cgtgctaaag ggggcgcctt caaatgcctc cccgaagagc tcttggagga   12660
ttcggaatct cccgaggaag gcccgcttca gcagcgcaaa ctgggtgtga acggcggcgg   12720
tggtctccgg ttccccgggg gtgtagtggc agtaaaacac gtcgagctgt tgttcgtcca   12780
gcccccgcgaa aataacgtcg aggtcgtcgt cgggaaaatc gtccgggccc ccgtcccgcg   12840
gccccagttg cttaaaatca aacgcacgct cgccgggggc gcctgcgtcg gctattaccg   12900
acgcctgcgt cggcgccccc gaagatttgg ggcgcagaga cagaatctcc gccgttagtt   12960
ctcccatgcg ggcgtaggcg agggtcctct ggctcgcatc caggcccggg cgctgcagaa   13020
agttgtaaaa ggagataagc ccgctaaata tgagccgcga caggaacctg taggcaaact   13080
ccaccgaagt ctccccctga gtctttacaa agctgtcgtc acgcaacact gcctcgaagg   13140
cccggaacgt cccactaaac ccaaaaacca gttttcgcag gcgcgcgtc accgcgatct   13200
ggctgttgag gacgtaagtg acgtcgttgc gggccacgac cagctgctgt ttgctgtgca   13260
cctcgcagcg catgtgcccc gcgtcctggt cctggctctg cgagtagttg gtgatgcggc   13320
tggcgttggc cgtgagccac ttttcaatag tcaggccggg ctggtgtcg agccgtcggt   13380
attcgtcaaa ctccttgacc gacacgaacg taagcacggg gagggtgaac acgacgaact   13440
cccccctcacg ggtcaccttc aggtaggcgt ggagcttggc catgtacgcg ctcacctctt   13500
tgtgggagga aacagccgc gtccagccgg ggaggttggc gggttggtg atgtagcttt   13560
ccgggacgac gaagcgatcc acgaactgca tgtgctcctc ggtgatgggc aggccgtagt   13620
ccagcacctt catgaggtta ccgaactcgt gctcgacgca ccgtttgttg ttaataaaaa   13680
tggcccagct atacgagagg cgggcgtact cgcgcagcgt gcggttgcag atgaggtacg   13740
tgagcacgtt ctcgctctgg cggacggaac accgcagttt ctggtgctcg aaggtcgact   13800
ccaggacgc cgtctgcgtc ggcgagccca cacacaccaa cacggggcgc aggcgggccg   13860
catactgggg ggtgtggtac agggcgttaa tcatccacca gcaatacacc acggccgtga   13920
ggaggtgacg cccaaggagc ccggcctcgt ctatgacgat cacgttgctg cgggtaaagg   13980
ccggcagcgc cccgtgggtg gccggggcca accgcgtcag ggcgccctcg ccaaccccca   14040
gggtccgttc cagggcggcc agggcggaa actcgttccg cgactcctcg cccccggagg   14100
cggccagggc gcgcttcgtg aggtccaaaa tcacctccca gtagtacgcc agatctcgtc   14160
gctgcaggtc ctccagcgag gcggggttgc tggtcagggt gtacgggtac tgtcccagtt   14220
gggcctggac gtgattcccg cgaaacccaa attcatgaaa gatggtgttg atgggtcggc   14280
tgagaaaggc gcccgagagt ttggcgtaca tgttttgggc cgcaatgcgc gtggcgcccg   14340
tcaccacaca cttccaagacc tcgttgattg tctgcacgca cgtgctcttt ccggagccag   14400
cgttgccggt gataagatac accgcgaacg gaaactccct gaggggcagg cctgcggggg   14460
actcaaggc cgccacgtcc cggaaccact gcagacgggg cacttgcgct ccgtcgagct   14520
gttgttgcga gagctctcgg atgcgcttaa ggattggctg caccccgtgc atagacgtaa   14580
aatttaaaaa ggcctcggcc ctccctggaa cggctggtcg gtcccggggt tgctgaaggt   14640
gcggcgggcc gggtctcgt ccgtctagct ggcgctcccc gccggccgcc gccatgaccg   14700
caccacgctc gcgggccccc actacgcgtg cgcgggggga cacggaagcg ctgtgctccc   14760
ccgaggacgg ctgggtaaag gttcacccca ccccggtac gatgctgttc cgtgagattc   14820
tccacggcca gctggggtat accgagggcc aggggtgta caacgtcgtc cggtccagcg   14880
aggcgaccac ccggcagctg caggcggcga tctttcacgc gctcctcaac gccaccacttt   14940
accgggacct cgaggcggac tggctcggcc acgtgcggc cctctgctg cagccccaac   15000
ggctggttcg ccggtacagg aacgcccggg aggcggatat cgccggggtg gccgagcggg   15060
tgttcgacac gtgcggaac acgcttagga cgacgctgct ggactttgcc cacgggttgg   15120
tcgcctgctt tgcccgggc ggcccagcg gccgtcaag cttccccaaa tatatcgact   15180
ggctgacgtg cctggggctg gtccccatat tacgcaagcg acaagaaggg ggtgtgacgc   15240
agggtctgag ggcgtttctc aagcagcacc cgctgacccg ccagctggcc acggtcgcgg   15300
```

```
aggccgcgga gcgcgccggc cccgggtttt ttgagctggc gctggccttc gactccacgc  15360
gcgtggcgga ctacgaccgc gtgtatatct actacaacca ccgccggggc gactggctcg  15420
tgcgagaccc catcagcggg cagcgcgag aatgtctggt gctgtggcct cccttgtgga   15480
ccggggaccg tctggtcttc gattcgcccg tccagcggct gtttcccgag atcgtcgcgt  15540
gtcactccct ccgggaacac gcgccacgct gccggctgca caataccgcg tccgtcaagg  15600
tgctgctggg gcgcaagagc gacagcgagc gcggggtggc cggcgccgcg cgggtcgtta  15660
acaaggtgtt gggggaggac gacgagacca aggccgggtc ggccgcctca cgcctcgtgc  15720
ggcttatcat caacatgaag ggcatgcgcc acgtaggcga cattaacgac accgtgcgtg  15780
cctacctcga cgaggccggg gggcacctga tagacgcccc ggccgtcgac ggtaccctcc  15840
ctggattcgg caagggcgga aacagccgcg ggtctgcggg ccaggaccag gggggcgggg  15900
cgccgcagct tcgccaggcc ttccgcacgg ccgtggttaa caacatcaac ggcgtgttgg  15960
agggctatat aaataacctg tttggaacca tcgagcgcct gcgcgagacc aacgcgggcc  16020
tggcgaccca attgcaggag cgcgaccgcg agctccggcg cgcaacagcg ggggccctgg  16080
agcgccagca gcgcgcggcc gacctggccg ccgagtccgt gaccggtgga tgcggcagcc  16140
gccctgcggg ggcggacctg ctccggggcg actatgacat tatcgacgtc agcaagtcca  16200
tggacgacga catgtacgtc gccaacagct ttcagcaccc gtacatccct tcgtacgccc  16260
aggacctgga gcgcctgtcg cgcctctggg agcacgagct ggtgcgctgt tttaaaattc  16320
tgtgtcaccg caacaaccag ggccaagaga cgtcgatctc gtactccagc ggggcgatcg  16380
ccgcattcgt cgcccctac tttgaggcag tgcttcgggc ccccgggta ggcgcgccca    16440
tcacgggctc cgatgtcatc ctggggggagg aggagttatg ggatgcgtg tttaagaaaa   16500
cctgcctgca aacgtacctg acagacatcg cggccctgtt cgtcgcggac gtccagcacg  16560
cagcgctgcc cccgccccc tcccccggtcg gccgattt ccggccccgg ccgtccccgc     16620
ggggccggtc cagatcgcgg tcgcccggaa gaactgcgcg aggcgcaccg gaccagggcg  16680
ggggcatcgg gcaccgggat ggccgccgcg acggccgacg atgaggggtc ggccgtcacc  16740
atcctcaagc aggccatcgc cggggaccgc agcctggtcg aggcggccga ggcgattagc  16800
cagcagagcg tgctccgcct ggcctgcgga gtgcgccagg tcggcgaccg ccagccgcgg  16860
tttaccgcca ccagcatcgc gcgcgtcgac gtcgcgcctg ggtgccggtt gcggttcgtt  16920
ctggacggga gtcccgagga cgcctatgtg acgtcggagg attactttaa gcgctgctgc  16980
ggccagtcca gttatcgcgg cttcgcgtg gcggtcctga cggccaacga ggaccacgtg   17040
cacagcctgg ccgtgccccc cctcgttctg ctgcaccggt tctccctgtt caaccccagg  17100
gacctcctgg actttgagct tgcctgtctg ctgatgtacc tggagaactg ccccccgaagc  17160
cacgccaccc cgtcgacctt tgccaaggtt ctggcgtggc tcggggtcgc gggtcgccgc  17220
acgtccccat tcgaacgcgt tcgctgcctt ttcatccgca gttgccactg gtcctaaac   17280
acactcatgt tcatggtgca cgtaaaaccg ttcgacgacg agttcgtcct gcccccactgg 17340
tacatggccc ggtacctgct ggccaacaac ccgccccccg ttctctcggc cctgttctgt  17400
gccaccccga cgagctcctc attccggctg ccggggccgc ccccccgctc cgactgcgtg  17460
gcctataacc ccgccgggat catggggagc tgctgggcgt cggaggaggt gcgcgcgcct  17520
ctggtctatt ggtggctttc ggagaccccaa aaacgacaga cgtcgtcgct gttttatcag  17580
ttttgttgaa ttttagtaaa taaaccggt tttgttttcta tggcctcctg acggatgcgc   17640
gtgtccttac tccgtttttgg tgggtgggtg gctgtgtatg gcgctcccatc tgtgcgggga  17700
ggggcaagt cggcacgtat tcggacagac tcaagcacac acgggggagc gctcttggct   17760
cagggcaatg ttttttattgg tcaaactcag gcaaacagaa acaacatctt gtcgtcaaag  17820
ggatacacaa acttccccccc ctcgcccccat actcccgcca cccccggt aaacaccaac    17880
tcaatctcgc gcaggatttc gcgcaggtga tgagcgcagt ccacggggg gagcacaagg    17940
ggccgcgggt atagatcgac ggggacgccg accgactccc cgcctccggg acagacacgc   18000
acgacgcgcc gccagtagtg ctctgcgtcc aacaaggcgc cgccgcggaa ggcagtgggg   18060
ggcaaggagt cgctggcctc aaagggggac accgaaccgc tccagtactc cgcgtccaac   18120
cgttatttaa acgcgtccac gataaggcgg tcgcaggcgt cctccataag gccccgggcc   18180
gtgagcgcgt cctcctccgg cacgcctgcc gttgtcaggc ccaggacccg tcgcagcgtg   18240
tcgcgtacga ccccggccgc cgtggtgtac gcgggcccgc ggagaggaaa tcccccaaga   18300
tggtcagtgt tgtcgcggga gttccagaac cacactcccg cttggctcca ggcgacgggg   18360
tgggtgtaga cgccctcgag cgccaggcac agtgggtgcc gcagccggga gccgttggcc   18420
ataagcacgg ctcccacggc cgtctcgatg gcccgccggg cgtcctcgat caccccggaa   18480
gccgcatccg cgtcttgggg gtccacgtta aagacacccc agaacgcacc cccatcgccc   18540
ccgcagaccg cgaacttaac cgagctggcc gtctcctcaa tctgcaggca gacggcggcc   18600
atcaccccgc ccaggagctg ccgcagcgca gggcaggcgt cgcacgtgtc cggggaccagg  18660
cgctccaaga cggcccggcc ccagggctct gagggagcgg ccaccaccag cgcgtccagt   18720
cttgctaggc ccgtccggcc gtggggttcc gccagcccgc tcccccgag gtcggccagg    18780
gccgccagga gctgggcgcg aagtccgggg aagcaaaacc gcgcgtgcca gacgggccgg   18840
acggccgcgg gcgggtctaa cagttggatg atttttagtgg cgggatgcca ccgcgccacc   18900
gcctcccgca ccgcgggcag gaggcatccg gctgccgccg aggccacgcc gggccaggct   18960
cgcgggggga ggacgaccct ggccccacc gcgggccagg ccccccagga gcgcggcgtaa  19020
gcggccgcgg ccccgcgcac caggtccgt gccgactcgg ccgtggccgg cacggtgaac    19080
gtgggccaac ccggaaaccc caggacggca aagtacggga cggtccccc ccggaccgca   19140
aactcgggcc ccagaaaggc aaagacgggg gccaggggccc cggggcggcc gtggaccgtg   19200
gtatgccact gccggaaaag ggcgacgagc gccggcgcgg agaacttctc gccggcgctt   19260
acaaagtagt cgtaatcgcg gggcagcagc acccgtgccg tgactcgttg cgggtgcccg   19320
cgtggccgca ggcccacctc gcacacctcg accaggtccc cgaacgctcc ctccttcttg   19380
atcggcggaa acgcaagagt ctggtattcg cgcgcaaata gcgcggttcc ggtggtgatg   19440
ttaacggtca gcgaagcggc ggacgcgcac tgggggggtgt cgcgaatggc cgccaggcgc   19500
gcccacgcca ccgcgcgtc gggatgctcg gcaacgcgcg ccgccagggc catagggtcg    19560
atgtcaatgt tggcctccgc gaccaggaga cggcgcgag gggcggcggg cgggcccac     19620
gacgctctct caactttcac caccagtccc gtgcgtgggt ccgagccgat acgcagcggg   19680
gcgaacaggg ccatccgccc cggggccgcg cccagcgacc accgacgacga gcgctacagc   19740
gcccacccaca gagtcgggtt ctccagggc tccagcgggg aggcggccgg cgtcgtcgcg     19800
gcgcgggcgg ccgccacgac ggcctggacg gagacgtccg cggagccgta gaaatcccgc   19860
agctccgtcg cggtgacgga gacctccgca agcgcgcgc gaccctcccc tgcggcgttg    19920
cgacatacaa aatacaccag ggcgtggaag tactcgcgag cgcggggggg cagccatacc   19980
gcgtaaaggg taatggcgct gacgctctcc tccacccaca cgatatctgc ggtgtccatc   20040
```

-continued

```
gcacggcccc taaggatcac gggcggtctg tgggtcccat gctgccgtgc ctggccgggc   20100
ccggtgggtc gcggaaaccg gtgacggggg gggcggttt ttggggttgg ggtgggggtg    20160
ggaaacggcc cggtccgggg ggccaacttg gccctcggt gcgttccggc aacagccgg     20220
ccggtccgcg gacgaccacg taccgaacga gtgcggtccc gagacttata gggtgctaaa   20280
gttcaccgcc ccctgcatca tgggccaggc ctcggtgggg agctccgaca gcgccgcctc   20340
caggatgatg tcagcgttgg ggttggcgct ggatgagtgc gtgcgcaaac agcgccccca   20400
cgcgggcacg cgtagcttga agcgcgcgcc cgcaaactcc cgcttgtggg ccataagcag   20460
ggcgtacagc tgcctgtggg tccggcaggc gctgtggtcg atgtggtggg cgtccaacaa   20520
ccccacgatt gtctgtttgg tgaggttttt aacgcgcgcc gccccgggaa acgtctgcgt   20580
gcttttggcc atctgcacgc caaacagttc gccccagatt atcttgaaca gcgccaccgc   20640
gtggtccgtc tcgctaacgg acccgcgcgg gggacagccg cttagggcgt cggcgacgcg   20700
cttgacggct tcctccgaga gcagaagtcc gtcggttacg ttacagtggc ccagttcgaa   20760
caccagctgc atgtagcggt cgtagtgggg ggtcagtagg tccagcacgt catcgggcc    20820
gaaggtcctc ccagatcccc cggccgccga gtccaatgc aggcgcgcgg ccatggtgct    20880
gcacaggcac aacagctccc agacggggggt tacgttcagg gtggggggca gggccacgag   20940
ctccagctct ccggtgacgt tgatcgtggg gatgacgccc gtggcgtagt ggtcatagat   21000
ccgccgaaat atggcgctgc tgcgggtggc catgggaacg cggagacagg cctccagcaa   21060
cgccaggtaa ataaaccgcg tgcgtcccat caggctgttg aggttgcgca tgaggcgac    21120
aatttccgcc ggcgcgacat cggaccggag gtatttttcg acgaaaagac ccacctcctc   21180
cgtctcggcg gcctgggccg gcagcgacgc ctcgggatcc cggcaccgca gctcccgtag   21240
atcgcgctgg gccctgaggg cgtcgaaatg tacgccccgc aaaaacagac agaagtcctt   21300
tggggtcagg gtatcgtcgt gtccccagaa gcgcacgcgt atgcagttta ggtcagcag    21360
catgtgaagg atgttaaggc tgtccgagag acacgccagc gtgcatctct caaagtagtg   21420
tttgtaacgg aatttgttgt agatgcgcga ccccgcccc agcgacgtgt cgcatgccga    21480
cgcgtcacag cgcccttga accggcgaca cagcaggttt tgacctggg agaactgcgc     21540
gggccactgg ccgcaggaac tgaccacgtg gttcaggagc atgggcgtaa agacgggctc   21600
cgagcgcgcc ccggagccgt ccatgtaaat cagtagctcc cccttgcgga gggtgcgcac   21660
ccgtcccagg gactggtaca cggacaccat gtccggtccg tagttcatgg gttcacgta    21720
ggcgaacatg ccatcaaagt gcaggggatc gaagctgagg cccacggtta cgaccgtcgt   21780
gtatataacc acgcggtatt ggccccacgt ggtcacgtcc cgagggggg tgagcgagtg    21840
aagcaacagc acgcggtccg taaactgacg gcagaaccgg gccacgatct ccgcgaagga   21900
gaccgtcgat gaaaaaatgc agatgttatc gcccccgcca aggcgcgctt ccagctcccc   21960
aaagaacgtg gccccccggg cgtcggaga ggcgtccgga acgggccgc ttggcggcc      22020
gggcgggcgc agggcagcct gcaggagctc ggtccccaga cgcgggagaa acaggcaccg   22080
gcgcgccgaa aacccgggca tggcgtactc gccgaccacc acatgcacgt tttttcgcc    22140
ccggagaccg cacaggaagt ccaccaactg cgcgttggcg gttgcgtcca tggcgatgat   22200
ccgaggacag gtgcgcagca ggcgtagcat taacgcatcc acgcggccca gttgctgcat   22260
cgttggcgaa tagagctggc ccagcgtcga cataacctcg tccgaacga ggacgtcgta    22320
gttgttcaga aggttgggc ccacgcgatg aaggcttcc acctggacga taagtcggtg    22380
gaaggggcgg tcgttcataa tgtaattggt ggatgagaag taggtgacaa agtcgaccag   22440
gcctgactca gcgaaccgcg tcgccagggt ctgggtaaaa ctccgacgac aggagacgac   22500
gagcacactc gtgtccggag agtggatcgc ttcccgcagc cagcggatca gcgcggtagt   22560
ttttcccgac cccattggcg cgcggaccac agtcacgcac ggcccgtcg ggcgctcgc    22620
gttggggaag gtgacgggtc cgtgctgctg ccgctcgatc gttgttttcg ggtgaacccg   22680
gggcacccat tcggccaaat ccccccgta caacatccgc gctagcgata cgctcgacgt    22740
gtactgttcg cactcgtcgt cccaatggg acgcccggcc cccagaggat ccccgactc    22800
cgcgccccc acgaaaggca tgaccggggc gcggacggcg tggtgggtct ggtgtgtgca   22860
ggtggcgacg tttgtggtct ctgcggtctg cgtcacgggg cttctcgtcc tggcctctgt   22920
gttccgggca cggtttccct gcttttatgc cacggcgagc tcttatgccg gggtgaactc   22980
cacggccgag gtgcgcgggg gtgtagccgt gccctcagg ttggacacgc agagcctgt    23040
gggcacttat gtaatcacgg ccgtgttgtt gttggccgcg gccgtgtatg ccgtggtcgg   23100
cgccgtgacc tcccgctacg accgcgcct ggacgcgggc cgccgtctgg ctgcggccg    23160
catgccatg ccgcacgcca cgctgatcgc cggaaacgtc tgctcttggt tgctgcagat   23220
caccgtcctg ttgctggccc atcgcatcag ccagctggcc cacctggttt acgtcctgca   23280
ctttgcgtgt ctggtgtatt tgcggcca ttttgcacc aggggggtcc tgagcgggac    23340
gtatctgcgt caggtgcacg gcctgatgga gccggcccg actcatcatc gcgtcgtcgg   23400
cccggctcga gccgtgctga caaacgcctt gctgttgggc gtcttcctgt gcacggccga   23460
cgccgcggta tccctgaata ccatcgccgc gttcaacttt aattttcgg ccccgggcat    23520
gctcatatgc ctgaccgtgc tgttcgccct tctcgtcgta tcgctgttgt tggtggtcga   23580
ggggtgtttg tgtcactacg tgcgcgtgtt ggtggcccc cacctgggg ccgtggccgg    23640
cacgggcatc gtcggcctgg cctgcgagca ctattacacc aacggctact acgttgtgga   23700
gacgcagtgg ccggggggccc agacgggagt ccgcgtcgcc ctcgcctggg tgccgcctt   23760
tgccctcggc atggccgtgc tccgctgcac ccgcgcctat ctgtatcaca ggcggcacca   23820
caccaaattt tttatgcgca tgcgcgacac gcacattccg ccctcaggcg                        23880
cgtacgcagt tccatgcgcg gatcgcgaga cggccgccac aggcccgcac ccggcagccc   23940
gcccgggatt cccgaatatg cggaagaccc ctacgcgatc tcatacgcg gccagctcga    24000
ccggtacgga gattccgacg gggagccgat ttacgacgag gtggctgacg accaaaccga   24060
cgtattgtac gccaagatac aacacccgcg gcacctgccc gacgacgagc ccatctatga   24120
caccgttggg gggtacgacc ccgagacccg cgaggacccc gtgtacagca ccgtccgcg    24180
ttggtagctg tttggttccg ttttaataaa ccgtttgtgt ttaacccgac cgtggtgtat    24240
gtctggtgtg tggcgtccga tcccgttact atcaccgttt ccccccccc cccctcaacc    24300
ccggcgattg tgggtttttt aaaaacgaca cgcgtcgac cgtatacaga acattgtttt    24360
ggttttatt cgctatcgga catggggggt ggaaactggg tggcggggca ggcgcctccg    24420
cccgccgtgg tgagtgtg cgcgaggggg gggtccgaca aacgcaggcg ctgtctcccc     24480
gggcccgcg taaccacgcg catatccggg ggcacgtaga aattaccttc ctcttccggac    24540
tcgatatcca cgacatcaaa gtcgtgggcg gtcagcgaga cgacctcccc gtcgtcggtg   24600
atgaggacgt tgtttcggca gcagcagggc cgggcccggg agaacgagag gcccatagct   24660
cggcgagcgt gtcgtcgaac gccaggcggc tgcttcgctg gatggcctta tagatctccg   24720
gatcgatgcg gacgggggta atgatcaggg cgatcggaac ggcctggttc gggagaatgg   24780
```

```
acgccttgct gggtcctgcg gccccgagag ccccggcgcc gtcctccagg cggaacgtta    24840
cgccctcctc cgcgctggtg cggtgcctgc cgataaacgt caccagatgc gggtgggggg    24900
ggcagtcggg gaagtggctg tcgagcacgt agccctgcac caagatctgc ttaaagttcg    24960
ggtgacgggg gttcgcgaag acgggctcgc ggcggaccag atccccggag ctccaggaca    25020
cgggggagat ggtgtggcgt ccgagtcgg gggcgccaaa cagaagcacc tccgagacaa     25080
cgccgctatt taactccacc aaggcccgat ccgcggcgga gcaccgcctt ttttcgcccg    25140
aggcgtgggc ctctgaccag gcctggtctt cgtgacgag agcctcctcc gggccggggga    25200
cgcgcccggg cgcgaagtat cgcacgctgg gcttcgggat cgaccggata aatgcccgga    25260
acgcctccgg ggaccggtgt gtcatcaagt cctcgtacgc ggaggccgtg gggtcgctgg    25320
ggtccatggg gtcgaaagcg tacttggccc ggcatttgac ctcgtaaaag gccagggggg    25380
tcttggggac tggggccagg tagccgtgaa tgtcccgagg acagacgaga atatccaggg    25440
acgcccgac catcccgtg tgaccgtcca tgaggacccc acacgtatgc acgttctctt      25500
cggtgaggtc gctgggttcg tggaagataa agcgccgcgt gtcggcgccg gcctcgccgc    25560
cgtcgtccgc gcggcccacg cagtagcgaa acagcaggct tcgggccgtc ggctcgttca    25620
cccgcccgaa catcaccgcc gaagactgta catccggccg caggctggcg ttgtgcttca    25680
gccactgggg cgagaaacac ggaccctggg ggccccagcg gagggtggat gcggtcgtga    25740
ggccccgccg gagcagggcc catagctggc agtcggcctg gttttgcgtg gccgcctcgt    25800
aaaaccccat gaggggccgg ggcgccacgg cgtccgcggc ggccggggggc ccgcggccgg   25860
tcaggcgcca taggtgccgg ccgagtccgc ggtccaccat acccgcctcc tcgaggacca    25920
cggcagggga acacagataa tccaggcggg cccagagggg accgatggcc agaggggcgc    25980
ggacgccgcg cagcaacccg cgcaggtggc gctcgaacgt ctcggctagt atatgggagg    26040
gcagcgcgtt ggggatcacc gacgccgacc acatagagtc aaggtccggg gagtcgggat    26100
cggcgtccgg gtcgcgggcg tgggtgcccc caggagatag cggaatgtct ggggtcggag    26160
gccctgaggc gtcagaaagt gccggcgacg cggcccgggg cttttcgtct gcggtgtcgg    26220
tggcgtgctg atcacgtggg gggttaacgg gcgaatggga gctcgggtcc acagctgacg    26280
tcgtctgggg tggggggggc aggggacgga aggtggttgt cagcggaaga ctgttaggcg    26340
gggggcgctt gggggggctg tcggggccac gagggggtgtc ctcggccagg gcccaggac    26400
gcttagtcac ggtgcgtccc ggcggacatg ctgggcctac cgtggactcc atttccgaga    26460
cgacgtgggg gagcggtggt tgagcgcgcc gccgggtgaa cgctgattct cacgacagcg    26520
cgtgccgcgc gcacgggttg gtgtgacaca ggcgggacac cagcaccagg agaggcttaa    26580
gctcgggagg cagcgccacc gacgacagta tcgccttgtg tgtgtgctgg taatttatac    26640
accgatccgt aaacgcgcgc cgaatcttgg gattgcggag gtggcgccgg atgccctctg    26700
gtacgtcata cgccaggccg tgggtgttgg tctcggccga gttgacaaac agggctgggt    26760
gcagcacgca gcgataggcg agcagggcca gggcgaagtc cggcgacagc tggttgttga    26820
aatactggta accgggaaac cgggtcacgg gtacgcccag gctcggggcg acgtacacgc    26880
taaccaccaa ctccagcagc gtctggccaa gggcgtacag gtcaaccgct aacccgacgt    26940
cgtgcttcag gcgtggttg gtaaattcgg cccgttcgtt gttaaggtat ttcaccaaca     27000
gctccggggg ctggttatac ccgtgaccca ccagggtgtg aaagttggct gtggttaggg    27060
cggtgggcat gccaaacatc cggggggact tgaggtccgg ctcctggagg caaaactgcc    27120
cccgggcgat cgtggagttg gagttgaggg tgacgaggct aaagtcggcg aggacggcc    27180
gccggagcga gacggcgtcc gaccgcagca tgacgaggat gttggcgcac ttgatatcca    27240
ggtggctgat cccgcaggtg gtgtttaaaa acacaacggc gcgggccagc tccgtgaagc    27300
actggtggag gccgtcgag accgaggggt ttgttgtgcg caggggacgc agttggccga    27360
tatacttacc gaggtccatg tcgtacgcgg ggaacactat ctgtcgttgt tgcagcgaga    27420
acccgagggg cgcgatgaag ccgcggatgt tgtgggtgcg gccggcgcgt agagcgcact    27480
ccccgaccaa caggtcgcg atgagctcaa cggcaaacca ctccttttcc tttatggtct    27540
taacgcaag cttatgttcg cgaatcagtt ggacgtccgc gtatccccca gaccccccga     27600
agcttcgggc cccggggatc tcgagggtcg tgtagtgtag ggcggggttg atggcgaaca    27660
cggggctgca tagcttgcgg atgcgcgtga gggtaaggat gtgcgagggg gacgaggggg    27720
gtgcggttaa cgccgcctgg gatctgcgca ggggcggggc gttcagtttg gccgccgtac    27780
cgggcgtctc gggggacgcg cggcgatgag acgagcggct cattcgccat cgggatagtc    27840
ccgcgcgaag ccgctcgcgg aggccggatc ggtggcggga cccgtgggag gagcgggagc    27900
cggcggcgtc ctggagagag gggccgctgg ggcgcccgga ggcccgtgt gggttggagt    27960
gtatgtagga tgcgagccaa tccttgaagg accgttggcg tgcaccttgg gggctgaggt    28020
tagctgccac atgaccagca ggtcgctgtc tgcgggactc atccatcctt cggccaggtc    28080
gccgtctccc cacagagaag cgttggtcgc tgcttcctcg agttgctcct cctggtccga    28140
aagacgatcg tccacggcgt ccaggcgctc accaagcgcc ggatcgaggt accgtcggtg    28200
tgcggttaga aagtcacgac gcgccgcttg ctcctccacg cgaattttaa cacaggtcgc    28260
gcgctgtcgc atcatctcta agcgccgcg ggacttagc cgcgcctcca attccaagtg      28320
gccgccttt gcagccataa aggcgccaac aaaccgagga tcttgggtgc tgacgccctc    28380
ccggtcgcagc tgcagggtct ggtccttgta aatctcggct cggaggtgcg tctcggcag    28440
gcgtcggcgc agggccgcgt gggcggcatc tcggtccatt ccgccaccct gcgggcgacc    28500
cgggggggtgc tctgatagtc tcgcgtgccc aaggcccgtg atcggggtac ttcgccgccg    28560
cgacccgcca cccggtgtgc gcgatgtttg gtcagcagct cggccgcccc cgtccgcagt    28620
acctggagcg cctcgagaaa cagaggcaac ttaaggtggg cgcggacgag gcgtcggcgg    28680
gcctcacaat gggcggcgat gccctacgag tgcccttttt agatttcgcg accgcgaccc    28740
ccaagcgcca ccagaccgtg gtcccgggcg tcggacgct ccacgactgc tgcgagcact     28800
cgccgctctt ctcggccgtg gcgcggcggc tgctgtttaa tagcctggtg ccggcgcaac    28860
taaaggggcg tgatttcggg ggcgaccaca cggccaagct ggaattcctg gaccccgagt    28920
tggtacgggc ggtggcgcga ctgcggttta aggagtgcgc gccggcggac gtggtgcctc    28980
agcgtaacgc ctactatagc gttctgaaca cgtttcaggc cctccaccgc tccgaagcct    29040
ttcgccagct ggtgcacttt gtgcgggact ttgcccagct gcttaaaacc tccttccggg    29100
cctccagcct cacggagacc acgggccccc caaaaaacg ggcaaggtg gacgtggcca     29160
ccacggggcg gacgtggagc tgttccaaaa aatgatccat atgcacgcca                29220
cctactttct ggccgccgtg ctcctcgggg accacgcgga gcaggtcaac acgttcctgc    29280
gtctcgtgtt tgagatcccc ctgtttagcg acgcggccgt gcgccacttc gccagcgcg     29340
ccaccgtgtt tctcgtcccc cggcgccacg gcaagacctg gtttctagtg cccctcatcg    29400
cgctgtcact ggcctccttt cggggatca agatcggcta cacggcgcac atccgcaagg     29460
cgaccgagcc ggtgtttgag gagatcgacg cctgcctgcg gggctggttc ggttcggccc    29520
```

```
gagtggacca cgttaaaggg gaaaccatct ccttctcgtt tccgacgggg tcgcgcagta   29580
ccatcgtgtt tgcctccagc cacaacacaa acgtaagtcc tcttttcttt cgcatggctc   29640
tcccaagggg ccccgggtcg acccgaccca cacccaccca cccacccaca tacacacaca   29700
accagacgcg ggaggaaagt ctgcccgtg ggcactgatt tttattcggg atcgcttgag    29760
gaggccgcgg caacgcccg ggcaacggtg gggcaactcg tagcaaatag gcgactgatg    29820
tacgaagaga agacacacag gcgccacccg gcgctggtcg gggggatgtt gtccgcgccg   29880
caccgtcccc cgacgacctc ttgcagacgt tccgtgatgc aaggacggcg ggggcctgc    29940
agcagggtga ccgtatccac gggatggcca aagagaagcg gacacaggct agcatccccc   30000
tggaccgcca gggtacactg ggccatcttg gcccacagac atggggcgac gcagggacag   30060
gactccgtta cgacggagga gagccacagt gcgttggcgg aatcgatgtg gggcggcggg   30120
gcgcaggact cgcagccccc cgggtggttg tgatcctgg ccaggagcca tcccagatgg    30180
cgggccctgc ttcccggtgg acagagcgac cccaggtcgc tgtccatggc ccagcagtag   30240
atctggccgc tggggaggtg ccaccaggcc cccgggccca aggcgcagca cgcgcccggc   30300
tccgggggg tcttcgcggg gaccagatac gcgccatcca gctcgccgac cactggctcc    30360
tccgcgagct gttcggtggt tgggtcgggg gtttcctccg ggggggtggc cgcccgtatg   30420
cgggcgaacg tgagggtgca caggagcggg gtcaggggt gcgtcacgct ccggaggtgg    30480
acgatcgcgc agtagcggcg ctcgcggtta aagaaaaaga gggcaaagaa ggtgttcggg   30540
ggcaaccgca gcgccttggg gcgcgtcaga tacagaaaaa tctcgcagaa gagggcgcg    30600
ccggggtctg ggttaggaag ggccacctga cacagaggct cggtgaggac cgttagacac   30660
cgaaagatct tgagccgctc gtccgcccga acgacgcgcc acacaaagac ggagttgaca   30720
atgcgcgcga tagagtcgac gtccgtcccc aggtcgtcga ctctgtcgcg cgtgccgcga   30780
gctccgcccc gggaatccgg ccgggggcaag gtccccgggg gaccaggcgg cgccagggg    30840
cgccgggggtc ccagctgcgc catgccgggg gcgggggggag ggcaaacccc agaggcgggg  30900
gccaacggcg cggggaggag tgggtgggcg aggtggccgg gggaaggcgc ccgctagcga   30960
gaacggccgt tccggacga caccttgcga caaaacctaa ggacagcggc ccgcgcgacg    31020
gggtccgaga ggctaaggta gcccgcgatg ttaatggtag acgcaaagcc gccgggaaag   31080
acaactatgc cacagaggcg gcgattaaac cccaggcaga ggtaggcgta gcttccccg    31140
ggcaggtatt gctcgcagac cctcgtgtg gctgtggagg ggacgccctc catgaagcga   31200
catttactct gctcgcgttt actgacgtca ccatccatcg ccacggcgat tggacgattg   31260
ttaagccgca gcgtgtctcc gcttgtgctg tagtagtcaa aaacgtaatg gccgtcggag   31320
tcggcaaagc gggccgggag gtcgtcgccg agcgggacga cccgccgccc ccgaccgccc   31380
cgtccccca ggtgtgccag gacgccagg gcatacgcgc tgtgaaaaaa ggagtcgggg    31440
gcggtcccct cgacgcgca catcaggttc tcgaggagaa tggggaagcg cctggtcacc   31500
tccccaacc acgcgcgttg gtcggggcca aagtcatagc gcaggcgctg tgagattcgc   31560
gggccgccct gaagcgcggc ccggatggcc tggccaaggg cccgaggcca cgccagatgt   31620
atgcgcgcgg taaaggcgac ctcggcggcg atgtcaaagg gcggcaggac ggggcgcggg   31680
tggcgcaggg gcacctcgag cgcgggaaag cgtagcagca gctccgcctg cccagcggga   31740
gacagctggt ggggcgcac gacgcgttct gcggcgcagg cctcggtcag ggccgtggcc    31800
agcgccgagg acagcagcgg aggggggcg cgtcgcccgc ccacgccac ggagttctcg     31860
taggagacga cgacgaagcg ctgcttggtt ccgtagtggt ggcgcaggac cacgagata    31920
gaacgacggc tccacagcca gtccggccgg tcgccgccgg ccaggcttc ccatccgcga    31980
tccaaccact cgaccagcga ccgcggcttt gcggtaccag gggtcagggt tagaacgtcg   32040
ttcaggatgt cctcgccccc gggccctgtg ggcacgggg ccacaaagcg gcccccgcct    32100
gggggctcca gacccgccaa caccgcatct gcgtcagccg cccccatggc gccccgctg    32160
acggcctggt gaaccagggc gccctggcgg agccccgatg caacgccaca ggccgcacgc   32220
ccggtccgag cgcggaccgg gtggcggcgg gtgacgtcct gcactgcccg ctgaaccaac   32280
gcgaggatct cctcgttctc ctgcgcgatg gacacgtcgc cgcgcgcgtt cgtgtcgccg   32340
ccggggggccg tcagctgctc ctccggggag atgggggggt cggacgcccc gacgatgggc   32400
gggtctgcgg gcgcccccgc gtggggccgg gccaagggct gcggacgcgg ggacgcgctt   32460
tccccagac ccatggacag gtgggccgca gcctccttcg cggccggcgg ggcggcggcg    32520
ccaagcagga cgacgtagcg gcacaaatgc cgacagacgc gcatgatgcg cgtgctgtcg   32580
gccgcgtagc gcgtgttggg ggggacgagc tcgtcgtaac taaacagaat cacgcgggca   32640
cagctcgccc ccgagcccca cgcaaggcgc agcgccgcca cggcgtacgg gtcatagacg   32700
ccctgcgcgt tacacaccac gggcaggag acgaacaacc ccccggcgct ggacgcacgc    32760
ggaaggaggc cagggtgtgc cagcgacacg ggggccagaa gctccccac cgcatccgcg    32820
ggcacgtagg cggcaaacgc cgtgcaccac ggggtacagt cgccggtggc atgagcccga   32880
gtctggattt cgacctggaa gtttgcggcc gtcccgagtc cggggtggcc gcgcatcagg   32940
gcggccagag ggattccgc ggccgccagg cactcgctgg atatgatgac gtgaaccaaa    33000
gacgagggcc gacccgggcc gtggccgaga tcgtactgga cctcgttgc caagtgcgcg    33060
ttcatggttc ggggggtggt gtgggtgtgt aggcgatgcg ggtccccga gtccgcggga    33120
agggcgtggg tttggcgcgc gtatgcgtat tcgccaacgg aggccgtcgt gcttatcgc    33180
ggcgcgtttc ttctgtctct agggaatccg aggccaggac tttaacctgc tctttgtcga   33240
cgaggccaac tttattcgcc cggatgcggt ccagacgatt atgggctttc tcaaccaggc   33300
caactgcaag attatcttcg tgtcgtccac caacaccggg aaggccagta cgagctttt    33360
gtacaacctc cgcggggccg cagacgagct tctcaacgtg gtgacctata tatgcgatga   33420
tcacatgccg agggtggtga cgcacacaaa cgccacggcc tgtcttcgtt atatcctcaa   33480
caagcccgtt ttcatcacga tggacgggc ggttcgccgg accgccgatt tgtttctggc    33540
cgattccttc atgcaggaga tcatcggggg ccaggccagg gagaccggcg acgaccggcc   33600
cgttctgacc aagtctgcgg gggagcggtt tctgttgtac cgccccctga ccaccaccaa   33660
cagcggcctc atggcccccg atttgtacgt gtacgtggat cccgcgttca ggcgcaacac   33720
ccgagcctcc gggaccggcg tcgctgtcgt cgggcggtac cgcgacgatt atatcatctt   33780
cgcccctggag cactttttc tccgcgcgct cacgggctcg gcccccgccg catcgccccg   33840
ctgcgtcgtc cacagtctga cgcaggtcct ggccctgcat cccggggcgt ttcgcggcgt   33900
ccggggtcgg gtcgagggaa atagcagcca ggactcggac gtcgccacga gggcgggcg    33960
gcacacagag atgcaccgcc tactggcctc ggagggggcc gacgcgggct cgggcccga    34020
gcttctcttc taccactgcg agcctccgg gagcgcggtc ctgtacccct ttttcctgct    34080
caacaaacag aagacgcccg cctttgaaca ctttattaaa aagtttaact ccggggggcgt   34140
catgcctcc caggagatcg tttccgcgac ggtgcgcctg cagaccgacc cggtcgagta    34200
tctgctcgag cagctaaata acctcaccga aaccgtctcc cccaacactg acgtccgtac   34260
```

```
gtattccgga aaacggaacg gcgcctcgga tgaccttatg gtcgccgtca ttatggccat   34320
ctacctcgcg gcccaggccg gacctccgca cacattcgct cctatcacac gcgtcttgtg   34380
agcgcccaat aaacacaccc aggtatgcta cgcacgacca cggtgtcgtc tgttaagggg   34440
ggggggaagg gggtgttggc gggaagcgtg ggaacacggg ggattctctc acgaccggca   34500
ccagtaccac cccctgtga acacagaaac cccaacccaa atcccataaa catacgacac   34560
acaggcatat tttggaattt cttaggtttt tatttattta ggtatgctgg ggttctcccc   34620
tggatgccca cccccacccc cccgtgggtc tagccgggcc ttagggatag cgtataacgg   34680
gggccatgtc tccggaccgc acaacggccg cgccgtcaaa ggtgcacacc cgaaccacgg   34740
gagccagggc caaggtgtct cctagttggc ccgcgtgggt cagccaggcg acgagcgcct   34800
cgtaaagcgg cagccttcgc tctccatcct gcatcagggc cggggcttcg gggtgaatga   34860
gctgggcggc ctcccgcgtg acactctgca tctgcaggag agcgttcacg tacccgtcct   34920
gggcacttag cgcaaagagc cgggggatta gcgtaaggat gatggtggtt ccctccgtga   34980
tcgagtaaac catgttaagg accagcgatc gcagctcggc gtttacggga ccgagttgtt   35040
ggacgtccgc cagcagcgag aggcgactcc cgttgtagta cagcacgttg aggtctggca   35100
gccctccggg gtttctgggg ctggggttca ggtcccggat gcccctggcc acgagcgcg   35160
ccacgatttc gcgcgccagg ggcgatggaa gcggaacggg aaaccgcaac gtgaggtcca   35220
gcgaatccag gcgcacgtcc gtcgcttggc cctgaacac gggcgggacg aggctgatgg    35280
ggtccccgtt acagagatct acgggggagg tgttgcaaag gttaacggtg ccggcgtggg   35340
tgaggcccac gtccaggggg caggcgacga ttcgcgtggg aagcaccggg gtgatgaccg   35400
cggggaagcg ccttcggtac gccagcaaca accccaacgt gtcgggactg acgcctccgg   35460
agacgaagga ttcgtgcgcc acgtcggcca gcgtcagttg ccggcggatg gtcggcagga   35520
ataccacccg cccttcgcag cgctgcagcg ccgcggcatc ggggcgcag atgcccgagg    35580
gtatcgcgat gtcagtttca aagccgtccg ccagcatggc gccgatccac gcggcaggga   35640
gtgcagtggt gggtcgggtg gcgggaggag cgcggtgggg gtcagcggcg tagcagagac   35700
gggcgaccaa cctcgcatag gacggggggt gggtcttagg gggttgggag gcgacaggga   35760
ccccagagca tgcgcgggga ggtctgtcgg gcccagacge accgagagcg aatccgtccg   35820
cggagtcccg gcttgggttt tatgggcgcc ggcctccgga atcgcggctt gtcggcgggg   35880
acaaaggggg cggggctagg ggcttgcgga aacagaagac gcgtgggata aaagaatcgc   35940
actaccccaa ggaagggcgg ggcggtttat tacagagcca gtcccttgag cggggatgcg   36000
tcatagacga gatactgcgc gaagtgggtc tcccgcgcgt gggcttcccc gttgcgggcg   36060
ctgcggagga gggcggggtc gctggcgcag gtgagcgggt aggcctcctg aaacaggcca   36120
cacgggtcct ccacgagttc gcggcacccc gggggcgcgt taaactgtac gtcgctggcg   36180
gcggtggccg tggacaccgc cgaacccgtc tccacgatca ggcgctccag gcagcgatgt   36240
ttggcggcga tgtcggccga cgtaaagaac ttaaagcagg ggctgagcac cggcgaggcc   36300
ccgttgaggt ggtaggcccc gttatagagc aggtcccccgt acgaaaatcg ctgcgacgcc   36360
cacgggttgg ccgtgccgc gaaggcccgg gacgggtcgc tctggccgtg gtcgtacatg   36420
agggcggtga catccccctc cttgtccccc gcgtaaacgc ccccggcggc gcgtccccgg   36480
gggttgcagg gccggcggaa gtagttgacg tcggtcgaca cggggggtggc gataaactca   36540
cacacgcgt cctgccgctg gtccatccct gcgcgccgcg gcacctgggc gcaccgaac    36600
acggggacgg gctgggccgg ccccaggcgg tttcccgcca cgaccgcgtt ccgcaggtac   36660
acggctgccg cgttgtccag gagagggga gccccgcggc ccaggtaaaa gtttttggga    36720
aggttgccca tgtcggtgac gggggttgcgg acggttgccg tggccacgac ggcggtgtag   36780
cccacgccca ggtccacgtt cccgcgcggc tgggtgaccg tgaagtttac ccccccgcca   36840
gtttcgtgcc gggccacctg gagctggccc aggaagtacg cctccgacgc gcgctccgag   36900
aacagcacgt tctcagtcac aaagcggtcc tgtcggacga cggtgaaccc aaacccggga   36960
tggaggcccg tcttgagctg atgatgcaag gccacggac tgatcttgaa gtaccccgcc    37020
atgacgccgt aggtcagcgc gttctccccg gccgcgctct aggtggcgtg ctgcacgacg   37080
ggctgtcgga tcgacgaaaa gtagttggcc cccagagccg gggggaccag ggggacctgc   37140
cgcgacaggt cgcgcagggc cggggggaaa ttgggcgcgt tcgccacgtg gtcggccccg   37200
gcgaacagcg cgtggacggg gaggggtaa aaatagtcgc catttggat ggtatggtcc     37260
agatgctggg gggccatcag caggattccg gcgtgcaacg ccccgtcgaa tatgcgcatg   37320
ttggtggtgg acgcggtgtt ggcgcccgcg tcgggcgccg ccgagcagag cagcgccgtt   37380
gtgcgttcgg ccatgttgtg ggccagcacc tgcagcgtga gcatggcggg cccgtccact   37440
accacgcgcc cgttgtgaaa catggcgttg accgtgttgg ccaccagatt ggccgggtgc   37500
aggggggtcg cgggggtccgt cacggggtcg ctggggcact cctcgccggg ggcgatctcc  37560
gggaccacca tgttctgcag ggtgcgtat acgcggtcga agcgaacccc cgcggtgcag   37620
cagcggcccc gcgagaaggc gggcaccatc acgtagtagt aaatcttgtg gtgcacggtc   37680
cagtccgccc cccggtgcgg ccggtcatcc gcggcgtccg cggctcgggc ctgggtgttg   37740
tgcagcagct ggccgtcgtt gcggttgaag tccgcggtcg ccacgttaca tgccgccgcg   37800
tacacgtggt cgtggccccc cgcgctaacc cggcagtcgc gatgcgcgtc cagggccgcg   37860
cgccgcatca gggcgtcaca gtcccacacg aggggtggca gcagcgcgg gtctcgcatt    37920
aggtgattca gctcggcttg cgcctgcccg cccagctccg ggccggtcag ggtaaagtca   37980
tcaaccagct gggccagggc ctcgacgtgc gccaccaggt cccggtacac ggccatgcac   38040
tcctcgggaa ggtctccccc gaggtaggtc acgacgtacg aggccagtga gtagtcgttc   38100
acgaacgccg cgcaccgcgt gttgttccag tagctggtga tgcactggac cacgagccgg   38160
gccagggcgc agaagacgtg ctcgctgccg tgtatgcggg cctgcagcag gtaaaacacc   38220
gccgggtagt tgcggtcgtc gaacgccccg cgaacggcgg cgatggtggc gggggccatg   38280
gcgtggcgtc ccaccccag ctccaggccc gggcgttgcc ggaacgccgc cggacatagc    38340
gccaggggca agttgccgtt caccacgcgc caggtggcct ggatctcccc cggccgagcc   38400
ggggaacgt ccccccccgg cagctccacg tcgccaccc ccacaaagaa gtcgaacgcg     38460
gggtgcagct caagagccag gttggcgttg tcgggctgca taaactgctc cggggtcatc   38520
tggccttccg cgacccatcg gacccgcccg tgggccaggc gctgccccca ggcgttcaaa   38580
aacagctgct gcatgtctgc ggcggggccg gccggggccg ccacgtacgc cccgtacgga   38640
ttggcggctt caacggggtc gcggttaagg ccccgagtca ac gttcatcagc           38700
gaagggtggc acacggtccc gatcgcgtgt tccagagaca ggcgcagcac ctggcggtcc   38760
ttccccccaaa aaaacagctg gcgggcggg aagcgcggg gatccgggtg gccggggcg     38820
gggactaggt ccccggcgtg cgcggcaaac cgttccatga ccggattgaa caggcccagg   38880
ggcaggacga acgtcaggtc catggcgccc accaggggt agggaacgtt ggtggcgcg     38940
tagatgcgct tctccagggc ctccagaaag accagcttct cgccgatgga caccagatcc   39000
```

```
gcgcgcacgc gcgtcgtctg gggggcgctc tcgagctcgt ccagcgtctg ccggttcagg   39060
tcgagctgct cctcctgcat ctccagcagg tggcggccca cgtcgtccag acttcgcacg   39120
gccttgccca tcacgagcgc cgtgaccagg ttggccccgt tcaggaccat ctcgccgtac   39180
gtcaccggca cgtcggcttc ggtgtcctcc gctttcagga aggactgcag gaggcgctgt   39240
ttgatcgggg cggtggtgac gagcaccccg tcgaccgccg gcccgcgcgt gtcggcatgc   39300
gtcagacggg gcacggccac ggagggctgc gtggccgtgg tgaggtccac gagccaggcc   39360
tcgacggcct cccggcggtg gcccgccttg cccaggaaaa agctcgtctc gcagaagctt   39420
cgctttagct cggcgaccag ggtcgcccgg gccaccctgg tggccaggcg gccgttgtcc   39480
aggtatcgtt gcatcggcaa caacaaagcc aggggcggcg ccttttccag cagcacgttg   39540
agcatctggt cggccgtgcc gcgctcaaac gccccgagga cggcctggac gttgcgagcg   39600
agctgttgga tggcgcgcaa ctggcgatgc gcgccgatac ccgtcccgtc cagggcctcc   39660
cccgtgagca gggcgatggc ctcggtggcc aggctgaagg cggcgttcag ggcccggcgg   39720
tcgataatct tggtcatgta attgtgtgtg ggttgctcga tgggtgcgg gccgtcgcgg    39780
gcaatcagcg gctggtggac ctcgaactgt acgcgcccct cgttcatgta ggccagctcc   39840
ggaaacttgg tacacacgca cgccaccgac aacccgagct ccagaaagcg cacgagcgac   39900
agggtgttgc aatacgaccc cagcagggcg tcgaactcga cgtcgtacag gctgttttgca   39960
tcggagcgca cgcgggaaaa aaaatcgaac aggcgtcgat gcgacgccac ctcgatcgtg   40020
ctaaggaggg acccggtcgg caccatggcc gcggcatacc ggtatcccgg agggtcgcgg   40080
ttgggagctg ccatgggtc gcgtggagat cggctggatc tagcgatatt tgcccgggga    40140
ggctaagatc caccccaacg cccggccacc cgtgtacgtg cccgacggcc caaggtccac    40200
cgaaagacac gacgggcccg gacccaaaaa ggcgggggat gctgtgtgag gggccggggtg   40260
tcggtcgggg gggaaaggca ccgggaggaag gctgcggcct cgttccagga gaacccagtg   40320
tccccaacag acccggggac gtgggatccc aggccttata tacccccccc gccccaccccc   40380
cgttagaacg cgacgggtgc attcaagatg gccctggtcc aaaagcgtgc caggaagaaa    40440
ttggcagagg cggcaaagct gtccgccgcc gccaccccaca tcgaggcccc ggccgcgcag   40500
gctatcccca gggcccgtgt gcgcagggga tcggtgggga gcagcatttg gttggtggca   40560
ataaagtgga aaagcccgtc cggactgaag gtctcgtggg cggcggcgaa caaggcacac   40620
agggccgtgc ctcccaaaaa cacgacatcc ccccaaaaca ctggcgccga caacggcaga   40680
cgatccctct tgatgttaac gtacaggagg acgcccgca ccgcccacgt aacgtagtag    40740
ccgacgatgg cggccaggat acaggccggc gccaccacc ttccggtcag cccgtaatac    40800
atgcccgctg ccaccatctc caacggcttc aggaccaaaa acgaccaaag gaacagaatc    40860
acgcgctttg aaaagaccgg ctgggtatgg ggcggaagac gcgagtatgc cgaactgaca    40920
aaaaaatcag aggtgccgta cgaggacaat gaaaactgtt cctccagcgg cagttctccc    40980
tcctccccc cgaaggcggc ctcgtcgacc agatctcgat ccaccagagg aaggtcatcc    41040
cgcatggtca tgggggtgtgc ggtggaggtg gggagaccga aaccgcaaag ggtcgcttac    41100
gtcagcagga tcccgagatc aaagacaccc gggttcttgc acaaacacca cccgggttgc    41160
atccgcggag gcgagtgttt tgataaggcc gttccgcgcc ttgatataac ctttgatgtt    41220
gaccacaaaa cccggaattt acgcctacgc cccaatgccc acgcaagatg aggtaggtaa    41280
ccccccgtg ggtgtgacgt tgcgtttagt tcattggagg ccaagggaa aaatgggtag    41340
gggaggaaac ggaaaaccca gtaggccgtg tcgggaacac gcccgggggtt gtcctcaaaa    41400
ggcagggtcc atactacgga agccgtcgtt gtattcgaga cctgcctgtg cgacgcacgt    41460
cggggttgcc tgtgtccggt tcggccccca ccgcgtgcgg cacgcacgag gacagagtccg    41520
cgtgctttat tggcgtttcca agcgttgccc tccagtttct ggttgtcggtg ttcccccata    41580
cccacgccca catccaccgt aggggggcctc tgggccgtgt tacgtcgccg cccgcgatgg    41640
agcttagcta cgccaccacc atgcactacc gggacgttgt gttttacgtc acaacggacc    41700
gaaaccgggc ctactttgtg tgcggggggt gtgtttattc cgtggggcgg ccgtgtgcct    41760
cgcagcccgg ggagattgcc aagtttggtc tggtcgttcg agggacaggc ccagacgacg    41820
gcgtggtcgc caactatgta cgaagcgagc tccgacaacg cggcctgcag gacgtcgtc    41880
ccattgggga ggacgaggtg tttctggaca gcgtgtgtct tctaaacccg aacgtgagct    41940
ccgagctgga tgtgattaac acgaacgacg tggaagtgct ggacgaatgt ctggccgagt    42000
actgcacctc gctgcgaacc agccccggggtg tgctaatatc cgggctgcgc gtgcgggcgc    42060
aggacagaat catcgagttg tttgaacacc caacgatagt caacgtttcc tcgcactttg    42120
tgtataccc gtcccatac gtgttcgccc tggcccaggc gcacctcccc cggctcccga    42180
gctcgctgga ggcctggtg agcggcctgt ttgacggcat cccgccccca cgccagccac    42240
ttgacgccca caacccgcgc acggatgtgg ttatcacggg ccgccgcgcc ccacgaccca    42300
tcgccgggtc ggggggcggggg tcggggggcg cgggcgccaa gcgggccacc gtcagcgagt    42360
tcgtgcaagt caaacacatt gaccgcgtgg gcccgctgg cgtttcgccg gcgcctccgc    42420
caaacaacac cgactcgagt tccctggtgc ccggggccca ggattccgcc ccgcccggcc    42480
ccacgctaag ggagctgtgg tgggtgtttt atgccgcaga cggggcgctg gaggagcccc    42540
gcgccgactc tggcctcacc cgcgaggagg tacgtgcgt acgtgggttc cgggagcagg    42600
cgtgaaaact gtttggctcc gcggggggccc cgcgggcgtt tatcggggcc gcgttgggcc    42660
tgagcccct ccaaaagctg gccgtttact actatatcat ccaccgagag aggcgcctgt    42720
ccccccttccc cgcgctagtc cggctcgtag gccggtacac acagcgccac ggcctgtacg    42780
tccctcgggcc cgacgaccca gtcttggccg atgccatcaa gggcgctgtt cgcgaccgcc    42840
tggcggccgg aaccagacc gagcagctcc tcatgttcga ccttctcccc ccaaaggacg    42900
tgccggtggg aagcgacgtg caggccgaca gcaccgctct gctgcgcttt atagaatcgc    42960
aacgtctcgc cgtccccggg gggtgatct ccccgagca cgtcgcgtac cttggtgcgt    43020
tcctgagcgt gctgtacgct ggccgcgggc gcatgtccgc agccacgcac accgccgggc    43080
tgacagggt gacctccctg gtgctagcgg tgggtgacgt ggaccgtctt tccgcgtttg    43140
accgcggagc ggcgggcgcg gccagccgca cgcgggccgc cgggtacctg gatgtgcttc    43200
ttaccgttcg tctcgctcgc tcccaacacg gacagtctgt gtaaaagacc ccaataaacg    43260
tatgtcgcta ctacacccctt gtgtgtcaat ggacgcctct ccggggggg gaaggggaag    43320
caaagagggg ctggggagc ggcaccaccg gggcctgaac aaaaaaccca cagacacggt    43380
tacagttttat tcggtcgggc ggagaaacg ccgaagccac gcccacttta ttcgcgtcct    43440
caaaaaaacg ggacacttgt tccggagaacc tttaggatgc cagccagggc ggcggtaatc    43500
ataaccacgc ccagcgcaga ggcggccaga aacccgggcg caattgcggc cacgggctgc    43560
gtgtcaaagg ctagcaaatg aatgacggtt ccgtttggaa atagcaacaa ggccgtggac    43620
ggcacgtcgc tcgaaaacac gcttggggcg ccctccgtcg gcccgcggc gatttgctgc    43680
tgtgtgttgt ccgtatccac cagcaacaca gacatgacct ccccggccgg ggtgtagcgc    43740
```

```
ataaacacgg cccccacgag ccccaggtcg cgctggtttt gggtgcgcac cagccgcttg   43800
gactcgatat cccgggtgga gccttcgcat gtcgcggtga ggtaggttag gaacagtggg   43860
cgtcggacgt cgacgccggt gagcttgtag ccgatccccc ggggcagagg ggagtgggtg   43920
acgacgtagc tggcgctgtg ggtgatgggt accaggatcc gtggctcgac gttggcagac   43980
tgcccccgc accgatgtga ggcctcaggg acgaaggcgc ggatcagggc gttgtagtgt   44040
gcccaacgcg tcagggtcga ggcgaggccg tgggtctgct gggccaggac ttcgaccggg   44100
gtctcggatc gggtggcttg agccagcgcg tccaggataa acacgctctc gtctagatca   44160
aagcgcaggg aggccgcgca tggcgaaaag tggtccggaa gccaaaagag ggttttctgg   44220
tggtcggccc gggccagcgc ggtccggagg tcgcgttgg tcgctgcggc gacgtcggac   44280
gtacacaggg ccgaggctat cagaaggctc cggcgggcgc gttcccgctg caccgccgag   44340
gggacgccag ccaagaacgg ctgccggagg acagccgagg cgtaaaatag cgcccggtgg   44400
acgaccgggg tggtcagcac gcggccccct agaaactcgg catacagggc gtcgatgaga   44460
tgggctgcgc tgggcgccac tgcgtcgtac gccgaggggc tatccagcac gaaggccagc   44520
tgatagccca gcgcgtgtaa tgccaagctc tgttcgcgct ccagaatctc ggccaccagg   44580
tgctggagcc gagcctctag ctgcaggcgg gccgtgggat ccaagactga cacattaaaa   44640
aacacagaat ccgcggcaca gcccgcgcc ccgcgggcgg ccaacccggc aagcgcgcgc   44700
gagtgggcca aaaagcctag caggtcggag aggcagaccg cgccgtttgc gtgggcggcg   44760
ttcacgaaag caaaacccga cgtcgcgagc agccccgtta ggcgccagaa gagagggggg   44820
cgcgggccct gctcggcgcc cgcgtccccc gagaaaaact ccgcgtatgc ccgcgacagg   44880
aactgggcgt agttcgtgcc ctcctccggg tagccgccca cgcggcggag ggcgtccagc   44940
gcggagccgt tgtcggcccg cgtcagggac cctaggacaa agacccgata ccgggggccg   45000
cccggggcc cggaagagc ccccggggg ttttcgtccg cggggtcccc gacccgatct   45060
agcgtctggc ccgcggggac caccatcact tccaccggag ggctgtcgtg catggatatc   45120
acgagcccca tgaattcccg cccgtagcgc gcgcgcacca gcgcggcatc gcacccgagc   45180
accagctccc ccgtcgtcca gatgcccacg ggccacgtcg aggccgacgg ggagaaatac   45240
acgtacctac ctggggatct caaccgagcc cgggtgccaa accaggtcgt ggacgcgttg   45300
tgcaggtgcg tgatgtccag ctccgtcgtc gggtgccgcc gggccccaac cggcggtcgg   45360
gggggcggtg tatcacgcgg cccgctcggg tggctcgccg tcgccacgtt gtctccccgc   45420
gggaacgtca gggcctcggg gtcagggacg gccgaaaacg ttacccaggc ccgggaacgc   45480
agcaacaggg aggcggctgg attgtgcaag agacccttaa ggggggcgac cgaggggga   45540
ggctgggcgg tcggctcgac cgtggtgggg gcgggcaggc tcgcgttcgg gggccggccg   45600
agcaggtagg tcttcgggat gtaaagcagc tggccgggt cccgcggaaa ctcggccgtg   45660
gtgaccaata caaaacaaaa gcgctcctcg taccagcgaa gaaggggcag agatgccgta   45720
gtcaggttta gttcgtccgg cggcgccaga aatccgcgcg gtggttttg ggggtcgggg   45780
gtgtttggca gccacagacg cccggtgttc gtgtcgccgc agtacatgcg gtccatgccc   45840
aggccatcca aaaaccatgg gtctgtctgc tcagtccagt cgtcgacctg accccacgca   45900
acgcccaaaa taataacccc cacgaaccat aaaccattcc ccatggggga ccccgtccct   45960
aacccacggg gcccgtggct atggcagggc ttgccgcccc gacgttggct gcgagccctg   46020
ggccttcacc cgaacttggg gggtgggtg gggaaaagga aaaacgcggg gcgtattgc   46080
cccaatgggg tctcggtggg gtatcgacga agtgccagcc ctgggaccga accccgcgtt   46140
tatgaacaaa cgacccaaca cccgtgcgtt ttattctgtc tttttattgc cgtcatagcg   46200
cgggttactt ccgtattgt ctccttccgt gttcagtta gcctcccca tctcccgggc   46260
aaacgtgcgc gccaggtcgc agatcgtcgg tatggagccg gggtggtga cgtgggctgg   46320
gaccatcccg gaggtaagtt gcagcagggc gtcccggcag ccgcggcg attggtcgta   46380
atccaggata aagacgtgca tgggacgag gcgtttggcc aagacgtcca aggcccaggc   46440
aaacacgtta tacaggtcgc cgttgggggc cagcaactcg ggggcccgaa acagggtaaa   46500
taacgtgtcc ccgatatggg gttgtgggcc cgcgttgctc tggggctcgg caccctgggg   46560
cggcacggcc gtcccgaaa gctgtcccca atcctcccgc cacgaccccgc cgccctgcag   46620
ataccgcacc gtattggcaa gcagctcgta aacgcggcga atcgcggcca acatagccag   46680
gtcaagccgc tcgccgggc gctggcgttt ggccaggcgg tcgatgtgtc tgtcctccgg   46740
aagggcccc aacacgatgt ttgtgccggg caaggtcggc gggatgaggg ccacgaaccgc   46800
cagcacgccc tgggggggtca tgctgcccat aaggtatcgc gcggccgggt aacacaggag   46860
ggcggcgatg ggatgcggt cgaagatgag ggtgagggcc gggggcgggg catgtgagct   46920
cccagcctcc ccccgatat gaggagccag aacggcgtcg gtcacggcat aaggcatgcc   46980
cattgttatc tgggcgcttg tcattaccac cgccgcgtcc ccggccgata tctcaccctg   47040
gtcgaggcgg tgttgtgtgg tgtagatgtt cgcgattgtc tcggaagccc caacacccg   47100
ccagtaagtc atcggctcgg gtacgtagac gatatcgtcg cgcgaaccca gggccaccag   47160
cagttgcgtg gtgtggttt tccccatccc gtggggaccg tctatataaa cccgcagtag   47220
cgtgggcatt ttctgctcca ggcggacttc cgtggctttt tgctgccggc gagggcgcaa   47280
cgccgtacgt cggttgttat ggccgcgaga gccgcagcc tggtcgaacg cagacgcgtg   47340
ttgatgcag gggtacgaag ccatacgcgc ttctacaagg cgctggccga agaggtgcgg   47400
gagtttcacg ccaccaagat ctgcggcacg ctgttgacgc tgttaagcgg gtcgctgcag   47460
ggtcgctcgg tattcgaggc cacacgcgtc accttaatat gcgaagtgga cctgggaccg   47520
cgcccccg actgcatctg cgtgttcgaa ttcgccaatg acaagacgct gggggggtt   47580
tgtgtcatca tagaactaaa gacatgcaaa tatatttctt ccggggacac cgccagcaaa   47640
cgcgagcaac gggccacggg gatgaagcag ctgcgccact ccctgaagct cctgcagtcc   47700
ctcgcgcctc cgggtgacaa gatagtgtac ctgtgcccg tcctggtgtt tgtcgcccaa   47760
cggacgctcc gcgtcagccg cgtgacccgg ctcgtccgc agaaggtctc cggtaatatc   47820
accgcagtcg tgcggatgct ccagagcctg tccacgtata cggtcccat tgagcctagg   47880
acccagcgag cccgtcgccg ccgcggcggc gccgcccggg ggtctgcgag cagaccgaaa   47940
aggtcacact ctggggcgcg cgacccgccc gagtcagcgg cccgcagtt accacccgcc   48000
gaccaaaccc ccgcctccac ggagggcggg ggggtgctta agaggatcgc ggcgtcttc   48060
tgcgtgcccg tggcaccaa gaccaaaccc cgagccgcct ccgaatgaga gtgtttcgtt   48120
ccttcccct ccccccgt cagacaaacc ctaaccaacg cttaagcggc cccgcgagg   48180
tccgaagact catttggatc cggcgggagc caccccgacaa cagccccggg ttttcccac   48240
gccagacgcc ggtccgctgt gccatcgcgc cccctcatcc cacccccat cttgtcccca   48300
aataaaacaa ggtctggtag ttaggacaac gaccgcagtt tcgtgtgtt attttcgctc   48360
tccgcctctc gcagatggac ccgtactgcc catttgacgc tctggacgtc tgggaacaca   48420
ggcgcttcat agtcgccgat tcccgaaact tcatcacccc cgagttcccc cgggactttt   48480
```

```
ggatgtcgcc cgtctttaac ctcccccggg agacggcggc ggagcaggtg gtcgtcctac  48540
aggcccagcg cacagcggct gccgctgccc tggagaacgc cgccatgcag gcggccgagc  48600
tcccgtcga tatcgagcgc cggttacgcc cgatcgaacg gaacgtgcac gagatcgcag   48660
gcgccctgga ggcgctggag acggcggcgg ccgccgccga agaggcggat gccgcgcgc   48720
gggatgagcc ggcgggtggg ggcgacgggg gggcgccccc gggtctggcc gtcgcggaga  48780
tggaggtcca gatcgtgcgc aacgaccgc cgctacgata cgacaccaac ctccccgtgg   48840
atctgctaca catggtgtac gcgggccgcg gggcgaccgg ctcgtcgggg gtggtgttcg  48900
ggacctggta ccgcactatc caggaccgca ccatcacgga cttcccctg accacccgca   48960
gtgccgactt tcgggacggc cggatgtcca agaccttcat gacggcgctg gtcctgtcct  49020
tgcagtcgtg cggccggctg tatgtgggcc agcgccacta ttccgccttc gagtcgcgcc  49080
tgttgtgtct ctacctgctg taccgaaaca cgcacggggc cgccgacgat agcgaccgcg  49140
ctccggtcac gttcggggat ctgctgggcc ggctgccccg ctacctggcg tgcctggccg  49200
cggtgatcgg gaccgagggc ggccggccac agtaccgcta ccgcgacgac aagctcccca  49260
agacgcagtt cgccggccgg ggggccgct acgaacacgg agcgctgggc tcgcacatcg  49320
tgatcgccac gctgatgcac cacggggtgc tccggcggc cccggggac gtccccggg    49380
acgcgagtac ccacgttaac cccgacgcg tggcgcacca cgacgacata aaccgcgccg  49440
ccgccgcgtt cctcagccgg ggccacaacc tattcctgtg ggaggaccag actctgctgc  49500
gggcaaccgc gaacaccata acggccctgg gcgttatcca gcggctcctc gcgaacggca  49560
acgtgtacgc ggaccgcctc aacaaccgcc tgcagctggg catgctgatc cccggagccg  49620
tcccttcgga ggccatcgcc cgtggggcct ccgggtccga ctcggggggcc atcaagagcg  49680
gagacaacaa tctggaggcg ctatgtgcca attacgtgct tccgctgtac cgggccgacc  49740
cggcggtcga gctgacccag ctgtttccgg gcctggccgc cctgtgtctt gacgcccagg  49800
cggggcggcc ggtcggtcg acgcggcggg tggtggatat gtcatcgggg gcccgccagg  49860
cggcgctggt gcgcctcacc gccctggaac tcatcaaccg cacccgcaca aaccccaccc  49920
ccgtggggga ggttatccac gcccacgacg ccctggcgat ccaatacgaa caggggcttg  49980
gcctgctggc gcagcaggca cgcattggct tgggctccaa caccaagcgt ttctccgcgt  50040
tcaacgttag cagcgactac gacatgttgt actttttatg tctggggttc attccacagt  50100
acctgtcggc ggtttagtgg gtggtgggcg aggggggagg gggcattagg gagaaagaac  50160
aagagcctcc gttgggtttt ctttgtgcct gtactcaaaa ggtcatacc cgtaaacggc   50220
gggctccagt cccggccccgg tggttggcgt gaacgcaacg gggggagctg ggttagcgtt  50280
tagtttagca ttcgctctcg ccttccgcc cgccccccga ccgttgcgcc ttttttttcg   50340
tccaccaaag tctctgtggg tgcgcgcatg cagccgatg cccgggagga ccggatggag   50400
gagccctgc ccgacagggc cgtgcccatt tacgtggctg ggttttttggc cctgtatgac   50460
agcgggact cgggcgagtt ggcattggat ccggatacgg tgcgggcgc cctgcctccg   50520
gataacccac tcccgattaa cgtggaccac cgcgctggct gcgaggtggg gcgggtgctg  50580
gccgtggtcg acgaccccg cgggccgttt tttgtgggc tgatcgcctg cgtgcagctg    50640
gagcgcgtcc tcgagacggc cgccagcgct gcgattttcg agcgccgcgg gccgccgctc  50700
tcccgggagg agcgcctgtt gtacctgatc accaactacc tgccctcggt ctcccctggcc 50760
acaaaacgcc tggggggcga ggcgcacccc gatcgcacgc tgttcgcgca cgtcgcgctg  50820
tgcgcgatcg ggcggcgcct cggcactatc gtcacctacg acaccggtct cgacgccgcc  50880
atcgcgcccct ttcgccacct gtcgccgcg tctcgcgagg gggcgcggcg actgccgcc   50940
gaggccgaga tcgcgctgtc cgggcgcacc tgggcgcccg gcgtggaggc gctgacccac  51000
acgctgcttt ccaccgccgt taacaacatg atgctgcggg accgctggag cctggtggcc  51060
gagcggcggc ggcaggccgg gatcgccgga cacacctacc tccaggcgag cgaaaaattc  51120
aaaatgtggg gggcggagcc tgtttccgcg cggcgcgcg ggtataagaa cggggcccg    51180
gagtccacgg acataccgcc cggctcgatc gctgccgcgc cgcagggtga ccggtgccca  51240
atcgtccgtc agcgcggggt cgccttgtcc ccggtactgc ccccatgaa ccccgttccg   51300
acatcgggca cccccgcccc cgcgccgccc ggcgacggga gctacctgtg gatccccggcc 51360
tcccattaca accagctcgt cgccggccat gccgcgcccc aacccagcc gcattccgcg   51420
tttggtttcc cggctgcggc ggggccgtg gcctatgggc ctcacggcgc gggtcttttcc  51480
cagcattacc ctccccacgt cgcccatcag tatcccgggt tgctgttctc gggaccagc   51540
ccactcgagg cgcagatagc cgcgttggtg ggggccatag ccgcggaccg ccaggcgggc  51600
ggtcagccgg ccgcgggaga ccctgggggtc cggggggtcgg gaaagcgtcg ccggtacgag  51660
gcggggccgt cggagtccta ctgcgaccag gacgaaccgg acgcggacta cccgtactac  51720
cccggggagg ctcgaggcgg gccgcgcggg gtcgactctc ggcgcgcggc ccgccagtct   51780
cccggggacca acgagaccat cacggcgctg atggggggcgg tgacgtcttt gcagcaggaa  51840
ctggcgcaca tgcgggctag gaccagcgcc ccctatggga tgtacacgcc ggtggcgcac  51900
tatcgccctc aggtgggggga gccggaacca acaacgaccc acccggccct ttgtcccccg  51960
gaggccgtgt atcgccccc accacacagc gcccctacg gtcctcccca gggtcgggcg   52020
tcccatgccc ccactccccc gtatgcccca gctgcctgcc cgccaggccc gccaccgcc   52080
ccatgtcctt ccaccagac gcgcgcccct ctaccgacgg agcccgcgtt ccccccgcc    52140
gccaccggat cccaaccgga ggcatccaac gcggaggccg ggcccttgt caacgccagc   52200
agcgcagcac acgtggacgt tgacacggcc cgcgccgccg atttgttcgt ctctcagatg  52260
atggggggccc gctgattcgc cccggtcttt ggtacctggg gatgtcttac tgtatatctt   52320
tttaaataaa ccaggtaata ccaaagaaga cccattggtg tatgttcttt ttttattggg   52380
aggcgcgggt aggcgggtag ctttacaatg caaaagcctt cgacgtggag gaaggcgtgg  52440
gggggaatcg gcactgacca aggggggtccg ttttgtcacg ggaaaggaaa gaggaaacag  52500
gccgcggaca cccgggggag tttatgtgtt ccctttctct tcttcccaca cacacaaaag  52560
gcgtaccaaa caaacaaacc aaaagatgca catgcggttt aacacccgtg gttttattt    52620
acaacaaacc ccccgtcaca ggtcgtcctc gtcgcgtcca ccgtcttttgt tgggaacttg  52680
ggtgtagttg gtgttgcggc gcttgcgcat gaccatgtcg gtgaccttgg cgctgagcag  52740
cgcgctcgtg cccttcttct tggccttgtg ttccgtgcgc tccatggcag acaccagggc  52800
catgtaccgt atcatctccc gggcctcggc tagcttggcc tcgtcaaagt cgccgccctc  52860
ctcgccctcc ccggacggct ccgggtttggt gggggttcttg agctccttgg tggttagcgg  52920
gtacagggcc ttcatggggt tgctctgcag ccgcatgacg tagcgaaagg tgaagaaggc  52980
cgccgccagg ccgccagga ccaacagacc cacggccagc gccccaaagg ggttggacat   53040
gaaggaggac acgcccgaca cggccgatac cacgccgccc acgatgccca tcaccacctt  53100
gccgaccgcg cgcccaggt cgcccatccc ctcgaagaac gcgcccaggc ccgcaaacat  53160
gcggcgcgttg gcgtcggcgt ggatgaccgt gtcgatgtcg gcgaagcgca ggtcgtgcag  53220
```

```
ctggttgcgg cgctggacct ccgtgtagtc cagcaggccg ctgtccttga tctcgtggcg   53280
ggtgtacacc tccagggggga caaactcgtg atcctccagc atggtgatgt tgaggtcgat   53340
gaaggtgctg acggtggtga tgtcggcgcg gctcagctgg tgggagtacg cgtactcctc   53400
gaagtacacg tagcccccac cgaaggtgaa gtagcgccgg tgtcccacgg tacacggctc   53460
gatcgcatcg cgcgtcagcc gcagtcgtt gtttctccccc agctgccct cgaccaacgg   53520
gccctggtct tcgtaccgaa agctgaccag ggggcggctg tagcaggccc cgggccgcga   53580
gctgatcgcg atcgagtttt ggacgatcac gtttgtccgcg gcgaccggca cgcacgtgga   53640
gacggccatc acgtcgccga gcatccgcgc gctcacccgc cggcccacgg tggccgaggc   53700
gatggcgttg gggttcagct tgcgggcctc gttccacagg gtcagctcgt gattctgcag   53760
ctcgcaccac gcgatggcaa cgcggcccaa catatcgttg acatggcgct gtatgtggtt   53820
gtacgtaaac tgcagcctgg cgaactcgat ggaggaggtg gtcttgatgc gctccacgga   53880
cgcgttggcg ctggccccgg gcggcggggg cgtggggttt gggggcttgc ggctctgctc   53940
tcggaggtgt tcccgcacgt acagctccgc gagcgtgttg ctgagaaggg gctggtacgc   54000
gatcagaaag cccccattgg ccaggtagta ctgcggccgg cccaccttga tgtgcgtcgc   54060
gttgtacctg cgggcgaaga tgcggtccat ggcgtcgcgg gcgtccttgc cgatgcagtc   54120
ccccaggtcc acgcgcgaga gcgggtactc ggtcaggttg tggtgaagg tggtggatat   54180
ggcgtcggag gagaatcgga aggagccgcc gtactcggag cgcagcatct cgtccacctc   54240
ctgccacttg gtcatggtgc agaccgacgg gcgctttggc accagtccc aggccacggt   54300
gaacttgggg gtcgtgagca ggttccgggt ggtcggcgcc gtgggcccggg ccttggtggt   54360
gaggtcgcgc gcgtagaagc cgtcgacctg cttgaagcgg tcggcggcgt agctggtgtg   54420
ttcggtgtgc gaccccctccc ggtagccgta aacggggac atgtacacaa agtcgccagt   54480
cgccagcaca aactcgtcgt acgggtacac cgagcgcgcg tccacctcct cgacgatgca   54540
gtttaccgtc gtcccgtacc ggtggaacgc ctccacccgc gaggggttgt acttgaggtc   54600
ggtggtgtgc cagcccccggc tcgtgcgggt cgcggcgttg gccggtttca gctccatgtc   54660
ggtctcgtgg tcgtcccggt gaaacgcggt ggtctccagg ttgttgcgca cgtacttggc   54720
cgtgaccga cagaccccct tggcgttgat ctttgtcgatc acctcctcga aggggacggg   54780
ggcgcggtcc tcaaagatcc ccataaactg ggagtagcgg tggccgaacc acacctgcga   54840
aacggtgacg tctttgtagt acatggtggc cttgaacttg tacggggcga tgttctcctt   54900
gaagaccacc gcgatgccct ccgtgtagtt ctgaccctcg gccgggtcg ggcagcggcg   54960
cggctgctcg aactgcacca ccgtggcgcc cgtggggcgt gggcacacgt aaaagtttgc   55020
atcggtgttc tccgccttga tgtcccgcag gtgctcgcgc agggtggcgt ggcccgcgcc   55080
gacggtcgcg ttgtcgccgg cggggcgcgg cggctttggg ggtttcggtt ttttgttctt   55140
cttcggtttc gggtcccccg ttgggggggc gccaggggcg ggcggcgccg gagtggcagg   55200
gccccgtc gccgcctggg tcgcggccgc gaccccagg gtgccggggg aactcggagc   55260
cgccgacacc accaaggacc ccagcgtcaa cccaagagc gcccatacga cgaaccaccg   55320
gcgccccgc gcggggggcgc cctgcgcat ggcgggacta cggggggccccg tcgtgccccc   55380
cgtcaggtag cctgggggcg aggtgctgga ggaccgagta gaggatcgag aaaacgtctc   55440
ggtcgtagac cacgaccgac cggggggccga tacagccgtc ggggggcgctc tcgacgatgg   55500
ccaccagcgg cagtcggag tcgtacgtga gatatacgcc gggcgggtaa cggtaacgac   55560
cttcggaggt cgggcggctg cagtccgggc ggcgcaactc gagctccccg caccggtaga   55620
ccgaggcaaa gagtgtggtg gcgataatca gctcgcgaat atatcgccag gcggcgcgct   55680
gagtgggcgt tattccggaa atgccgtcaa aacagtaaaa cctctgaaat tcgctgacgg   55740
cccaatcagc acccgagccc cccgccccca tgatgaaccg ggctgcctc tccttcaggt   55800
gcggcaggag ccccacgttc tcgacgctgt aatacgcgc ggtgttgggg ggctgggcga   55860
agctgtgggt ggagtgatca aagaggggcc cgttgacgag ctcgaagaag cgatgggtga   55920
tgctggggag cagggccggg tccacctggt gtcgcaggag agacgctcgc atgaaccggt   55980
gcgcgtcgaa cacgcccggc gccgagcggt tgtcgatgac cgtgccccgc gcggccgtca   56040
gggcgcagaa gcgcgcgcgc gccgcaaagc cgttggcgac cgcggcgaac gtcgcgggca   56100
gcacctcgcc gtgacgctg acccgcagca tcttctcgag ctccccgcgc tgctcgcgga   56160
cgcagcgccc caggctggcc aacgaccgct tcgtcaggcg gtccgcgtac agccgccgtc   56220
gctcccgcac gtccgcgggc gcttgcgtgg cgatgtcccc ccacgtctcg ggccccgcc   56280
ccccgggccc gcggcgacgg tcttcgtcct cgcccccgcc cccggagct cccaaccccc   56340
gtgccccttc ctctacggcg acacggtccc cgtcgtcgtc ggggcccgcg ccgcccttgg   56400
gcgcgtccgc cgcgcccccc gccccatgc gcgccagcac gcgacgcagc gcctcctcgt   56460
cgcactgttc ggggctgacg aggcgccgca agagccgcat cgtcaggtgg tggtcgtagc   56520
acgcgcggat gagcgcctcg atctgatcgt cgggtgacgt ggcctgaccg ccgattatta   56580
gggcgtccac catatccagc gccgccaggt ggctcccgaa cgcgcgatcg aaatgctccg   56640
cccgccgccc gaacagcgcc agttccacgg ccaccgcggc ggtctcctgc tgcaactcgc   56700
gccgcgccag cgcggtcagg ttgctggcaa acgcgtccat ggtggtctgg ggcgcgcggt   56760
cgccggacgc gagccagaat cgcaattcgc tgatggccga caggccggc gtggtggcct   56820
gaaacacgtc gtgcgcctcc agcagggcgt cggcctcctt gcggaccgag tcattccgg   56880
gcgacgggtg gggctgcccg tcgccccccg cggtccgggc cagcgcatgg tccaacacgg   56940
agagcgcccg cgcgcggtcg gcgtccgaca gcccggcggc gtggggcagg taccgccgca   57000
gctcgttggc gtcagccgc acctgcgcct gctgggtgac tggttacag atacggtccg   57060
ccaggcggcg ggcgatcgtc gcccctggt tcgccgtcac acacagttcc tcgaaacaga   57120
ccgcgcaggg gtgggacggg tcgctaagct ccgggggggac gataaggccc gacccaccg   57180
cccccaccat aaactcccga acgcgctcca gcgcggcggt ggcgccgcgc gaggggggtga   57240
tgaggtggca gtagtttagc tgctttagaa agttctcgac gtcgtgcagg aaacacagct   57300
ccatatggac ggtcccgcca tacgtatcca gcctgacccg ttggtgatac ggacagggtc   57360
gggcaggcc catggtctcg gtgaaaaacg ccgcgacgtc tcccgcggtc gcaacgtct   57420
ccaggctgcc caggagccgc tcgccctcgc gccacgcgta ctctagcagc aactccaggg   57480
tgaccgacag cggggtgaga aaggcccggg cctgggcctc caggcccggc tcagacgac   57540
gccgcagcgc ccgcacctga agcgcgttca gcttcagttg ggggagcttc cccgtccga   57600
tgtggggtc gcaccgccgg acgcagctcta tctgaaacac ataggtctgc acctgcccga   57660
gcagggctaa caacttttga cgggccacgg tgggctcgga caccggggcg gccatctcgc   57720
ggcgccgatc tgtaccgcgg ccggagtatg cggtggaccg aggcggtccg tacgctaccc   57780
ggcgtctggc tgaccccgg ggtccccctc ttcggggcgg cctccgcgg gcccgccgac   57840
cggcaagccc ggagtcggcg gcgcgtgcgt ttctgctcta ttcccagaca ccgcggagag   57900
gaatcacggc ccgcccagag atatagacac ggaacacaaa caagcacgga tgtcgtagca   57960
```

```
ataatttatt ttacacacat tccccgcccc gccctaggtt cccccacccc caacccctca   58020
cagcatatcc aacgtcaggt ctcccttttt gtcgggggc ccctcccaa acgggtcatc     58080
cccgtggaac gcccgtttgc ggccggcaaa tgccggtccc ggggcccccg ggccgccgaa   58140
cggcgtcgcg ttgtcgtcct cgcagccaaa atccccaaag ttaaacacct ccccggcgtt   58200
gccgagttgg ctgactaggg cctcgcgcct gtgcgccacc tccaggcg cgtccgtcga    58260
ccactcgccg ttgccgcgct ccagggcacg cgcggtcagc tccatcatct cctcgcttag   58320
gtactcgtcc tccaggagcg ccagccagtc ctcgatctgc agctgctggg tgcggggccc   58380
caggctttc acggtcacca cgaacacgct actggcgacg gccgcccgc cctcggagat    58440
aatgccccgg agctgctcgc acagcgagct ttcgtgcgct ccgccgccga ggctcgaggc   58500
cgcgcacaca aacccggccc ggggacaggc caggacgaac ttgcgggtgc ggtcaaaaat   58560
aaggagcggg cacgcgtttt tgccgcccat caggctggcc cagttccgg cctgaaacac    58620
acggtcgttg ccgccatgc cgtagtactt gctgatgctc aaccccaaca cgaccatggg    58680
gcgcgccgcc atgacgggcc gcagcaggtt gcagctggcc aacatggacg tccacgcgcc   58740
cggatgcgcg tccacggcgt ccatcagcgc gcgggcccg gcctccaggc cgcccccgcc   58800
ctgcgcggac cacgcggccg cagcctgcac gctggggga cggcgggacc cgcgatgat    58860
ggccgtaagg gtgttgatga agtacgtcga gtgatcgcag taccgcagaa tctggtttgc   58920
catgtagtac atcgccagct cgctcacgtt gttggggggcc aggttaataa agtttatcgc   58980
gccgtagtcc agggaaaact ttttaatgaa cgcgatggtc tcgatgtcct cgccgacag    59040
gagccgggcg ggaagctggt tgcgttggag ggccgtccag aaccactgcg ggttcggctg   59100
gttggacccc gggggcttgc cgttgggaa gatggccgcg tggaactgct tcagcagaaa    59160
gcccagcggt ccgaggagga tgtccacgcg cttgtcgggc ttctggtagg cgctctggag   59220
gctggcgacc cgcgccttgg cgcgttggg cgcgttgcg ctcgcgcccg cgaacaacac    59280
gcggctcttg acgcgcagct ccttgggaaa ccccaggggtc acgcgggcaa cgtcgccctc   59340
gaagctgctc tcggcggggg ccgtctgcc ggccgttagg ctgggggcgc agatagccgc    59400
cccctccgag agcgcgaccg tcagcgtttt ggccgacaga aacccgttgt taaacatgtc   59460
catcacgcgc cgccgcagca ccggttgaa ttgattgcga aagttgcgcc cctcgaccga    59520
ctgcccggcg aacaccccgt ggcactggct cagggccagg tcctgataca cggcgaggtt   59580
ggatcgccgc ccgagaagct gaagcagggg gcatggcccg cacgcgtacg ggtccagcgt   59640
cagggacatg gcgtggttgg cctcgcccag accgtcgcga aacttgaagt tcctcccctc   59700
caccaggttg cgcatcagct gctccacctc gcggtccacg acctgcctga cgttgttcac   59760
caccgtatgc agggcctcgc ggttggtgat gatggtctcc agccgcccca tggccgtggg    59820
gaccgcctgg tccacgtact gcagggtctc gagttcggcc atgacgcgct cggtcgccgc   59880
gcggtacgtc tcctgcatga tggtccgggc ggtctcggat ccgtccgcgc gcttcagggc   59940
cgagaaggcg gcgtagtttc ccagcacgtc gcagtcgctg tacatgctgt tcatggtccc   60000
gaagacgccg atggctccgc gggcggcgct ggcgaacttg ggatgcgcg cccggaggcg    60060
catgagcgtc gtgtgtacgc aggcgtggcg cgtgtcgaag gtgcacaggt tgcagggcac   60120
gtcggtctgt tggagtccg cgacgtatcg aaacacgtcc atctcctggc gcccgacgat    60180
cacgccgccg tcgcagcgct ccaggtaaaa cagcatcttg ccagcagcg ccggggaaaa    60240
cccacacaga atggccaggt gctcgcccgc aaattcctgg gttccgccga cgaggggcgg   60300
ggtgggccga ccctcgaacc cgggcaccac gtgtccctcg cggtccacct gtgggttggc   60360
cgccacgtgg gtcccgggca cgaggaagaa gcgtaaaag gagggtttgc tgtggtcctt    60420
tgggtccgcc ggaccggcgt cgtccacctc ggtgagatgt agggccgagt tggtgctaaa   60480
taccatggcc cccacgagtc ccgcggccgg cgccaggtac gccccgacgg cgttggcgcg   60540
ggccgcggcc gtgtcctggc cctcgcacag cggccatgcg gagatgtcgg tgggcggctc    60600
gtcgaagacg gccatcgaca cgatagactc gagggccagg gcggcgtctc cggccatgac   60660
ggaggccagg cgctgttcga acccgcccgc cgggcccttg ccgccgccgt cgcgcccacc    60720
ccggcgggtc ttacccctggc tggcttcgaa ggccgtgaac gtaatgtcgg cggggagggc    60780
ggcgccctcg tggttttcgt caaacgccag gtgggcggcc gcgcgggcca cggcgtccac   60840
gtttcggcat cgcagtgcca cggcggcggg tccacgacc gcctcgaaca ggaggcggtt    60900
gaggggggcgg ttaaaaaacg gaagcgggta ggtaaaattc tccccgatcg atcggtggtt   60960
ggcgttgaac ggctcggcga tgaccgcgct aaaatccggc atgaacagct gcaacggata   61020
cacgggtatg cggtgcacct ccgcccgcc tatggttacc ttgtccgagc ctcccaggtg    61080
cagaaaggtg ttgttgatgc acacggcctc cttgaagccc tcggtaacga ccagatacag    61140
gagggcgcgg tccgggtcca ggccgaggcg ctcacacagc gcctcccccg tcgtctcgtg   61200
tttgaggtcg ccgggccggg gggtgtagtc cgaaaagcca aaatggcggc gtgcccgctc    61260
gcagagtcgc gtcaggtttg gggcctgggt gttgggtcc aggtgccggc cgccgtgaaa    61320
gacgtacacg gacgagctgt agtgcgatgg cgtcagtttc agggacaccg cggtaccccc   61380
gagccccgtc gtgcgagaac ccacgaccac ggctacgttg gcctcaaagc cgctctccac   61440
ggtcaggccc acgaccaggg gcgccaacggc gacgtcggca tcgccgctgc gcgccgacag   61500
taacgccaga agctcgatgc cttcggatgg acacgcgca gcgtacacgt atccccaggg    61560
cccgggggggg accttgatgg tggttgccgt cttgggctttt gtctccatgt cctcctggca    61620
atcggtccgc aaacgaggt aatcccggca cgacgacgga cgcccgacga ggtatgtctc    61680
ccgagcgtca aaatccggg gggcggcga cggtcaaggg gagggtggga gaccggggtt    61740
ggggaatgaa tccctaccct tcaccgacaa ccccccgagcg accaggagt ggccgatgaac    61800
cccggcggct ggcaacgcgg ggtccctgcg agaggcacag atgcttacgg tcaggtgctc    61860
cgggccgggt gcgtctgata tgcgttggt atatgtacac tttacctggg ggcgtgccgg   61920
accgcaccag cccctcccac accccgcgcg tcatcagccg gtgggcgnnn nnnnnnnnn    61980
nnnnnnnnnn nnnnnnnnnn nnnnnnnnnn nnnnnnnnnn nnnnnnnnnn nnnnnnnnnn    62040
nnnnnnnnnn nnnnnnnnnn nnnnnnnnnt ttttataata gcggccacgc ccaccggcta    62100
cgtcacgctc ctgtcggccg ccggcggtcc ataagcccgg ccggccggc cgacgcgaat    62160
aaaccgggcc gccggccggg gcgccgcgca gcagctcgcc gcccggatcc gccagacaaa   62220
caaggccctt gcacatgccg gcccgggcga gcctgggggt ccggtaattt tgccatccca   62280
cccaagcggc ttttgggggtt tttcctcttc ccccctcccc acctcccccc tctttagggg   62340
ttcgggtggg aacaaccgcg atgttttccg gtggcgggca ggcctgtcc ccgggaggaa    62400
agtcggcggc cagggcggcg tccgggtttt ttgcgcccgc cggccctcgc ggagccggcc   62460
ggggaccccc gccttgtttg aggcaaaact tttacaaccc ctaccctgcc ccagtcggga    62520
cgcaacagaa gccgaccggg ccaacccagc gccatacgta ctatagcgaa tgcgatgaat   62580
ttcgattcat cgccccgcgg gtgctggacg aggatgcccc cccggagaag cgcgccgggg   62640
tgcacgacgg tcacctcaag cgcgccccca aggtgtactg cgggggggac gagcgcgacg   62700
```

```
tcctccgcgt cgggtcgggc ggcttctggc cgcggcgctc gcgcctgtgg ggcggcgtgg   62760
accacgcccc ggcggggttc gaccccaccg tcaccgtctt tcacgtgtat gacatcctgg   62820
agaacgtgga gcacgcgtac ggcatgcgcg cggcccagtt ccacgcgcgg tttatggacg   62880
ccatcacacc gacggggacc gtcatcacgc tcctgggcct gactccgaa ggccaccggg    62940
tggccgttca cgtttacggc acgcggcagt acttttacat gaacaaggag gaggttgaca   63000
ggcacctaca atgccgcgcc ccacgagatc tctgcgagcg catggccgcg gccctgcgcg   63060
agtccccggg cgcgtcgttc cgcggcatct ccgcggacca cttcgaggcg gaggtggtgg   63120
agcgcaccga cgtgtactac tacgagacgc gccccgctct gttttaccgc gtctacgtcc   63180
gaagcgggcg cgtgctgtcg tacctgtgcg acaacttctg cccggccatc aagaagtacg   63240
agggtggggt cgacgccacc acccggttca tcctgacaa ccccgggttc gtcaccttcg    63300
gctggtaccg tctcaaaccg ggccggaaca acacgctagc ccagccgcgg gccccgatcg   63360
ccttcgggac atccagcgat gtcgagttta actgtacggc ggacaacctg gccatcgagg   63420
ggggcatgag cgacctaccg gcatacaagc tcatgtgctt cgatatcgaa tgcaaggcgg   63480
gggggaggga cgagctggcc tttccggtgg ccgggcaccc ggacgacctg gtcatccaga   63540
tatcctgtct gctctacgac ctgtccacca ccgcccgga gcacgtcctc ctgtttcgc    63600
tcggttcctg cgacctcccc gaatcccacc tgaacgagct ggcggccagg ggcctgccca   63660
cgcccgtggt tctggaattc gacagcgaat cgagatgct gttggcttc atgacccttg    63720
tgaaacagta cggccccgag ttcgtgaccg ggtacaacat catcaacttc gactggccgt   63780
tcttgctggc caagctgacg gacatttaca aggtcccccct ggacgggtac ggccgcatga   63840
acggccgggc cgtgtttcgc gtgtgggaca taggccagag ccacttccag aagcgcagca   63900
agataaaggt gaacggcatg gtgaacatcg acatgtacgg gattataacc gacaagatca   63960
agctctcgag ctacaagctc aacgccgtgg ccgaagccgt cctgaaggac aagaagaagg   64020
acctgagcta tcgcgacatc cccgcctact acgccgccgg gcccgcgcaa cgcggggtga   64080
tcggcgagta ctgcatacag gattccctgc tggtgggcca gctgtttttt aagttttgc    64140
cccatctgga gctctcggcc gtcgcgcgct tggcgggtat taacatcacc cgcaccatct   64200
acgacggcca gcagatccgc gtctttacgt gcctgctgcg cctggccgac cagaagggct   64260
ttattctgcc ggacacccag gggcgattta ggggcgccgg ggggaggcg cccaagcgtc     64320
cggccgcagc ccgggaggac gaggagcggc cagaggagga ggggaggac gagaacgaac     64380
gcgaggaggg cggggcgag cgggagccgg agggcgcgcg ggagaccgcc ggccggcacg    64440
tggggtacca ggggcccagg gtccttgacc ccacttccgg gtttcacgtg aacccgtgg    64500
tggtgttcga ctttgccagc ctgtaccca gcatcatcca ggcccacaac ctgtgcttca    64560
gcacgctctc cctgagggcc gacgcagtgg cgcacctgga ggcgggcaag gactacctgg   64620
agatcgagat ggggggggcga cggctgttct tcgtcaaggc tcacgtgcga gagagcctcc   64680
tcagcatcct cctgcgggac tggctcgca tgcgaaagca gatccgctcg cggattcccc    64740
agagcagccc cgaggaggcc gtgctcctgg acaagcagca ggccgccatc aaggtcgtgt   64800
gtaactcggt gtacgggttc acgggagtgc agcacggact cctgccgtgc ctgcatgttg   64860
ccgcgacggt gacgaccatc ggccgcgaga tgctgctcgc gacccgcgag tacgtccacg   64920
cgcgctgggc ggccttcgaa cagctcctgg ccgatttccc ggaggcggcc gacatgcgcg   64980
cccccgggcc ctattccatg cgcatcatct acggggacac ggactccata tttgtgctgt   65040
gccgcggcct cacggccgcc gggctgacgg ccatggcaca caagatgcgc agccacatct   65100
cgcgcgcgct gtttctgccc cccatcaaac tcgagtgcga aaagacgttc accaagctgc   65160
tgctgatcgc caagaaaaag tacatcggcg tcatctacgg gggtaagatg ctcatcaagg   65220
gcgtggatct ggtgcgcaaa aacaactgcg cgtttatcaa ccgcacctcc aggggccttgc  65280
tcgacctgct gttttacgac gataccgtat ccggagcggc cgccgcgtta gccgagcgcc   65340
ccgcagagga gtggctggcg cgaccctgc ccgagggact gcaggcgttc ggggccgtcc    65400
tcgtagacgc ccatcggcgc atcaccgacc cggagaggga catccaggac tttgtcctca   65460
ccgccgaact gagcagacac ccgcgcgcgt acaccaacaa gcgcctggcc cacctgacgg   65520
tgtattacaa gctcatggcc cgccgcgcgc aggtccgtc catcaaggac cggatcccgt     65580
acgtgatcgt ggcccagacc cgcgaggtag aggagacggt cgcgcggctg gccgcctcc    65640
gcgagctaga cgccgccgcc caggggacg agcccgcccc ccgcggcc ctgccctccc       65700
cggccaagcg ccccgggag acgccgtcgc atgccgaccc ccggggaggc gcgtccaagg    65760
cccgcaagct gctggtgtcc gagctggccg aggatcccgc atacgccatt gcccacggcg   65820
tcgccctgaa cacggactat tacttctccc acctgttggg ggcggcgtgc gtgacattca   65880
aggccctgtt tgggaataac gccaagatca ccgagagtct gttaaaaagg tttattcccg   65940
aagtgtggca ccccccggac gacgtgccg cgccgctcca ggccgcaggg ttcggggcgg    66000
tgggtgccgg cgctacggcg gaggaaactc gtcgaatgtt gcatagagcc tttgatactc   66060
tagcatgagc ccccgtcga agctgatgtc cctcattta caataaatgt ctgcggccga    66120
cacggtcgga atctccgcgt ccgtgggttt ctctgcgttg cgccggacca cgagcacaaa   66180
cgtgctctgc cacacgtggg cgacgaacct gtacccggg cacgcggtga gcatccggtc    66240
tatgagccgg tagtgcaggt gggcggacgt gccgggaaag atgacgtaca gcatgtggcc   66300
cccgtaagtg gggtccgggt aaaacaacag ccgcgggtcg cacgccccgc ctccgcgcag   66360
gatcgtgtgtg acgaaaaaaa gctcgggttg gccaagaatc ccggccaaga ggtcctggag   66420
gggggcgttg tggcggtcgg ccaacacgac caaggaggcc aggaaggcgc gatgctcgaa   66480
tatcgtgttg atctgctgca cgaaggccag gattagggcc tcgcgcttg tggccgcaa    66540
ccgcccgtct cccgcgttgc acgcgggaca gcaaccccg atgcctaggt agtagcccat    66600
cccggagagg gtcaggcagt tgtcggccac ggtctggtcc agacagaagg gcagccgacac   66660
gggagtggtc ttcaccaggg gcaccgagag cgagcgcacg atgcgatct cctcggaggg    66720
cgtctgggcg agggcggcga aaaggcccg atagcgctgg cgctcgtgta aacacagctc    66780
ctgtttgcgg gcgtgaggcg gcaggctctt ccgggaggcg cgacgcacca cgcccagagt   66840
cccgccggcc gcagaggagc gcgaccgccg gcgctccttg ccgtgatagg gcccgggccg   66900
ggagccgcgg cgatggggt cggtatcata cataggtaca cagggtgtgc tcagggaca     66960
ggagcgagat cgagtggcgt ctaagcagcg cgcccgcctc acggacaaat gtggcgagcg   67020
cggtgggctt tggtacaaat acctgatacg tcttgaaggt gtagatgagg gcacgcaacg   67080
ctatgcagac acgccctcg aactcgttcc cgcaggccag cttgccttg tggagcagca    67140
gctcgtcggg atgggtggcg gggggatggc cgaacagaac ccaggggtca acctccatct    67200
ccgtgatggc gcacatgggg tcacagaaca tgtgcttaaa gatggcctcg ggccccgcgg   67260
cccgcagcag gctcacaaac cggcccccgt ccccgggctg cgtctcgggg tccgcctcga   67320
gctggtcgac gacgggtacg atacagtcga agaggctcgt gttgttttcc gagtagcgga   67380
ccacggaggc ccggagtctg cgcagggcca gccagtaagc ccgcaccagt aacaggttac   67440
```

```
acagcaggca ttctccgccg gtgcgcccgc gcccccggcc gtgtttcagc acggtggcca   67500
tcagagggcc caggtcgagg tcgggctggg catcgggttc ggtaaactgc gcaaagcgcg   67560
gagccacgtc gcgcgtgcgt gccccgcgat gcgcttccca ggactggcgg accgtggcgc   67620
gacgggcctc cgcggcagcg cgcagctggg gccccgactc ccagacgcg ggggtgccgg    67680
cgaggagcag cgaggaccaga tccgcgtacg cccacgtatc cggcgactcc tccggctcgg  67740
ggtccccggc gaccgtctcg aattcccgt tgcgagcggc ggcgcgcgta cagcagctgt    67800
ccccgccccc gcgccgaccc tccgtgcagt ccaggagacg ggcgcaatcc ttccagttca   67860
tcagtgcggt ggtaagcgac ggctgcgtgc cggataccgc cgccgacccc gccccctcct   67920
cgccccggga ggccaaggtt ccgatgaggg cccgggtggc agactgcgcc aggaacgagt   67980
agttggagta ctgcaccttg gcggctcccg ggagggcgg gggcttgggt tgcttctggg    68040
catgccgccc gggcacccg ccgtcggtac ggaagcagca gtggagaaaa aagtgccggt    68100
ggatgtcgtt tatggtgagg gcaaagcgtg cgaaggagcc gaccagggtc gccttcttgg   68160
tgcgcagaaa gtggcggtcc atgacgtaca caaactcgaa cgcggccacg aagatgctag   68220
cggcgcagtg gggcgcccc aggcattgg cacagagaaa gcgtaatcg gccacccact      68280
gaggcgagag gcgtaggtt tgcttgtaca gctcgatggt gcggcagacc agacagggcc    68340
ggtccagcgc gaaggtgtcg atggccgccg cggaaagggg cccggtgtcc aaaagcccct   68400
ccccacaggg atccggggc gggttgcggg gtcctccgcg cccgcccgaa cccctccgt     68460
cgcccgcccc cccgcgggcc cttgagggg cggtgaccac gtcggcggcg acgtcctcgt    68520
cgagcgtacc gacgggcggc acacctatca cgtgactggc cgtcaggagc tcggcgcaga   68580
gagcctcgtt aagagccagg aggctgggat cgaaggccac atacgcgcgc tcgaacgccc   68640
ccgccttcca gctgctgccg ggggactctt cgcacaccgc gacgctcgcc aggacccgg    68700
ggggcgaagt tgccatggct gggcgggagg ggcgcacgcg ccagcgaact ttacgggaca   68760
caatccccga ctgcgcgctg cggtcccaga ccctggagag tctagacgcg cgctacgtct   68820
cgcgagacgg cgcgcatgac gcggccgtct ggttcgagga tatgaccccc gccgagctgg   68880
aggttgtctt cccgactacg gacgccaagc taaactacct gtcgcggacg cagcggctgg   68940
cctccctcct gacgtacgcc gggcctataa aagcgcccga gccgccgcc gccccgcaga    69000
ccccggacac cgcgtgtgtg cacgcgagc tgctcgcccg caagcgggaa agattccgcg    69060
cggtcattaa ccgttcctg gacctgcacc agattctgcg gggctgacgc gcgcgctgtt    69120
gggcgggacg gttcgcgaac cctttggtgg gtttacgcgg gcacgcacgc tcccatcgcg   69180
ggcgccatgg cgggactggg caagccctac accggccacc caggtgacgc cttcgaggt    69240
ctcgttcagc gaattcggct tatcgtccca tctacgttgc ggggcgggga cggggaggcg   69300
ggcccctact ctccctccag cctccctcc aggtgcgcct ttcagtttca tggccatgac    69360
gggtccgacg agtcgtttcc catcgagtat gtactgcggc ttatgaacga ctgggccgag   69420
gtcccgtgca acccttacct gcgcatacag aacaccggca tgtcggtgct gtttcagggg   69480
ttttttcatc gcccacacaa cgccccccggg ggcgcgatta cgcagagcg gaccaatgtg   69540
atcctgggt ccaccgagac gacggggttg tccctcggcg acctggacac catcaagggg    69600
cggctcggcc tggatgcccg gccgatgatg gccagcatgt ggatcagctg ctttgtgcgc   69660
atgccccgcg tgcagctcgc gtttcggttc atgggccccg aagatgccgg acggacgaga   69720
cggatcctgt gccgcgccgc cgagcaggct attacccgtc gccgccgaac ccggcggtcc   69780
cgggaggcgt acggggccga ggccgggctg ggggtggccg gaacgggttt ccgggccagg   69840
ggggacggtt ttggcccgct ccccttgtta acccaagggc cctcccgccc gtggcaccag   69900
gccctgcggg gtcttaagca cctacggatt ggcccccccg cgctcgtttt ggcggcggga   69960
ctcgtcctgg gggccgctat ttggtgggtg gttggtgctg gccgcgcct ataaaaaagg    70020
acgcaccgcc gccctaatcg ccagtgcgtt ccggacgcct tcgccccaca cagccctccc   70080
gaccgacacc cccatatcgc tccccgacct ccggtcccga tggccgtccc gcaatttcac   70140
cgccccagca ccgttaccac cgatagcgtc cgggcgcttg gcatgcgcgg gctcgtcttg   70200
gccaccaata actctcagtt tatcatggat aacaaccacc cacaccccca cggcacccaa   70260
ggggccgtgc gggagtttct ccgcggtcag gcggcggcac tgacggacct tggtctggcc   70320
cacgcaaaca cacgtttac cccgcagcct atgttcgcgg gcgacgcacc ggccgcctgg    70380
ttgcggcccg cgtttggcct gcggcgcacc tattcacctt ttgtcgttcg agaaccttcg   70440
acgcccggga cccgtgagg cccagggagt tccttctggg gtgttttaat caataaaaga    70500
ccacaccaac gcacgagcct tgcgtttaat gtcgtgttta ttcaagggag tgggataggg   70560
ttcgacggtt cgaaacttaa cacaccaaat aatcgagcgc gtctagccca gtaacatgcg   70620
cacgtgatgt aggctggtca gcacggcgtc gctgtgatga agcagcgccc ggcgggtccg   70680
ctgtaactgc tgttgtaggc ggtaacaggc gcggatcagc accgccaggg cgctacgacc   70740
ggtgcgttgc acgtagcgtc gcgacagaac tgcgtttgcc gatacggcgg ggggccgaa    70800
ttgtaagcgc gtcacctctt gggagtcatc ggctataac gcactgaatg gttcgttggt    70860
tatggggag tgtggttccc cagggagtgg gtcgagcgcc tcggcctcgg aatccgagag    70920
gaacaacgag gtggcgtcgg agtcttcgtc gtcagagaca tacagggtct gaagcagcga   70980
cacgggcgtg ggggtagcgt cgatgtgtag cgcgagggag gatgcccacg aagacaccc    71040
agacaaggag ctgcccgtgc gtggatttgt ggaagacgcg gaagccggga cggatgggcg   71100
gttttgcggt gcccggaacc gaaccgccgg atactccccg ggtgctacat gcccgttttg   71160
gggctggggt tggggctggg gcgcggacag gcggctgacg gtcaaatgcc cccggggcg    71220
cgcagatgtg gcgggcgtgg ccaccggctg ccgtgtagtg gggcggcggg aaaccgggcc   71280
tccgggcgta acaccgccct ccagcgtcaa gtatgtgggg ggcgggcctg acgtcggggg   71340
cggggtgacg ggttggaccg cgggaggcgg gggagaggga cctgcgggag aggatgaggt   71400
cggctcggcc gggttgcggc ctaaacagg ggccgtgggg tcgcggggt cccagggtga    71460
agggagggat tcccgcgatt cggacagcga cgcgacagcg gggcgcgtaa ggcgccgctg   71520
ccgccccgcct acgggaaccc tggggggggt tggcgcgggg cccgaggtta gcgggggggcg 71580
gcggttttcg ccccccgggca aaaccgtgcc ggttgcgacc ggggcggaa cgggatcgat   71640
agggagagcg ggagaagcct ggccggcgga ctggggaccg agcgggaggg gcacaccaga   71700
caccaaagcg tggggcgctg gctctggggg tttgggaggg gccggggggc gcgcgaaatc   71760
ggtaaccggg gcgaccgtgt cggggagggc aggcggccgc caaccctggg tggtcgcgga   71820
agcctggggtg gcgcgcgcaa gggagcgtgc ccggcggtcg ggcgaccgga   71880
cgaagaagcg gcagaagcgc gggaggaggc ggggcggtcgg ggggcggtgg catcgggggg   71940
cgccggggaa cttttggggg acggcaagcg ccggacgtcg tcgcggggc ccacgggcgc    72000
cggccgcgtg ctttcggccg ggacgcccgg tcgtgcttcg cgagccgtga ctgccggccc   72060
agggggccgc ggtgcacact gggatgtggg gacggactga tcggcggtgg gcgaaagggg   72120
gtccggggca aggagggggcg cggggccgcc ggagtcgtca gacgcgagct cctccaggcc  72180
```

```
gtgaatccat gcccacatgc gagggggac gggctcgccg ggggtggcgt cggtgaatag  72240
cgtgggggcc aggcttccgg gccccaacga gccctccgtc ccaacaaggt ccgccgggcc  72300
gggggtcggg ttcggaccg aggggctctg gtcgtcgggg gcgcgctggt acaccggatg  72360
cccgggaat agctcccccg acaggaggga ggcgtcgaac ggccgcccga ggatagctcg  72420
tgcgaggaag gggtcctcgt cggtggcgct ggcggcgagg acgtcctcgc cgcccgccac  72480
aaacgggagc tcctcggtgg cctcgctgcc aacaaaccgc acgtcggggg ggccggggg  72540
tccgggtttt cccacaacac cgcgaccggg gtcatggaga tgtccacgag caccagacac  72600
ggcgggcccc gggcgagggg ccgctcggcg atgagcgcgg acaggcgcgg gagctgtgcc  72660
gccagacacg cgttttcgat cgggttcagg tcggcgtgca ggaggcggac ggcccacgtc  72720
tcgatgtcgg acgacacggc atcgcgcaag gcggcgtccg gcccgcgagc gcgtgagtca  72780
aacagcgtga ggcacagctc cagctccgac tcgcgggaaa aggccgtggt gttgcggagc  72840
gccacgacga cgggcgcgcc caggagcact gccgccagca ccaggtccat ggccgtaacg  72900
cgcgccgcgg gggtgcggtg ggtggcggcg gccgcacgg cgacgtgctg gcccgtgggc  72960
cggtagaggg cgttgggggg agcggggggt gacgcctcgc gcccccccga ggggctcagc  73020
gtctgcccag attccagacg cgcggtcaga agggcgtcga aactgtcata ctctgtgtag  73080
tcgtccggaa acatgcaggt ccaaagagcg gccagcgcgg tgcttgggag acacatgcgc  73140
ccgaggacgc tcaccgccgc cagcgcctgg gcgggactca gctttcccag cgcggcgccg  73200
cgctcggttc ccagctcggg gaccgagcgc caggggcgca gggggtcggt ttcggacaac  73260
ttgccgcggc gccagtctgc cagccgcgtg ccgaacatga ggccccgggt cggagggcct  73320
ccggccgaaa acgctggcag cacgcggatg cgggcgtctg gatgcggggt caggcgctgc  73380
acgaatagca tggaatctgc tgcgttctga acgcacggg ggagggtgag atgcatgtac  73440
tcgtgttggc ggaccagatc caggcgccaa aagtgtaaa tgtgttccgg cggagctggcc  73500
accagcgcca ccagcacgtc gttctcgtta aggaaacgg ggtgcctagt ggagctctgg  73560
ggtccgagcg gcgccccgg ggcgccgcg tcaccccccc attccagctg ggcccagcga  73620
cacccaaact cgcgcgtgag agtggtcgcg acgagggcga cgtagagctc ggccgccgca  73680
tccatcgagg ccccccatct cgcctgcgg tggcacaa agcgtccgaa agctgaaag  73740
ttggcggcct gggcgtcgct gagggccagc tgaagccggt tgatgacgat gaggacgtac  73800
atggccgtga cggtcgaggc cgactccagg gtgtccgtcg gaagcggggg gcgaatgcat  73860
gccgcctcgg gacacatcag cagcgcgccg agcttgtcgg tcacggccgg gaagcagagc  73920
gcgtactgca gtggcgttcc atccgggacc aaaaagctgg agcgaacgg ccgatccagc  73980
gtactggtgg cctcgcgcag caccaggggc cccgggcctc cgctcactcg caggtacgg  74040
tcgcccggc ggcgcagcat ctgcgggtcg gcctcttggc cgggtggggc ggacgcccgg  74100
gcgcgggcgt ctagggcgcg aagatccacg agcaggggcg cgggcgcggc ggccgcgccc  74160
gcgcccgtct ggcctgtggc cttggcgtac gcgctatata agcccatgcg gcgttggatg  74220
agctcccgcg cgccccggaa ctcctccatc gcccatgggg ccaggtcccc ggccaccgcg  74280
tcgaattccg ccaacaggcc cccaggggta tcaaagttca tctcccaggc caccctttggc  74340
accacctcgt cccgcagccg ggcgctcagg tcggcgtgtt gggccacgcg cccccccgagc  74400
tcctccacgg ccccggcccg ctcggcgctc ttggcgccca ggacgccctg gtacttggcg  74460
ggaaggcgct cgtagtcccg ctgggcgtc agccccgaca cagtgttggt ggtgtcctga  74520
agggcgcgaa gctgctcgca tgccgcgcga aatccctcgg gcgatttcca ggccccccg  74580
cgaacgcggc cgaagcgacc ccataccctcg tcccactccg cctcggcctc ctcgagagac  74640
ctccgcaggg cctcgacgcg gcgacgggtg tcgaagagcg cctgcaggcg cgcgcctgt  74700
cgcgtcagga ggcccggcgc ctcgctgctg gccgcgctta gcgggtcgcgt ctcaaaggta  74760
cgctgggcat gttccaacca ggcgaccgcc tgcacgtcga gctcgcgcgc cttctccgtc  74820
tggtccaaca gaatttcgac ctgatccgcg atctcctccg ccgagcgcgc ctggtccagc  74880
gtcttggcca cggtcgccgg gacggcgacc accttcagca gggtcttcag attggccaga  74940
ccctccggct ccgagctggc ccggcgctcg cgccggccca gcacatcccg cagccccgc  75000
gtgacccgct ccggtggcttc ggcgcgctgc tgtttggcgc gcaccacggc gtccttggta  75060
tcggccaggt cctgtcgggt cacgaatgcg acgtagtcgg agtacgccgt gtccttcacg  75120
gggctctggt ccacgcgctc cagcgccgcc acgcacgcca ccagcgcgtc ctcgctcggg  75180
cagggcaggt tgaccctgc ccggacaagc tcggccgccg ccgccgggtc gttgcgcgg  75240
gcggatatct cctccgcgc ggcggccagg tccagcgcca cgcttccgat cgcgcgccgc  75300
gcgtcggccc ggagggcgtc caggcgatcg cggatatcca cgtactcggc gtagcccttt  75360
tgaaaaaacg gcacgtactg gcgcagggcc ggcacgcccc caagtcttc cgacaggtgt  75420
agtacggcct cgtggtagtc gataaacccg tcgttccgct gggcccgctc cagcagcccg  75480
cccgcgagcc gcagaagccg cgccaggggc tcggtgtcca cccgaaacat gtcggcgtac  75540
gtgtcggccg cggccccaaa ggccgcgctc cagtcgatgc ggtgaatggc tgcgagcggg  75600
gggagcatgg ggtggcgctg gttctcgggg gtgtatgggt taaacgcaag ggccgtctcc  75660
agggcaaggg tcaccgcctt ggcgttggtt cccagcgcct gctcggcccg ctttcggaag  75720
tccggggt tgtagccgtg cgtgcccgcc agcgctgca ggcgacggag ctcgaccacg  75780
tcaaactcgg cactgctttc cacgcggtcc agcacggcct ccacgtcggc ggcccagcgc  75840
tcgtggctac tgcgggcgcg ctgggccgcc atcttctctc tgaggtcggc ggtggcggcc  75900
tcaagttcgt cggcgcggcg tcgcgtggcg ccgatgacct ttcccagctc ctgcaggcg  75960
cgcccgctgg gggagtggtc cccggccgtc cttcggcgt gcaacaggcc cccgaacctg  76020
ccctcgtggc ccgcgaggct ttcccgcgcg ccggtggtcg cgcgcgtcgc ggcttggatc  76080
agggaggcat gctctcctt cggttggttg gcggcccggc gcacctggac gacaaggtcg  76140
gcggcagcca accctaaggt cgtgagctgg gcgatggccc ccgcgcgtc cagggccaac  76200
cgagtcgcct tgacgtatcc cgcggcgctg tcggccatgg ccgctaggaa ggcaggggg  76260
gaggccggt cgctggcggc cgctgcgcgg gccgtcaccg gtcgaccag gacgcggttg  76320
gcccgcacgg ccgcatccac cgtcgacgcg gggtctccgc tcgcgacggg ggcgctgccg  76380
gcgttgatgg cgttcgagac ggcgtgggct atgatcgggg cgtgatcggc gaagaactgc  76440
aagagaaacg gagtctcggg ggcgtcggcg aacaggttct tcagcaccac cacgaagctg  76500
ggatgcaagc cggacagagc cgtcgccgtg tccgagtcgg ggtgctccag ggcatctcgg  76560
tactgcccca gcagcccca catgtccgcc cgcacgccgg ccgtaacctc aggggcgcgc  76620
ccccgaacgg cctcggggag gtccgaccag ccccgccgga gggagcccgg cagggtcgcc  76680
aggacgccg gacaggcctt tagccccaca aagtcaggga gggggcgcag gacccctgg  76740
agtttgtgca agaacttctc ccgggcgtcg cgggccacct tcgcccgctc ccgcgctccc  76800
tcgagcattg cctccaggga gcgcgcgcgc tcccgcaaac ggacacgcgc atcggggcg  76860
agctctgccg tcagcttggc ggcatccatg gcccgcgcct gccgcagcgc ttcctcggcc  76920
```

```
atgcgcgtgg cctctggcga cagcccgccg tcgtcggggt agggcgacgc gccgggcgca   76980
ggaacaaagg ccgcgtcgct gtccagctgc tggcccaggg ccgcatctag ggcgtcgaag   77040
cgccgcagct cggccagacc cgagctgcgg cgcgcctgct ggtcgttaat gtcgcggatg   77100
ctgcgcgcca gctcgtccag cggcttcgt tctatcagcc cttggttggc ggcgtccgtc    77160
aggacggaga gccaggccgc caggtcctcg ggggcgtcca gcgtctggcc ccgctgtatc   77220
agatcccgca acaggatggc cgtggggctg gtcgcgatcg ggggcggggc gggaatggcc   77280
gcgcgctgcg cgatgtcccg cgtgtgctgg tcgaagacag gcagggactc gagcagctgg   77340
accacgggca cgacggcggc cgaagccacg tgaaaccggc ggtcgttgtt gtcgctggcc   77400
tgtagagcct tggcgctgta tacgcccccc cggtaaaagt actccttaac cgccccctcg   77460
atcgcccgac gggcctgggt ccgcacctcc tccagccgaa cctgaacggc ctcggggccc   77520
agggggggtg ggcgcggagc ccctgcgggg gccgcccgg ccggggcggg cattacgccg     77580
aggggccccg cgtgctgtga gaccgcgtcg acccgcgag cgaggcgtc gagggcctcg     77640
cgcatctggc gatcctccgc ctccaccta atctcttcgc cacgggcaaa tttggccaga    77700
gcctgactc tatacagaag cggttctggc tgcgtcgggg tggcggggca aaaagggtg     77760
tccgggtggg cctgcgagcg ctccagaagc cactcgccga ggcgtgtata cagattggcc   77820
ggcggggccg cgcgaagctg cagctccagg tccgcgagtt ccccgtaaaa ggcgtccgtc   77880
tcccgaatga catccctagc cacaaggatc agcttcgcca cgccaggcg accgatcaga    77940
gagttttcgt ccagcacgtg ctggacgagg ggcagatggg cggccacgtc ggccaggctc   78000
aggcgcgtgg aggccagaaa gtcccccacg gccgttttcc ggggcagcat gctcagggta   78060
aactccaaca gggcggcggc cgggccggcc accccggcct gggtgtgcgt ccgggccccg   78120
ttctcgatga gaaaggcgag gacgcgttca agaaaaaaa taacacagag ctccagcagc    78180
cccggagaag ccggatacgg cgaccgtaag gcgctgatgg tgagccgca acacgcgggg   78240
acctcgcggg ccagggcggc ggagcacgcg gtgaacttaa ccgccgtggc ggccacgttt   78300
gggtgggcct cgaacagctg ggcaaggtct gcgcccgggg gctcgggtga gcggcgagtc   78360
ttcagcgcct cgagggcctg cgaggacgcc ggaaccgtgg gcccgtcgtc ctcgcccgcc   78420
tcggcgaccg gcgcgccggc gggtcgggg ggtgccgagg cgaggacagg ctccggaacg    78480
gaggcgggga ccgcggcccc gacggggtt ttgcctttgg gggtggattt cttcttggtt    78540
ttggcagggg gggccgagcg tttcgttttc tcccccgaag tcaggtcttc gacgctggaa   78600
ggcggagtcc aggtgggtcg gcggcgcttg ggatggccgg ccgagtagcg tgcccggtgc   78660
cgaccaaccg ggacgacgcc catctccagg acccgcatgt cgtcgtcatc ttcttcggcc   78720
gcctctgcgg cggggggctt gggggcggag ggaggcggtg gtgggatcgc ggagggtggg   78780
tcggcggagg ggggatccgt gggtggggta ccctcaggg ccaccgccca tacatcgtcg    78840
ggcgcccgat tcgggcgctt ggcctctggt tttgccgacg gaccgccgt ccccccggat    78900
gtctcggagg ccctgtcgtc gcgacgggcc cgggtcggtg gcggcgactg ggcggctgtg   78960
ggcgggtgtg gcccgcgtgcc ccctaccccc tcccggggcc ccacgccgac gcagggctcc  79020
cccaggcccg cgatccgcc ccgcagggg tgcgtgatgg ccacgcgccg ttcgctgaac     79080
gcttcgtcct gcaggtaagt ctcgctggcc ccgtaaagat gcagagccgc ggccgtcaag   79140
tccgcaggag ccgcgggttc cgggcccgac ggcacgaaaa acaccatggc tcccgcccac   79200
cgtacgtccg ggcgatcgcg ggtgtaatac gtcaggtatg gatacatgtc ccccgcccgc   79260
actttggcga tgaacgcggg ggtgccctcc ggaaggccgt gcgggtcaaa aaggtatgcg   79320
gtgtcgcgt ccctgaacag cccccatccct agggggccaa tggttaggag cgtgtacgac   79380
agggggcgca gggcccacgg gccggcgaag aacgtgtgtg cggggcattg tgtctccagc   79440
aggcccgcgc cgggctcccc gaagaagccc acctcgccgt atacgcgcga gaagacacag   79500
cgcagtccgc cgcgcgcccc tgggtactcg aggaagttgg ggagctcgac gatcgaaac    79560
atgcgcggcg gcccagggcc cgcggtcgcg cgcgtccact cgccccctc gaccaaacaa    79620
ccctcgatgg cctccgcgga cagaacgtcg cgagggccca catcaaatat gaggctgaga   79680
aaggacagcg acgagcgcat gcacgatacc gaccccccg gctccaggtc gggcgcgaac    79740
tggttccgag caccggtgac cacgatgtcg cgatcccccc cgcgttccat cgtggagtgc   79800
ggtgggggtgc ccgcgatcat atgtgcccta ctggccagag acccggcctg tttatggacc  79860
ggaccccgg ggttagtgtt gtttccgcca cccatgcccc cgtaccatgg ccccggttcc    79920
cctgattagg ctacgagtcg cggtgatcgc ttcccaaaaa ccgagctgcg tttgtctgtc   79980
ttgatcttcc ccccccccc cgccgcccg ccccgcccgcc cgcccgcaca ccataacacc    80040
gagaacaaca cacggggtg ggcgtaacat aataaagctt tattggtaac tagttaacgg    80100
caagtccgtg ggtggcgcga cggtgtcctc cgggctcatc tcgtcgtcct cgacgggggt   80160
gttggaatga ggcgccccct gccggtccgc ctggcgtggg ccgtgcccat aggcctccgg   80220
ctttctgtgcg tccatgggca taggcgcggg gagactgttt ccggcgtcgc ggacctccag  80280
gtccctggga gactccggtc cggctaacgg acgaaacgcg gaagcgcgaa acacgccgtc   80340
ggtgacccgc aggagctcgt tcatcagtaa ccaatccata ctcagcgtaa cggccagccc   80400
ctggcgagac agatccacgg agtccggaac cgcggtcgtc tggcccaggg ggccgaggct   80460
gtagtccccc caggccccta ggtcggacgg gctcgtaagc acgacgcggt cggcccggcg   80520
gctttgcggg ggggcgtcct cgggcgcatg cgccattacc tctcggatgg ccgcggcgcg   80580
ctggtcggcc gagctgacca agggcgccac gaccacggcg cgctccgtct gcaggccctt   80640
ccacgtgtcg tggagttcct ggacaaactc ggccacgggc tcgggtcccg cggccgcgcg   80700
cgcggcttga tagcaggccg agagacgccg ccagcgccgt agaaactgac ccatgaagca   80760
aaacccgggg acctggtctc ccgacagcag cttcgacgcc cgggtgtgaa tgccggacac   80820
aacgacagaa aacccgtgaa tttcgcgccg gaccacggcc agcacgttgt cctcgtgcga   80880
cacctgggcc gccagctcgt cgcacacctc caggtgcgcc gtggtttcgg tgatgacgga   80940
acgcaggctc gcgagggacg cgaccagcgc gcgcttggcg tcgtgataca tgctgcagta   81000
ctgactcacc gcgtccccca tggcctcggg gggccaggcc cccaggcgcgt cgggagtgtc  81060
cccgaccacc gcatacaggc ggcgcccgtc gctctcgaac cgacactcga aaaaggcgga   81120
gagcgtgcgc atgtgcagcc gcagcagcac gatggcgtcc tccagttggc gaatcagggg   81180
gtctgcgcgc tcgcgaggt cctgcagcac ccccgggcg gccagggcgt acatgctaat    81240
caacaggagg ctggtgccca cctcgggggg cgggggggc tgcagctgga ccagggggccg  81300
cagctgctcg acggcaccc gtgagatcac gtacagccagct gctctatgtt             81360
gtcggccatc tgcatagtgg ggccgaggcc gccccgggcg gccggttcga gagggtaat    81420
cagcgcgccc agtttggtgc gatgcccctc gaccgtgggg agatagccca gcccaaagtc   81480
ccgggcccag gccaacacac gcagggcgaa ctcgaccggg cgtggaaggt aggccgcgct   81540
acacgtggcc cccaacgcgt ccccgaccac cagggccaga acgtagggga cgaagcccgg   81600
gtcggcgagg acgttgggt gaatgccctc gagggcgggg aagcggatct gggtcgccgc    81660
```

```
ggccaggtgg acagagggggg cgtggctggg ctgcccgacg gggagaagcg cggacagcgg    81720
cgtggccggg gtggtggggg tgatgtccca gtgggtctga ccatacacgt cgatccagat    81780
gagcgccgtc tcgcggagaa ggctgggttg accggaacta aagcggcgct cggccgtctc    81840
aaactccccc acgagcgccc gccgcaggct cgccagatgt tccgtcggca cggccggacc    81900
catgatacgc gccagtgtct ggctcagaac gccccccgac aggccgaccg cctcgcagag    81960
ccgcccgtgc gtgtgctcgc tggcgccctg gacccgcctg aaagtttttta cgtagttggc    82020
atagtacccg tattccgcgc ccagaccaaa cacgttcgac cccgcgaggg caatgcaccc    82080
aaagagctgc tggacttcgc cgagtccgtg gccggcgggc gtccgcgcgg ggacgcccgc    82140
cgccagaaac ccctccaggg ccgaaaggta gtgcgtgcag tgcgagggcg tgaacccagc    82200
gtcgatcagg gtgttgatca ccacggaggg cgaattcgta ttctggatca acgtccacgt    82260
ctgctgcagc agagccagca gccgctgctg ggcgccggcg gagggctgct ccccgagctg    82320
cagcaggctg gagacggcag gctggaagac tgccagtgcc gacgaactca ggaacggcac    82380
gtcgggatca aacacggcca cgtccgtccg cacgcgcgcc attagcgtcc ccgggggcgc    82440
acaggccgag cgcggggctga cgcggctgag ggccgtcgac acgcgcacct cctcgcggct    82500
gcgaaccatc ttgttggcct ccagtggcgg aatcattatg gccgggtcga tctcccgcac    82560
ggtgtgctga aactgcgcca acaggggcgg cgggaccaca gcccccgct cggggtcgt    82620
caggtactgg tccaccaggg ccaacgtaaa gagggcccgt gtgaggggag tgagggtcgc    82680
gtcgtctatg cgctggaggt gcgccgagaa cagcgtcacc cgattactca ccagggccaa    82740
gaaccggagg ccctcttgca cgaacggggc ggggaagagc aggctgtacg ccggggtggt    82800
aaggttcgcg ctgggctgcc ccaacgggac cggcgccatc ttgagtgacg tctccccaag    82860
ggcctcgatg gaggtccgcg ggctcatggc caagcagctc ttggtgacgg tttgccagcg    82920
gtctatccac tccacggcgc actggcggac gcggaccggc gcgaacccgg ccgcggtgcg    82980
caggccggcg gaatccagcg catgggacgt gtcggagccg gtgaccgcga ggatggtgtc    83040
cttgatgacc tccatctccc ggaaggcctg tcgggggcc tcggggagag ccaccaccaa    83100
gcggtgtacg agcaacccgg ggaggttctc ggccaagagc gccgtctccg gaagcccgtg    83160
ggcccggtgg agcgcgcaca ggtgttccag cagcggccgc cagcatgccc gcgcgtctac    83220
cggggcaatg gccgttcccg acaacagaaa cgccgccatg gcggcgcgca gcttggccgt    83280
ggccagaaac gccgggtcgt ccgccccgtt tgccgtctcg gccgtggggg ttggcggttg    83340
gcgaaggccg gctaggctcg ccaataggcg ctgcataggt ccgtccgagg gcggaccggc    83400
gggtgaggtc gtgacgacgg gggcctgcga cgggagaccg cggtctgcca tgacgcccgg    83460
ctcgcgtggg tggggacag cgtagaccaa cgacgagatc gggcgggaat gactgtcgtg    83520
cgctgtaggg agcggcgaat tatcgatccc ccgcggccct ccaggaaccc cgcaggcgtt    83580
gcgagtaccc cgcgtcttcg cggggtgtta tacggccact taagtcccgg catcccgttc    83640
gcggacccag gcccgggga ttgtccggat gtgcgggcag cccggacggc gtgggttgcg    83700
gactttctgc ggggcgggcc aaatggccct ttaaacgtgt gtatacggac gcgccgggcc    83760
agtcggccaa cacaacccac cggaggcggt agccgcgttt ggctgtgggg tgggtggttc    83820
cgccttgcgt gagtgtcctt tcgaccccc tccccgggt tttgttaggt cgcgatctgc    83880
agtcgcaatg aagaccaatc cgctaccgc aaccccttcc gtgtggggcg ggagtaccgt    83940
ggaactcccc cccaccacac gcgataccgc gggacagggc ctgcttcggc gcgtcctgcg    84000
cccccccgatc tctcgccgcg acggcccagt gctccccagg gggtcgggac cccggaggc   84060
ggccagcacg ctgtggttgc ttggcctgga cggcacagac gcgccccctg gggcgctgac   84120
ccccaacgac gataccgaac aggccctgga caagatcctg cggggcacca tgcgcgggggg   84180
ggcggccctg atctgctccc cgcgccatca tctaacccgc caagtgatcc tgacggatct   84240
gtgcaaccc aacgcggatc gtgccgggac gctgcttctg cgcgctgcggc accccgccga   84300
cctgcctcac ctgccccacc agcgcgcccc gccaggccgg cagaccgagc ggctgggcga   84360
ggcctggggc cagctgatgg aggcgaccgc cctgggggtcg gggcgagccg agagcggggtg   84420
cacgcgcgg ggcctcgtgt cgtttaactt cctggtggcg gcgtgtgcg cctcgtacga   84480
cgcgcgcgac gccgccgatg cggtacgggc ccacgtcacg gccaactacc gcggacgcg   84540
ggtgggggcg cgcctggatc gttttttccga gtgtctgcgc gccatggttc acacgcacgt   84600
cttccccccac gaggtcatgc ggtttttcgg ggggctggtg tcgtgggtca cccaggacga   84660
gctagcgagc gtcaccgccg tgtgccgggg gccacaggag gcacaccggcc cggccaccg   84720
gggccggccc cgctcggccg tgatcctccc ggcgtgtgcg ttcgtggacc tggacgccga   84780
gctggggctg gggggcccgg gtgcggcgtt tctgtacctg gtattcactt accgccagcg   84840
ccgggaccag gagctgtgtt gtgtgtacgt gatcaagagc cagctccccc cgcgcgggtt   84900
ggagccggcc ctggagcggc tgtttgggcg cctccggatc accaacacga ttcacggcac   84960
cgaggacatg acgcccccgg cccaaaccg aaacccgac ttcccccctcg cgggcctggc   85020
cgccaatccc caaacccgc gttgctcggc tggccaggtc acgaaccccc agttcgcgga   85080
caggctgtac cgctggcagc cggacctgcg ggggcgcccc accgcacgca cctgtacgta   85140
cgccgccttt gcagagtccg gcatgatgcc cgaggatagt cccccgctgcc tgcaccgcac   85200
cgagcgcttt ggggcggtca gcgtccccgt tgtcatcctg gaaggcgtgg tgtggccgcc   85260
cggcgagtgg cgggcatgcg cgtgagcgta gcaaacgccc cgcccacaca acgtccgcc   85320
cccaaccect tccccgctgt cactcgtggt tcgttgaccc ggacgtccgc caaataaagc   85380
cactgaaacc cgaaacgcga gtgttgtaac gtccttgggc cgggaggaag ccacaaaatg   85440
caaatgggat acatggaagg aacacacccc cgtgactcag gacatcggcg tgtccttttg   85500
ggtttcactg aaactggccc gcgcccace cctgcgcgat gtggataaaa agccagcgcg   85560
ggtggttag ggtaccacag gtgggtgctt tggaaacttg tcgtcgccg tgctcctgtg   85620
agcttgcgtc cctccccggt ttcctttgcg ctcccgcctt ccggacctgc tcttgcctat   85680
cttcttttggc tctcggtgcg attcgtcagg cagcggcctt gtcgaatctc gaccccacca   85740
ctcgccggac ccgccgacgt cccctctcga gccaccgaa acccgccgg tctgttgaaa   85800
tggccagccg cccagccgca tcctctcccg tcgaagcgcg ggccccggtt ggggggacagg   85860
aggccggcgg ccccagcgca gccacccagg ggaggccgc cggggcccct ctcgcccacg   85920
gccaccacgt gtactgccag cgagtcaatg gcgtgatggt gctttccgac aagacgcccc   85980
ggtccgcgtc ctaccgcatc agcgatagca actttgtcca atgtggttcc aactgcacca   86040
tgatcatcga cggagacgtg gtgcgcggac gcccccgaagg cgggcatccc   86100
ccgctccctt cgttgcggtg acaaacatcg gagccggcag cgacggcggg accgccgtcg   86160
tggcattcgg gggaacccca cgtgctcgg cggggacgtc taccggtacc cagacggccg   86220
acgtccccac cgaggccctt gggggcccc ctcctcctcc ccgcttcacc ctgggtggcg   86280
gctgttgttc ctgtcgcgac acacggcgcc gctctgcggt attcgggggg gaggggatc   86340
cagtcggccc cgcggagttc gtctcggacg accggtcgtc cgattccgac tcggatgact   86400
```

```
cggaggacac ggactcggag acgcctgtcac acgcctcctc ggacgtgtcc ggcggggcca   86460
cgtacgacga cgcccttgac tccgattcgt catcggatga ctccctgcag atagatggcc   86520
ccgtgtgtcg cccgtggagc aatgacaccg cgcccctgga tgtttgcccc gggaccccg    86580
gcccgggcgc cgacgccggt ggtccctcag cggtagaccc acacgcgccg acgccagagg   86640
ccggcgctgg tcttgcggcc gatcccgccg tggcccggga cgacgcggag gggctttcgg   86700
acccccggcc acgtctggga acgggcacgg cctaccccgt cccctggaa  ctcacgcccg   86760
agaacgcgga ggccgtggcg cgcttctgg  gagatgccgt gaaccgcgaa cccgcgctca   86820
tgctggagta ctttgccgg  tgcgcccgcg aggaaaccaa gcgtgtcccc ccaggacat    86880
tcggcagcgc ccctcgcctc acggaggacg actttgggct tctcaactac gcgctcgtgg   86940
agatgcagcg cctgtgtctg gacgttcctc cggtcccgcc gaacgcatac atgcctatt    87000
atctcaggga gtatgtgacg cggctggtca acggtttcaa gccgctggtg agccggtccg   87060
ctcgcctttta ccgcatcctg ggggttctgg tgcacctgcg gatccggacc cgggaggcct   87120
cctttgagga gtggctgcga tccaaggaag tgggcctgga ttttggcctg acggaaaggc   87180
ttcgcgagca cgaagcccag ctggtgatcc tggcccaggc tctggaccat tacgactgtc   87240
tgatccacag caccacacac acgctggtcg agcggggct  gcaatcggcc ctgaagtatg   87300
aggagttta  cctaaagcgt tttggcgggc actacatgga gtccgtcttc cagatgtaca   87360
cccgcatcgc cggcttttg  gcctgccggg ccacgcgcgg catgcgccac atcgccctgg   87420
ggcgagaggg gtcgtggtgg gaaatgttca agttcttttt ccaccgcctc tacgaccacc   87480
agatcgtacc gtcgaccccc gccatgctga acctggggac ccgcaactac tacacctcca   87540
gctgctacct ggtaaaccc  caggccacca caaacaaggc gaccctgcgg gccatcacca   87600
gcaacgtcag tgccatcctc gcccgcaacg ggggcatcgg gctatgcgtg caggcgttta   87660
acgactccgg ccccgggacc gccagcgtca tgcccgcct  caaggtcctt gactcgctgg   87720
tggcggcgca caacaaagag agcgcgcgtc cgaccgccgc gtgcgtgtac ctggagccgt   87780
ggcacaccga cgtgcgggcc gtgctccgga tgaaggggt  cctcgccggc gaagaggccc   87840
agcgctgcga caatatcttc agcgccctct ggatgccaga cctgttttc  aagcgcctga   87900
ttcgccacct ggacggcagg aagaacgtca catggaccct gttcgaccgg gacaccagca   87960
tgtcgctcgc cgactttcac ggggaggagt tcgagaagct ctaccagcac ctcgaggtca   88020
tggggttcgg cgagcagata cccatccagg agctggccta tggcattgtg cgcagcgcgg   88080
ccacgaccgg gagcccctc  gtcatgttca aagacgcggt gaaccgccac tacatctacg   88140
acaccccaggg ggcggccatc gccggctcca acctctgcac cgagatcgtc catccggcct   88200
ccaagcgatc cagtgggtc  tgcaacctgg gaagcgtgaa tctggcccga tgcgtctcca   88260
ggcagacgtt tgactttggg cggctccgcg acgccgtgca ggcgtgcgtg ctgatggtga   88320
acatcatgat cgacagcacg ctacaaccca cgccccagtg cacccgcggc aacgacaacc   88380
tgcggtccat gggaatcggc atgcagggcc tgcacacgcg ctgcctgaag gtggggctgg   88440
atctggagtc tgccgaattt caggacctga acaaacacat cggcagggtg atgctcggga   88500
cggcgatgaa gaccagcaac gcgctgtgcg ttcgcggggc ccgtccctc  aaccactta    88560
agcgcagcat gtatcgcgcc ggccgctttc actgggagcg cttttccggac gcccggccgc   88620
ggtacgaggg cgagtgggag atgctacgcc agagcatgat gaaacacggc ctgcgcaaca   88680
gccagtttgt cgcgctgatg cccaccgccg cctcggccga gatctcggac gtcagcgagg   88740
gctttgcccc cctgttcacc aacctgttca gcaaggtgca ccgggacggc gagacgctgc   88800
gccccaacac gctcctgcta aaggaactgg aacgcacgtt tagcgggaag cgcctcctgg   88860
aggtgatgga cagtctcgac gccaagcagt ggtccgtggc gcaggcgctc ccgtgcctgg   88920
agcccaccca ccccctccgg cgattcaaga ccgcgtttga ctacgaccag aagttgttga   88980
tcgacctgtg tgcggaccgc gcccctacg  tcgaccatag ccaatccatg accctgtatg   89040
tcacggagaa ggcggacggg accctccag  cctccaccct ggtccgcctt ctggtccacg   89100
catataagcg cggactaaaa acaggatgt  actactgcaa ggttcgcaag gcgaccaaca   89160
gcggggtctt tggcggcgac gacaacattg tctgcacgag ctgcgcggtg tgaccgacaa   89220
accccctccg cgccaggccc gccgccactg tcgtcgccgt cccacgctct cccctgctgc   89280
catggattcc gcggccccag ccctctcccc cgctctgacg gccttacgg  gccagagcgc   89340
gacggcggac ctggcgatcc agattccaaa gtgcccgac  cccgagaggt acttctacac   89400
ctcccagtgt cccgacatta accacctgcg ctccctcagc atccttaacc gctggctgga   89460
aaccgagctt gttttcgtgg gggacgagga ggacgtctcc aagctttccg agggcgagct   89520
cagcttttac cgcttcctct tcgctttcct gtcggccgcc gacgacctgg ttacggaaaa   89580
cctgggcggc ctctccggcc tgtttgagca gaaggacatt ctccactact acgtggagca   89640
ggaatgcatc gaagtcgtac actcgcgcgt gtacaacatc atccagctgg tgcttttcca   89700
caacaacgac caggcgcgcc gcgagtacgt ggccggcacc atcaaccacc cggccatccg   89760
cgccaaggtg gactggttgg aagcgcgggt gcgggaatgc gcctccgttc cggaaaagtt   89820
cattctcatg atcctcatcg agggcatctt ttttgccgcc tcgtttgccg ccatccgcta   89880
ccttcgcacc aacaaccttc tgcgggtcac ctgccagtca aacgacctca tcagccggga   89940
cgaggccgtg cacacgacgg cctcgtgtta catctacaac aactacctcg gcgggcacgc   90000
caagcccccg cccgaccgcg tgtacgggct gttccgccag gcggtcgaga tcgagatcgg   90060
atttatccga tcccaggcgc cgacggacag ccatatcctg agcccggcgg cgctggcggc   90120
catcgaaaac tacgtgcgat tcagcgcgga tcgcctgttg ggccttatcc acatgaagcc   90180
actgttttcc gccccacccc ccgagccgcag cttccgctg agcctcatgt ccaccgacaa   90240
acacaccaat ttttcgagt  gtcgcagcac ctcctacgcc ggggcggtcg tcaacgatcc   90300
gtgagtgtcg cggcgcgctt ctaccgtgt  ttgcccataa taaacctctg aaccaaactt   90360
tgggtctcat tgtgattctt gtcagggacg cggggtggg  agaggataaa aggcggcgca   90420
aaaagcagta accaggtccg tccagattct gcgggcatag aataccataa ttttattggt   90480
gggtcgtttg ttcggggaca agcgcgtcg  tctgacgttt gggctactcg tcccagaatt   90540
tggccaggac gtccttgtag aacgcgggtg gggggggcctg ggtccgcaac tgctccagaa   90600
acctgtcggc gatatcaggg gccgtgatat gccgggtcac gatagatcgc gccaggtttt   90660
cgtcgcggat gtcctggtag ataggcaggc gtttcagaag agtccacggc cccgctcct    90720
tgggggccgat aagcgatatg acgtacttaa tgtagcggta ttccaccagc tcggtgatgg   90780
tcatgggata ggggagccag tccagggact ctgggacggt ggtgatgacg tggcgtccac   90840
ggttggccac ataactcggg tgctcttcca gcagctgcgc gttcgggacc tggacgagct   90900
cgggcggggt gagtatctcc gaggaggacg acctgggggcc ggggtggccc ccggtaacgt   90960
cccgggggatc caggggggagg tcctcgtcgt cttcgtatcc gccggcgatc tgttgggtta   91020
gaatttcggt ccacgagacg cgcgtctcgg tgccgccggc ggccgccggc agaggggcc    91080
tggtttccgt ggagcgcgag ctggtgtgtt cccggcggat ggcccgccgg gtctgagagc   91140
```

-continued

```
gactcggggg ggtccagtga cattcgcgca gcacatcctc cacgcgaggcg taggtgttat  91200
tgggatggag gtcggtgtgg cagcggacaa agagggccag gaactggggg tagctcatct  91260
taaagtactt cagtatatcg cgacagttga tcgtgggaat gtagcaggcg ctaatatcca  91320
acacaatatc acagcccatc aacaggaggt cagtgtccgt ggtgtacacg tacgcgaccg  91380
tgttggtgtg atagaggttg gcgcaggcat cgtccgcctc caactgaccc gagttaatgt  91440
aggcgtaccc cagggcccgg agaacgcgaa tacagaacag atgcgccaga cgcagggccg  91500
gcttcgaggg cgcggcggac ggcagcgcgg ctccggaccc ggccgtcccc cgggtccccg  91560
aggccagaga ggtgccgcgt cggcgcatgt tggaaaaggc agagctgggt ctggagtcgg  91620
tgatggggga aggcggtgga gaggcgtcca cgtcactggc ctcctcgtcc gtccggcact  91680
gggccgtcgt gcgggccagg atgggccttgg ctccaaacac aaccggctcc atacaattga  91740
ccccgcgatc ggtaacgaag atggggaaaa gggactttttg ggtaaacacc tttaataagc  91800
gacagaggca gtgtagcgta atggcctcgc ggtcgtaact ggggtatcgg cgctgatatt  91860
tgaccaccaa cgtgtacatg acgttccaca ggtccacgtg aatgggggtg aagtacccgg  91920
ccggggcccc aaggcccggg cgcttgacca gatggtgtgt gtgggcaaac ttcatcatcc  91980
cgaacaaacc catgtcaggt cgattgtaac tgcggatcgg cctaactaag gcgtggttgg  92040
tgcgacggtc cgggacaccc gagcctgtct ctctgtgtat ggtgacccag acaacaacac  92100
cgacacaaga ggacaataat ccgttagggg acgtctcttta taatttcgat ggcccaactc  92160
cacgcggatt ggtgcagcac cctgcatgcg ccggtgcggg ccaaccttcc ccccgctcat  92220
tgcctcttcc aaaagggtgt ggcctaacga gctgggggcg tatttaatca ggctagcgcg  92280
gcgggcctgc cgtagtttct ggctcggtga gcgacggtcc ggttgcttgg gtcccctggc  92340
tgccatcaaa acccccaccct cgcagcggca tacgcccccct ccgcgtcccg cacccgagac  92400
cccggcccgg ctgccctcac caccgaagcc cacctcgtca ctgtggggtg ttcccagcce  92460
gcgttgggat gacggattcc cctgcggtg tggcccccgc ctcccacgtg gaggacgcgt  92520
cggacgcgtc cctcgggcag ccggaggagg gggcgccctg ccaggtggtc ctgcagggcg  92580
ccgaacttaa tggaatccta caggcgtttg ccccgctgcg cacgagcctt ctggactcgc  92640
ttctggttat gggcgaccgg ggcatccttta tccataacac gatcttttgg gagcaggtgt  92700
tcctgccct ggaacactcg caattcagtc ggtatcgctg gcgcggaccc acggcggcgt  92760
tcctgtctct cgtggaccag aagcgctccc tcctgagcgt gtttcgcgcc aaccagtacc  92820
cggacctacg tcgggtggag ttggcgatca cgggccaggc cccgtttcgc acgctggttc  92880
agcgcatatg gacgacgacg tccgacggcg aggccgttga gctagccagc gagacgctga  92940
tgaagcgcga actgacgagc tttgtggtgc tggttcccca gggaaccccc gacgttcagt  93000
tgcgcctgac gaggccgcag ctcaccaagg tccttaacgc gaccggggcc gatagtgcca  93060
cgcccaccac gttcgagctc ggggttaacg gcaaaatttc cgtgttcacc acgagtacct  93120
gcgtcacatt tgctgcccgc gaggagggcg tgtcgtccag ccacagcacc caggtccaga  93180
tcctgtccaa cgcgctcacc aaggcgggcc aggcggccgc caacgccaag acggtgtacg  93240
gggaaaatac ccatcgcacc ttctctgtgg tcgtcgacga ttgcagcatg cgggcggtgc  93300
tccggcgact gcaggtcggc gggggcaccc tcaagttctt cctcacgacc cccgtcccca  93360
gtctgtgcgt caccgccacc ggtcccaacg ctgtatcgg ggtatttctc ctgaaacccc  93420
agaagatttg cctggactgg ctgggtcata gccagggtc tccttcagcc gggagctcgg  93480
cctcccgggc ctctgggagc gagccaacag acagcaagga ctccgcgtcg gacgcggtca  93540
gccacgcgca tccggaagac ctcgatgcgc ctgcccgggc gggagaggcg ggggcctcgc  93600
acgcctgtcc gatgccgtcg tcgaccacgc gggtcactcc cacgaccaag cggggcgct  93660
cggggggcgg ggatgccgcg gcggacacgg ccctaaagaa acctaagacg gggtcgccca  93720
ccgcacccce gcccgcagat ccagtccccc tggacacgga ggacgactcc gatgcggcgg  93780
acgggacggc ggcccgtccc gccgctccag acgcccggag cggaagccgt tacgcgtgtt  93840
actttcgcga cctcccgacc ggagaagcaa gccccgcgc cttctccgcc ttcgggggg  93900
ggcccaaac cccgtatggt tttggattcc cctgacgggg cgggccttg gcggccgccn  93960
aactctcgca ccatcccggg ttaatgtaaa taaacttggt attgcccaac actctcccgg  94020
gtgtcgcgtg tggttcatgt gtgtgcctgg cgtcccccac cctcgggttc gtgtatttcc  94080
tttccctgtc cttataaaag ccgtatgtgg ggcgctgacg gaaccacccc gcgtgccatc  94140
acggccaagg cgcgggatgc tccgcaacga cagccaccgg gccgcgtccc cggaggacgg  94200
ccagggacgg gtcgacgacg gacgccaca cctcgcgtgc gtgggggccc tggcgcgggg  94260
gttcatgcat atctggcttc aggccgccaa gctgggtttt gcgggatcgg tcgttatgtc  94320
gcgcgggccg tacgcgaatg ccgcgtctgg ggcgttcgcc gtcgggtgcg ccgtgctggg  94380
ctttatgcgc gcaccccctc cctcgccgcg gcccaccgcg cggatatacg cctggctcaa  94440
actggcggcc ggtggagcgg cccttgttct gtggagtctc ggggagcccg gcacgcagcc  94500
gggggccccg gccccgggcc cggccaccca gtgcctggcg ctgggcgccc cctatgcggc  94560
gctcctggtc ctcgccgatg acgtctatcc gctctttctc ctcgcccggg gcccctgtt  94620
cgtcggcacc ctggggatgg tcgtcggcgg gctgacgatc ggagcagcg cgcgctactg  94680
gtggatcggt gggcccgcg cggccgcctt ggccgcgcg gtgttggcgg gcggggcgc  94740
gaccaccgcc agggactgct tctccaggc gtgcccgac caccgccgcg tctgcgtcat  94800
cgtcgcaggc gagtctgttt cccgccgccc ccggaggac ccagagcgac ccggggaccc  94860
cgggccaccg tccccccga caccccaacg atcccagggg ccgccggccg atgaggtcgc  94920
accggccggg gtagcgcggc ccgaaaacgt ctgggtgccc gtgtcacct ttctggggcg  94980
gggcgcgctc gccgtcaaga cggtgcgaga acatgcccgg ggaacgccgg gcccgggcct  95040
gccgctgtgg ccccaggtgt ttctcggagg ccatgtggcg gtgcccctga cggagctgtg  95100
tcaggcgctt gcgccctggg accttacgga cccgctgctg tttgttcacg ccggactgca  95160
ggtcatcaac ctcgggttgg tgtttcggtt ttccgaggtt gtcgtgtatg cggcgctagg  95220
gggtgcgctg tggattcgt tggcgcaggt gctggggctc cggcgtcgc tgcggcaggaa  95280
ggaccccggg gacggggccc ggttggcggc gacgcttcgg ggcctcttct tctccgtgta  95340
cgcgctgggg tttggggtgg gggcgctgct gtgcctccg gggtcaacgg gcgggcggtc  95400
gggcgattga tatatttttc aataaaaggc attagtcccg aagaccgccg gtgtgtgatg  95460
atttcgccat aacacccaaa ccccggatgg ggcccgggta taaattccgg aaggggacac  95520
gggctaccct cactaccgag ggcgcttggt cgggaggccg gtcgaacgc acaccccccat  95580
ccggtggtcc gtgtgaggt cgttttcagt gccggtctc gctttgccgg gaacgctagc  95640
cgatccctcg cgaggggagg gcgtagggca tggcccgggg gcgggtgggc cttgccgtgg  95700
tcctgtggag cctgttgtgg ctcggggcgg gggtgtccgg gggctcggaa actgcctcca  95760
ccgggcccac gatcaccgcg ggagcggtga cgaacgcgag cgaggccccc acatcggggt  95820
cccccgggtc agccgccagc ccggaagtca cccccacatc gaccccaaac cccaacaatg  95880
```

```
tcacacaaaa caaaaccacc cccaccgagc cggccagccc ccaacaacc cccaagccca    95940
cctccacgcc caaaagcccc cccacgtcca ccccgaccc caaacccaag aacaacacca    96000
cccccgccaa gtcgggccgc cccactaaac ccccgggcc cgtgtggtgc gaccgccgcg    96060
acccattggc ccggtacggc tcgcgggtgc agatccgatg ccggtttcgg aattccaccc    96120
gcatggagtt ccgcctccag atatggcgtt actccatggg tccgtccccc ccaatcgctc    96180
cggctcccga cctagaggag gtcctgacga acatcaccgc cccacccggg ggactcctgg    96240
tgtacgacag cgcccccaac ctgacgacc cccacgtgct ctgggcgag ggggccggcc    96300
cgggtgccga ccctccgttg tattctgtca ccgggccgct gccgacccag cggctgatta    96360
tcggcgaggt gacgcccgcg acccaggaaa tgtattactt ggcctggggc cggatggaca    96420
gcccgcacga gtacgggacg tgggtgcgcg tccgcatgtt ccgcccccg tctctgaccc    96480
tccagcccca cgccggtgatg gagggtcagc cgttcaaggc gacgtgcacg gccgacgcct    96540
actaccccgcg taaccccgtg gagttggtct ggttcgagga cgaccgccag gtgtttaacc    96600
cgggccagat cgacacgcag acgcacgagc accccgacgg gttcaccacc gtctctaccg    96660
tgacctccga ggctgtcggc ggccaggtcc ccccgcggac cttcacctgc cagatgacgt    96720
ggcaccgcga ctccgtgaca ttctcgcgac gcaatgccac cgggctggcc ctggtgctgc    96780
cgcggccaac catcaccatg gaatttgggg tccggcatgt ggtctgcacg gccggctgcg    96840
tccccgaggg cgtgacgttt gcctggttcc tgggggacga cccctcaccg gcggctaagt    96900
cggccgttac ggcccaggag tcatgcgacc accccggcgc ggctacggtc cggtccaccc    96960
tgcccatttc gtacgactac agcgagtaca tctgtcggtt gaccggatat ccggccggga    97020
ttcccgttct agaacaccac ggcagtcacc agccccacc cagggaccc accgagcggc    97080
aggtgatcga ggcgatcgag tgggtgggga ttggaatcgg ggttctcgcg gcgggggtcc    97140
tggtcgtaac ggcgatcgtg tacgtcgtcc gcacatcaca gtcgcggcag cgtcatcggc    97200
ggtaacgcga gaccccccg ttaccttttt aatatctata tagtttggtc ccccctctat    97260
cccgccacc gctgggcgct ataaagccgc caccctctct tccctcaggt catccttggt    97320
cgatcccgaa cgacacacgg cgtggagcaa aacgcctccc cctgagccgc tttcctacca    97380
acacaccggc atgcctctgc gggcatcgga acacgccac cggccctgg gccccgggca    97440
accccccatg cgggctcggc tccccgccgc ggcctgggtt ggcgtcggga ccatcatcgg    97500
gggagttgtg atcattgccg cgttggtcct cgtgccctcg cgggcctcgt gggcactttc    97560
cccatgcgac agcggatggc acgagttcaa cctcgggtgc atatcctggg atccgacccc    97620
catggagcag gagcaggcgg tcggcggctg tagcgcccgg cgcgaccctga tccccgacgg    97680
ggctgccaaa cagctggccg ccgtcgcacg cgtccagtcg gcaagatcct cgggctactg    97740
gtgggtgagc ggagacggca ttcgggcctg cctgcggctc gtcgacgcg tcggcggtat    97800
tgaccagttt tgcgaggagc ccgcccttcg catatgctac tatccccgca gtcccggggg    97860
ctttgttcag tttgtaactt cgacccgcaa cgcgctgggg ctgccgtgag gcgcgtgtac    97920
tgcggtctgt ctcgtctcct ctttctcccct tccctccccc tccgcatccc aggatcacac    97980
cggcaacga gggttggggg gtccggcacg gacccaaaat aataaacaca caatcacgtg    98040
cgataaaaag aacacgcggt cccctgtggt gttttttggtt attttttatta aatctcgtcg    98100
acaaacaggg ggaagggcc gtggtctagc gacggcagca cgggcggagg cgttcaccgg    98160
ctccggccgtc cttcgcgttt aagcttggtc aggagggcgc tcaggcggc gacgttggtc    98220
gggccgtcgt tggtcagggc gttggctcga tggcgggcga ggacgggcga ggggctcaac    98280
ggcgggggcg ggggcccggt gcggcccggg gggaaaaata gggcggatcc cccccagtcg    98340
tacagggat tttccgcctc aatgtacggg gaggccggcc ctgcattcgc cgtgttcacg    98400
cagacgtttt cgtagacccg catccatggt atttcctcgt agacacgccc cccgtcctcg    98460
cgcaccgtct cgtatattga ctcgtcgtcc tcgtaggggg cgtgccgttc gcgggccgag    98520
gcggcgtggg tggctttgcg gcgggcgtcg tcgtcgtcgt cgtcggccgt cagatacgtg    98580
gcttccatct ggtcgggttc tccctccggg gcgggtcccc acaccgtgg ccgatcgagg    98640
ctccccagag acgcgcgcg gacgaggagg gggcacgtcg ccgccggcgg tcgcctgtcg    98700
ggtcccgcga cgttacgggc cgggaggcgc gggggcacct ccccccatgtg cgtgtaatac    98760
gtggccggct gtgcggccgc agcggggggc tcggcgaccg ggtcgttcgc atccggaagc    98820
gggggccccg cgccgtccgc gcggcgcctc cggaacctcc gggtggacgc gggggtcgag    98880
tgtaggcgag gtcgggggag gggcgggcgc tcgttgtcgc gccgcgcccg ctgaatcttt    98940
tcccgacagg tcccacccc cgcgcgatgc cccccgggc cgctggccat gtcgtccggg    99000
ggaggcccccg cggaccacgt cgtccggcga gacgccacga gccgcaggat ggactcgtag    99060
tggagcgacg gcgcccccgct gcggagcaga tccgcgccca gggcggcccc gaaccaagcc    99120
ttgatgctca actccatccg ggcccagctg ggggcggtca tcgtggggaa caggggggcg    99180
gtggtccgac agaaacgctc ctggctgtcc accgcggccc gcagatactc gttgttcagg    99240
ctgtcggtgg cccagacgcc gtaccccggtg agggtcgcgt tgatgatata ctgggcgtgg    99300
tgatggacga tcgacagaac ctccaccgtg gatacgacgg tatccacggt cccgtacgta    99360
ccgccgctcc gcttgccggt ctgccacagg ttggctaggc gcgtcaggtg gcccaggacg    99420
tcgctgaccg ccgccatgac tgcatggagc cggttgtgc gctgggaccc    99480
cggtccagat ggcgcgcgaa cgtttccgcg ggccgcctccg ggctgccgcc gagcgggagg    99540
aaccggcgat tggagggact cagccggtga catacgtgct tgtctgtcgt ccacagcatc    99600
caggacgccc accggtacag cacggagacg taggccagga gctcgttgag ccgcagtgcg    99660
gtgtcggtgc tggggcggct tgggtccgcc gggcgcataa agaacatgta ctgctgaatc    99720
cgatggaggg cgtcgcgcag gccggccacg gtgcggcgc acttggccgc cacgccccg    99780
ctcttgaacg gggtgcgcgc cagcagcttt ggcgccaggg tggccgcag cagcacgtga    99840
aggctggggt cgcagtcgcc cacggggtcc tcggggacgt ccaggccgct gggcaccacc    99900
gtcgcaggt acttccagta ctgcgtgagg atggcgcggc tcaactggcc gccgggcagc    99960
tccacctcgc ccagccgtcg ggtggccgcc gaagcgtagt ggccggatgta ctcgtagtgc  100020
gggtcgctgg cgagcccgtc cacgatcaaa ctctcgggaa ccgtgttgtg ttgccgcgcg  100080
gccaaccgga cgctgcgatc ggtcgcaggtc agaaacgccg gctgcgcgtc gtcggagcgc  100140
tgccgcaagg cgcccacggc cgcgctaagg agcccctccg gggtggggag cagacacccg  100200
ccgaagatgc gccgctcggg aacgcccgcg ttgtcgcgc ggatcaggtt ggcaggcgtc  100260
aggcaccgcg ccagccgcag ggagctcgcg ccgccgtcg cggcgtgcat ggtgacgccg  100320
gttcggtcgg gacccgccgg tcggagttat gccgcgtcca gggccatcgg ggcgcttttt  100380
atcgggagga gcttatggc gtggcgggcc tcccagcccg gtcgcgcgcc tcccgacac  100440
gtgcgcccgc agggcggcgg cccctcgtc tcccatcagc agtttcctaa actgggacat  100500
gatgtccacc acgcggaccc gcgggcccaa cacgacccg ccgcttacgg ggcgggggg  100560
gaagggctcc aggtccttga gaagaaaggc ggggtctgcc gtcccggaca cggggggccg  100620
```

```
gggcgctgag gaggcggggc gcagatccac gtgctccgcg gccgcgcgga cgtccgccca   100680
gaacttggcg ggggtggtgc gcgcgtacag gggctgggtc gctcggagga cgcacgcgta   100740
gcgcaggggg gtgtacgtgc ccacctcggg ggccgtgaat cccccgtcaa acgcggccag   100800
tgtcacgcac gccaccacgg tgtcggcaaa gcccagcagc cgctgcagga cgagcccggc   100860
ggccagaatg gcgcgcgtgg ccgccagcgt gtcccggccg cggtgcgcgt ccccgcacgc   100920
ccgggcgtac tttaaggtca cggtcgccag ggccgtgtgc agcgcgtaca ccgcagcgcc   100980
cagcacggcg ttgagcccgc tgttggcgag cagccggcgc gctgcggtgt cgcccagcgc   101040
ctcgtgctcg gcccccacga ccgcggggct tcccaggggc agggcgcgaa acagctcctc   101100
ccgcgccacg tccgcaaagg cggggtggtg cacgtgcggg tgcaggcgcg ccccccacgac   101160
caccgagagc cactggaccg tctgctccgc catcaccgcc agcacatcca gcacgcgccc   101220
caggaaggcg gcctcccgcg tcaaaacgca ccggacggcg tcgggattga agcgggcgag   101280
cagggccccg gtgccaggt acgtcatgcg gccggcatag cgggcggcca cgcgacagtc   101340
gcggtccagc agcgcgcgca ccccgggcca gtacagcagg accccagcg agctgcggaa   101400
caccgcgagc tcggggccgg attgggggga cactaacccc ccgcgctca gtaacggcaa   101460
ggccgcggcc ccgacgggac gcaacgccgt gaggctcgcg aactgccgcc tcagctcggc   101520
cgccctgtcg tccaggtcag acccgcgcgc ctccgcgtga aggcgcgtcc cgcacaccca   101580
cccgttgatg gccagccgca cgacggcatc cgccaaaaag ctcatcgcct gggcggggct   101640
ggttttttgtt cgacgatccg tcaggtcaag aatcccatcg cccgtgatat accaggccaa   101700
cgcctcgccc tgctgcaggg tttgcggaa aaacaccgcg gggttgtcgg ggagggcgaa   101760
gtgcatgacc cccacgcgcg ataacccgaa cgcgctatcc ggacacgggt aaaacccggc   101820
cggatgcccc agggctaggg cggagcgcac ggactcgtcc cacacggcaa cctgaggggc   101880
cagtcgatcc aacgggaatg ccgcccggag ctccggccgt gcgcacgcgtc cctccagaac   101940
ctccaccttg ggcggggaac gggcccgcc gccggtcctcc ggcccgacgg cttccgggta   102000
gtcgtcctcc tcgtactgca gctcctctag gaacagcggc gacggcgcca cccgcgaacc   102060
gccgacccgc cccaaaatag cccgcgcgtc gacgggaccc aggtatcccc cctgccgggc   102120
ctgcggagga ccgcggggaa cctcatcatc atcgtccagg cgcacgcgca ccgactggct   102180
acgggccgca tcgggcccgg ggcgctgccg ggacgctcgg cgatgggatg tgggcgggggc   102240
ttccgacgcg cgccgtcgtc gggctcgcgg gccttcccgt cgacgcgcca cgggcggctc   102300
gtcgcccgcc atctcctcca gagcctctag ctcgctgtcg tcatcccgc ggaacaccgc   102360
acgcaggtac cccatgaacc ccaccccatc gcccgctgc tcgtccgcca cgggcgaggc   102420
gcggggggcgg gtggatgcgc gcctcctgcg ccccgcgggt tcgcgagccg acatggtggc   102480
gatagacgcg ggttatcgga tgtccgctac cccccaaaaa agaaaaagac cccacagcgc   102540
ggatggaggc cgggggtaggt gccgccggac cccctcgcga tgggaatgga cgggagcgac   102600
ggggccggcg caaaaaaacg cagtatctcc cgcgaaggct acccgccgcc ccgccccccg   102660
gccaaatgcg gaaacggtcc cgcgctctcg cctttatacg cgggccgccc tgcgacacaa   102720
tcacccgtcc gtggtttcga atctacacga caggcccgca gacgcggcta acacacacgc   102780
cggcaacca gaccccagtg ggttggttgc gcggtcccgt ctcctggcta gttctttccc   102840
ccaccaccaa ataatcagac gacaaccgca ggttttgtaa tgtatgtgct cgtgtttatt   102900
gtggatacga accggtgacg ggaggggaaa acccagacgg gggatgcggg tccggtcggg   102960
cccctaccc accgtactcg tcaattccaa gggcatcggt aaacatctgc tcaaactcga   103020
agtcggccat atccagagcg ccgtagggggg cggagtcgtg gggggtaaat cccggccccg   103080
gggaatcccc gtccccaaac atgtccagat cgaaatcgtc tagcgcgtcg gcatgcgcca   103140
tcgccacgtc ctcgccgtct aagtggagct cgtccccag gctgacatcg gctcggggggg   103200
ccgtcgacag tctgcgcgtg tgtcccgcgg ggagaaagga caggcgcgga gccgccagcc   103260
ccgcctcttc gggggcgtcg tcgtccggga gatcgagcag gccctcgatg gtagacccgt   103320
aattgttttt cgtacgcgcg cggctgtacg cgtgttccg catgaccgcc tcggagggcg   103380
aggtcgtgaa gctggaatac gagtccaact tcgcccgaat caacaccata aagtacccag   103440
aggcgcgggc ctgggtgcca tgcagggtgg gaggggtcgt caacggcgcc cctggctcct   103500
ccgtagccgc gctgcgcacc agcgggaggt taaggtgctc gcgaatgtgg tttagctccc   103560
gcagccggcg ggcctcgatt ggcactcccc ggacggtgag cgctccgttg acgaacatga   103620
agggctggaa cagacccgcc aactgacgcc agctctccag gtcgcaacag aggcagtcaa   103680
acaggtcggg ccgcatcatc tgctcggcgt acgcggccca taggatctcg cgggtcaaaa   103740
atagatacaa atgcaaaaac agaacacgcg ccagacgagc ggtctctcgg tagtacctgt   103800
ccgcgatcgt ggcgcgcagc atttctccca ggtcgcgatc gcgtccgcgc atgtgcgcct   103860
ggcggtgcag ctgccggaca ctgccggaca ggtaccggta cagggccgag cagaagttgg   103920
ccaacacggt tcgatagctc tcctcccgcg cccgtagctc ggcgtggaag aaacgagaga   103980
gcgcttcgta gtagagcccg aggccgtcgc gggtggccgg aagcgtcggg aaggccacgt   104040
cgccgtgggc gcgaatgtcg atttgggcgc gttcggggac gtacgcgtcc ccccattcca   104100
ccacatcgct gggcagcgtt gataggaatt tacactccgg tacaggtcg gcgttggtcg   104160
gtagcgccga aaacagatcc tcgttccagg tatcgagcat ggtacatagc gcgggccccg   104220
cgctaaagcc caagtcgtcg aggagacggt taaagagggc ggcgggggg acgggcatgg   104280
gtggggaggg catgagctgg gcctggctca ggcgccccgt tgcgtacagc ggggggggccg   104340
ccggggtgtt tttgggaccc ccggctgggc ggggggggcgg tggcgaagcg ccgtccgcgt   104400
tcatgtcggc aaacagctcg tcgaccaaga ggtcattgg gtgggggttga tacgggaaag   104460
acgatatcgg gcttttgatg cgatcgtccc cgcccgccca gagagtgtgg gacgcccgac   104520
ggcgcgggaa gagaaaaacc cccaaacgcg ttagaggacc ggacggacct tatgggggga   104580
agtgggcagc gggaaccccg tccgttcccg aggaatgaca gcccgtggtc gccaccacgg   104640
atttaagcaa cccgcacggg ccgccccgta cctcgtgact tcccccccaca ttggctcctg   104700
tcacgtgaag gcgaaccgag ggcggctgtc caacccaccc cccgccaccc agtcccggtc   104760
cccgtcggat tggaaacaa aggcacgcaa cgccaacacc gaatgaaccc ctgttggtgc   104820
tttattgtct gggtacggaa gttttcactc gacgggccgt ctgggggcgag aagcggagcg   104880
ggctgggggct cgaggtcgct cggtggggcg cgacgccgca gaacgccctc gagtcgccgt   104940
ggccgcgtcg acgtcctgca ccacgtctgg attcaccaac tcgttggcgc gctgaagcag   105000
gttttttcgg tcgcagaccg tcacgcggat ggtggtgatg ccaaggagtt cgttgaggtc   105060
ttcgtctgtg cgcggacgcg acatgtccca gagctggacc gccgccatcc gggcatgcat   105120
ggcgccagg cgcccgaccg cggcgcagaa gacgcgcttg ttaaagcggg ccacccgggg   105180
ggtccatggc gcgtcggggt ttgggggggc ggtgctaaag tgcagctttc tggccagccc   105240
ctgcgcgggt gtcttggatc gggttggcgc cgtcgacgcg ggggcgtctg ggagtgcggc   105300
ggattctggc tgggccgatt tcctgccgcg ggtggtctcg gccgccgggg ccgcggggggc   105360
```

```
cttagtcgcc acccgctggg ttcggggggc ccgggggggcg gtggtgggtg tgcgtccggc   105420
ccctccggac ccagcgggtg gcggaggtgc ccgcgcaggc cccgggccgg acaaaaccgc   105480
cccggaaacg ggacgccgcg tccggggggac ctccgggtgt tcgtcgtctt cggatgacga   105540
gcccccgtag agggcataat ccgactcgtc gtactggacg aaacggacct cgcccctctg   105600
gcgcgagcgt gtctgtaggg cgccacggcg ggaggtgtca ggcggactgc tggggactcgc   105660
catacctgaa gacggggtgt agtacagatc ctcgtactca tcgcgcggaa cctcccgcgg   105720
acccgacttc acggagcggc gagaggtcat ggttccacga acacgctagg gtcggatgcg   105780
cggacaatta ggcctgggtt cggacggcgg gggtggtgca ggtgtggaga ggtcgagcga   105840
taggggcggc ccgggagaga agagagggtc cgcaaaaccc actggggatg cgtgagtggc   105900
cctctgtggg cggtggggga gagtcttata ggaagtgcat ataaccacaa cccatgggtc   105960
taaccaatcc ccaggggcca agaaacagac acgcccaaa cggtctcggt ttccgcgagg   106020
aaggggaagt cctgggacac cctccacccc caccctcac cccacacagg gcgggttcag   106080
gcgtgccccgg cagccagtag cctctggcag atctgacaga cgtgtgcgat aatacacacg   106140
cccatccgagg ccatgcctac ataaaagggc accagggccc cggaggcaga catttggcca   106200
gtgttttggg tctcgcaccg cgcgccccg atcccatcgc gcccgcccctc ctcgccgggc   106260
ggctccccgt gcgggcccgc gtctcccgcc gctaaggcga cgagcaagac aaacaacagg   106320
cccgcccgac agacccttct gggggggccc atcgtcccta acaggaagat gagtcagtgg   106380
ggatccgggg cgatccttgt ccagccggac agcttgggtc ggggtacga tggcgactgg   106440
cacacgccg tcgctactcg cgggggcgga gtcgtgcaac tgaacctggt caacaggcgc   106500
gcggtggctt ttatgccgaa ggttagcggg gactccggat gggccgtcgg gcgcgtctct   106560
ctggacctgc gaatgctat gccggctgac ttttgcgcga ttattcacgc cccgcgcta   106620
gccagccccg ggcaccacgt aatactgggt cttatcgact cggggtaccg cggaaccgtt   106680
atggccgtgg tcgtagcgcc taaaaggacg cgggaatttg ccccggggac cctgtgggtc   106740
gacgtgacgt tcctggacat cctgcgacc ccccgggccc tcaccgagcc gatttccctg   106800
cggcagttcc cgcaactggc gcccccccct ccaaccgggg ccgggatacg cgaagatcct   106860
tggttggagg gggcgctcgg ggccccaagc gtgactacgg ccctaccggc gcgacgccga   106920
gggcggtccc tcgtctatgc cggcgagctg acgccggttc agacggaaca cgggacgga   106980
gtacgagaag ccatcgcctt ccttccaaaa cgcgaggagg atgccggttt cgacattgtc   107040
gtccgtcgcc cggtcaccgt cccggcaaac ggcaccacgt tcgtgcagcc atccctccgc   107100
atgctccacg cggacgccgg gcccgccgcc tgctatgtgt tggggcggtc gtcgctcaac   107160
gcccgcggcc tcctggtcgt cctacgcgc tggctcccg ggcacgtatg tgcgtttgtt   107220
gtttacaacc ttacgggggt tcctgtgacc ctcgaggccg gcgccaaggt cgcccagctc   107280
ctggttgcgg gggcggacgc tcttccttgg atccccccgg acaactttca cgggaccaaa   107340
gcgcttcgaa actaccccag gggtgttccg gactcaaccg ccgaacccag gaacccgccg   107400
ctcctggtgt ttacgaacga gtttgacgcg gaggcccccc cgagcgagcg cgggaccggg   107460
ggttttggct ctaccggtat ttagcccaca gctttgggtt cgttccgggc aataaaaaac   107520
gtttgtatcg catctttcct gtgtgtagtt gtttatgttg gatgcctgtg ggtctatcac   107580
acccgcccct ccatcccaca aacacaaaac acacggggttg gatgaaaaca cgcatttatt   107640
gacccaaaac acacggagct gctcgagatg ggcaggggcg aggtgcggtt ggggaggctg   107700
taggtctggg aacggacacg cggggacacg attccggttt ggggtccggg agggcgtcgc   107760
cgtttcgggc ggcaggcgcc agcgtaacct ccggggggcgg cgtgtggggg tgccccaagg   107820
agggcgcctc ggtcaccccca atccccccg accgggttcc cccggcaacc ccgaaggcgg   107880
agaggccaag ggccgttcg gcgatggcca catcctccat gaccacgtca ctctcggcca   107940
tgctccgaat agcctgggag acgagcacat ccgcggactt gtcagccgcc cccacggaca   108000
tgtacatctg caggatggtg gccatacacg tgtccgccag gcgccgcatc ttgtcctgat   108060
gggccgccac ggccccgtcg atcgtgggggg cctcgagccc ggggtggtgg cgcgccagtc   108120
gttctaggtt caccatgcaa gcgtggtacg tgccggccaa ggcgccccg ttcacgaggc   108180
gtcgggtgtc gtccagggac cccagggcgt catcgagcgt gatgggggcg ggaagtagcg   108240
cgttaacgac cgcccagggcc tcctgcagcc gcggctccgc ctccgagggc ggaacggccg   108300
gcggatcat ctcatattgt tcctcgggc gcgctcccca gccacatata gccccgagaa   108360
gagaagccat gccgggcggg tactgccct tgggcgcgcg gacgcaatgg ggcaggaaga   108420
cgggaaccgc ggggagaggc gggcggccgg gactccgtg gaggtgaccg cgctttatgc   108480
gaccgacggg tgcgttatta cctcttcgat cgccctcctc acaaactctc tactgggggc   108540
cgagccggtt tatatattca gctacgacg atacacgcac gatggccgtg ctgacgggcc   108600
cacggagcaa gacaggttcg aagagagtcg ggcgctctac caagcgtcgg gcgggctaaa   108660
tggcgactcc ttccgagtaa cctttttgttt attgggggacg gaagtgggtg ggacccacca   108720
ggcccgcggg cgaacccgac ccatgttcgt ctgtcgcttc gagcgagcgg acgacgtcgc   108780
cgcgctacag gacgccctgg cgcacgggac cccgctacaa ccggaccaca tcgccgccac   108840
cctgacgcg gaggccacgt tcgcgctgca tgcgaacatg atcctggctc tcaccgtggc   108900
catcaacaac gccagccccc gcaccggacg cgacgccgcc gcggccgcagt atgatcaggg   108960
cgcgtcccta cgctcgctcg tggggcgcac gtccctggga caacgcggcc ttaccacgct   109020
atacgtccac cacgaggcgc gcgtgcttgc gcgtaccgc agggcgtatt atggaagcgc   109080
gcagagtccc ttctggtttc ttagcaaatt cgggccggac gaaaaaagcc tggtgctcac   109140
cactcggtac tacctgcttc aggccagcg tctgggggggc gcggggggcca cgtacgacct   109200
gcaggccatc aaggacatct gcgccaccta cgcgattccc cacgcccccc gcccgacac   109260
cgtcagcgct gcgtccctga cctcgtttgc cgccatcacg cggttctgtt gcacgagcca   109320
gtacgcccgc ggggccgcgg cggccgggtt tccgctttac gtggagcgcc gtattgcggc   109380
cgacgtccgc gagaccagtg cgctggagaa gttcataacc cacgatcgca gttgcctgcg   109440
cgtgtccgac cgtgaattca ttacgtacat ctacctggcc catttgagt gtttcagccc   109500
cccgcgccta gccacgcatc ttcgggccgt gacgacccac gacccaacc ccgcggccag   109560
cacggagcag ccctcgcccc tgggcaggga ggccgtggaa caattttttt gtcacgtgcg   109620
cgcccaactg aatatcgggg agtacgtcaa acacaacgtg accccccggg agaccgtcct   109680
ggatggcgat acgccaagg cctacctgcg cgctcgcacg tacgcgcccg ggccgctgac   109740
gcccgccgc gcgtattgcg ggccggtgga ctccgccaac aaaatgatgg ggcgttttgg   109800
ggacgccgaa aagctcctgg tcccccgcgg gtgccccgcg tttgcgcccg ccagtccccgg   109860
ggaggacacg gcggggcggca cgccgccccc acagacctgc ggaattgtca agcgcctcct   109920
gagactggcc gccacggaac agcagggcac cacacccccg gcgatcgcgg cgcttatccg   109980
taatgcggcg gtgcagactc ccctgcccgt ctaccggata tccatggtcc ccacgggaca   110040
ggcatttgcc gcgctggcct gggacgactg ggcccgcata acgcggacg ctcgcctggc   110100
```

```
cgaagcggtc gtgtccgccg aagcggcggc gcaccccgac cacgcgcgc tgggcaggcg   110160
gctcacggat cgcatccgcg cccagggccc cgtgatgccc cctggcgcc tggatgccgg   110220
ggggcagatg tacgtgaatc gcaacgagat attcaacggc gcgctggcaa tcacaaacat   110280
catcctggat ctcgacatcg ccctgaagga gcccgtcccc tttcgccggc tccacgaggc   110340
cctggccac tttaggcgcg gggctctggc tgcggttcag ctcctgtttc ccgcggcccg   110400
cgtggacccc gacgcatatc cctgttattt tttcaaaagc gcatgtcggc ccggcccggc   110460
gtccgtgggt tccggcagcg gactcggcaa cgacgacgac ggggactggt ttccctgcta   110520
cgacgacgcc ggtgatgagg agtgggcgga ggacccgggc gccatggaca catcccacga   110580
tcccccggac gacgaggttg cctactttga cctgtcgcac gaagtcggcc cacggcgga   110640
acctcgcgaa acggattcgc ccgtgtgttc ctgcaccgac aagatcggac tgcgggtgtg   110700
catgccgtc cccgccccgt acgtcgtcca cggttctcta acgatgcggg gggtggcacg   110760
ggtcatccag caggcggtgc tgttggaccg agattttgtg gaggcatcg ggagctacgt   110820
aaaaaacttc ctgttgatcg atacgggagt gtacgcccac ggccacagcc tgcgcttgcc   110880
gtattttgcc aaaatcgccc ccgacgggcc tgcgtgcgga aggctgctgc cagtgtttgt   110940
gatccccccc gcctgcaaag acgttccggc gtttgtcgcc gcgcacgccg acccgcggcg   111000
cttccatttt cacgccccgc ccacctatct cgcttccccc cggagatcc gtgtcctgca   111060
cagcctgggt ggggactatg tgagcttctt tgaaaggaag gcgtcccgca acgcgctgga   111120
acactttggg cgacgcgaga ccctgacgga ggtcctgggt ggtacaacg tacagccgga   111180
tgcgggaggg accgtcgagg ggttcgcatc ggaactgctg gggcggatag tcgcgtgcat   111240
cgaaacccac tttcccgaac acgcggcga atatcaggcc gtatccgtcc ggcgggccgt   111300
cagtaaggac gactgggtcc tcctacagct agtcccgtt cgcggtaccc tgcagcaaag   111360
cctgtcgtgt ctgcgcttta agcacgggcg ggcgagtcgc gccacggcgc ggacattcgt   111420
cgcgctgagc gtcggggcca caaccgcct gtgcgtgtcc ttgtgtcagc agtgctttgc   111480
cgccaaatgc gacagcaacc gcctgcacac gctgtttacc attgacgccg gtacgccatg   111540
ctcgccgtcc gttccctgca gcacctctca accgtcgtct tgataacggc gtacggcctc   111600
gtgctcgtgt ggtacaccgt cttcggttgcc agtccgctgc accgatgtat ttacgcggta   111660
cgccccaccg gcaccaacaa cgacaccgcc ctcgtgtgga tgaaaatgaa ccagaccta   111720
ttgttctgg gggcccgac gcaccccccc aacgggggct ggcgcaacca cgcccatatc   111780
tgctacgcca atcttatcgc gggtagggtc gtgccctcc aggtcccacc cgacgccatg   111840
aatcgtgaa tcatgaacgt ccacgaggca gttaactgtc tggagaccct atggtacaca   111900
cgggtgcgtc tggtggtcgt aggggtggttc ctgtatctgg cgttcgtcgc cctccaccaa   111960
cgccgatgta tgtttggtgt cgtgagtccc gcccacaaga tggtggcccc ggccacctac   112020
ctcttgaact acgcaggccg catcgtatcg agcgtgttcc tgcagtaccc ctacacgaaa   112080
attaccccgcc tgctctgcga gctgtcggtc cagcggcaaa acctggttca gttgtttgag   112140
acggacccgg tcaccttctt gtaccaccgc cccgccatcg gggtcatcgt aggctgcgag   112200
ttgatgctac gctttgtggc cgtgggtctc atcgtcggca ccgctttcat atcccggggg   112260
gcatgtgcga tcacataccc cctgtttctg accatcacca cctggtgttt tgtctccacc   112320
atcggcctga cagagctgta ttgtattctg cggcggggcc cggcccccaa gaacgcagac   112380
aaggccgccg cccccggggcg atccaagggg cgtgtctgcg tctgcgggcg ctgttgttcc   112440
atcatcctct cgggcatcgc agtgcgattg tgttatatcc ccgtggtggc cggggtggtg   112500
ctcgtggcgc ttcactacga gcaggagatc cagaggcgcc tgtttgatgt atgacgtcac   112560
atccaggccg gcggaaaccg gaacggcata tgcaaattgg aaactgtcct gtcttggggc   112620
ccacccaccc gacgcgtcat atgcaaatga aaatcgctcc cccgaggccc gctgtagcct   112680
ggatcccaac gaccccgccc atgggtccca attggccgtc ccgttaccaa gaccaaccca   112740
gccagcgtat ccaccccgc ccgggtcccc gcggaagcgg aacggtgtat gtgatatgct   112800
aattaaatac atgccacgta cttatggtgt ctgattggtc cttgtctgtg ccggaggtgg   112860
ggcggggccc ccgccggggg ggcggaacga ggaggggttt gggagagccg gccccggcac   112920
cacgggtata aggacatcca ccaccccggcc ggtggtggtg tgcagccgtg ttccaaccac   112980
ggtcacgctt ctgtgcctct ccccgattcg ggccggtcg ctcgctaccg gtgcaccacc   113040
accagaggcc atatccgaca ccccagcccc gacggcagcc gacagcccgg tcatggcgac   113100
tgacattgat atgctaattg acctcggcct ggacctctcc gacagcgatc tggacgagga   113160
ccccccgag ccggcggaga gccgccgcga cgacctggca tcggacagca gcggggagtg   113220
ttcctcgtcg gacgaggaca tggaagaccc ccacgagag gacggaccgg agccgatact   113280
cgacgccgct cgcccggcgg tccgcccgtc tcgtccagaa gaccccggcg tacccagcac   113340
ccagacgcct cgtccgacgg agcggcaggg ccccaacgag cctcaaccag cgcccccacag   113400
tgtgtggtcg cgcctcgggg cccggcgacc gtcttgctcc cccgagcagc acgggggcaa   113460
ggtggcccgc ctccaacccc caccgaccaa agcccagcct gccgcggcg gacgccgtgg   113520
gcgtcgcagg ggtcggggtc gcggtggtcc cggggccgcc gatggtttgt cggacccccg   113580
ccggcgtgcc cccagaacca atcgcaaccc gggggggacc cgcccgggg cggggtggac   113640
ggacggcccc ggcccccccc ggcgcgaggc gtggcgcgga agtgagcagc ccgacccacc   113700
cggaggcccg cggacacggg gcgtgcgcca agcacccccc ccgctaatga cgctggcgat   113760
tgcccccccg cccgcggacc cccgcgcccc ggccccggag cgaaaggcgc ccgccgcga   113820
caccatcgac gccaccacgc ggttggtcct gcgctccatc tccgagcgcg cggcggtcga   113880
ccgcatcagc gagagctttg gccgcagcgc acaggtcatg cacgaccct ttgggggcga   113940
gccgtttccc gccgcgaata gccctgggc cccggtgttg gcgggccaag gagggccctt   114000
tgacgccgag accagacggg tctcctggga aaccttggtc gcccacggcc cgagcctcta   114060
tcgcactttt gccggcaatc ctcgggccgc atcgaccgcc aaggccatgc gcgactgcgt   114120
gctgcgccaa gaaaatttca tcgaggcgct ggcctccgcc gacgacgcg tggcgtggtg   114180
caagatgtgc atccaccaca acctgccgct gcgccccgca gcacccatta tcgggacggc   114240
cgcggctgtg ctggataacc tcgcacgcg cctgcggccc tttctccagt gctacctgaa   114300
ggcgcgaggc ctgtcggcc tggacgaact gtgttcgcgc cggcgtctgg cggacattaa   114360
ggacattgca tccttcgtgt ttgtcattct ggccaggctc gccaaccgcg tcgagcgtgg   114420
cgtcgcggag atcgactacg cgacccttgg tgtcggggtc ggagagaaga tgcatttcta   114480
cctccccggg gcctgcatgg cgggcctgat cgaaatccta gacacgcacc gccaggagtg   114540
ttcgagtcgt gtctgcgagt tgacggccag tcacatcgtc gccccccgt acgtgcacgg   114600
caaatatttt tattgcaact ccctgttttta ggtacaataa aaacaaaaca tttcaaacaa   114660
atcgccccac gtgttgtcct tctttgctca tggccggcgg ggcgtgggtc acggcagatg   114720
gcggggtgg gcccggcgta cggcctgggt gggcggaggg aactaaccca acgtataaat   114780
ccgtccccgc tccaaggccg gtgtcatagt gcccttagga gcttccgcc cgggcgcatc   114840
```

-continued

```
cccccttttg cactatgaca gcgaccccc  tcaccaacct gttcttacgg gccccggaca 114900
taacccacgt tgccccccct tactgcctca acgccacctg gcaggccgaa acggccatgc 114960
acaccagcaa aactgactcc gcttgcgtgg ccgtgtggag ttacctggtc cgcgcctcct 115020
gtgagaccga cggcacaatc cactgctttt tctttgtggt atacaaggac acccaccata 115080
cccctccgct gattaccgag ctccgcaact ttgcggaacc ggttaaccac gtccgccgtc  115140
tacgcgaact ggaggataag cgcggggtgc ggctgcggtg tgcgcggccg tttagcgtcg 115200
ggacgattaa ggacgtctct gggtccggcg cgtcctcggc gggagagtac acgataaacg 115260
ggatcgtgta ccactgccac tgtcggtatc cgttctcaaa aacatgctgg atgggggcct 115320
ccgcggccct acagcacctg cgctccatca gctccagcgg catggccgcc cgcgcggcag 115380
agcatcgacg cgtcaagatt aaaattaagg cgtgatttcc aaccccat gaatgtgtgt 115440
aaccccccc aaaaaaataa agagccgtaa cccaaccaaa ccaggcgtgg tgtgagtttg 115500
tggacccaaa gccctcagag acaacgcgac aggccagtat ggaccgtgag acttttattt 115560
attaactcac aggggcgctt accgccacag gaataccaga ataatgacca ccacaatggt 115620
gaccacccca aatacagcat ggcgcccac cacgccacaa cagccctgtc gccggtatgg 115680
ggcatgatca gacgagccgc gagccgcgcg ttgggccctg tacagctcgc gcgaattgac 115740
cctaggaggc cgccacgcgc ccgagttttg cgttcgtcgc tggtcgtcgg gcaccaaagc 115800
cccggacggc tgttcggtcg aacgaacggc cacgacagtg gcataggttg gggggtggtc 115860
cgacatagcc tcggcgtacg tcgggaggcc cgacaaggagg tccctttgtga tgtcgggtgg 115920
ggccacaagc ctggtttccg gaagaaacag ggggggttgcc aataacccgc caggggccaaa 115980
actccggccc tggcgcacgt cgttcggcgc ggcgccgggc gcgccgagcg gctcgctggg 116040
cggcttggcg tgagcggccc cgctccgacg cctcgccctc tccggaggag gttggtggaa 116100
ttggcacgga cgacaggggc ccagcagagt acggtggagg tgggtccgtg ggggtgtcca 116160
gatcaataac gacaaacggc ccctcgttcc taccagacaa gctatcgtag ggggcgggg 116220
gatcaacaaa cgcgttcccc gcgctccata gacccgcgtc gggttgcgcc gcctccgaag 116280
ccatggatgc gccccaaagc cacgactccc gcgcgctagg tccttgggggt aagggaaaag 116340
gccctactcc ccatccaagc cagccaagtt aacgggctac ccgcttcgggg atgggactgg 116400
caccccggcg gatttttgttg ggctggcatg cgtcgcccaa ccgagggccg cgtccacgtg 116460
acgcgccttt tataacccg ggggtcattc ccaacgatca catgcaatct aactggctcc 116520
cctctcctcc cctctcccct ctcccctctc ccctctcccc tctccctct cctctcttag 116580
gttgggggt ggtccgacat agcctcggcg tacgtcggga gcccgacaa gaggtccctt 116640
gtgatgtcgg gtgggggccac aagcctggtt tccggaagaa acaggggggt tgccaagcgg 116700
cccggccgc gctcccccc ccccggggcc gtgtccttgc tttccccccg tctccccccc 116760
cctcctcctc cttctcctcc tcctcgtttt tccaaaccc gcccaccgg cccggcccgg 116820
cccggccacc gccgcccacc caccccacgc gggagccgca cccggcggtcc cccgttcccc 116880
gggggccgtt atctccagcg cccccgtccgg cgcgccgccc ccgccgcta aacccccatc 116940
cgcccccggg accccacata taagccccca gccacacgca agaacagaca cgcagaacgg 117000
ctgtgtttat ttaaataaac cgatgtcgga ataacaaac acaaacaccc gcgacggggg 117060
gacggaggga gggggggtgac ggggggacggg aacagacaca aaaaacaacc acaaaaaaac 117120
agccacccccc gacaccccccc accccagtct cctcgccttt tcccaccac cccacgcccc 117180
cactgagccc ggtcgatcga cgagcacccc cgccccgcc cctgcccgg cgaccccgg 117240
cccgcacgat cccgacaaca ataacaaccc caacggaaag cggcgggtg ttggggagg 117300
cgaggaacaa ccgaggggaa cggggatgg aaggacggga agtggaagtc ctgatacccaa 117360
tcctacaccc ccctgccttc caccctccgg ccccccggga gtccacccgc cggccccgcta 117420
ccgagaccga acacgcggc cgccgcagcc gccgcagccg ccgccgacac cgcagagccg 117480
gcgcgcgcac acacaagcgg cagaggcaga aaggccccga gtcattgttt atgtggccgc 117540
gggccagcag acggccgcg cacccccccc gcccgtgtgg gtatccggcc cccgccccg 117600
cgccggtcca ttaagggcgc gcgtgcccgc gagatatcaa tccgttaagt gctctgcaga 117660
caggggcacc gcgcccggaa atccattagg ccgcagacga ggaaaataaa attacatcac 117720
ctacccacgt ggtgctgtgg cctgttttg ctgcgtcatc tgagcctta taaaagcggg 117780
ggcgcggccg tgccgatcgc gggtggtgcg aaagacttc cggcgcgtc cggtgccgc 117840
ggctctcggg gcccccctgc agccggggcg gccaaggggc gtcgcgaca tcctcccctt 117900
aagcgccggc cggccgctgg tctgttttt gttttccccg tttcggggt ggggggggtt 117960
acggtttctg ttttttaaac ccgtctgggg tgttttcgt tccgtcgccg ggatgtttcg 118020
ttcgttcggc ccctcacggg gcgaaggccg cgtacggccc gggacgaggg gccccccgacc 118080
gcggcggtcc gggccccgtc cgggccccgct cgccggcacg cgacgcgaaa aaggccccc 118140
ggaggctttt ccgggttccc ggccccggggc ctgagataaa caatcggggt taccgccaac 118200
ggccggcccc cgtggcggcc cggccgggg ccccggccga cccaagggggc ccggcccgg 118260
ggccccacaa cggcccggcg catgcgctgt gttttttttt tcctcggtgt tctgccgggc 118320
tccgtcgcct ttcctgttct cgcttcttcc ccccccctt cttcaccccc agtaccctcc 118380
tccctccctt cctcccccgt tatcccactc gtcgagggcg cccggtgtc gttcaacaaa 118440
gacgccgcgt ttccaggtag gttagacacc tgcttctccc caatagaggg gggggaccc 118500
aaacgacagg gggcgcccca gaggctaagg tcggccacgc cactcgcggg tgggctcgtg 118560
ttacagcaca ccagcccgtt cttttccccc cctcccaccc ttagtcagac tctgttactt 118620
acccgtccga ccaccaactg ccccccttatc taagggccgg ctggaagacc gccaggggct 118680
cggccggtgt cgctgtaacc ccccacgcca atgaccacg tactccaaga aggcatgtgt 118740
cccacccgc ctgtgttttt tgtgcctggct ctctatgctt gggtcttact gcctgggggg 118800
ggggatgcgg gggagggggg gtgtggaagg aaatgcacgg cgcgtgtgta cccccccccc 118860
aaagttgttc ctaaagcgag gatatggagg agtggcgggt gccgggggac gggggtgatc 118920
tctggcacgc ggggggggaa gggtcgggg aggggggat gggtaccggg ccccacctggc 118980
cgacgcgggt gcgcgtgcct ttgcacacca accccacgtc cccggcggtt ctctaagaag 119040
caccgccccc cctccttcat accaccgagc atgcctgggt gtgggttggt aaccaacacg 119100
cccatccct cgtctcctgt gattctctggg ctgcaccgca ttcttgtttt ctaactatgt 119160
tcctgttct gtctccccc caccctccg ccccacccc caacacccac gtctgtggtg 119220
tggccgtcc cttttgggc ccctcgtccc gccaccctc ccgtccttg ttgccctata 119280
gtgtagttaa cccccccccc gcccttttgtg gcggccagag gccaggtcag tccgggcggg 119340
caggcgctcg cggaaactta acacccccac ccagccccact gtggttctgg ctccatgcca 119400
gtggcaggat gcttcggggg atcggtggtc aggcagcccg ggccgcgct ctgtggttaa 119460
caccagagcc tgcccaacat ggcaccccca ctccacgca cccccactcc cacgcacccc 119520
cactccacg cacccccact cccacgcacc cccactccca cgcaccccca ctcccacgca 119580
```

```
ccccactcc cacgcacccc cactcccacg caccccact cccacgcacc cccactccca    119640
cgcaccccca ctcccacgca ccccactcc cacgcacccc cactcccacg caccccaag    119700
atccatccaa cacagacagg gaaaagatac aaaagtaaac ctttatttcc caatagacag   119760
caaaaatccc ctgagttttt tattagggcc aacactaaag acccgctggt gtgtggtgcc   119820
cgtgtctttc acttttccct ccccgacacg gattggctgg tgtagtgggc gcggccagag   119880
accacccagc acccgacccc cctcccaca aacacggggg gcgtcccctta ttgttttccc   119940
tcgtcccggg tcgacgcccc ctgctcccg gaccacgggt gccgagaccg caggctgcgg    120000
aagtccaggg cgcccactag ggtgccctgg tcgaacagca tgttcccccac gggggtcatc   120060
cagaggctgt tccactccga cgcggggggcc gtcgggtact cggggggcat cacgtggtta    120120
cccggggtct cggggagcag ggtgcggcgg ctccagcgg ggaccgcggc ccgcagccgg    120180
gtcgccatgt ttcccgtctg gtccaccagg accacgtacg ccccgatgtt cccgtctcc    120240
atgtccagga tgggcaggca gtcccccgtg atagtcttgt tcacgtaagg cgacagggcg    120300
accacgctag agacccccga gatgggcagg tagcgcgtga ggccgcccgc ggggacggcc    120360
ccggaagtct ccgcgtggcg cgtcttccgg gcacacttcc tcggccccg cggcccagaa    120420
gcagcgcggg ggccgaggga ggtttcctct tgtctccctc ccagggcacc gacggccccg    120480
cccgaggagg cggaagcgga ggaggacgcg gccccggcgg cggaagaggc ggcccccgcg    120540
ggggtcgggg ccgaggagga agaggcagag gaggaagagg cggaggccgc cgaggacgtc    120600
agggggtgtcc cgggccacc ctggccgcgc cccccggcc ctgagtcgga ggggggtgc    120660
gtcgccgccc tcttggcccc tgccggcgcg aggggggac gcgtggactg ggggagggg    120720
ttttcctggc ccgacccgcg cctcttcctc ggacgcaccg ccgcctcctg ctcgacagag    120780
acggcggagg ggagcggggc ggcgccgag ggggtgcggc cgcgggaggg cccgtgccca    120840
ccctccacgc ccggcccccc cgagccgccg gccaccgtcg gccgcccg gcacagactc    120900
tgttcttggt tcgcggcctg agccaggac gagtgcgact ggggcacacg gcgcgcgtcc    120960
gcggggcggg cggccggctc cgccccgggg gccggggcgc ggggccggg cccggaggc    121020
ggcgctcgca cgcacggggc cacggccgcg cggggggcgcg cgggtcccga cgcggccgag    121080
gacgcggggg ccccggggcg ggggcggag cctggccatgg gcgccgcgg gggcctgtgg    121140
ggagaggccg gggggagtc gctgatcact atgggtctc tgttgtttgc aaggggggcg    121200
ggtctgttga caaggggcc cgtccggcc ctcggccgcc ccgcctccgc ttcaacaacc    121260
ccaacccccaa ccccaacccc cccggagggg ccagacgccc ccgcggcgc cgcggctcgc    121320
gactgggcag agccgccgcc gccgctgctg ttggtggtgg tgttggtgtt actgctgccg    121380
tgtggcccga tgggcgccga ggggggcgct gtccgagccg cggccggctg gggggctgcg    121440
ttagacgccc cgcccgtcac gggggcgcg gcggtgcctc tgcgtggggg ggcgcggggc    121500
gtccggcggg gggcggcgg gacgtagtct gctgcaagag acaacggggg gcgcgatcag    121560
gttacgccgc ctcccggcc cgccctttcc tcgccgccc gccattcct ccctcctcc    121620
ctccccccag ggtccttgcc gcccccgcc tcaccgtcgt ccaggtcgtc gtcatcctcg    121680
tccgtggtgg gctccgggtg ggtgggcgac agggccctca ccgtgtgccc ccccagggtc    121740
aggtaccgcg gggcgaaccg ctgattgccc gtccagataa agtccacggc cgtgcccgcc    121800
ctgacggcct cctcggcctc catgcgggtc tgggggtcgt tcacgatcgg gatggtgctg    121860
aacgccgcgc tgggcgtcac gcccactatc aggtacacca gcttggcgtt gcacagccgg    121920
caggtgttgc gcaattgcat ccaggttttc atgcacggga tgcagaagcg gtgcatgcac    121980
gggaaggtgt cgcagcgcag gtggggcgcg atctcatccg tgcacacggc gcacacgtcg    122040
ccctcgtcgc tccccccgtc ctctcgaggg ggggcgcccc cgcaactgcc ggggtcttcc    122100
tcgcggggcg ggctccccc cgagaccgcc ccccatcca cgccctgccg ccccagcagc    122160
cccgtctcga acagttccgt gtccgtgctg tccgcctcgg aggcggagtc gtcgtcatgg    122220
tggtcggcgt cccccccgcc cccacttcg gtctccgcct cagagtcgct gctgtccggc    122280
aggtctcggt cgcaggggaaa cacccagaca tccggggcgg gctaagggga aaaaggggg    122340
gcgggtaaga atgggggggg atttcccgcg tcaatcagcg cccacgagtt cccctctcc    122400
ccccccgcct cacaaagtcc tgcccccctg ctggcctcgg aagaggggg agaaagggggt    122460
ctgcaaccaa aggtggtctg ggtccgtcct ttggatcccg accctcttc ttccctcttc    122520
tcccgccctc cagacgcacc ggagtcgggg gtcccacggc gtcccccaaa tatggcgggc    122580
ggctcctccc caccccccta gatgcgtgtg agtaagggg gcctgcgtat gagtcagtgg    122640
ggaccacgcc cccaacacgg cgaccccggt ccctgtgtgt ttgttgtggg ggcgtgtctc    122700
tgtgtatgag tcagggggtc ccacggcgac cccgggccct gcgtctgagt caagggggcc    122760
atgtgtatgt gttgggggtc tgtatatata aagtcagggg gtcacatggc gacccccaac    122820
agggcgaccc cggtccctgt atatatagg tcagggggtt ccgcgcccc taacatggcg    122880
ccccggtcc ctgtatatat agtgtcacgg ggttccacgc ccctaacat ggcgcccaa    122940
catggcgccc ggctcccgtg tatgagtggg ggtccccaa catggggggcc ggttccaggg    123000
taagggtcgg gggtccccca acatggcgcc cccaatatg gcgccccaga catggcgccc    123060
ggccctcac ctcgcgctgg ggggcggccct caggccggcg ggtactcgct ccggggcggg    123120
gctccatggg ggtcgtatgc ggctgggagg tcgcggacgg agggtccctg ggggtcgcaa    123180
cgtaggcggg gcttctgtgg tgatgcggag aggggcggc ccgagtccgc ctggctgctg    123240
cgtctcgctc cgagtgccga ggtgcaaatg cgaccagacc gtcgggccag gctaactta    123300
taccccacgc ctttcccctc cccaagggg cggcagtgac gattccccca atggccgcgc    123360
gtccagggg aggcaggccc accgcgggc ggcccgtcc ccaggaccca accggcgcc    123420
cccaaagaat atcattagca tgcacgcccc ggccccgat ttggggggacc aaccggtgt    123480
ccccaaaga accccattag catgccctc ccgccgacgc aacaggggct tggcctgcgt    123540
cggtgccccg gggcttcccg ccttcccgaa gaaactcatt accatacccg gaaccccagg    123600
ggaccaatgc gggttcattg agcgacccgc gggccaatgc gcgagggg gtgtgttccg    123660
ccaaaaagc aattagcata acccggaacc ccaggggagt ggttacgcgg ggtgcggag    123720
gcggggaata ccggggttgc ccattaaggg ccgcggggaat tgccggaagc gggaagggcg    123780
gccgggggccg cccattaatg agtttctaat taccataccg ggaagcggaa caaggcctct    123840
tgcaagtttt taattaccat accggaagt gggcggcccg gccattggg cggtaactcc    123900
cgcccaatgg gccgggcccc gaagactcgg cggacgctgg ttggccgggc cccgccgcgc    123960
tggcgcccg cgattggcca gtcccgcccc cgaggcgggc ccgccttggg ggcggaccgg    124020
ctccagccgt atatatgcgc ggctcctgcc atcgtctctc cggagagcgg cttggtgcgg    124080
agctcccggg agctccgcgg aagacccagg cgcctcgggt gtaacgttag accgagttcg    124140
ccgggccgg tccgcgggcc agggcccggg cacgggcctc gggcccagg cacggcccga    124200
tgaccgcctc ggcctccgcc acccggcgcc ggaaccgagc ccggtcggcc cgctcgcggg    124260
cccacgagcc gcggcgcgcc aggcgggcgg ccgaggccca gaccaccagg tggcgcaccc    124320
```

```
ggacgtgggg cgagaagcgc acccgcgcgg gggtcgcggg ggtcgcgggg gtcgcggggg   124380
tcgcgggggt cgcggggtc gcggggtcg cggggtcgc gggggctcc ggcgcccct       124440
ccccgcccgc gcgtcgcagg cgcaggcgcg ccaggtgctc cgcggtgacg cgcaggcgga   124500
gggcgaggcg cggcggaagg cggaaggggc gcgaggggg gtgggagggg tcagcccgc    124560
ccccgggcc cacgccgggc ggtgggacc gggccgggg gcgcgggcg gtgggccgg       124620
cctctggcgc cggctcggc gggggctgt ccggccagtc gtcgtcatcg tcgtcgtcg     124680
acgcggactc gggaacgtgg agccactggc gcagcagcag cgaacaagaa ggcgggggcc  124740
caccggcggg gggcggcggc ggggcggccg cgggcgcgct cctgaccgcg ggttccgagt   124800
tgggcgtgga ggttacctgg gactgtgcgg ttgggacggc gcccgtgggc ccgggcggc   124860
ggggcggcg ggggccgcga tggcggcggc ggcgggccat ggagacagag agcgtgccga   124920
ggtggtagag tttgacaggc aagcatgtgc gtgcagaggc gagtagtgct tgcctgtcta   124980
actcgctagt ctcggccgcg gggggccgg gctgccgcc gccgcgcttt aaagggccgc    125040
gcgcgacccc cgggggtgt gtttcgggg ggcccgtttt tggggtctgg ccgctcctcc   125100
cccgctcctc ccgtctgtg ggtggggctc ctccccgct cctccccgc tcctccccg     125160
ctcctcccg tctgtgggtg gggctcctcc cccgctcccg cggccccgcc ccccacgccc  125220
gccgcgcgcg cgcacgccgc ccggaccgcc gcccgcttt tttgcgcgcc gccccgcgcg   125280
cgggggccc gggctgccac aggtgtaaca acaccaacag aacaccaaca gcacggcgca   125340
ccggcgactc cggttcctca tccacacgtc acgtcatcca acacacctgc ccaacaacac  125400
aactcacagc gacaactcac cgcgcaacaa ctcctgttcc tcatccacac gtcaccgcgc   125460
acccccgct cctccagacg tccccagcg caacacgccg ctcctgtcac acaccacagc   125520
cccagccctc cccagcccca gccctcccca gcccagccc tccccagccc cagccctccc  125580
cagccccagc cctccccagc cccagcccct ccagccccca gccccagccc ccagccccc  125640
tccccagccc cagccctccc cagccccagc cctcccagc cccagccctc cccagcccca   125700
gccctcccca gccgcgtccc gcgctccctc gggggggttc gggcatctct acctcagtgc  125760
cgccaatctc aggtcagaga tccaaacct cggggggcgc ccgcgcacca ccaccgcccc   125820
tcgccccctc ccgccctcg ccccctcccg cccctcgcc cctcccgcc ctcgccccc    125880
cccgccccct cgccccctcc ccccctcgcc cctcccgcc cctcgcccc tcccgccc    125940
cgccccctcc cgccctcga ataaacaacg ctactgcaaa acttaatcag gtcgttgccg   126000
tttattgcgt cttcgggttt cacaagcgcc ccgcccgtc ccggcccgtt acagcacccc   126060
gtccccctcg aacgcgccgc cgtcgtcttc gtcccaggcg ccttcccagt ccacaacgtc   126120
ccgtcgcgcg ggcgtggcca agccgcctc cgcccccagc acctccacgg ccccccgcgc   126180
cgccagcacg gtgccgctgc ggccgtggc cgaggccag cgaatcccgg gcggcgccgg   126240
cggcagggcc cccgggccgt cgtcgtcgcc gcgcagcacc agcggggggg cgtcgtcgtc   126300
gggctccagc agggcgcggg cgcaaaagtc cctccgcggc ccgcgcggcg gggccgggcc  126360
ggcgcgcacc ggctcgcgcc gccagcgcac gtacacggc cgcagcggcg cgcccaggcc  126420
ccagcgcgcg caggcgcggt gcgagtgggc ctcctcctcg cagaagtccg gcgcgccggg   126480
cgccatggcc tcggtggtcc ccgaggccgc cgcccgccg tccagcgccg gcagcacggc   126540
ccggcggtac tcgcgcgggg acatgggcac cggcgtgtcc gggccgaagc gcgtgcgcac   126600
gcggtagcgc acgttgccgc cgcggcacag cgcagccggc ggcgtcgtgg ggtacaggcg   126660
cgcgtgcgcg gcctcacgc gcgcgaagac cccggggccg aacacgcggc ccgaggccag   126720
caccgtgcgg cgcaggtcgc gcgccgccgg ccagcgcacg gcgcactgca cggcgggcag   126780
caggtcgcac gccaggtagg cgtgctgccg cgacaccgcg ggccgtcgg cgggccagtc   126840
gcaggcgcac ggcggtgttga ccacgatgag ccgccggtcg ccggcgctgg cggcagccc   126900
cagaaactcc acggcccgg cgaaggccag gtcccgcgtg gacagcagca gcacgccctg   126960
cgcgcccagc gccgacacgt cggggggcgcc ggtccagttg ccgcccagg cggccgtgtc   127020
cggcccgcac agccggttgg ccaggccgc cagcaggcag gacagcccgc cgcgctcggc   127080
ggaccagtcc ggcggccccc ccgaggcccc gccgccggcc aggtcctcgc ccggcagcgg  127140
cgagtacagc accaccacgc gcacgtcctc ggggtcgggg atctggcgca tccaggccgc   127200
catgcggcgc agcgggcccg aggcgcgcag ggggccaaag aggcggcccc cggcggcccc   127260
gtgggggtgg gggttctcgt cgtcgtcgcc gccgccgcac gcggcctggg cggcggggggc  127320
gggcccgggc caccgcgcgg cgatcgaggc caggggccgc gggtcaaaca tgagggccgg  127380
tcgccagggg acgggaaca gcgggtggtc cgtgagctcg gccacggcgc gcggggagca   127440
gtaggcctcc agggcggcgg ccgcgggcgc cgccgtgtgg ctgggccccg ggggctgccg   127500
ccgccagccg cccaggggt cggggccctc ggcgggccgg cgcgacagcg ccacggggcg   127560
cgggcgggcc tgccgccgga ccggcggggg cgccgcgggc tgggcgggc cgggctcggg  127620
ccccgggggc gtggagggg gcgcgggcgg gggagggggg gcgcgggcgt ccgagccggg  127680
ggcgtccgcg ccgctcttct tcgtcttcgg gggtcgcggg ccgccgcctc cgggcggccg   127740
ggccggggccg ggactcttgc gcttgcgccc ctcccgcggc gcggcggagg cggcggccgc   127800
gaccccgaa gacgaagaag agcggcgcgg acccgccgc agcaggggc gcaggctctg   127860
gttctcaaac agcaggtccg cggccggcgc ggccgcaggc gtcggcaggc cgggttcccg   127920
cggcagcgcg ggaccagggc cccggcgac caggctcacg gcgcgcacgg cggccacggc   127980
ggcctcgctg ccgccggcca cgcgcaggtc cccgcgcagg cgcatgagca ccagcgcgtc   128040
gcgcacgaac cgcagctcgc gcagccacgc gcgcaggcgg ggcgcgtcgg cgtgcggcgg   128100
cggcgggaa ggcggggccg cgggtccctc cggccgcggg ggctggcgg gccgggcccc  128160
ggccagcccc gggacgccg ccaggtcgcc gtcgaagccc tcggccagcg cctccaggat   128220
cccgcggcag gcggccaggc actccacggc cacgcggccg gcctgggcgc ggcgcccggc   128280
gtcgtcgtcg gcgtcggcgt ggcgggcggc gtcgggtcg tcgccccccg cggggggaggc   128340
gggcgcggcg gacagccgcc ccaggcggc gaggatcccc gcggcgccgt accggcgggg  128400
caccggcgcg tcgcccggtg cggcggcggg ggcgacgacg gcggcggcca ccccctcgtc  128460
atctgccgcc gcgccgggc tcccgcggc cccgtcagc gccgcgttct cgcgcgccaa   128520
cagggcgcg taggcgcggc gcaggctgct cagcaggaag ccttctgcg cgccggtcgta   128580
tcggcggctc atgccacggc cggccgccgc gtgcgccagg cccagccgga gcggccggc    128640
cgccatggcc tagcccaggt ggggcacggc ccgccacg ctgccggtga tgaaggagct   128700
gctgtttgc gcggcgccg agatccggaa gcaggcctgg tccagcgcca cgtccagggc    128760
gaccacgcgc gggttctgga gccacccat ggcctccgcg tccggggtgt acagcagccg  128820
cgtgatcagg gcgtactgct gccggccgtc gcccagctcg ggcgcccaca ccggccgcgg   128880
ggcgcccgag gcctcgaacc ggcgtcgcgc ctcctccgcc tcgggcgccc cagaggccc    128940
cgggcggctg tcgcccaggc cgccgtacag caccccgccc ggggcgggg gccggccgcc   129000
gggccacggc tccccgctga cgtacccgtc gcgatagcgc gcgtagaagg cgccggaggc   129060
```

-continued

```
cgcgtcggcg tccagctcga cccgccgggg ctgcccggcc gtgaagcggc ccgtggcgtc   129120
gcggccggcc accgccgcgc gggcccggcg gcgctcgatg cggcccgcgg aggccgcggg   129180
ggtcctcgcc gccgcccggg gcttgggcgc ggcctcggag aggggggggtg gcccgggcgg   129240
gggcggcgtc cgcccggggg cttccggcgc cgcgctcgac ggaccccgcc cgacggcccg   129300
cgcctcgcgt gcgtggtcgg ccgcgtcgtt gccgtcgtcg tcctcgtcct cgtcggacga   129360
cgaggacgaa gaggatgcgc acgacgagga cgaggacccg gagtccgacg aggtcgatga   129420
cgccgatggc cgccgccggc cgtgacgacg tctctgcggc ggctgggccg gcgggcgcgg   129480
cgacaggcgg tccgtggggt ccggatacgc gccgcgtagc ggggcctccc gtgcgcggcc   129540
ccgggccggg gcccggtcgc cggcggcgtc ggctgcgtcg tcgtactcgt ccccgtcatc   129600
gtcgtcggct cgaaaggcgg gggtccgggg cggcgaggcc gcggggtcgg gcgtcgggat   129660
cgtccggacg gcctcctcta ccatggaggc cagcagggcc agctgtcgcg gcgagacggg   129720
gtccccggcg tcctcgccgg cgtcggtgcc cgccgcgggg gccctccgt cccgccgggc   129780
gtcgtcgagg tcgtgggggt ggtcggggtc gtggtcgggg tcgtccccgc cctcctccgt   129840
ctccgcgcgg caccgaggg cccccgcgctc gtcgcggtct gggctcgggg tgggcggcgg   129900
cccgtcggtg gggccggggg agccggggcg ctgcttgttc tccgacgcca tcgccgatgc   129960
ggggcgatcc tccggggata cgactgcgac ggcggacgta gcacggtagg tcacctacgg   130020
actctcgatg ggaggggggc gagacccacg accccgacg accccgcg tcgacgcgga    130080
actagcgcgg accggtcgat gcttggctgg gaaaaaggac agggacggcc gatcccctc    130140
ccgcgcttcg tccgcgtatc ggcgtcccgg cgcggcgagc gtctgacggt ctgtctctgg   130200
cggtcccgcg tcgggtcgtg gatccgtgtc ggcagccgcg ctccgtgtgg acgatcgggg   130260
cgtcctcggg ctcatatagt cccagggggcc ggcgggaagg aggagcagcg gaggccgccg   130320
gcccccgccc cccacgcgg gcccgccccg aacggaattc cattatgcac gaccccgccc   130380
cgacgccggc acgccggggg cccgtggccg cggcccgttg gtcgaacccc ggccccgcc    130440
catccgcgcg atctgccatg ggcgggcgc tagggcgggt gggcccgcgc ccgcccccgc    130500
atggcatctc attaccgccc gatccggcgg tttccgcttc cgttccgcat gctaacgagg   130560
aacgggcagg gggcggggcc cgggccccga cttcccggtt cggcggtaat gagatacgag   130620
ccccgcgcgc ccgttggccg tcccccgggcc cccgtcccg cccgccgac gccgggacca    130680
acgggacggc gggcggccca agggccgccc gccttgccgc ccccccattg gccggcgggc   130740
gggaccgccc caaggggcg gggccgccgg gtaaagaag tgagaacgcg aagcgttcgc    130800
acttcgtccc aatatatata tattattagg gcgaagtgcg agcactggcg ccgtgcccga   130860
ctccgcgccg gccccggggg cgggcccggg cggcggggg cgggtctctc cggcgcacat   130920
aaaggcccgg cgccgaccgac gcccgcagac ggcgccggcc acgaacgacg ggagctgctg   130980
cggagcacgc ggaccgggag cgggactcgc agagggccgt cggagcggac ggcgtcggca   131040
tcgcgacgcc ccggctcggg atcgggatcg catcggaaag ggacacgcgg aaagacccac   131100
ccaccccacc acgaaaacac aggggacgca ccccgggggc ctccgacgac agaaaacccac   131160
cggtccgcct ttttgcacgg gtaagcacct tgggtgggcg gaggagggcg gaggagggggg   131220
gacgcggggg cggaggaggg gggacgcggg ggcggaggag gggggacgcg ggggcggagg   131280
agggggacg cggggggcgga ggaggggcct caccgcgtt cgtgccttcc cgcaggagga    131340
acgtcctcgt cgaggcgacc ggcggcgacc gttgcgtgga ccgcttcctg ctcgtcgggg   131400
cgaccggcgg cgaccgttgc gtggaccgct tcctgctcgt cggggcgacc ggcggcgacc   131460
gttgcgtgga ccgcttcctg ctcgtcgggg ggggggggg gaagcactg tggtcctccg     131520
ggacgttttc tggatggccg acatttcccc aggcgctttt gcgccttgtg taaaagcgcg   131580
gcgtcccgct ctccgatccc cgcccctggg cacgcgcaag ccaagcgcc ctgcccgccc    131640
cctctcatcg gagtctgagg tcgaaaccga tacagccttg gagtctgagg tcgaatccga   131700
gacagcatcg gattcgaccg agtctgggga ccaggaggaa gccccccgca tcggtggccg   131760
tagggccccc cggaggcttg gggggcggtt ttttctggac atgtcggcgg aatccaccac   131820
ggggacggaa acggatacgg cggtgtcgga cgaccccgac gacacgtcg actggtctta   131880
tgacgacatt cccccacgac ccaagcgggc ccgggtaaac ctgcggctca cgagctctcc   131940
cgatcggcgg gatggggtta ttttttcctaa gatgggggcgg gtccggtcta cccgggaaac   132000
gcagccccgg gccccaaccc cgtcggcccc aagcccaaat gcaatgctac ggcgctcggt   132060
gcgccaggcc cagaggcgga gcagcgcacg atggaccccc gacctgggct acatgccgga   132120
gtgtatcaat cagctgtttc gggtcctgcg ggtcgcccgg gaccccacg gcagtgccaa    132180
ccgcctgcgc cacctgatac gcgactgtta cctgatggga tactgccgag cccgtctggc   132240
cccgcgcacg tggtgccgct tgctgcaggt gtccggcgga acctgggggca tgcacctgcg   132300
caacaccata cgggaggtgg aggctcgatt cgacgccacc gcggaacccg tgtgcaaact   132360
tccttgtttg gaggcagac ggtacggcc ggagtgtgat cttagtaatc tcgagattca     132420
tctcagcgcg acaagcgatg atgaaatctc cgatgccacc gatctggagg ccgccggttc   132480
ggaccacacg ctcgcgtccc agtccgacac ggaggatgcc ccctcccccg ttacgctgga   132540
aacccagaa cccgcgggt ccctcgctgt gcgtctggag gatgagtttg gggagtttga    132600
ctggaccccc caggaggggct ccagccctg gcgtctgccg gtcgtggccg ataccagctc   132660
cgtgaacgc ccgggcccat ccgattctgg ggcgggtcgc gccgcagaag accgcaagtg    132720
tctgacggc tgccggaaaa tgcgcttctc caccgcctgc ccctatcgt gtagcgacac     132780
gtttctccgg ccgtgagtcc ggtcgccccg accccttgt atgtcaccaa aataaaagac   132840
caaaatcaaa gcgtttgtcc cagcgtctta atggcgggaa ggcggagag aaacagacca    132900
cgcggacatg ggggggtgttt gggggtttat tggcacgggg ggctaaaggg tggtaaccgg   132960
atagcagatg tgaggaagtc ggggccgttc gccgcgaacg gcgatcagag ggtcagtttc   133020
ttgcggacca cggcccggcg atgtggggttg ctcgtctggg acctcgggca tgcccataca   133080
cgcacaacac ggacgccgca ccggatggga cgtcgtaagg gggctgggg tagctgggtg    133140
gggtttgtgc agagcaatca gggaccgcag ccagcgcata caatcgcagg ccctccgctt   133200
tgtcccggc agtaccacgc cgtactggta ttcgtaccgg ctgagcaggg tctccagggg   133260
gtggttgggg gccgcgggga acgggtccca cgccacggtc cactcgggca aaaaccgagt   133320
cggcacggcc cacggttctc ccacccacgc gtctgggggtc ttgatggcga taaatcttac   133380
cccgagccgg attttttggg cgtattcgag aaacggcaca cacagatccg ccgcgcctac   133440
cacccacaag tggtagatgc gagggggggct gggttggtct cggtgcagca gtcgaagca   133500
cgccacggcc tccacgacct cggtgctctc caagggggctg tcctccgcaa acaggcccgt   133560
ggtggtgttt gggggggcagc gacaggacct agtgcgcacg atcgggcggg tgggtttggg   133620
taagtccatc agcggctcgg ccaaccgtcg aaggttggcc ggacgaacga cgaccggggt   133680
acccaggggt tctgatgcca aaatgcggca ctgcctaagc aggaagctcc acagggccgg   133740
gcttgcgtcg acggaagtcc ggggcagggc gttgttctgg tcaaggaggg tcattacgtt   133800
```

```
gacgacaaca acgcccatgt tggtatatta caggcccgtg tccgatttgg ggcacttgca   133860
gatttgtaag gccacgcacg gcggggagac aggccgacgc gggggctgct ctaaaaattt   133920
aagggcccta cggtccacag acccgccttc ccggggggg ggcccttgga gcgaccggca    133980
gcgtaggcgt ccgggggagg ggagggtgat ttacggggg gtaggtcagg gggtgggtcg    134040
tcaaactgcc gctccttaaa accccggggc ccgtcgttcg gggtgctgtt tggttggcac   134100
tcacggtgcg gcgaatggcc tgtcgtaagt tttgtcgcgt ttacggggga caggggcagga  134160
ggaaggagga ggccgtcccg ccggagacaa agccgtcccg ggtgtttcct catgcccct    134220
tttatacccc agccgaggac gcgtgcctgg actcccgcc cccggagacc cccaaacctt    134280
cccacaccac accacccagc gaggccgagc gcctgtttca tctgcaggag atccttgccc   134340
agatgtacgg aaaccaggac taccccatag aggacgaccc cagcgcggat gccgcgacg    134400
atgtcgacga ggacgccccg gacgacgtgg cctatccgga ggaatacgca gaggagcttt   134460
ttctgcccgg ggacgcgacc ggtcccctta tcggggccaa cgaccacatc cctccccgt    134520
gtggcgcatc tcccccggt atacgacgac gcagccggga tgagattggg gccacgggat    134580
ttaccgcgga agagctggac gccatggaca gggaggcggc tcgagccatc agccgcggcg   134640
gcaagccccc ctcgaccatg gccaagctgg tgactggcat gggctttacg atccacggag   134700
cgctcacccc aggatcggag gggtgtgtct ttgatagcag ccacccagat tacccccaac   134760
gggtaatcgt gaaggcgggg tggtacacga gcacgagcca cgaggcgcga ctgctgaggc   134820
gactggacca ccccgcgatc ctgccccctcc tggacctgca tgtcgtctcc ggggtcaggg   134880
gtctggtcct ccccaagtac caggccgacc tgtataccta tctgagtagg ggcctgaacc   134940
cgctgggacg cccgcagatc gcagcggtct cccggcagct cctaagcgcc gttgactaca   135000
ttcaccgcca gggcattatc caccgcgaca ttaagaccga aaatattttt attaacacc    135060
ccgaggacat ttgcctgggg gactttggtg ccgcgtgctt cgtgcaggt tcccgatcaa    135120
gcccccttccc ctacgaatc gccgaaccga tcgacaccaa cgcccccgag gtcctggccg   135180
gggatccgta taccacgacc gtcgacattt ggagcgccgg tctggtgatc ttcgagactg   135240
ccgtccacaa cgcgtccttg ttctcggcc cccgcgccc caaaaggggc ccgtgtgaca    135300
gtcagatcac cgcatcatc cgacagcccc aggtccacgt tgacgagttt tccccgcatc    135360
cagaatcgcg cctcacccctcg cgctaccgct cccgcgccg cgggaacaat cgcccgcctt   135420
acaccgacc ggcctggacc cgctactaca agatggacat agacgtcgaa tatctggttt    135480
gcaaagccct caccttcgac ggcgcgcttc gcccagcgc cgcagagctg cttttgtttgc   135540
cgctgtttca acagaaatga ccgccccgg ggggcggtgc tgtttgcggg ttggcacaaa    135600
aagacccga cccgcgtctg tggtgttttt ggcatcatgt cgccgggcgc catgcgtgcc    135660
gttgttccca ttatcccatt cctttggtt cttgtcggtg tatcgggggt tcccaccaac    135720
gtctcctcca ccacccaacc ccaactccag accaccggtc gtccctcgca tgaagccccc   135780
aacatgacc agaccggcac caccgactct cccaccgcca tcagccttac cacgcccgac   135840
cacacaccc ccatgccaag tatcggactg gaggaggag aggaagagga ggaggggccc    135900
ggggatggcg aacatcttaa gggggagat gggacccgtg acaccctacc ccagtccccg    135960
ggtccagccg tcccgttggc cggggatgac gagaaggaca aacccaaccg tcccgtagtc   136020
ccaccccccg gtcccaacaa ctcccccgcg cgccccgaga ccagtcgacc gaagacaccc   136080
cccaccagta tcgggccgct ggcaactcga cccacgacc aactccctc aaaggggcga    136140
cccttggttc cgacgcctca acatacccg ctgttctcgt tcctcactgc ctcccccgcc    136200
ctggacaccc tcttcgtcgt cagcaccgtc atccacacct tatcgttttt gtgtattggt   136260
gcgatggcga cacacctgtg tggcggttgg tccagacgcg ggcgacgcac acaccctagc   136320
gtgcgttacg tgtgcctgcc gtccgaacgc gggtagggta tggggcgggg gatggggaa    136380
gcccacatgc ggaaagcaag aacaataaag gcggtggtat ctagttgata tgcatctctg    136440
ggtgtttttg gggtgtggcg gacgcggggc ggtcattgga cggggtgcag ttaaatacat   136500
gcccgggacc catgaagcat gcgcgacttc cgggcctcgg aacccacccg aaacggccaa   136560
cggacgtctg agccaggcct ggctatccgg agaaacagca cacgacttgg cgttctgtgt   136620
gtcgcgatgt ctctgcgcgc agtctggcat ctgggggcttt tggaagcct cgtgggggct   136680
gttcttgccg ccacccatcg gggacctgcg gccaacacaa cggacccctt aacgcacgcc   136740
ccagtgtccc ctcacccag cccctgggg ggctttgccg tcccctcgt agtcggtggg     136800
ctgtgccgca tagtcctggg ggcggcgtgt ctgcttgagc tcctgcgtcg tacgtgccgc   136860
gggtggggc gttaccatcc ctacatggac ccagttgtcg tataattccc cccccccctt     136920
ctccgcatgg gtgatgtcgg gtccaaactc ccgacaccac cagctggcat ggtataaatc   136980
accggtgcgc ccccaaacc atgtccggca gggggatggg ggggcgaatg cggagggcac   137040
ccaacaacac cgggctaacc aggaaatccg tggcccccgc cccaataaaa gatcgcggta   137100
gcccggccgt gtgacactat cgtccatacc gaccacaccg acgaatcccc taaggggag    137160
gggccatttt acgaggagga ggggtataac aaagtctgtc tttaaaaagc aggggttagg   137220
gagttgttcg gtcataagct tcagcgcgaa cgaccaacta ccccgatcat cagttatcct   137280
taaggtctct tttgtgtggt gcgttccggt atggggggg ctgccgccag gttggggcc     137340
gtgattttgt ttgtcgtcat agtgggcctc catggggtcc gcggcaaata tgccttgcg    137400
gatgcctctc tcaagatggc cgaccccaat cgctttcgcg gcaaagacct tccggtcctg   137460
gaccagctga ccgaccctcc gggggtccgg cgcgtgtacc acatccaggc gggcctaccg   137520
gaccgttcc agccccccag cctcccgatc acggtttact acgccgtgtt ggagcgcgcc   137580
tgccgcagcg tgctcctaaa cgcaccgtcg gaggccccccc agattgtcgg cggggcccc   137640
gaagacgtcc ggaaacaacc ctacaacctg accatcgctt ggtttcggat gggaggcaac   137700
tgtgctatcc ccatcacggt catggagtac accgaatgct cctacaacaa gtctctgggg   137760
gcctgtccca tccgaacgca gcccccgctgg aactactatg acagcttcag cgccgtcagc   137820
gaggataacc tgggggttcct gatgcacgcc cccgcgtttg agaccgccgg cacgtacctg   137880
cggctcgtga agataaacga ctggacggag attaccctgg ggcaccgagcc              137940
aagggctcct gtaagtacgc cctcccgctg cgcatccccc cgtcagcctg cctgtccccc   138000
cagggcctacc agcaggggtt gacggtggac agcatcggga tgctgccccg cttcatcccc   138060
gagaaccagc gcaccgtcgc cgtatacagc ttgaagatcg ccgggtggca cgggcccaag   138120
gccccataca cgagcaccct gctgcccccg gagctgtccc agaccccaa cgccacgcag    138180
ccagaactgc ccccggaaga ccccgaggat tcggccctct tgtgaggacc gtggggacg    138240
gtggcgccgc aaatcccacc aaactggcac ataccgtcga tccaggacgc cgcgacgcct   138300
taccatcccc cggccaccccc gaacaacatg ggcctgatcg ccgtcggt gggcggcagt    138360
ctcctggcag ccctggtcat ttgcggaatt gtgtactgga tgcgccgcg cactcaaaaa    138420
gcccaaagc catacgcct ccccacatc cgggaagacg accagccgtc ctcgcaccag      138480
cccttgtttt actagatacc cccccttaat gggtgcgggg gggtcaggtc tgcggggttg   138540
```

```
ggatgggacc ttaactccat ataaagcgag tctggaaggg gggaaaggcg gacagtcgat   138600
aagtcggtag cggggggacgc gcacctgttc cgcctgtcgc acccacagct ttttttgcga   138660
accgtcccgt tccgggatgc cgtgccgccc gttgcagggc ctggtgctcg tgggcctctg   138720
ggtctgtgcc accagcctgg ttgtccgtgg ccccacggtc agtctggtat caaactcatt   138780
tgtggacgcc ggggccttgg ggcccgacgg cgtagtgcga gaagacctgc ttattctcgg   138840
ggagcttcgc tttgtggggg accaggtccc ccacaccacc tactacgatg gggtcgtaga   138900
gctgtggcac tacccatgg gacacaaatg cccacgggtc gtgcatgtcg tcacggtgac   138960
cgcgtgccca cgtcgcccg ccgtggcttt cgccctgtgt cgcgcgaccg acaacactca   139020
cagccccgca tatcccaccc tggagctgaa tctggcccaa cagccgcttt tgcgggtcgg   139080
gagggcgacg cgtgactatg ccggggtgta cgtgttacgc gtatggtcg tggacgcacc   139140
aaacgccagc ctgttttgtcc tggggatggc catagccgcc gaagggactc tggcgtacaa   139200
cggctcggcc catggctcct gcgacccgaa actgcttccg tattcggccc cgcgtctggc   139260
cccgcgagc gtataccaac ccgcccctaa cccggcctcc accccctcga ccaccacctc   139320
caccccctcg accaccacct ccaccccctc gaccaccacc tccaccccct cgaccaccac   139380
ctccacccccc tcgaccacca cctccacccc ctcgaccacc acctccaccc cctcgaccac   139440
catcccccgct cccaagcat cgaccacacc cttcccacg ggagacccaa aaccccaacc   139500
tcacgggggtc aaccacgaac cccatcgaa tgccacgcga gcgacccgcg actcgcgata   139560
cgcgctaacg gtgacccaga taatccagat agccatcccc gccgtcatta tagccctggt   139620
gtttctgggg agctgtattt gctttataca cagatgtcaa cgccgctacc gacgctcccg   139680
ccgcccgatt tacaaccccc agatacccac gggcatctca tgcgcggtga acgaagcggc   139740
catggcccgc ctcggagccg agctcaaatc gcatccgagc acccccccca aatcccggcg   139800
ccggtcgtca cgcacgccaa tgccctccct gacggccatc gccgaagagt ggagcccgtc   139860
gggggcgggct gggcttccga cgcccccccgt ggacccacg acatccacccc caacgcctcc   139920
cctgttggta taggtccacg gccactggcc gggggcacca cataaccgac cgcagtcact   139980
gagttgggaa taaaccggta ttatttacct atatccgtgt atgtccattt ctttccccc   140040
cccccccccc cggaaaccca aagaaggaag caaagaatgg atgggaggag ttcaggaagc   140100
cggggagagg gcccgcggcg catttaaggc gttgttgtgt tgactttggc tcttctggcg   140160
ggttggtgcg gtgctgttg ttgggctccc atttttaccccg aagatcggct gctatccccg   140220
ggacatggat cgcggggcgg tggtgggggtt tcttctcggt gttgtgttg tatcgtgctt   140280
ggcgggaatg cccaaaacgt cctggagacg ggtgagtgtc ggcgaggacg tttcgttgct   140340
tccagctccg gggcctacgg ggcgcggccc gacccagaaa ctactatggg ccgtggaacc   140400
cctggatggg tgcggcccct tacacccgtc gtgggtctcg ctgatgcccc ccaagcaggt   140460
gcccgagacg gtcgtggatg cggcgtgcat gcgcgctccg gtcccgctgg cgatggcgta   140520
cgcccccccg gccccatctg cgaccggggg tctacgaacg gacttcgtgt ggcaggagcg   140580
gcggccgtg gttaaccgga gtctggttat tcacgggggtc cgagagacgg acagcggcct   140640
gtataccctg tccgtgggcg acataaagga cccggctcgc caagtggcct cggtggtcct   140700
ggtggtgcaa ccgccccag ttccgacccc accccccgacc ccagccgatt acgacgagga   140760
tgacaatgac gagggcgagg gcgaggacga aagtctagcc ggcactcccg ccagcgggac   140820
ccccccggctc ccgcctcccc ccgccccccc gaggtcttgg cccagcgccc ccgaagtctc   140880
acacgtgcgt ggggtgaccg tgcgtatgga gactccggaa gctatcctgt tttcccccgg   140940
ggaggcgttt agcacgaacg tctccatcca tgccatcgcc cacgacgacc agacctacac   141000
catgacgtc gtctggttga ggttcgacgt gccgacctcg tgtccgaga tgcgaatata   141060
cgaatcgtgt ctgtatcacc cgcagtcccc agagtgtctg tcccccggccg acgctccgtg   141120
cgccgcgagt acgtgacgt ctcgcctggc cgtccgcagc tacgcggggt gttccagaac   141180
aaaccccccg ccgcgctgtt cggcgaggc tcacatggag cccttccggg ggctggcgtg   141240
gcaggcggcc tccgtcaatc tggagttccg ggacgcgtcc ccacaacact ccggcctgta   141300
tctgtgcgtg gtgtacgtca acgaccatat tcacgcatgg ggccacatta ccatcagcac   141360
cgcggcgcag taccggaacg cggtggtgga acagcccctc ccacagcgcg gcgcggattt   141420
ggccgagccc acccaccccgc acgtcggggc ccctccccac gcgcccccaa cccacggcgc   141480
cctgcgggtta ggggcggtga tgggggccgc cctgctgctg tctgcgctgg ggttgtcggt   141540
gtgggcgtgt atgacctgtt ggcgcaggcg tgcctggcgg gcggttaaaa gcagggcctc   141600
gggtaagggg cccacgtaca ttcgcgtggc cgacagcgag ctgtacgcgg actgagctc   141660
ggacagcgag ggagaacgcg accaggtccc gtggctggcc ccccggaga gcccgactc   141720
tccctccacc aatggatccg gctttgagat cttatcacca acggctccgt ctgtatacccc   141780
ccgtagcgat gggcatcaat ctcgccgcca gctcacaacc tttggatccg gaaggcccga   141840
tcgccgttac tccaggcct ccgattcgtc cgtcttctgg taaggcgccc catcccgagg   141900
ccccacgtcg gtcgccgaac tggcgaccg ccggcgaggt ggacgtcgga gacgagctaa   141960
tcgcgatttc cgacgaacgc ggacccccccc gacatgaccg cccgccctc gccacgtcga   142020
ccgcgccctc gccacacccg cgaccccgg gctacacgcc cgttgtctcc ccgatgccct   142080
tccaggctgt cgacgcccct tccctgtttg tcgcctggct ggccgctcgg tggctccgag   142140
gggcttccgg cctgggggcc gtcttgtgtg ggattgcgtg gtatgtgacg tcaattgccc   142200
gaggcgcata aagggccggt ggtccgccta gccgcagcaa attaaaaatc gtgagtcact   142260
gcgaccgcaa cttcccaccc ggagctttct tccggcctcg atgacgtccc ggctctccga   142320
tcccaactcc tcagcgcgat cgacatgtc cgtgccagtt tatcccacgg cctcgccagt   142380
ttcggtcgaa gcctactact cggaaagcga agacgaggcg gccaacgact tcctcgtacg   142440
catgggccgc caacagtcgg tattaaggcg tcgacgcaga cgcacccgct gcgtcggcat   142500
ggtgatcgcc tgtctcctcg tggccgttct gtcgggcgga tttggggcgc tcctgatgtg   142560
gctgctccgc taaaagaccg catcgacacg cgcgtccttc ttgtcgtctc tcttccccca   142620
atcaccccgc aatttgaac cagccttta ctacattaaa ttgggttcga ttggcaatgt   142680
tgtctccccgg ttgattttttg ggtgggtggg gagtgggtgg gtggggagtg ggtgggtggg   142740
gagtgggtgg gtggggagtg ggtgggtggg gagtgggtgg gtggggagtg ggtgggtggg   142800
gagtgggtgg gtggggagtg ggtgggtggg gagtgggtgg gtggggagtg ggtgggtggg   142860
gagtgggtgg gtggggagtg ggtgggtggg gagtgggtgg gtggggagtg ggtgggtggg   142920
gagtgggtgg gtggggagtg gcaaggaaga aacagcccg accaccagac agaaaatgta   142980
accatcccca aaccgactct gggggctgtt tgtggggtcg gaaccatagg atgaacaaac   143040
caccccgtac ctcccgcacc cttgggtgcg ggtggctcat cggcatctgt ccggtatggg   143100
ttgttcccca cccactcgcg ttcggacgtc ttagaatcat ggcggtttct atgccgacat   143160
cggtttctcc cccgcaataa gacacgatgc gataaaatct gtttgtgaaa tttattaagg   143220
gtacaaattg ccctagcaca ggggtggggt tagggccggg tccccacacc caaacgcacc   143280
```

```
aaacagatgc aggcagtggg tcgagtacag ccccgcgtac gaacacgtcg atgcgtgtgt  143340
cagacagcac cagaaagcac aggccatcaa caggtcgtgc atgtgtcggt gggtttggac  143400
gcggggggcc atggtgggtg ataaagttaa tggccgccgt ccgccagggc cacaggggcg  143460
acgtctcttg gttggcccgg agccactggg tgtggaccag ccgcgcgtgg cggcccaaca  143520
tggccctgt agccggggc gggggatcgc gcacgtttgc agcgcacatg cgagacacct  143580
cgaccacggt tcggaagaag gcccggtggt ccgcgggcaa catcaccagg tgcgcaagcg  143640
cccgggcgtc cagagggtag agccctgagt catccgaggt tggctcatcg cccgggtcat  143700
gccgcaagtg cgtgtgggtt gggcttccgg tgggcgggac gcgaaccgcg gtgtggagcc  143760
cgacgcgggc ccgagcgtac gctccatctt gtggggagaa ggggtctggg ctcgccaggg  143820
gggcatactt gcccgggcta tacagacccg cgagccgtac gtggttcgcg gggggtgcgt  143880
ggggtccggg gctcccgggg aggccggggc tcccgggggtt gtcgtggatc cctgggtca  143940
cgcggtaccc tggggtctct gggagctcgc ggtactctgg gttccctagg ttctcggggt  144000
ggtcgcggaa cccgggggctc ccggggaaca cgcggtgtcc tggggattgt tggcggtcgg  144060
acggcttcag atggcttcga gatcgtagtg tccgcaccga ctcgtagtag acccgaatct  144120
ccacattgcc ctgccgcttg atcattatca ccccgttgcg ggggtccgga gatcatgcgc  144180
gggtgtcctc gaggtgcgtg aacacctctg gggtgcatgc cggcggacgg cacgcctttt  144240
aagtaaacat ctggggtcgcc cggcccaact gggggccggg gttgggtctg gctcatctcg  144300
agagccacgg gggaaccac cctccgccca gaaacttggg cgatggtcgt acccgggact  144360
caacgggtta ccggattacg gggactgtcg gtcacggtcc cgccggttct tcgatgtgcc  144420
acacccaagg atgcgttggg ggcgattttg ggcagcagcc cggagagcg cagcaggaga  144480
cgctccgggt cgtgcacggc ggttctggcc gcctccggt cctcacgccc cctttattg  144540
atctcatcgc gtacgtcggc gtacgtcctg ggccaaccc gcatgttgtc caggaaggtg  144600
tccgccattt ccaggggccca cgacatgctc cccccccc cccgacgag caggaagcgg  144660
tccacgcaac ggtcgccgcc ggtcgccccg acgagcagga agcggtccac gcaacggtcg  144720
ccgccggtcg ccccgacgag caggaagcgg tccacgcaac ggtcgccgcc ggtcgccctcg  144780
acgaggacgt tcctccctgcg ggaaggcacg aacgcggtg agccccctcc tccgccccga  144840
cgtcccccct cctccgcccc cgcgtccccc ctcctccgcc cccgcgtccc ccctcctccg  144900
cccccgcgtc cccctcctc cgccctcctc cgcccaccca aggtgcttac ccgtgcaaaa  144960
aggcggaccg gtgggttct gtcgtcgag gccccgggg tgcgtcccct gtgtttcgtg  145020
ggtggggtgg gtgggtctt ccgcgtgtcc ctttcgatg cgatcccgat cccgagccgg  145080
ggcgtcgcga tgccgacgcc gtccgctccg acgccctct gcgagtcccg ctccccggtcc  145140
gcgtgctccg cagcagctcc cgtcgttcgt ggccggcgcc gtctgcggc gtcggtcgcg  145200
ccgggccttt atgtgcgccg gagagacccg ccccccgccg cccgggcccg ccccccgggc  145260
cggcgcggag tcgggcacgg cgccagtgct cgcacttcgc cctaataata tatatatt  145320
gggacgaagt gcgaacgctt cgcgttctca cttctttac ccggcgcccc cgccccctg  145380
gggcggtccc gcccgccggc caatgggggg gcggcaaggc gggcggccct tgggccgccc  145440
gccgtcccgt tggtcccggc gtccggcggg cgggaccggg ggcccgggga cggcaaacgg  145500
gcgcgcgggg ctcgtatctc attaccgccg aaccgggaag tcggggccg ggccccgccc  145560
cctgccgtt cctcgttagc atgcggaacg gaagcggaaa cccgccggatc ggcggtaat  145620
gagatgccat gcggggcggg gcgcgggcc accgcccta gcgccccgcc catggcagat  145680
ggcgcggatg ggcggggccg ggggttcgac caacgggccg cggccacggg ccccccggcgt  145740
gccggcgtcg gggcggggtc gtgcataatg gaattccgtt cgggggcggc cgccgtggg  145800
ggccgggggc cggcggccctc cgctgctcct ccttcccgcc ggccctggg actatatgag  145860
cccgaggacg ccccgatcgt ccacacggag cgcggctgcc gacacggatc cacgacccga  145920
cgcggggaccg ccagagacag accgtcgac gctcgccgcg ccgggacgcc gatacggga  145980
cgaagcgcg gaggggatc ggccgtccct gtccttttc ccacccaagc atcgaccggt  146040
ccgcgctagt tccgcgtcga cgggcgggt cgtcgggtc cgtgggtctc gcccccctcc  146100
catcgagagt ccgtaggtga cctaccgtgc tacgtccgcc gtcgcagtcg tatccccgga  146160
ggatcgcccc gcatcggcga tggcgtcgga gaacaagcag cgcccggct ccccggggccc  146220
caccgacggg ccgccgccca ccccgagccc agaccgcgac gagcggggg ccctcggtg  146280
gggcggcggag acggaggagg gcggggacga ccccgaccac gaccccgacc acccccaggg  146340
cctcgacgac gccggcggg acgggaggc cccgcggcg ggcaccgacg ccggcgagga  146400
cgccgggac gccgtctcgc cgcgacagct ggccctgctg gcctccatgg tagaggaggc  146460
cgtccggacg atcccgacgc ccgacccgc ggcctcgccg ccccgggccc ccgcttcg  146520
agccgacgac gatgacgggg acgagtacga cgacgcagcc gacgccgccg gcgaccgggc  146580
cccggcccgg ggccgcgcac gggaggcccc gctacgcggc gcgtatccgg accccacgga  146640
ccgcctgtcg ccgcgcccgc cggcccagcc gccgcagaga cgtcgtcacg gccggcggcg  146700
gccatcggcg tcatcgacct cgtcggactc cgggtcctcg tcctcgtcgt ccgcatcctc  146760
ttcgtcctcg tcgtccgacg aggacgagga cgacgacggc aacgacgcgg ccgaccacgc  146820
acgcgaggcg cggggggtcg ggcggggtcc gtcgagcgcg gccggaaag ccccgggcg  146880
gacgccgccc ccgccgggc cacccccct ctccgaggcc gcgcccaagc cccgggcggc  146940
ggcgaggacc cccgcggcct ccgcgggcg catcgagcgc cgccgggccc gcgcggcggt  147000
ggccggccgc gacgccacgg gccgcttcac ggccgggcag ccccgggcg tcgagctgga  147060
cgccgacgcg gcctccggcg cctttctacg cgcgtatacg gacgggtacg tcagcgggga  147120
gccgtggccc ggcgccgcc ccccgccccc gggcgggtg ctgtacgcg gcctgggcga  147180
cagccgcccg ggcctctggg gggcgccga ggcggaggag gcgcgacgcc ggttcgaggc  147240
ctcgggcgcc ccggcggccg tgtgggcgcc cgagctgggc gacgccgcgc agcagtacgc  147300
cctgatcacg cggctgctgt acaccccgga gcggaggcc atggggtggc tccagaaccc  147360
gcgcggtggtc cccggggacg tggcgtcgga ccaggcctgg ttccggatct ccgggcccg  147420
gcgcaacagc agctccttca tcaccggcag cgtggcgcg gccgtgcccc acctgggcta  147480
cgccatggcg gccgccgct tcggctgggg cctggcgcac gcggcggccg ccgtggccat  147540
gagccgccga tacgaccgcg cgcagaaggg cttcctgctg accagcctgc gccgcgccta  147600
cgcgcccctg ttggcgcgcg agaacgcggc gctgacgggg gccgcggga gccccggcgc  147660
cgcgcagat gacgaggggg tcgccgacgc cgtcgtccgc gccgccgccg gcgaccgggc  147720
gccgcggtg cccgccggt acggcgccgc gggatcctc gccgccctgg ggcggctgtc  147780
cgccgcgccc gcctcccccg cgggggggcga cgacccgac gccgcccgcc acgccgacgc  147840
cgacgacgac gccgggcgcc gcgcccaggc cggccgcgtg gccgtggagt gcctggccgc  147900
ctgccgcggg atcctggagg cgctggccga gggcttcgac ggcgacctgg cggccgtccc  147960
ggggctggcc ggggcccggc ccgccagccc ccgcgcgccg gagggacccg cgggcccgc  148020
```

```
ttccccgccg   ccgccgcacg   ccgacgcgcc   ccgcctgcgc   gcgtggctgc   gcgagctgcg    148080
gttcgtgcgc   gacgcgctgg   tgctcatgcg   cctgcgcggg   gacctgcgcg   tggccggcgg    148140
cagcgaggcc   gccgtggccg   ccgtgcgcgc   cgtgagcctg   gtcgccgggg   ccctgggtcc    148200
cgcgctgccg   cgggacccgc   gcctgccgag   ctccgcggcc   gccgccgccg   cggacctgct    148260
gtttgagaac   cagagcctgc   gccccctgct   ggccgccggg   ccgccgccgct  cttcttcgtc    148320
ttcgggggtc   gcggccgccg   cctccgccgc   gccgcgggag   gggcgcaagc   gcaagagtcc    148380
cggcccggcc   cggccgcccg   gaggcggcgg   cccgcgaccc   ccgaagacga   agaagagcgg    148440
cgcggacgcc   cccggctcgg   acgcccgcgc   ccccctcccc   gcgcccgcgc   cccctccac    148500
gcccccgggg   cccgagcccg   ccccccgccca  gccgcgggcc   ccccgggccg   ccgcggcgca    148560
ggccgcccgg   cgcccgcctgg  cgctgtcgcg   ccggcccgcc   gagggccccg   acccctggg    148620
cggctggcgg   cggcagcccc   cggggcccag   ccacacggcg   gcgcccgcgg   ccgccgccct    148680
ggaggcctac   tgctccccgc   gcgccgtggc   cgagctcacg   gaccaccgc    tgttccccgt    148740
cccctggcga   ccggccctca   tgtttgaccc   gcgggccctg   gcctcgatcg   ccgcgcggtg    148800
cgccggcccc   gccccgccgc   ccaggccgc    gtgcggcggc   ggcgacgacg   acagaaccc    148860
ccacccccac   ggggccgccg   ggggccgcct   ctttggcccc   ctgcgcgcct   cgggcccgct    148920
gcgccgcatg   gcggcctgga   tgcgccagat   ccccgacccc   gaggacgtgc   gcgtggtggt    148980
gctgtactcg   ccgctgccgg   gcgaggacct   ggccggcggc   ggggcctcgg   gggggccgcc    149040
ggagtggtcc   gccgagcgcg   gcgggctgtc   ctgcctgctg   gccctcgctg   ccaaccggct    149100
gtgcgggccg   gacacggccg   cctgggcggg   caactggacc   ggcgcccccg   acgtgtcggc    149160
gctgggcgcg   cagggcgtgc   tgctgctgtc   cacgcgggac   ctggccttcg   ccggggccgt    149220
ggagtttctg   gggctgctcg   ccagcgccgg   cgaccggcgg   ctcatcgtgg   tcaacaccgt    149280
gcgcgcctgc   gactggccgg   ccgacgggcc   cgcggtgtcg   cggcagccga   cctacctggc    149340
gtgcgacctg   ctgccgccg    tgcagtgcgc   cgtgcgctgg   ccggcggcgc   gcgacctgcg    149400
ccgcacggtg   ctggcctcgg   gccgcgtgtt   cggccgggg    gtcttcgcgc   gcgtggaggc    149460
cgcgcacgcg   cgcctgtacc   ccgacgcgcc   gccgctgcgc   ctgtgccgcg   gcggcaacgt    149520
gcgctaccgc   gtgcgcacgc   gcttcggccc   ggacacgccg   gtgcccatgt   cccgcgagcga   149580
gtaccgccgg   gccgtgctgc   cggcgctgga   cggccgggcg   gcggcctcgg   ggaccaccga    149640
cgccatggcg   cccggcgcgc   cggacttcg    cgaggaggag   gcccactcgc   accgcgcctg    149700
cgcgcgctgg   ggcctgggcg   cgccgctgcg   gcccgtgtac   gtgcgctgg    ggcgcgaggc    149760
ggtgcgcgcc   ggcccgcccc   ggtggccgg    gccgcgaggc   gacttttcg    ccgcccgcct    149820
gctggagccc   gacgacgacg   cccccccgct   ggtgctgagg   ggcgacgacg   acggcccgcg    149880
ggccctgccg   ccggcgccgc   ccgggattcg   ctgggcctcg   gccacgggcc   gcagcggcac    149940
cgtgctggcg   gcggcggggg   ccgtggaggt   gctgggggcg   gagcgggct   tggccacgcc    150000
cccgcgacgg   gacgttgtgg   actgggaagg   cgccgtgggac  gaagacgacg   gcggcgcgtt    150060
cgagggggac   gggtgctgt   aacggccgg    gacggggcgg   ggcgcttgtg   aaaccgcaag    150120
acgcaataaa   cggcaacgac   ctgattaagt   tttgcagtag   cgttgtttat   tcgaggggcg    150180
ggagggggcg   agggggcggga  gggggcgagg   ggcgggaggg   ggcgaggggc   gggaggggc    150240
gaggggcggg   aggggggcgag  gggcgggagg   gggcgagggg   cgggaggggg   cgaggggcgg    150300
gaggggcgtgg  ggggcggtgg   tggtgcgcgg   gcgccccggg   agggtttgga   tctctgacct    150360
gagattggcg   gcactgaggt   agagatgccc   gaacccccc    gagggagcgc   gggacgcggc    150420
tggggagggc   tgggctggg   gagggctggg   gctggggagg   gctggggctg   ggagggctg    150480
gggctgggga   gggctgggc   tggggaggc    tgggctggg   gagggctggg   gctggggagg    150540
gctggggctg   gggaggctg    gggctgggga   gggctggga   tggggaggc    tggggctgg    150600
gagggctggg   gctgtggtgt   gtgacaggag   cggcgtgtg    cgctggggga   cgtctgagg    150660
agcgggggt    gcgcggtgac   gtgtggatga   ggaacaggag   ttgttgcgcg   gtgagttgtc    150720
gctgtgagtt   gtgttgttgg   gcaggtgtgt   tggatgacgt   gacgtgtgga   tgaggaaccg    150780
gagtcgtcgc   tgtcgccgtgc  tgttggtgtt   ctgttggtgt   tgttacacct   gtggcagccc    150840
gggcccccg    cgcgcggggc   ggcgcgcaaa   aaaggcggc    ggcggtccgg   gcggcgtgcg    150900
cgcgcgcggc   gggcgtgggg   ggcggggccg   cgggagcggg   ggaggagccc   acccacaga    150960
cggggaggag   cggggagga    gcgggggagg   agcggggag    gagccccacc   cacagacggg    151020
gaggagcggg   ggaggagcgg   ccagacccca   aaaacgggcc   ccccgaaac    acacccccg    151080
ggggtcgcgc   gcggcccttt   aaagcgcggc   ggcgggcagc   ccgggccccc   cgcgg         151135
```

```
SEQ ID NO: 2            moltype = AA   length = 1300
FEATURE                 Location/Qualifiers
source                  1..1300
                        mol_type = protein
                        note = human herpesvirus 1 strain McKrae ICP4
                        organism = unidentified
SEQUENCE: 2
MASENKQRPG  SPGPTDGPPP  TPSPDRDERG  ALGWGAETEE  GGDDPDHDPD  HPHDLDDARR    60
DGRAPAAGTD  AGEDAGDAVS  PRQLALLASM  VEEAVRTIPT  PDPAASPPRT  PAFRADDDDG   120
DEYDDAADAA  GDRAPARGRA  REAPLRGAYP  DPTDRLSPRP  PAQPPQRRRH  GRRRPSASST   180
SSDSGSSSSS  SASSSSSSSD  EDEDDDGNDA  ADHAREARAV  GRGPSSAAPE  APGRTPPPPG   240
PPPLSEAAPK  PRAAARTPAA  SAGRIERRRA  RAAVAGRDAT  GRFTAGQPRR  VELDADAASG   300
AFYARYRDGY  VSGEPWPGAG  PPPPGRVLYG  GLGDSRPGLW  GAPEAEEARR  RFEASGAPAA   360
VWAPELGDAA  QQYALITRLL  YTPDAEAMGW  LQNPRVVPGD  VALDQACFRI  SGAARNSSSF   420
ITGSVARAVP  HLGYAMAAGR  FGWGLAHAAA  AVAMSRRYDR  AQKGFLLTSL  RRAYAPLLAR   480
ENAALTGAAG  SPGAGADDEG  VAAAVVAAAA  APGERAVPAG  YGAAGILAAL  GRLSAAPASP   540
AGGDDPDAAR  HADADDDAGR  RAQAGRVAVE  CLAACRGILE  ALAEGFDGDL  AAVPGLAGAR   600
PASPPPRPEGP  AGPASPPPPH  ADAPRLRAWL  RELRFVRDAL  VLMRLRGDLR  VAGGSEAAVA   660
AVRAVSLVAG  ALGPALPRDP  RLPSSAAAAA  ADLLFENQSL  RPLLAAGPRR  SSSSSGVAAA   720
ASAAPREGRK  RKSPGPARPP  GGGGPRPPKT  KKSGADAPGS  DARAPLPAPA  PPSTPPGPEP   780
APAQPAAPRA  AAAQARPRPV  ALSRRPAEGP  DPLGGWRRQP  PGPSHTAAPA  AAALEAYCSP   840
RAVAELTDHP  LFPVPWRPAL  MFDPRALASI  AARCAGPAPA  AQAACGGDD   DENPHPGHAA   900
GGRLFGPLRA  SGPLRRMAAW  MRQIPDPEDV  RVVVLYSPLP  GEDLAGGGAS  GGPPEWSAER   960
GGLSCLLAAL  ANRLCGPDTA  AWAGNWTGAP  DVSALGAQGV  LLLSTRDLAF  AGAVEFLGLL  1020
ASAGDRRLIV  VNTVRACDWP  ADGPAVSRQH  AYLACDLLPA  VQCAVRWPAA  RDLRRTVLAS  1080
GRVFGPGVFA  RVEAAHARLY  PDAPPLRLCR  GGNVRYRVRT  RFGPDTPVPM  SPREYRRAVL  1140
```

```
PALDGRAAAS GTTDAMAPGA PDFCEEEAHS HRACARWGLG APLRPVYVAL GREAVRAGPA   1200
RWRGPRRDFC ARALLEPDDD APPLVLRGDD DGPGALPPAP PGIRWASATG RSGTVLAAAG   1260
AVEVLGAEAG LATPPRRDVV DWEGAWDEDD GGAFEGDGVL                        1300

SEQ ID NO: 3             moltype = AA  length = 420
FEATURE                  Location/Qualifiers
source                   1..420
                         mol_type = protein
                         note = human herpesvirus 1 strain McKrae ICP22
                         organism = unidentified
SEQUENCE: 3
MADISPGAFA PCVKARRPAL RSPPLGTRKR KRPARPLSSE SEVETDTALE SEVESETASD   60
STESGDQEEA PRIGGRRAPR RLGGRFFLDM SAESTTGTET DTAVSDDPDD TSDWSYDDIP   120
PRPKRARVNL RLTSSPDRRD GVIFPKMGRV RSTRETQPRA PTPSAPSPNA MLRRSVRQAQ   180
RRSSARWTPD LGYMRQCINQ LFRVLRVARD PHGSANRLRH LIRDCYLMGY CRARLAPRTW   240
CRLLQVSGGT WGMHLRNTIR EVEARFDATA EPVCKLPCLE ARRYGPECDL SNLEIHLSAT   300
SDDEISDATD LEAAGSDHTL ASQSDTEDAP SPVTLETPEP RGSLAVRLED EFGEFDWTPQ   360
EGSQPWLSAV VADTSSVERP GPSDSGAGRA AEDRKCLDGC RKMRFSTACP YPCSDTFLRP   420

SEQ ID NO: 4             moltype = AA  length = 88
FEATURE                  Location/Qualifiers
source                   1..88
                         mol_type = protein
                         note = human herpesvirus 1 strain McKrae ICP47
                         organism = unidentified
SEQUENCE: 4
MSWALEMADT FLDNMRVGPR TYADVRDEIN KRGREDREAA RTAVHDPERP LLRSPGLLPK   60
IAPNASLGVA HRRTGGTVTD SPRNPVTR                                     88

SEQ ID NO: 5             moltype = DNA  length = 4020
FEATURE                  Location/Qualifiers
source                   1..4020
                         mol_type = genomic DNA
                         note = human herpesvirus 1 strain McKrae ICP4
                         organism = unidentified
SEQUENCE: 5
tttattgcgt cttcgggttt cacaagcgcc ccgccccgtc ccggcccgtt acagcacccc   60
gtccccctcg aacgcgccgc cgtcgtcttc gtcccaggcg ccttccagt ccacaacgtc    120
ccgtcgcggg ggcgtggcca agcccgcctc cgccccccagc acctccacgg ccccgccgc   180
cgccagcacg gtgccgctgc ggcccgtggc cgaggcccag cgaatccggg cggcgccgg    240
cggcagggcc cccgggccgt cgtcgtcgcc gcgcagcacc agcgggggggg cgtcgtcgtc   300
gggctccagc agggcgcggg cgcaaaagtc cctccgcggc ccgcgccacc gggccgggcc   360
ggcgcgcacc gcctcgcgcc gcagcgccac gtacacgggc gcagcggcg cgcccaggcc   420
ccagcgcgcg caggcgcggt gcgagtgggc ctcctcctcg cagaagtccg gcgcgccggg   480
cgccatggcg tcgtggtgcc cgaggccgcg cccggccg tccagcgccg gcagcacggc     540
ccggcggtac tcgcgcgggg acatgggcac cggcgtgtcc gggccgaagc gcgtgcgcac   600
gcggtagcgc acgttgccgc cgcggcacag cgcagcggc cgtcgcgtcgg ggtacagggcg   660
cgcgtgcgcg gcctccacgc gcgcgaagac ccccgggccg aacacgcggc ccgaggccaa   720
caccgtgcgg cgcaggtcgc gcgccgccgg ccagcgcacg gcgcactgca cggcgggcag   780
caggtcgcac gccaggtagg cgtgctgccg cgacaccgcg ggcccgtcgg cgggccagtc   840
gcaggcgacc acggtgttga ccacgatgag cgccgtgcgg ccggcgctgg cgagcagccg   900
cagaaactcc acggcccggg cgaaggccag gtcccgcgtg acagcagca gcacgccctg    960
cgcgcccagc gccgacacgt cggggggcgcc ggtccagttg cccgcccagg cggccgtgtc   1020
cggcccgcac agccggttgg ccagggccgc cagcaggcag gacagcccgc cgcgctcggc   1080
ggaccactcc ggcggccccc ccgaggcccc gccgccgccc aggtcctcgc ccggcagcgg   1140
cgagtacagc accaccacgc gcacgtcctc ggggtcgggg atctggcgca tccaggccgc   1200
catgcggcgc agcgggccccg aggcgcgcag ggggccaaag aggcggcccc cggcggcccc   1260
gtgggggtgg gggttctcgt cgtcgtcgcc gcgccgccac gcggcctggg cggcggggggc   1320
gggcccggcg caccgcgcgg cgatcgaggc cagggcccgc gggtcaaaca tgagggccgg   1380
tcgccagggg acggggaaca gcgggtggtc cgtgagcgg gccacggcgc gcggggagca    1440
gtaggcctcc agggcggcgg ccgcgggcgc cgccgtgtgg ctgggccccg gggcgctgccg   1500
ccgccagccc ccagggggt cggggccctc ggcgggccgg cgcgacagcg ccacggggcg    1560
cgggcggggcc tgcgccgcgg cggccgggg cgccgcgggc tggcgggggg cgggctcggg   1620
ccccgggcgc gtgaggggg gcgcgggcgc ggggagggg gcgcggcggg ccgagcgggg     1680
ggcgtccgcg ccgctcttct tcgtcttcgg ggtcgcggg ccgccgcctc cgggcggccg    1740
ggccgggccg ggactcttgc gcttgcgccc ctcccgcggc gcggcggagg cggcggccgc   1800
gacccccgaa gacgaagaag agcggcgcgg acccgccgcc agcagggggc gcaggctctg   1860
gttctcaaac agcaggtccg cggcggcggc ggccgcggag ctcggcaggc gcgggtcccg   1920
cggcagcgcg ggaccccaggg cccccggcggac caggctcacg gcgcggcacgg cccacgcg   1980
ggcctcgctg ccgccggcca cgcgcaggtc cccgcgcagg cgcatgagca ccagcgcgtc   2040
gcgcacgaac cgcagctcgc gcagccacgc gcgcaggcgg ggcgtcgg cgtgcggcgg     2100
cggcgggaa gcggggcccg cgggtcctcg cggccgcggg gggctggcgg ccgggccc      2160
ggccagcccc gggacggccg ccaggtcgcc gtcgaagccc tcggcagcg cctccaggat    2220
cccgcggcag ccgggcaggc actccacggc cacggcgcgg cggggcgagc              2280
gtcgtcgtcg gcgtcggcgt ggcgggcggc gtcggggtcg tcgccccccg ggggcgaggc   2340
gggcgcggcg gacagccgcc ccaggcggcg gaggatcccg cggcgccgt accccggcggg    2400
caccgcgcgc tcgcccggtg cggcggcggc ggcgacgacg gcggcggcga ccccctcgtc   2460
atctgcgccg cgccggggc tcccgcggc cccgtcagc gccgcgttct cgcgcgccaa     2520
cagggggcgc taggcgcgcg gcg gcaggctggt cagcaggaag cccttctgcg cgcggtcgta  2580
```

```
tcggcggctc atggccacgg cggccgccgc gtgcgccagg ccccagccga agcggccggc  2640
cgccatggcg tagcccaggt ggggcacggc ccgcgccacg ctgccggtga tgaaggagct  2700
gctgttgcgc gcggcgcccg agatccggaa gcaggcctgg tccagcgcca cgtcccgg    2760
gaccacgcgc gggttctgga gccacccat ggcctccgcg tccggggtgt acagcagccg   2820
cgtgatcagg gcgtactgct gcgcggcgtc gcccagctcg ggcgcccaca cggccgccgg  2880
ggcgcccgag gcctcgaacc ggcgtcgcgc ctcctccgcc tcgggcgccc cccagaggcc  2940
cgggcggctg tcgcccaggc cgccgtacag caccccgccc ggggggcggg gcccggcgcc  3000
gggccacggt tccccgctga cgtacccgtc gcgatagcgc gcgtagaagg cgccggaggc  3060
cgcgtcggcg tccagctcga cccgccgggg ctgcccgacg gtgaagcggc ccgtggcgtc  3120
gcggccggcc accgccgcgc ggggccggcg gcgctcgatg cggcccgcgg aggccgcggg  3180
ggtcctcgcc gccgcccggg gcttgggcgc ggcctcggag aggggggtg gcccgggcgg   3240
gggcggcgtc cgcccggggg cttccggcgc cgcgctcgac ggaccccgcc cgacggcccg  3300
cgcctcgcgt gcgtggtcgg ccgcgtcgtt gccgtcgtcg tcctcgtcct cgtcggacga  3360
cgaggacgaa gaggatgcgg acgacgagga cgaggaccg gagtccgacg aggtcgatga   3420
cgccgatggc cgccgccggc cgtgacgacg tctctgcggc ggctgggccg gcgggcgcgg  3480
cgacaggcgg tccgtggggt ccggatacgc gccgcgtagc ggggcctccc gtgcgcggcc  3540
ccgggccggg gcccggtcgc cggcggcgtc ggctgcgtcg tcgtactcgt cccgtcatc   3600
gtcgtcggct cgaaaggcgg gggtccgggg cggcgaggcc ggggcgtgg gcgtcgggat   3660
cgtccggacg gcctcctcta ccatggaggc cagcagggcc agctgtcgcg gcgagacggc  3720
gtccccggcg tcctcgccgg cgtcggtgcc cgccgcgggg gccctccgt cccgccgggc   3780
gtcgtcgagg tcgtgggggt ggtcggggtc gtggtcgggg tcgtcccgc cctcctccgt   3840
ctccgcgccc cacccgaggg ccccccgctc gtcgcgggct gggctcgggg tgggcggcgg  3900
cccgtcggtg gggcccgggg agccggggcg ctgcttgttc tccgacgcca tcgccgatgc  3960
ggggcgatcc tccgggga ta cgactgcgac ggcggacgta gcacggtagg tcacctacgg  4020

SEQ ID NO: 6              moltype = DNA  length = 1320
FEATURE                   Location/Qualifiers
source                    1..1320
                          mol_type = genomic DNA
                          note = human herpesvirus 1 strain McKrae ICP22
                          organism = unidentified
SEQUENCE: 6
ggtcctccgg gacgttttct ggatggccga catttcccca ggcgcttttg tgccttgtgt   60
aaaagcgcgg cgtcccgctc tccgatcccc gccctgggc acgcgcaagc gcaagcgccc   120
tgcccgcccc ctctcatcgg agtctgaggt cgaatccgaa acagccttg agtctgaggt   180
cgaatccgag acagcatcgg attcgaccga gtctggggac caggaggaag ccccccgcat  240
cggtggccgt agggcccccc ggaggcttgg ggggcggttt tttctggaca tgtcggcgga   300
atccaccacg gggacggaaa cggatgcgtc ggtgtcggac gaccccgacg acacgtccga   360
ctggtcttgt gacgacattc cccacgacc caagcggccc cgggtaaacc tgccggctcac  420
tagctctccc gatcggcggg atgggggttat ttttcctaag atgggcggg tccggtctac    480
ccgggaaacg cagcccccggg ccccccaccc gtcgggccca agcccaaatg caatgctccg   540
gcgctcggtg cgccaggccc agaggcggag cagcgcacga tggaccccg acctgggcta   600
catgccagg tgtatcaatc agctgttttc ggtcctgcgg gtcgcccggg accccacgg     660
cagtgccaac cgcctgcgcc acctgatacg cgactgttac ctgatgggat actgccgagc   720
ccgtctggcc ccgcgcacgt ggtgccgctt gctgcaggtg tccggcggaa cctggggcat   780
gcacctgcgc aacaccatac gggaggtgga ggctcgattc gacgccaccg cagaacccgt   840
gtgcaagctt ccttgtttgg aggccagacg gtacggcccg ggtgtgatc ttagtaatct    900
cgagattcat ctcagcgcga caagcgatga tgaaatctcc gatgccaccg atctggaggc   960
cgccggttcg gaccacacgc tcgcgtccca gtccgacacg gaggatgccc cctcccccgt  1020
tacgctggaa accccagaac cccgcgggtc cctgctgtg cgtctggagg atgagtttgg   1080
ggagttttgac tggacccccc aggagggctc ccagccctgg ctgtctgcgg tcgtggccga  1140
taccagctcc gtggaacgcc cgggcccatc cgattctggg gcgggtcgcg cagcagaaga  1200
ccgcaagtgt ctggacggct gccggaaaat gcgcttctcc accgcctgcc cctatccgtg  1260
cagcgacacg tttctccggc cgtgagtccg gtcgccccga ccccttgta tgtccccaaa   1320

SEQ ID NO: 7              moltype = DNA  length = 360
FEATURE                   Location/Qualifiers
source                    1..360
                          mol_type = genomic DNA
                          note = human herpesvirus 1 strain McKrae ICP47
                          organism = unidentified
SEQUENCE: 7
tccgcccaga gactcgggtg atggtcgtac ccgggactca acgggttacc ggattacggg   60
gactgtcggt cacggtcccg ccggttcttc gatgtgccac acccaaggat ggtttggggc   120
cgatttcggg cagcagcccg ggagagcgca gcagggacg ctccgggtcg tgcacggcgg   180
ttctggccgc ctcccggtcc tcacgcccc ttttattgat ctcatcgcgt acgtcggcgt    240
acgtcctggg cccaacccgc atgttgtcca ggaaggtgtc cgccatttcc agggcccacg   300
acatgctttt cccccgacg agcaggaagc ggtccacga acggtcgccg ccggtcgcct    360

SEQ ID NO: 8              moltype = DNA  length = 523
FEATURE                   Location/Qualifiers
source                    1..523
                          mol_type = genomic DNA
                          organism = Human cytomegalovirus
SEQUENCE: 8
gaagatcttt ggttatatag cataaatcaa tattggctat tggccattgc atacgttgta   60
tccatatcat aaatatgtaca tttatattgg ctcatgtcca acattaccgc catgttgaca  120
ttgattattg actagttatt aatagtaatc aattacgggg tcattagttc atagcccata  180
tatggagttc cgcgttacat aacttacggt aaatggcccg cctggctgac cgcccaacga   240
```

```
cccccgccca ttgacgtcaa taatgacgta tgttcccata gtaacgccaa tagggacttt   300
ccattgacgt caatgggtgg agtatttacg gtaaactgcc cacttggcag tacatcaagt   360
gtatcatatg ccaagtacgc ccccatttga cgtcaatgac ggtaaatggc ccgcctggca   420
ttatgcccag tacatgacct tatgggactt tcctacttgg cagtacatct acgtattagt   480
catcgctatt accatggtga tgcggttttg gcagtacatc aat                     523

SEQ ID NO: 9          moltype = DNA  length = 1199
FEATURE               Location/Qualifiers
source                1..1199
                      mol_type = genomic DNA
                      organism = Homo sapiens
SEQUENCE: 9
aatgggtttg ggtgtgtgta aatgagtgtg accggaagcg agtgtgagct tgatctaggc    60
agggaccaca cagcactgtc acacctgcct gctctttagt agaggactga agtgcggggg   120
tgggggtacg gggccggaat agaatgtctc tgggacatct tggcaaacag cagccggaag   180
caaaggggca gctgtgcaaa cggctcaggc aggtgatgga tggcagggta ggaaggggga   240
ggtccagagg tctggatgga ggcttccgca tctgtacctt gcaactcacc cctcaggccc   300
agcaggtcat cggccccctc ctcacacatg taatgacgta gaagagtacc cgggacagt   360
ccggggagat ggagattcgg aaagtatcca tggagctctt acagaatccc ctgtgcggac   420
caggaaactc ttgtagatcc ctgcctatct gaggcccagg cgctgggctg tttctcacaa   480
tattccttca agatgagatt gtggtcccca tttcaaagat gagtacactg agcctctgtg   540
aagttacttg cccatgatca cacaaccagg aattgggcca actgtaattg aactcctgtc   600
taacaaagtt cttgctccca gctccgtctc ttgtttccca cgagcctggg cctctgtgg   660
gtaataccag ctactggagt cagatttctt gggcccagaa cccacccttta ggggcattaa   720
cctttaaaat ctcacttggg caggggtctg ggatcagagt tggaagagtc cctacaatcc   780
tggaccctt ccgccaaatc gtgaaaccag gggtggagtg gggcgagggt tcaaaaccag   840
gccggactga gaggtgaaat tcaccatgac gtcaaactgc cctcaaattc ccgctcactt   900
taagggcgtt acttgttggt gccccaccca tcccccacca tttccatcaa tgacctcaat   960
gcaaatacaa gtgggacggt cctgctgacg cctccaggtt ctggaagcat gagggtgacg  1020
cacccagggg caaaggaccc ctccgcccat tggttgctgt cgactggcgg aactttcccg  1080
acccacagcg gcgggaataa gagcagtcgc tggcgctggg aggcatcaga gacactgccc  1140
agcccaagtg tcgccgccgc ttccacaggg ctctggctgg acgccgccgc cgccgctgc   1199

SEQ ID NO: 10         moltype = DNA  length = 225
FEATURE               Location/Qualifiers
misc_feature          1..225
                      note = bovine growth hormone polyadenylation signal
source                1..225
                      mol_type = other DNA
                      organism = synthetic construct
SEQUENCE: 10
ggatcccgac tgtgccttct agttgccagc catctgttgt ttgcccctcc cccgtgcctt    60
ccttgaccct ggaaggtgcc actcccactg tcctttccta ataaaatgag gaaattgcat   120
cgcattgtct gagtaggtgt cattctattc tggggggtgg ggtggggcag gacagcaagg   180
gggaggattg ggaagacaat agcaggcatg ctggggaaga tcttc                   225

SEQ ID NO: 11         moltype = AA  length = 7
FEATURE               Location/Qualifiers
source                1..7
                      mol_type = protein
                      note = human herpesvirus 1 strain McKrae
                      organism = unidentified
SEQUENCE: 11
STPSTTT                                                                7

SEQ ID NO: 12         moltype = DNA  length = 16
FEATURE               Location/Qualifiers
source                1..16
                      mol_type = genomic DNA
                      note = human herpesvirus 1 strain McKrae
                      organism = unidentified
SEQUENCE: 12
gcaccccac tcccac                                                      16

SEQ ID NO: 13         moltype = DNA  length = 16
FEATURE               Location/Qualifiers
source                1..16
                      mol_type = genomic DNA
                      note = human herpesvirus 1 strain McKrae
                      organism = unidentified
SEQUENCE: 13
ccccagccct ccccag                                                     16

SEQ ID NO: 14         moltype = DNA  length = 17
FEATURE               Location/Qualifiers
source                1..17
                      mol_type = genomic DNA
                      note = human herpesvirus 1 strain McKrae
                      organism = unidentified
```

```
SEQUENCE: 14
ccctcgccc cctcccg                                                                  17

SEQ ID NO: 15          moltype = AA  length = 14
FEATURE                Location/Qualifiers
source                 1..14
                       mol_type = protein
                       note = human herpesvirus 1 strain KOS
                       organism = unidentified
SEQUENCE: 15
AASAPDAADA LAAA                                                                    14

SEQ ID NO: 16          moltype = AA  length = 13
FEATURE                Location/Qualifiers
source                 1..13
                       mol_type = protein
                       note = human herpesvirus 1 strain McKrae
                       organism = unidentified
SEQUENCE: 16
GPRRSSSSSG VAA                                                                     13

SEQ ID NO: 17          moltype =     length =
SEQUENCE: 17
000

SEQ ID NO: 18          moltype =     length =
SEQUENCE: 18
000

SEQ ID NO: 19          moltype = AA  length = 9
FEATURE                Location/Qualifiers
source                 1..9
                       mol_type = protein
                       note = human herpesvirus 1
                       organism = unidentified
SEQUENCE: 19
TAATGARAT                                                                           9
```

What is claimed is:

1. A gene therapy vector comprising a replication-defective variant of herpes simplex virus (HSV) McKrae strain whose genome contains an alteration such that the variant fails to express a functional ICP4 protein comprising SEQ ID NO: 16, wherein the gene therapy vector is capable of expressing a payload in a cell susceptible to McKrae strain infection for at least 18 days.

2. The gene therapy vector of claim 1, wherein the gene therapy vector comprises a neuron specific promoter.

3. The gene therapy vector of claim 2, wherein the neuron specific promoter is a calcitonin gene-related peptide (CGRP) promoter.

4. The gene therapy vector of claim 1, wherein the gene therapy vector comprises a human cytomegalovirus (HCMV) enhancer.

5. The gene therapy vector of claim 1, wherein the gene therapy vector comprises a bovine growth hormone (BGH) polyadenylation signal.

6. The gene therapy vector of claim 1, further comprising a nucleic acid that encodes a therapeutic polypeptide.

7. The gene therapy vector of claim 1, wherein the functional ICP4 protein has an amino acid sequence of SEQ ID NO: 2.

8. The gene therapy vector of claim 1, wherein the gene therapy vector is capable of expressing a payload in a cell susceptible to McKrae strain infection for at least 50 days.

9. The gene therapy vector of claim 1, wherein the gene therapy vector is capable of expressing a payload in a cell susceptible to McKrae strain infection for at least 100 days.

10. The gene therapy vector of claim 1, wherein the gene therapy vector is capable of producing in neurons a mean genome copy number of greater than 5,000 transcripts.

11. The gene therapy vector of claim 1, wherein the gene therapy vector is capable of producing in neurons a mean genome copy number of greater than 10,000 transcripts.

12. The gene therapy vector of claim 1, wherein the gene therapy vector is capable of producing in neurons a mean genome copy number of greater than 15,000 transcripts.

13. A cell transduced with a gene therapy vector according to claim 1.

14. A pharmaceutical composition comprising a gene therapy vector according to claim 1 and a pharmaceutically acceptable carrier.

* * * * *